US012656350B2

(12) United States Patent
Lei et al.

(10) Patent No.: US 12,656,350 B2
(45) Date of Patent: Jun. 16, 2026

(54) METHODS AND COMPOSITIONS FOR TREATING AND DIAGNOSING A SAGE1-RELATED CONDITION

(71) Applicants: SHANGHAI NINTH PEOPLE'S HOSPITAL, SHANGHAI JIAO TONG UNIVERSITY SCHOOL OF MEDICINE, Shanghai (CN); SHANGHAI JIAOTONG UNIVERSITY SCHOOL OF MEDICINE, Shanghai (CN)

(72) Inventors: Ming Lei, Shanghai (CN); Wei Deng, Shanghai (CN); Yanjie Zhang, Shanghai (CN); Yang Song, Shanghai (CN); Chao Zheng, Shanghai (CN)

(73) Assignees: SHANGHAI NINTH PEOPLE'S HOSPITAL, SHANGHAI JIAO TONG UNIVERSITY SCHOOL OF MEDICINE, Shanghai (CN); SHANGHAI JIAOTONG UNIVERSITY SCHOOL OF MEDICINE, Shanghai (CN)

( * ) Notice: Subject to any disclaimer, the term of this patent is extended or adjusted under 35 U.S.C. 154(b) by 925 days.

(21) Appl. No.: 17/783,439

(22) PCT Filed: Dec. 14, 2020

(86) PCT No.: PCT/CN2020/136081
§ 371 (c)(1),
(2) Date: Jun. 8, 2022

(87) PCT Pub. No.: WO2021/115478
PCT Pub. Date: Jun. 17, 2021

(65) Prior Publication Data
US 2023/0031980 A1     Feb. 2, 2023

(30) Foreign Application Priority Data

Dec. 13, 2019   (CN) .......................... 201911282487.6
Dec. 13, 2019   (CN) .......................... 201911282566.7
Dec. 13, 2019   (CN) .......................... 201911282567.1

(51) Int. Cl.
| | |
|---|---|
| *G01N 33/574* | (2006.01) |
| *A61K 39/395* | (2006.01) |
| *A61K 45/06* | (2006.01) |
| *A61P 35/00* | (2006.01) |
| *C07K 14/47* | (2006.01) |
| *C07K 16/30* | (2006.01) |
| *C12Q 1/6886* | (2018.01) |
| *G01N 33/50* | (2006.01) |
| *A61K 39/00* | (2006.01) |

(52) U.S. Cl.
CPC . *G01N 33/57492* (2013.01); *A61K 39/39558* (2013.01); *A61K 45/06* (2013.01); *A61P 35/00* (2018.01); *C07K 14/4748* (2013.01); *C07K*

*16/3069* (2013.01); *C12Q 1/6886* (2013.01); *G01N 33/5023* (2013.01); *A61K 2039/505* (2013.01); *C07B 2200/13* (2013.01); *C07K 2317/76* (2013.01); *C07K 2319/02* (2013.01); *C07K 2319/03* (2013.01); *C07K 2319/33* (2013.01); *C12Q 2600/106* (2013.01); *C12Q 2600/118* (2013.01); *C12Q 2600/154* (2013.01); *C12Q 2600/158* (2013.01)

(58) Field of Classification Search
CPC ................................................ G01N 33/57492
USPC ......................................................... 424/134.1
See application file for complete search history.

(56) References Cited

U.S. PATENT DOCUMENTS

| | | | |
|---|---|---|---|
| 2002/0128188 A1* | 9/2002 | Wei .......................... | C12N 9/90 |
| | | | 435/325 |
| 2016/0060709 A1 | 3/2016 | Wilhelm et al. | |
| 2018/0346536 A1* | 12/2018 | Powlesland ........ | C07K 14/4748 |
| 2019/0160115 A1 | 5/2019 | Falb et al. | |
| 2019/0292601 A1 | 9/2019 | Smith | |

FOREIGN PATENT DOCUMENTS

| | | | |
|---|---|---|---|
| AU | 2016201170 A1 | 3/2016 | |
| CN | 107936109 A | 4/2018 | |
| CN | 107987156 A | 5/2018 | |
| CN | 108218977 A | 6/2018 | |
| CN | 110951874 A | 4/2020 | |
| CN | 110960677 A | 4/2020 | |
| CN | 110974963 A | 4/2020 | |
| IN | 109251243 A | 1/2019 | |
| WO | 2012/031008 A2 | 3/2012 | |
| WO | WO 2017/203526 A1 * | 11/2017 | |
| WO | 2018/161092 A1 | 9/2018 | |

OTHER PUBLICATIONS

Poeta et al (NEJM, 2007, 357: 2552-2561).*
Milner et al (Cancer Research, 1993, 53: 2128-2132).*
Ahmed et al (Journal of Pathology, 2010, 221: 49-56).*

(Continued)

*Primary Examiner* — Sean E Aeder

(74) *Attorney, Agent, or Firm* — Oliff PLC

(57) ABSTRACT

The present disclosure provides methods and kits for diagnosing and assessing SAGE1-positive disorders, and compositions and methods for treating SAGE1-positive disorders. The present disclosure further provides SAGE1 complexes and methods and composition for inhibiting SAGE1 complexes and treating SAGE1-positive disorders.

28 Claims, 58 Drawing Sheets
Specification includes a Sequence Listing.

(56) References Cited

OTHER PUBLICATIONS

Vidhyasagar et al (Biochemical Journal, 2018, 475: 45-60).*

Zhang et al (Journal of Cell Science, 2013, 126: 4850-4855).*

Aug. 23, 2023 Office Action issued in Japanese Patent Application No. 2022-534358.

Maheswaran et al., "Lack of ADAM2, CALR3 and SAGE1 Cancer/Testis Antigen Expression in Lung and Breast Cancer," PLOS One, Aug. 7, 2015, pp. 1-10.

Pu et al., "Research progress of tumor testis antigen gene," Journal of Basic and Clinical oncology, Aug. 2014, vol. 27, No. 4, pp. 366-369.

Atanackovic et al., "Expression of cancer-testis antigens as possible targets for antigen-specific immunotherapy in head and neck squamous cell carcinoma," Cancer Biology & Therapy, 2006, vol. 5, Issue 9, pp. 1218-1225.

Lim et al., "OCT2, SSX and SAGE1 reveal the phenotypic heterogeneity of spermatocytic seminoma reflecting distinct subpopulations of spermatogonia," Journal of Pathology, 2011, vol. 224, pp. 473-483.

Chen et al., "Cancer-Testis Antigen Expression in Digestive Tract Carcinomas: Frequent Expression in Esophageal Squamous Cell Carcinoma and Its Precursor Lesions," Cancer Immunology Research, May 2014, vol. 2, No. 5, pp. 480-486.

Soga et al., "Limited expressino of cancer-testis antigens in renal cell carcinoma patients," Molecular and Clinical Oncology, 2013, vol. 1, pp. 326-330.

Lan et al., "Structural insight into precursor tRNA processing by yeast ribonuclease P," Science, 2018, pp. 1-21.

Feb. 22, 2021 Search Report issued in Chinese Patent Application No. 2019112824876.

Feb. 22, 2021 Search Report issued in Chinese Patent Application No. 2019112825671.

Mar. 15, 2022 Search Report issued in Chinese Patent Application No. 2019112825667.

Mar. 23, 2021 International Search Report issued in International Patent Application No. PCT/CN2020/136081.

Apr. 14, 2021 Supplementary Search Report issued in Chinese Patent Application No. 2019112825671.

* cited by examiner

HCC15

SAGE1:  N — 1  76 ... 766  818  904  I3BD — C hSSB1  INIP

INTS3:  N — 1 34  NTD  498 572  CTD  976 1042 — C

INTS6:  N — 1  160  vWA  803  887  I3BD — C

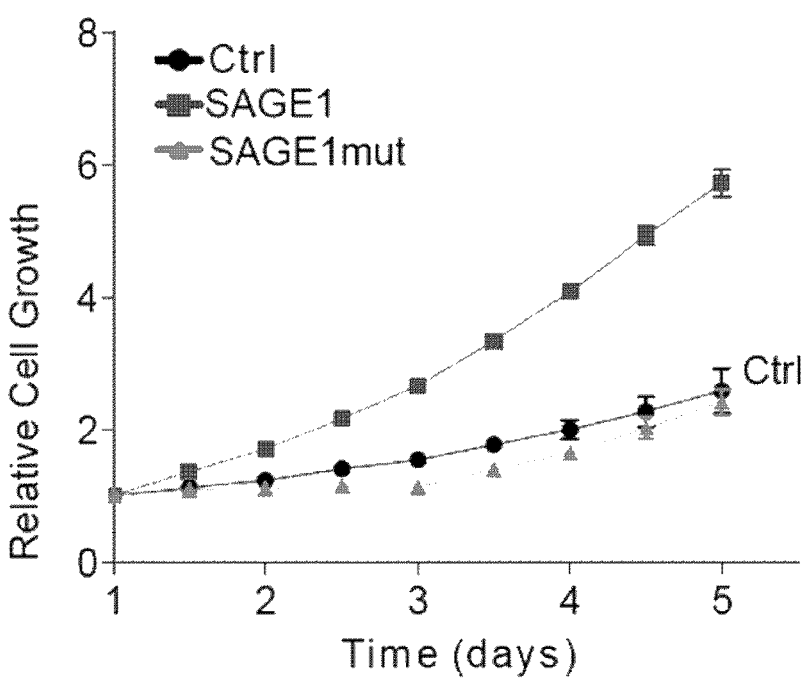
Figure 7J
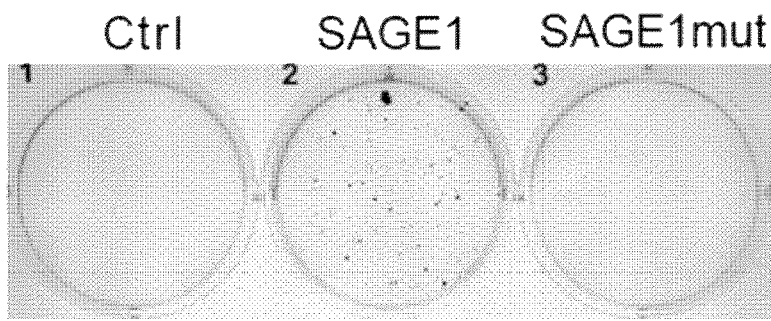
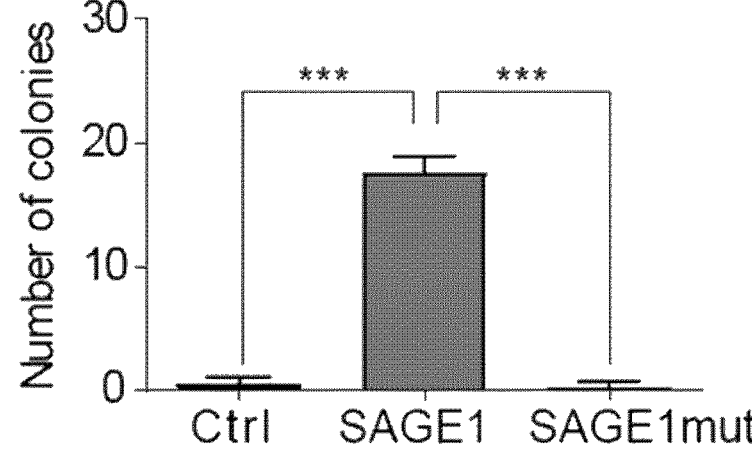
Figure 7K

INTS3$_{CTD}$ (contour level = 1s)

INTS3$_{CTD}$-SAGE1$_{I3BD}$ (contour level = 1s)

Crystal data collection and refinement statistics

|  | INTS3$_{CTD}$ (SeMet-SAD) | INTS3$_{CTD}$-SAGE1$_{I3BD}$ (Native) |
|---|---|---|
| Data collection | | |
| Wavelength (Å) | 1.07817 | 0.97872 |
| Space group | $P6_322$ | $C2$ |
| Cell dimensions | | |
| $\quad$ a, b, c (Å) | 135.3, 135.3, 110.6 | 260.1, 46.2, 103.1 |
| $\quad$ α, β, γ (°) | 90.0, 90.0, 120.0 | 90.0, 113.3, 90.0 |
| Resolution (Å) | 2.3 | 3.0 |
| $R_{merge}$ (%) | 8.0 (81.2) * | 8.9 (51.8) * |
| $I / \sigma I$ | 21.4 (1.5) * | 15.1 (2.0) * |
| Completeness (%) | 98.7 (95.0) * | 97.4 (84.1) * |
| Redundancy | 4.9 (3.5) * | 4.1 (3.6) * |
| | | |
| Refinement | | |
| Resolution (Å) | 42.86-2.30 | 47.40-3.00 |
| No. of reflections | 26,682 | 22,585 |
| $R_{work}$ / $R_{free}$ (%) | 17.3/21.4 | 21.5/25.7 |
| No. of atoms | | |
| $\quad$ INTS3 | 3,185 | 6,384 |
| $\quad$ SAGE1 | - | 718 |
| $\quad$ Water | 94 | - |
| $B$-factors (Å$^2$) | | |
| $\quad$ INTS3 | 77.8 | 114.5 |
| $\quad$ SAGE1 | - | 71.5 |
| $\quad$ Water | 73.4 | - |
| R.m.s. deviations | | |
| $\quad$ Bond lengths (Å) | 0.002 | 0.003 |
| $\quad$ Bond angles (°) | 0.843 | 0.975 |
| Ramachandran plot (%) | | |
| $\quad$ Favored region | 97.7 | 93.9 |
| $\quad$ Allowed region | 100.0 | 100.0 |
| $\quad$ Outlier region | 0.0 | 0.0 |

*Highest resolution shell is shown in parenthesis

Figure 12

Residues involved in interaction between INTS3CTD dimer

| ChainA | ChainA' | Distance(Å) |
|---|---|---|
| Hydrogenbonds | | |
| SER841[OG] | GLN773[OE1] | 2.58 |
| SER874[OG] | CYS777[O] | 3.72 |
| ASN936[ND2] | MSE781[O] | 3.15 |
| ASN933[ND2] | MSE781[O] | 3.02 |
| ASN936[ND2] | ASN783[OD1] | 3.74 |
| ARG848[NH1] | LEU815[O] | 2.88 |
| SER769[OG] | GLU838[OE2] | 2.95 |
| ARG849[NH1] | GLN846[OE1] | 3.42 |
| ARG849[NH2] | GLU850[OE2] | 3.62 |
| GLN773[OE1] | SER841[OG] | 2.58 |
| CYS777[O] | SER874[OG] | 3.72 |
| MSE781[O] | ASN933[ND2] | 3.02 |
| MSE781[O] | ASN936[ND2] | 3.15 |
| ASN783[OD1] | ASN936[ND2] | 3.74 |
| LEU815[O] | ARG848[NH1] | 2.88 |
| GLU838[OE2] | SER769[OG] | 2.95 |
| GLN846[OE1] | ARG849[NH1] | 3.42 |
| GLU850[OE2] | ARG849[NH2] | 3.62 |
| Saltbridges | | |
| ARG849[NH2] | GLU850[OE2] | 3.62 |
| GLU850[OE2] | ARG849[NH2] | 3.62 |

Figure. 13A

Residues involved in interaction between INTS3ᴄᴛᴅ-SAGE1ɪ3ʙᴅ

| ChainA (Ints3) | ChainB (Sage1) | Distance(Å) |
|---|---|---|
| Hydrogenbonds | | |
| GLN773[OE1] | SER841[OG] | 2.33 |
| SER769[OG] | THR804[OG1] | 3.18 |
| MET781[SD] | SER874[N] | 3.75 |
| MET781[O] | ASN933[ND2] | 3.70 |
| ASN818[OD1] | LYS882[NZ] | 3.65 |
| ARG849[O] | ARG849[NH2] | 3.51 |
| GLU838[OE2] | SER769[OG] | 2.85 |
| SER874[OG] | MET781[SD] | 3.16 |
| PHE871[N] | CYS777[SG] | 3.77 |
| SER841[OG] | GLN773[OE1] | 2.60 |
| SER874[OG] | CYS777[O] | 3.20 |
| ASN933[ND2] | MET781[O] | 3.30 |
| ARG848[NH1] | ALA816[O] | 3.58 |
| ARG848[NH1] | ASN818[OD1] | 2.93 |
| ARG849[NH1] | ARG849[O] | 3.83 |
| SER769[OG] | GLU838[OE2] | 3.29 |
| ARG849[NH2] | ARG849[O] | 3.80 |
| ARG849[NH2] | GLU850[OE2] | 2.99 |
| Saltbridges | | |
| GLU850[OE2] | ARG849[NH2] | 3.29 |
| ARG849[NH2] | GLU850[OE2] | 2.99 |
| GLU850[OE2] | ARG849[NH1] | 3.68 |
| ARG849[NH1] | GLU850[OE2] | 3.40 |
| GLU850[OE1] | ARG849[NH2] | 3.38 |

Figure. 13B

The spectral counts of the high-confidence SAGE1 interactors in HuTu 80 cells identified by IP-MS analysis.

| | Gene name | IgG[a] | | | SAGE[a] | | |
|---|---|---|---|---|---|---|---|
| | | rep1 | rep2 | rep3 | rep1 | rep2 | rep3 |
| Q9NXZ1 | SAGE1 | 0 | 0 | 0 | 41 | 32 | 49 |
| Q68E01 | INTS3 | 0 | 0 | 0 | 13 | 6 | 14 |
| Q9NRY2 | INIP | 0 | 0 | 0 | 3 | 2 | 2 |
| Q9BQ15 | NABP2 | 0 | 0 | 0 | 0 | 1 | 1 |
| Q96AH0 | NABP1 | 0 | 0 | 0 | 0 | 0 | 0 |
| Q8N201 | INTS 1 | 0 | 0 | 0 | 0 | 0 | 0 |
| Q9H0H0 | INTS 2 | 0 | 0 | 0 | 0 | 0 | 0 |
| Q96HW7 | INTS 4 | 0 | 0 | 0 | 0 | 0 | 0 |
| Q6P9B9 | INTS 5 | 0 | 0 | 0 | 0 | 0 | 0 |
| Q5JSJ4 | INTS 6 | 0 | 0 | 0 | 0 | 0 | 0 |
| Q9NVH2 | INTS 7 | 0 | 0 | 0 | 0 | 0 | 0 |
| Q75QN2 | INTS 8 | 0 | 0 | 0 | 0 | 0 | 0 |
| Q9NV88 | INTS 9 | 0 | 0 | 0 | 0 | 0 | 0 |
| Q9NVR2 | INTS 10 | 0 | 0 | 0 | 0 | 0 | 0 |
| Q5TA45 | INTS 11 | 0 | 0 | 0 | 0 | 0 | 0 |
| Q96CB8 | INTS 12 | 0 | 0 | 0 | 0 | 0 | 0 |
| Q9NVM9 | INTS 13 | 0 | 0 | 0 | 0 | 0 | 0 |
| Q96SY0 | INTS 14 | 0 | 0 | 0 | 0 | 0 | 0 |
| Q04724 | TLE1 | 0 | 0 | 0 | 10 | 8 | 12 |
| Q04725 | TLE2 | 0 | 0 | 0 | 0 | 0 | 0 |
| Q04726 | TLE3 | 0 | 0 | 0 | 38 | 40 | 48 |
| Q04727 | TLE4 | 0 | 0 | 0 | 0 | 0 | 0 |
| Q08117 | TLE5 | 0 | 0 | 0 | 5 | 5 | 5 |
| Q92793 | CREBBP | 0 | 0 | 0 | 20 | 20 | 38 | a: The antibody used in the IP experiment

Figure. 14A

The spectral counts of the high-confidence SAGE1 interactors in K562 cells identified by IP-MS analysis.

| | Gene name | IgG[a] | | | SAGE[a] | | |
|---|---|---|---|---|---|---|---|
| | | rep1 | rep2 | rep3 | rep1 | rep2 | rep3 |
| Q9NXZ1 | SAGE1 | 0 | 0 | 0 | 36 | 33 | 49 |
| Q68E01 | INTS3 | 0 | 0 | 0 | 4 | 3 | 14 |
| Q9NRY2 | INIP | 0 | 0 | 0 | 1 | 2 | 1 |
| Q9BQ15 | NABP2 | 0 | 0 | 0 | 0 | 0 | 0 |
| Q96AH0 | NABP1 | 0 | 0 | 0 | 0 | 0 | 0 |
| Q8N201 | INTS 1 | 0 | 0 | 0 | 0 | 0 | 0 |
| Q9H0H0 | INTS 2 | 0 | 0 | 0 | 0 | 0 | 0 |
| Q96HW7 | INTS 4 | 0 | 0 | 0 | 0 | 0 | 0 |
| Q6P9B9 | INTS 5 | 0 | 0 | 0 | 0 | 0 | 0 |
| Q5JSJ4 | INTS 6 | 0 | 0 | 0 | 0 | 0 | 0 |
| Q9NVH2 | INTS 7 | 0 | 0 | 0 | 0 | 0 | 0 |
| Q75QN2 | INTS 8 | 0 | 0 | 0 | 0 | 0 | 0 |
| Q9NV88 | INTS 9 | 0 | 0 | 0 | 0 | 0 | 0 |
| Q9NVR2 | INTS 10 | 0 | 0 | 0 | 0 | 0 | 0 |
| Q5TA45 | INTS 11 | 0 | 0 | 0 | 0 | 0 | 0 |
| Q96CB8 | INTS 12 | 0 | 0 | 0 | 0 | 0 | 0 |
| Q9NVM9 | INTS 13 | 0 | 0 | 0 | 0 | 0 | 0 |
| Q96SY0 | INTS 14 | 0 | 0 | 0 | 0 | 0 | 0 |
| Q04724 | TLE1 | 0 | 0 | 0 | 11 | 11 | 15 |
| Q04725 | TLE2 | 0 | 0 | 0 | 0 | 0 | 0 |
| Q04726 | TLE3 | 0 | 0 | 0 | 37 | 28 | 58 |
| Q04727 | TLE4 | 0 | 0 | 0 | 0 | 0 | 15 |
| Q08117 | TLE5 | 0 | 0 | 0 | 15 | 12 | 24 |
| Q92793 | CREBBP | 0 | 0 | 0 | 5 | 2 | 10 | a: The antibody used in the IP experiment

Figure. 14B

The spectral counts of the high-confidence SAGE1 interactors in U2OS cells identified by IP-MS analysis.

| | Gene name | IgG[a] | | | SAGE[a] | | |
|---|---|---|---|---|---|---|---|
| | | rep1 | rep2 | rep3 | rep1 | rep2 | rep3 |
| Q9NXZ1 | SAGE1 | 0 | 0 | 0 | 29 | 21 | 35 |
| Q68E01 | INTS3 | 0 | 0 | 0 | 8 | 7 | 15 |
| Q9NRY2 | INIP | 0 | 0 | 0 | 3 | 2 | 2 |
| Q9BQ15 | NABP2 | 0 | 0 | 0 | 0 | 0 | 0 |
| Q96AH0 | NABP1 | 0 | 0 | 0 | 1 | 0 | 1 |
| Q8N201 | INTS 1 | 0 | 0 | 0 | 0 | 0 | 0 |
| Q9H0H0 | INTS 2 | 0 | 0 | 0 | 0 | 0 | 0 |
| Q96HW7 | INTS 4 | 0 | 0 | 0 | 0 | 0 | 0 |
| Q6P9B9 | INTS 5 | 0 | 0 | 0 | 0 | 0 | 0 |
| Q5JSJ4 | INTS 6 | 0 | 0 | 0 | 0 | 0 | 0 |
| Q9NVH2 | INTS 7 | 0 | 0 | 0 | 0 | 0 | 0 |
| Q75QN2 | INTS 8 | 0 | 0 | 0 | 0 | 0 | 0 |
| Q9NV88 | INTS 9 | 0 | 0 | 0 | 0 | 0 | 0 |
| Q9NVR2 | INTS 10 | 0 | 0 | 0 | 0 | 0 | 0 |
| Q5TA45 | INTS 11 | 0 | 1 | 1 | 0 | 0 | 0 |
| Q96CB8 | INTS 12 | 0 | 0 | 0 | 0 | 0 | 0 |
| Q9NVM9 | INTS 13 | 0 | 0 | 0 | 0 | 0 | 0 |
| Q96SY0 | INTS 14 | 0 | 0 | 0 | 0 | 0 | 0 |
| Q04724 | TLE1 | 0 | 0 | 0 | 9 | 10 | 13 |
| Q04725 | TLE2 | 0 | 0 | 0 | 6 | 0 | 0 |
| Q04726 | TLE3 | 0 | 0 | 0 | 23 | 26 | 26 |
| Q04727 | TLE4 | 0 | 0 | 0 | 0 | 0 | 0 |
| Q08117 | TLE5 | 0 | 0 | 0 | 12 | 12 | 17 |
| Q92793 | CREBBP | 0 | 0 | 0 | 11 | 11 | 17 | a: The antibody used in the IP experiment

Figure. 14C

The spectral counts of the high-confidence SAGE1 interactors in KYSE30 cells identified by IP-MS analysis.

| | Gene name | IgG[a] | | | SAGE[a] | | |
|---|---|---|---|---|---|---|---|
| | | rep1 | rep2 | rep3 | rep1 | rep2 | rep3 |
| Q9NXZ1 | SAGE1 | 0 | 0 | 0 | 9 | 11 | 9 |
| Q68E01 | INTS3 | 0 | 0 | 0 | 7 | 3 | 5 |
| Q9NRY2 | INIP | 0 | 0 | 0 | 2 | 2 | 0 |
| Q9BQ15 | NABP2 | 0 | 0 | 0 | 0 | 0 | 0 |
| Q96AH0 | NABP1 | 0 | 0 | 0 | 0 | 0 | 0 |
| Q8N201 | INTS 1 | 0 | 0 | 0 | 0 | 0 | 0 |
| Q9H0H0 | INTS 2 | 0 | 0 | 0 | 0 | 0 | 0 |
| Q96HW7 | INTS 4 | 0 | 0 | 0 | 0 | 0 | 0 |
| Q6P9B9 | INTS 5 | 0 | 0 | 0 | 0 | 0 | 0 |
| Q5JSJ4 | INTS 6 | 0 | 0 | 0 | 0 | 0 | 0 |
| Q9NVH2 | INTS 7 | 0 | 0 | 0 | 0 | 0 | 0 |
| Q75QN2 | INTS 8 | 0 | 0 | 0 | 0 | 0 | 0 |
| Q9NV88 | INTS 9 | 0 | 0 | 0 | 0 | 0 | 0 |
| Q9NVR2 | INTS 10 | 0 | 0 | 0 | 0 | 0 | 0 |
| Q5TA45 | INTS 11 | 0 | 1 | 1 | 0 | 0 | 0 |
| Q96CB8 | INTS 12 | 0 | 0 | 0 | 0 | 0 | 0 |
| Q9NVM9 | INTS 13 | 0 | 0 | 0 | 0 | 0 | 0 |
| Q96SY0 | INTS 14 | 0 | 0 | 0 | 0 | 0 | 0 |
| Q04724 | TLE1 | 0 | 0 | 0 | 21 | 18 | 18 |
| Q04725 | TLE2 | 0 | 0 | 0 | 0 | 0 | 0 |
| Q04726 | TLE3 | 0 | 0 | 0 | 30 | 37 | 41 |
| Q04727 | TLE4 | 0 | 0 | 0 | 0 | 0 | 0 |
| Q08117 | TLE5 | 0 | 0 | 0 | 10 | 14 | 13 |
| Q92793 | CREBBP | 0 | 0 | 0 | 42 | 55 | 45 | a: The antibody used in the IP experiment

Figure. 14D

Prevalence of SAGE1 expression in pan-cancer (estimated by IHC staining)

| Tumor | Case Number (n) | SAGE1 positive (n) |
|---|---|---|
| Melanoma | 155 | 12 |
| Head and neck cancer | 43 | 4 |
| Pancreatic cancer | 43 | 3 |
| Colorectal caner | 36 | 2 |
| Neuroblastoma | 34 | 3 |
| Hepatocellular carcinoma | 31 | 1 |
| Bladder Cancer | 14 | 2 |
| Leukemia | 12 | 6 |
| Ovary Cancer | 10 | 1 |
| Kidney Cancer | 10 | 0 |
| Non-Small cell lung cancer | 9 | 3 |
| Breast cancer | 9 | 1 |
| Lymphoma | 9 | 0 |
| Esophageal carcinoma | 8 | 1 |
| Prostate Cancer | 4 | 1 |
| Cervical Cancer | 4 | 0 |
| Endometrial Carcinoma | 4 | 0 |
| Nephroblastoma | 3 | 1 |
| Osteosarcoma | 3 | 0 |
| Stomach adenocarcinoma | 3 | 0 |
| Thyroid carcinoma | 3 | 0 |
| Glioma | 3 | 0 |
| Cholangiocarcinoma | 2 | 0 |
| Small cell lung cancer | 2 | 0 |
| Adrenal Cancer | 2 | 0 |
| Testicular germ cell tumors | 2 | 0 |
| Rhabdomyosarcoma | 1 | 1 |
| Gallbladder Cancer | 1 | 1 |
| Small intestinal adenocarcinoma | 1 | 0 |
| Cholangiocarcinoma | 1 | 0 |
| Skin carcinoma | 1 | 0 |
| Vaginal Cancers | 1 | 0 |
| Hepatoblastoma | 1 | 0 |
| Total | 465 | 43 |

Figure. 15

Inhibition of SAGE1 expression by human SAGE1 shRNA

| shRNA | SEQ ID NO: | Inhibition (%) of SAGE1 expression |
|---|---|---|
| shRNA Y12660 | 106 | 35% |
| shRNA Y12661 | 107 | 18% |
| shRNA Y12662 | 108 | 38% |
| shRNA Y12663 | 109 | 31% |
| shRNA Y12664 | 110 | 45% |
| shRNA Y12665 | 111 | 20% |
| shRNA Y12666 | 112 | 24% |
| shRNA Y12667 | 113 | 22% |
| shRNA Y12668 | 114 | 43% |
| shRNA Y12669 | 115 | 26% |
| shRNA Y12670 | 116 | 19% |
| shRNA Y12671 | 117 | 37% |
| shRNA Y12672 | 118 | 52% |
| shRNA Y12673 | 119 | 55% |
| shRNA Y12674 | 120 | 39% |
| shRNA Y12675 | 121 | 42% |
| shRNA Y12676 | 122 | 56% |
| shRNA Y12677 | 123 | 38% |
| shRNA Y12678 | 124 | 48% |
| shRNA Y12679 | 125 | 28% |
| shRNA Y12680 | 126 | 35% |
| shRNA Y12681 | 127 | 37% |
| shRNA Y12682 | 128 | 7% |
| shRNA Y12683 | 129 | 40% |
| shRNA Y12684 | 130 | 32% |
| shRNA Y12685 | 131 | 36% |
| shRNA Y12686 | 132 | 30% |
| shRNA Y12687 | 133 | 25% |
| shRNA Y12688 | 134 | 60% |
| shRNA Y12689 | 135 | 14% |
| shRNA Y12690 | 136 | 68% |
| shRNA Y12691 | 137 | 22% |
| shRNA Y12692 | 138 | 28% |
| shRNA Y12693 | 139 | 26% |
| shRNA Y12694 | 140 | 35% |
| shRNA Y12695 | 141 | 31% |
| shRNA Y12696 | 142 | 61% |
| shRNA Y12697 | 143 | 67% |
| shRNA Y12698 | 144 | 32% |
| shRNA Y12699 | 145 | 45% |

Figure. 16

Target sequences of SAGE1 mRNA transcript variant 1

| SEQ ID NO: | Target Sequence | Sites on SAGE1_transcript variant 1 (SEQ ID NO:2) |
|---|---|---|
| 11 | GCAGTCACTCACAGCATTT | 292-310 |
| 12 | CCAACCAGTAGCTGATAAT | 333-351 |
| 13 | CCTGATAACGTCTTGTCAA | 577-595 |
| 14 | CCACAGGGCTTATTAATAT | 602-620 |
| 15 | GCACCTGATAACGTGTTGT | 715-733 |
| 16 | GGGATCCATATGCTACCAT | 794-812 |
| 17 | CCTGATAACATCTTGTCAA | 859-867 |
| 18 | GCTTCAACAGGGCTTATTA | 880-898 |
| 19 | CCCTCACAATGTCTGTGAA | 954-972 |
| 20 | CCGCAACCTAATAACGTAT | 994-1012 |
| 21 | GGGATCAGTATGCTACCAT | 1076-1094 |
| 22 | CCTAGTAACGCCTTGTCAA | 1141-1159 |
| 23 | GGGCTTGCTTATTTGGCAA | 1171-1189 |
| 24 | GGGATCAGCATGCTACCAT | 1217-1235 |
| 25 | GCTGTTACACCAGAGCTTA | 1300-1318 |
| 26 | GGATAACGTCTTGTCAAAT | 1425-1443 |
| 27 | GGAGCTAGTATTCCAGCAA | 1471-1489 |
| 28 | GGGATCTGTATGCTACCAT | 1499-1517 |
| 29 | GCACCACAGCTTGGTCATA | 1588-1606 |
| 30 | GGTATTCCATCCATGAGTA | 1618-1636;490-508 |
| 31 | CCAAGCAGCATCCGATAAT | 1836-1854 |
| 32 | GGTGTTTCATCCATGAGTA | 1900-1918 |

Figure 17A

| 33 | GCTGCAGTCACTCACAACA | 1933-1951 |
| 34 | CCTGGTAACATCTTGTCAA | 1987-2005 |
| 35 | GGAATTTCATCCACGATTA | 2041-2059 |
| 36 | GAAGATGACAAATGGCCAA | 2103-2121 |
| 37 | CCTGATAACTCCTTGTCAA | 2128-2146 |
| 38 | GGTTCCACCTGGTTGTATT | 2148-2166 |
| 39 | GCTGGTATTTCATGCAGAA | 2179-2197 |
| 40 | GCTACTGTCATTCACGATA | 2215-2233 |
| 41 | GCCACCCAATGCATTGGAT | 2331-2349 |
| 42 | GCCAAATACACCACAAATA | 2493-2511 |
| 43 | CTTCTCACACAGCGGGATA | 43-61(5'UTR) |
| 44 | GAGCTGGTATTCCACCCAT | 1331-1349 |
| 45 | TCAGTATGCTACCGTCAAT | 1362-1380 |
| 46 | GGAGCTAGTATTCCAGCAA | 1471-1489 |
| 47 | CCTCCATGGCTTCGTCATA | 2011-2029 |
| 48 | CCACGATTACCAGGGATCT | 2051-2069 |
| 49 | GAGAAGGCGCTTAAAGAAA | 2713-2731 |
| 50 | GGAACAGGTTATTGCTGAA | 2897-2915(3'UTR) |
| 51 | GCTGATAATGTCTTGTCAA | 343-361 |
| 52 | CACTCTTCATCTAAGAGAA | 232-250 |
| 53 | CACTCACAATGTCTGTGAA | 672-690 |
| 54 | CCAAGGAGAAACAAGGACATA | 2799-2819(3 'UTR) |
| 55 | GCTGCCTATGTGTTTACAAAT | 124-144 |
| 56 | CCCAAACTGATAAGGTCATAT | 1559-1579 |
| 57 | GCTGGAATTTCATCCACGATT | 2038-2058 |
| 58 | CTGCTGCCTATGTGTTTACAA | 122-142 |

Figure 17A
CONTINUED

| 59 | GTCCCACAGGGCTTATTAA | 599-617 |
| 60 | TGGTATTTCATGCAGAAGT | 2181-2199 |
| 61 | GTTCCACCTGGTTGTATTA | 2149-2167 |
| 62 | GCTGGAATTTCATCCACGATT | 2038-2058 |
| 63 | CTGCTGCCTATGTGTTACAA | 122-142 |
| 64 | CCAAGGAGAAACAAGGACATA | 2799-2819 |
| 65 | GCTGCCTATGTGTTACAAAT | 124-144 |
| 66 | CCCAGACTGATAAGGTCATAT | 1559-1579 |
| 67 | CCCAAACTGATAAGGTCATAT | 1559-1579 |

Figure 17A
CONTINUED

Target sequences of SAGE1 genome

| SEQ ID NO: | Sequence |
| --- | --- |
| 68 | AAGGAAGAGTATGTCCTCG |
| 69 | AAGTAAATCTGGTTGCAAC |

Figure 17B

SAGE1 siRNA

| SEQ ID NO: | Sequence | Description |
|---|---|---|
| 70 | GCUGAUAAUGUCUUGUCAATT | hs-SAGE1-si-1 sense strand |
| 71 | UUGACAAGACAUUAUCAGCT T | hs-SAGE1-si-1 antisense strand |
| 72 | CACUCUUCAUCUAAGAGAATT | hs-SAGE1-si-2 sense strand |
| 73 | UUCUCUUAGAUGAAGAGUGTT | hs-SAGE1-si-2 antisense strand |
| 74 | CACUCACAAUGUCUGUGAATT | hs-SAGE1-si-3 sense strand |

| 75 | UUCACAGACAUUGUGAGUGTT | hs-SAGE1-si-3 antisense strand |
|---|---|---|
| 76 | CCAAGGAGAAACAAGGACAUA | si752 sense strand |
| 77 | UAUGUCCUUGUUUCUCCUUGG | si752 antisense strand |
| 78 | CCCAAACUGAUAAGGUCAUAU | si754 sense strand |
| 79 | AUAUGACCUUAUCAGUUUGGG | si754 antisense strand |
| 80 | GCUGCAGUCACUCACAACATT | Y82 sense strand |
| 81 | UGUUGUGAGUGACUGCAGCTT | Y82 antisense strand |

Figure 17C

SAGE1 shRNA

| SEQ ID NO: | Sequence | Description |
|---|---|---|
| 82 | CCGGCCAAGGAGAAACAAGGACAUACUCGAGU AUGUCCUUGUUUCUCCUUGGUUUUUG | shRNA 115752 |
| 83 | CCGGGCUGCCUAUGUGUUUACAAAUCUCGAGA UUUGUAAACACAUAGGCAGCUUUUUG | shRNA 115753 |
| 84 | CCGGCCCAAACUGAUAAGGUCAUAUCUCGAGA UAUGACCUUAUCAGUCUGGGUUUUUG | shRNA 115754 |
| 85 | CCGGGCUGGAAUUUCAUCCACGAUUCUCGAGA AUCGUGGAUGAAAUUCCAGCUUUUUG | shRNA 115755 |
| 86 | CCGGCUGCUGCCUAUGUGUUUACAACUCGAGU UGUAAACACAUAGGCAGCAGUUUUUG | shRNA 115756 |
| 87 | UGCUGUUGACAGUGAGCGCGGUCCCACAGGGC UUAUUAAUUAGUGAAGCCACAGAUGUAAUUA AUAAGCCCUGUGGGACCAUGCCUACUGCCUCG GA | shRNA sequence |
| 88 | UGCUGUUGACAGUGAGCGACUGGUAUUUCAU GCAGAAGUAUAGUGAAGCCACAGAUGUAUAC UUCUGCAUGAAAUACCAGCUGCCUACUGCCUC GGA | shRNA sequence |

Figure 17D

| 89 | UGCUGUUGACAGUGAGCGAGGUUCCACCUGGU UGUAUUAAUAGUGAAGCCACAGAUGUAUUAA UACAACCAGGUGGAACCGUGCCUACUGCCUCG GA | shRNA sequence |
| 90 | CCGGGCUGGAAUUUCAUCCACGAUUCUCGAGA AUCGUGGAUGAAAUUCCAGCUUUUUG | shRNA sequence |
| 91 | CCGGCUGCUGCCUAUGUGUUUACAACUCGAGU UGUAAACACAUAGGCAGCAGUUUUUG | shRNA sequence |
| 92 | CCGGCCAAGGAGAAACAAGGACAUACUCGAGU AUGUCCUUGUUUCUCCUUGGUUUUUG | shRNA sequence |
| 93 | CCGGGCUGCCUAUGUGUUUACAAAUCUCGAGA UUUGUAAACACAUAGGCAGCUUUUUG | shRNA sequence |
| 94 | CCGGCCCAGACUGAUAAGGUCAUAUCUCGAGA UAUGACCUUAUCAGUCUGGGUUUUUG | shRNA sequence |
| 95 | CCGGCCCAAACUGAUAAGGUCAUAUCUCGAGA UAUGACCUUAUCAGUCUGGGUUUUUG | shRNA sequence |
| 106 | CCGGGCAGUCACUCACAGCAUUUUCAAGAGA AAAUGCUGUGAGUGACUGCUUUUUG | shRNA Y12660 |
| 107 | CCGGCCAACCAGUAGCUGAUAAUUUCAAGAGA AUUAUCAGCUACUGGUUGGUUUUUG | shRNA Y12661 |
| 108 | CCGGCCUGAUAACGUCUUGUCAAUUCAAGAGA UUGACAAGACGUUAUCAGGUUUUUG | shRNA Y12662 |
| 109 | CCGGCCACAGGGCUUAUUAAUAUUUCAAGAGA AUAUUAAUAAGCCCUGUGGUUUUUG | shRNA Y12663 |
| 110 | CCGGGCACCUGAUAACGUGUUGUUCAAGAGA ACAACACGUUAUCAGGUGCUUUUUG | shRNA Y12664 |
| 111 | CCGGGGAUCCAUAUGCUACCAUUUCAAGAGA AUGGUAGCAUAUGGAUCCCUUUUUG | shRNA Y12665 |
| 112 | CCGGCCUGAUAACAUCUUGUCAAUUCAAGAGA UUGACAAGAUGUUAUCAGGUUUUUG | shRNA Y12666 |
| 113 | CCGGGCUUCAACAGGGCUUAUUAUUCAAGAGA UAAUAAGCCCUGUUGAAGCUUUUUG | shRNA Y12667 |

Figure 17D
CONTINUED

| 114 | CCGGCCCUCACAAUGUCUGUGAAUUCAAGAGA UUCACAGACAUUGUGAGGGUUUUUUG | shRNA Y12668 |
| 115 | CCGGCCGCAACCUAAUAACGUAUUCAAGAGA AUACGUUAUUAGGUUGCGGUUUUUUG | shRNA Y12669 |
| 116 | CCGGGGGAUCAGUAUGCUACCAUUCAAGAGA AUGGUAGCAUACUGAUCCCUUUUUUG | shRNA Y12670 |
| 117 | CCGGCCUAGUAACGCCUUGUCAAUUCAAGAGA UUGACAAGGCGUUACUAGGUUUUUUG | shRNA Y12671 |
| 118 | CCGGGGGCUUGCUUAUUUGGCAAUUCAAGAG AUUGCCAAAUAAGCAAGCCCUUUUUUG | shRNA Y12672 |
| 119 | CCGGGGGAUCAGCAUGCUACCAUUCAAGAGA AUGGUAGCAUGCUGAUCCCUUUUUUG | shRNA Y12673 |
| 120 | CCGGGCUGUUACACCAGAGCUUAUUCAAGAGA UAAGCUCUGGUGUAACAGCUUUUUUG | shRNA Y12674 |
| 121 | CCGGGAUAACGUCUUGUCAAAUUCAAGAG AAUUUGACAAGACGUUAUCCUUUUUUG | shRNA Y12675 |
| 122 | CCGGGGAGCUAGUAUUCCAGCAAUUCAAGAGA UUGCUGGAAUACUAGCUCCUUUUUUG | shRNA Y12676 |
| 123 | CCGGGGGAUCUGUAUGCUACCAUUCAAGAGA AUGGUAGCAUACAGAUCCCUUUUUUG | shRNA Y12677 |
| 124 | CCGGGCACCACAGCUUGGUCAUAUUCAAGAGA UAUGACCAAGCUGUGGUGCUUUUUUG | shRNA Y12678 |
| 125 | CCGGGGUAUUCCAUCCAUGAGUAUUCAAGAGA UACUCAUGGAUGGAAUACCUUUUUUG | shRNA Y12679 |
| 126 | CCGGCCAAGCAGCAUCCGAUAAUUCAAGAGA AUUAUCGGAUGCUGCUUGGUUUUUUG | shRNA Y12680 |
| 127 | CCGGGGUGUUUCAUCCAUGAGUAUUCAAGAG AUACUCAUGGAUGAAACACCUUUUUUG | shRNA Y12681 |
| 128 | CCGGGCUGCAGUCACUCACAACAUUCAAGAGA UGUUGUGAGUGACUGCAGCUUUUUUG | shRNA Y12682 |
| 129 | CCGGCCUGGUAACAUCUUGUCAAUUCAAGAGA UUGACAAGAUGUUACCAGGUUUUUUG | shRNA Y12683 |

Figure 17D
CONTINUED

| 130 | CCGGGGAAUUUCAUCCACGAUUAUUCAAGAGA UAAUCGUGGAUGAAAUUCCUUUUUG | shRNA Y12684 |
|---|---|---|
| 131 | CCGGGAAGAUGACAAAUGGCCAAUUCAAGAG AUUGGCCAUUUGUCAUCUUCUUUUUG | shRNA Y12685 |
| 132 | CCGGCCUGAUAACUCCUUGUCAAUUCAAGAGA UUGACAAGGAGUUAUCAGGUUUUUG | shRNA Y12686 |
| 133 | CCGGGGUUCCACCUGGUUGUAUUUCAAGAGA AAUACAACCAGGUGGAACCUUUUUUG | shRNA Y12687 |
| 134 | CCGGGCUGGUAUUUCAUGCAGAAUUCAAGAG AUUCUGCAUGAAAUACCAGCUUUUUG | shRNA Y12688 |
| 135 | CCGGGCUACUGUCAUUCACGAUAUUCAAGAGA UAUCGUGAAUGACAGUAGCUUUUUG | shRNA Y12689 |
| 136 | CCGGGCCACCCAAUGCAUUGGAUUUCAAGAGA AUCCAAUGCAUUGGGUGGCUUUUUUG | shRNA Y12690 |
| 137 | CCGGGCCAAAUACACCACAAAUAUUCAAGAGA UAUUUGUGGUGUAUUUGGCUUUUUG | shRNA Y12691 |
| 138 | CCGGCUUCUCACACAGCGGGAUAUUCAAGAGA UAUCCCGCUGUGUGAGAAGUUUUUG | shRNA Y12692 |
| 139 | CCGGGAGCUGGUAUUCCACCCAUUUCAAGAGA AUGGGUGGAAUACCAGCUCUUUUUG | shRNA Y12693 |
| 140 | CCGGUCAGUAUGCUACCGUCAAUUUCAAGAGA AUUGACGGUAGCAUACUGAUUUUUG | shRNA Y12694 |
| 141 | CCGGGGAGCUAGUAUUCCAGCAAUUCAAGAGA UUGCUGGAAUACUAGCUCCUUUUUG | shRNA Y12695 |
| 142 | CCGGCCUCCAUGGCUUCGUCAUAUUCAAGAGA UAUGACGAAGCCAUGGAGGUUUUUG | shRNA Y12696 |
| 143 | CCGGCCACGAUUACCAGGGAUCUUCAAGAGA AGAUCCCUGGUAAUCGUGGUUUUUG | shRNA Y12697 |
| 144 | CCGGGAGAAGGCGCUUAAAGAAAUUCAAGAG AUUUCUUUAAGCGCCUUCUCUUUUUG | shRNA Y12698 |
| 145 | CCGGGGAACAGGUUAUUGCUGAAUUCAAGAG AUUCAGCAAUAACCUGUUCCUUUUUG | shRNA Y12699 |

Figure 17D
CONTINUED

SAGE1 sgRNA

| SEQ ID NO: | Sequence | Description |
|---|---|---|
| 146 | AAACCGAGGACAUACUCUUCCUU | Hum SAGE1 sg1 |
| 147 | AAACGUUGCAACCAGAUUUACUU | Hum SAGE1 sg2 |

Figure 17E

SEQUENCE LISTING

<160> NUMBER OF SEQ ID NOS: 147

<210> SEQ ID NO 1
<211> LENGTH: 19363
<212> TYPE: DNA
<213> ORGANISM: Homo sapiens

<400> SEQUENCE: 1

```
tctacaggtg gccttcacta tcaactgcac agcgggcaga ggcagaggaa cacagaacct      60
tctcacacag cgggataaaa gggtgaattt ggagctgaca ggcaaatata tcttgtgata     120
tatttctctg gctttgatat cagggtaata ttggccgcat agaatgaagt agtgttcctc     180
cgttattttt tggaagacat tgctaagtac tggtattatt tcttccttaa atgtttgata     240
gaatttgcac gcgaagccat cttggcttgg cttgtatttc tggggagatt ttaaattact     300
aattaaatct cttttcatgc tatagtccta agtcgatttt ctacttatta tttatttatt     360
tatttattca tttattttga gacggagttt cactcttgtt gttcgctctt gttgcccggg     420
gtggagtgca atggcatgat cttggctcac ccaacctccg cctcccgggt tcaagtgatt     480
```

-continued

```
ctcctgcctc agcctcccaa atagctggga ttacaggcat gcgccaccac gcccagctaa      540
ttttgtattt gtagtagaga cggagtttct ccatgtttgt caggctggtc tcaaactccc      600
aacctcaggt gatccgcccg ccttggcctc ccaaagtgct gggattacag gcgtgagcca      660
ctgcacccag cctgtttctt cttgagtcgg taatttgtct tccaagaatt ttttccattt      720
tacctaagtt gtttagtttg ttggcgtaaa gttgttcata atgtattcct tttaatttct      780
gtaaggtcag tattaataac cccccttttca tttttgattt tgataatctg tgtagtcctt      840 tctattttc ttggtcagtc aagctaaaag attgttagat ttttttttttc accttttcgg      900 tgaaccaact tttgatttca ttgatttttc tgtttcttat ttcattgatt ttcttctact      960
ctaattttca tcattccccct ccttctgctt gcttgtatta aatacatcag tttaaaactt     1020
caggaataac aaaagatttg tttcgcaaag gaagatttga aatgttagac atgtagaaat     1080
gcttatgata ttgcaagtag cagtcatttc gaccagttaa ccagaaggaa attcggtgtg     1140
ctgaaaccaa acaagtgttt ttttgtgccg ggcttttact gattttgaaa atatcaagtc     1200
tagtttgtgg gaagctgttt attgcatgag cagtttattt ttttaatgtt ttaatataga     1260
gaatgcccat gttcactaaa tcccacaagt ttgtttgttt gtttgtttgt tttttaactt     1320
aaaggaaagt atgtattaac cagcacatac actatcctct ttgtgcttta tctctggtaa     1380
tccttataag agcaccatga gttagatact gtttttatgcc cttttttatgg aaatagaatc     1440 ttagagtgta catttaagta gctctcccag gtataactag ctggaaaagt gacagaacct     1500
aggtctctca gattccagag attgcacaca cgaatactat atcacactgc ttactgctgt     1560
gagttcagca gagaattcct tgtttatatg gaaataacaa aattgatagt atccaggata     1620
attggcaaca gtttacaaac cctctttacc cccactttgg tgattttaag tggggtcatc     1680
tgtccactaa attaaacaga tcttaggctg gtcacacttc taaaattgta caccaagttt     1740
gtgtgtaaag gtactttccc agggaaaaat atctgtagat ttaatcaaat tatccaaaga     1800
gggttaggcc cactacccag tgttccctgg atgataagag aatgccatgg agcctacacc     1860
cttccagtgg gaagaatagt gccaatttac ttgccattta tgttctagtt tttaatcaga     1920
gtgttctagt cacacacaca tagttagcta tgaggaatat ctgaagatgc tggttcctcc     1980
acttcaaacg agtcagctaa ctctaggtga agagctttat actttggact atgtggttat     2040
aaatgatggg caggtaggat aactagaaca gtgtatatgc tcattaatac atacttatcc     2100
tttaagtctg aaaaaatgaa cttgtggaat tcagtgaaaa ttggcattct aaatattaaa     2160
gtattaatat ttagaattat agattttttag ttgggatggt ggtataagga aggtcagccc     2220
attctcaaac tgggttggag gcataaggga cttgtttaac ctaacctagt ggtgtgaacc     2280
tacaggaagt agtgatggtg gactgagtca tgacttaggt aaagggagat gattctagat     2340
catggaacat gatatagatt ctagacatga gattctaaac tctggtacca aggcacacat     2400
tgctaagaca atctgtgatc atgtactctc aagaggatca tatatttcag ctgtatagcg     2460
ccaatttatg tgccagttac gttccagtta taaatcaaag tgttctagta acacacatag     2520
ttaattatga ggactatctg cagatgcagg cttctccact tcaaacgagt caaccaactc     2580
cacctgaaga acttcatgct gctgcctatg tgtttacaaa tgatgggcag gtaagataac     2640 tcttttctatt tctgccctaa ttgtgacatt cttcgtataa ttattttctc attggaaaga     2700
tgaatataaa ctatatgtgt taattctctt gatttaaaag ataaaatatg acacaggaaa     2760
tcttatgtga acataaaatg ggaacttttt gatccaagag tggattggtt gtactaggaa     2820
```

-continued

```
ctgatttatt ttattttatt ttattttatt ttatttatat cttttttttt tttttttgaga    2880 tggagtttca ctcttgttgc ccaggctgga gtgcaatggc acgatctcag ctcaccgcaa    2940
cctccacttc ccgggttcaa gtgattctcc tgccttagcc ttctgagtag ctgggattac    3000
aggcatgcgc caccacaccc agcttatttt ttgtattttt agtagagaca gggtttctcc    3060
attttggaca ggctgctctc gaactcccga cctcaggtga tccgcccacc tcgcctccca    3120
aagtgctggg attacaggca tgagccaccg cacctggccg aactgatgtt tttaattatc    3180
acatttaatg ctcatagttg ttctgcagat atgtattact atctaccctt taataagaaa    3240
tcaaggctga cagtggtcaa atggcttgcc ccatgtgaca caagatagga ggtagagcca    3300
gggtttgaac gcatatcttt ctgactccag agtctatatt ctttcccact ccccacaata    3360
actcctttaa tatcgagatt gcagtctaca gtctctcttt ctgttatcca agtcactagt    3420
gctctgccta aaaaaatgac taagtattcc tcgtggaata tgaagcacta ggtgatgttg    3480
ccatgattgg attgtcctga tggagatctt aatgtgagtt ttgtgttgtg tatgagagag    3540
acttactaac ttcaccatta gaacatgaag acaaaggaga ttgcatctgc actaggacac    3600
aattaggcaa taatctcttc tgtaacaaaa ccagactaaa gttattccac cacattccca    3660
aaactcctca attaattagg cttttcctta attttctgtg cctttatttt ctcttttta    3720 acaatagtca taagaatcac acctcactca tagggattgg ccaaggattg agttaataca    3780
tgtaaagcat tgagaacagt acctggaggg tagtaaatgt tcagtaaaaa tgttttcaca    3840
cattctccac tctgctttta taggaaatga aaatggtttg gaaaattttt taatcaaaat    3900
tatatatttg aatataattt tcattaaata tgctcctgca tatttaatgc aagagcatat    3960
tctttatttc ttcaactttt actttaagtc ctggggtaca tgtgcaggat gtgcaggttt    4020
attacatagg taaacgtgtg gcatggtggc ttactgcacc tatgaaccca tcaccttggt    4080
attaagccca gcacccagta gctatttttc ctgatgcatt ccctccccca actcctcccc    4140
caacaggccc agtgtgtgtt gccctgcccg acgtgtccat gtgttctcat cattcagctc    4200
ccacttataa gtgagaacac gtgctgtttg gttttctttt cttgcgttag tttcctgatg    4260
ataacggctt ctagctccat ccatgtttct gcaaaggaca tgatctcatt cctttttttat    4320 tttttttctt ttttttgaga cggagtcacg ctctgtcgcc caggctggag tgcagtggca    4380
tgatctcggc tcactgcaag ctccgcctcc cgggctcatg ccattctcct gcctcagcct    4440
cccgagtagc tggtactgca agcgcccgcc accacacctg gctaattttt tttgtatttt    4500
tagtagagac ggggtttcac cgtgttagcc aggatggtct ccatctcctg acctcgtgat    4560
ccgcccgcct tggcctccca aagtgctggg attacaggcg tgagccaccg cacccggccg    4620
atctcattcc tttttatggc tgcatagtat tccgtggtgt atatgtacta catttttcttt    4680 atccagtcta tcattgatgg gcatttgggt tgattccaca tctttgctat tgtgaatagt    4740
gctgcaatga acatacatgt gcatgtatct ttataataga atgatttata tttctctggg    4800 tatatacccca gtaatgagat tgctggatca aatgatattt ctgcctctag atctttcagg    4860
aatcaccaca ctgtcatcca catggttgaa gtaatttaca ctcccaccaa cagtgtaaaa    4920
gcagtccttt ttctccacag ccttgccagc atctgtagtt ttttgacgtt ttagtaatcg    4980
ccattctgac tggcatgaga tgttatctca ttgtggtttc gagttgcatt tctctaatga    5040
tcagtgatgt tgagcttttt ttcatatttt tgttgcccgc gtgaatatct tcttttgaga    5100
cgtgtctgtt catgtccttt gcccactttt taatgggggt tgtttggtttt cttttgtaaa    5160 tttgtttaag tttcttgtag actctggata gtagaccttt gtcagatggg cagattgcaa    5220
```

```
aagttttctc ccattctgta ggctgtctat tcactctgat gatagtttat tttgctatgc   5280
atatgctctt tagtttaatt agatcccatt tgtcaacttt tgcttttgtt gccattgctt   5340
ttggcatttt tgtcatgaaa tctttgccgg tgcctatgtc ctgaatagta ttgcctattt   5400 tttttttctag ggtttgtata gttttgtgtt ctacatttaa gtctttaatc catcttgagt   5460
aaatttttgt ataaggtgta aggaaggagc ccagtttcaa attttgcata cagctagcca   5520
gttctcccag caccattaat taaatatggga atcctgtccc cattgcttgt ttttgtcagg   5580
tttgtcgaag atcagataat tatcactgtg tgatcttatt tccgagttct ctattctgtt   5640
ccattggtcc atgtatctgt ttttctgcca gcaccatgct gctttggtta ctgtagccct   5700
gtagtatagt ttgaagttag gtagcgtgat gcctccagct ttgttcttat tgcttaggat   5760
tgtcttggct attctggctc tttttttcgtt ccatatgcat tttaaaatag ctccttctaa   5820
cttggtgaag aatatcaatg atagtttaat ggaaatagca ttgaatttct aaattacttt   5880
gggcagtatg gccattttca caatattgat tcttcctatc catgagcatg gaatgttttt   5940
ccattcattt atttgctctc tgatttcctt gagcagtggt ttgtagttct ctctgaagag   6000
gtctttcact tcccttgtta gccatattcc taggtaattt attctttttg taggaattgt   6060
taatgggagt tcattcatga tttgtctctc tgcttgcctg ttttttggtgt agaggaatgc   6120 tagcaatttt tgcacatgga ttttgtatcc cgagactttg ctgaaattgc ttatcagctt   6180
aagaagcttt tgggctgaga caacgggatt ttctagatat agggtcatgt catctgcaaa   6240
caaaggtaat ttgacttcct ttctcccttt ttgaatactc tttatttctt tgccttgccc   6300
gattcccctg gacagaacgt gtaatactat gttgaatagg cgaggtgagg gagggcatcc   6360
ttgttttgtg ccagtttcaa gggtaatgct tccaggtttt tcccattcag tatgatattg   6420
gctgtgggtt tgtcatatat ggctcttatt attttgaggt atgttccttc aatacctggt   6480
ttattgagag cttttaatat aaggggatgt tgaattttat caaaggcctt ttctgcatct   6540
attgagataa gcgtgtggtt tttgtcttta gttctgttta tgtgatgaat tacattcatt   6600
gattggccta ttctgaaatg accttgcatc ccggggatga agccaacttg atcatgggga   6660
ataagctttt tgatgtgctg ctggattcag ttttccagta ttttattgag gattttgcat   6720
cgatgttcat caggaatact ggcctgaagt ttttttttgt tgtatctctg ccaggttttg   6780
gtatcagggt gatgctggtc tcataaaatg agttaggtag gagtccctcc tttttaattt   6840
tttggaatag tttcggtagt aatattacca gctcttcttg gtacctctag taggcaggaa   6900
catattcttg ggttatcctt tgatgaaaac agcttttagt taacatacat actataccct   6960
tcattttcat gttttatttta ccactaacat tgtaaagctc gccctacccc tacctgattc   7020
caagatcaac atatcggaat ctccataagg ttggaggtgg gaaaatttat cttttcaatc   7080
tatcctaccc ttcattatct atatgtatca tctaataaag tattaatgat tattggttaa   7140
taagtaactt taaagcacta aaagaggccg ggtgtggtgg ctcgcacctg taatcccagc   7200
actttgggag gccgaggtgg gaggatcagg aggtcaggag atcaagacca tcctggctaa   7260
cacggtgaaa ccccatctct actaaaaata caaaatagcc gggcgtggtg gcgggtgcct   7320
gtagtcccag gaactcggga agctgaggca gtagaatggc gtgacttggg gaagcagagc   7380
ttgcagtgag ccgagatcat gcaattgcaa tccagcctgg gcgacagagc aagactccgt   7440
ctaaaaaaaa aaaaaaaaaa aaaaagcact aaaagataaa aaaggtattt ctttttttttt   7500 ctcccctaac aagggctgag acaaaatgat gtgtacttca tgagagagat aaccatatgt   7560
```

-continued

```
ttataccttt ggatgatgaa agccactcat tccccaagca ttctgattta tcatgactgt    7620
accatgtttg actttggata acaccttgta ttttaccttc ccttgtttca ctgagacttg    7680
actaaaatta gcttgccttt tctgagagca tcgtgtatgt tcagggatga gaaatctttg    7740
acctgtgact aaaacttaca ttaatgatat aaatgcatgg ctgtgtatgc atatgaagac    7800
tgtgactttg cagtggttgg atttgtcttt aatggaatat gttcactgat gtttttcagc    7860
aaatgaggag tgatgaagta aatctggttg caacagggca tcaaagcaaa aagaaacatt    7920
ccagaaaatc caagagacac tcttcatcta agagaaggaa gagtatgtcc tcgtggttag    7980
acaaacagga aggtgagggg gaatccaatc tttgggcctc aaccatgtca aaggacattt    8040
gtagtcatgt ccttgaggga tgaacagata tgagcacatt tgcaagtgga agggcaaggt    8100
tctaattagg tgcaacaatt tggagttgtt gcaagcgtta gatgaatgaa gcaggttcct    8160
gaggcagaag gagatggtgg gctcaacaag aggatgggtc tgctcacttt ctgcctgtcc    8220
tcacattccg ctctaaccca gtgtggtctg gcttcttagt gtactccaat gaaactacta    8280
tcatcaaggt caccagtgtt tgctacactt tggcgttaat gtctcagcag catgcgacac    8340
agttgtttac tccctcctgc acggaaagct tcttgggtcc ccagacacct ggatttctta    8400
ccctgttact agagactcat tttccttctc ttttttgttt ttctcctctc ccttcccacc    8460
tctaaatatt tcggaacccc aaagcttaat cctagactct cttctcttca gtatactatc    8520
tatttaggcg atgccgtgct gtcttagaat tttaaatgat tcacactata agaactctca    8580
ccattatact tctacactac aacttgctcc tgaaatccag actcaaatac gactacactc    8640
gcggtatctt tactgggtgt ctaataggca tgtaaaattc aactgactct acatgctcaa    8700
atttctgacc tccctctctc caaaaatact ctacttttag ctttcactat ttcaattaaa    8760
gatactgtcc attaggtgaa acatccacaa aggtgtaaca accagctgtt cacaggtatg    8820
ggggattgag gaatcctggt ttttacagtt tgcagctatc catcgggcaa ataatcccac    8880
catggcctag ttcaagctgt caacataagg tcactgaacc agattcagga agagttggca    8940
gcactcagct ctcatggtcg gttgcctaac acctcctgaa cacccctggt gtacttttac    9000
ttagtagttc tagtcaaaat acttaaagtc acttatgagt tatctcatga ttcttttatt    9060
actctctcat ttcccatttc ttagcaagtc cagcagtaga tgcccagtat aaattctgca    9120
tccaaccatt tctctctatg cctccagtgc atgctgccgt gatctgtctc caggctagta    9180
caatgccttc ttagctctgt gtttctaatc ttcgctcatc tatcgcatac tctctaaccc    9240
tgtggctaga taattatttc agcacgtaaa tcacatcatg ccatgtccct cctgaaaacc    9300
catcctcatc tctcctaagc actcagaaca gaccctgaac cggctttggt ctccaagcct    9360
ctgcacagcc tggcctctgt caccctctcc taacatgggt cccatccatt tcctcctggc    9420
tctctctgcc tctgaccttc acctctgtag tgcccggtcc atccccactc cattccctac    9480
ccttggcctc actgcagcct ggaactctcc ctctgcctct gcacaggagg ctctgcttct    9540
ttctccaagc cctgcccaat ggcacttctt cagaagcctc tgccaaacca gctgcagccc    9600 cagggctcc ctctgctgct gtctcccaca ggcctgtgga ctgcttttcc aacaccagcc    9660
caatgctgct tgtttcattt gctcattgtg catgtactgt ctgactgccc catgaggatg    9720
tgagctccac aagggcaggg aacgttgctc cctgggctgt ttactgctga tccctgggtc    9780
ctggcatgct gcctgccaca gatgatgaat aaatgaaaga ggcgtcgac ctggagtgaa    9840 aagaaagtca cttttttctag ataaaaggga aggatctgta gaatcatata aaaatacaga    9900
tgtgtgatga tggagtggtg ataagagtgt tcaactccaa tagccacgtg tattttctca    9960
```

-continued

```
gagtatttgg ggtagaaagg aggcaggtta aggagggctc acttagtctg gcttcctgct   10020
gtgcacagca tggcatttat aggtgaacta tacaaataat atcaagtgag aattatcatc   10080
ttgctgccta tcaagggcag caagatgata caaaatgacg aatacaaaaa cctgtgaatg   10140
tttattctgc tgtcgtactt ctttactgca tatattcatt atgccaagag gtaaaaaggt   10200
agttttattg tattatctga cctgatctct gtcacaagat ctgagatttc cacgtggtaa   10260
atccttctgt ttcatgaaat aaataattct ttagaacctg attaatacac agctgtccct   10320
ctgggggagg atgggacaaa acacacctat cttgcagctc aacctcttca tttggtttcc   10380
agctgctagc atcactcaca atgtccatga agagaaggta aaaaatggcc aatctgcaca   10440
caataatgtc attgcaactg ttccatcagt gcttattagt atggcagcag ctggtatttc   10500
atccatgagt accagggacc agtgtaaatt tgctcacttg ttatactgtc ctacgaggat   10560
tccactacgc accatatatg catagtgtcg tgagggaaga aggtaatttt gttgtattat   10620
cttttctggc ctcaatttta gggttctcag attgctacct ggtatatcct tcttctttat   10680
gagataattt cctagatact gagcatcagt ggggcatgcc tgtgccattg acataatgca   10740
cttacctcac agctcaacca cttcatttgg tttccagatg ctgcagtcac tcacagcatt   10800
tgtgaagaga ggataaataa cggccaacca gtagctgata atgtcttgtc aactgctcca   10860
ccatggcctg gtaatatggc agcagcagga atttcatcca tgagtatgaa attcatccat   10920
gagtacttat taattgtact gtcctacttg gtttccataa gcaggcatat tttcatgaat   10980
tatagaaggt ggttttgttg tatattcttt cttagcctca atttgagggg tatcagatgg   11040
ccagctggca tatcctcccc tgctttttta gataatttcc tagaaattga acacagagga   11100
atatacctgt ggggttgaca taatgcactt acctcacagc tcaacctctt cacttggttt   11160
ccacacgcta ctgtcaatca cagtgtccat gaggagggga tggaaaatgg tcaaccccaa   11220
cgagataatg tcatgtcaaa tgttctatca gggcttatta atatgacagg agctggtatt   11280
ccagcgatga gtaccaggga tctgtgtgtg tttgtttatt agttgtagtg tcctccttgg   11340
tttccatgtg catgcataat gtcatgaagg gaagaaggtg gtttttgttga attatctttc   11400 gtgacctcaa cttaagtgga ctcaaatcat tatatgatgt attctcctgc attaggggat   11460
aatttcctag aaaccgagca tcagtgggat atactggttc aattgtcata atgcacatac   11520
ctcacaactc aacctgttcc atcggtttcc agatgctacc atcgctcaca atatccgtga   11580
agagaggatg gaaaatggcc aatctcgaac tgacaaagtc ttgtcaactg ctccaccaca   11640
gcttgttcat atggctgcag ctggtattcc atccatgagt accagggatc tgcgtatgtc   11700
tgctaattag ttgtactgtc atacttgttt tccataagca tggatatttt catgaaaggt   11760
agaagtcact tttgttgcat atactttcct agtctcaatt tgaggggtct cagatggcca   11820
cctggcaaat cctcccctga tttcctagat aatttcctag aaactgagca tcagagggat   11880
atacctgttg ggctgacata gtggacttac ctcacagttc aaactcttcg tttgtttttcc   11940 agattcaact gttactcaca ttatctgtga agagaagata aaaaatgaac aaatggcacc   12000
tgataaattc ttgtctacta ttacagcggg gcttatgaat ttcacagggg ctgatattcc   12060
acccctgagt accagggatc agtgtgtgtt tactagttgc actgacctac ttgctttttcg   12120 tacgcatgca gtgtcatgca gggaagaagg tggtttcgtt ttattatctt ttctggccta   12180
aaattcaggg gtctcaaatc accacctgat atgtcctcct ggtttatggg ataatttcct   12240
agaaactgag catcagaggg atatacctgt ggcactgacg taatgcactt acctcacagc   12300
```

-continued

```
ttgaactctt catttggttt ccagattcta ccgtcactca caatatccgt gaagagagaa    12360
tggaaaatgg ccaaccccaa cctgataacg tcttgtcaac tggtcccaca gggcttatta    12420
atatggcagc aactcctatt ccagccatga gtgccagaga tctctgtatg tccacttata    12480
aattgtgctg tcttacttgg ttttcatatg catacatagt gccatgaagg gagttaggtg    12540
gttttgttgt gttatcgttt ctggcctaaa tctgaggggt ctcacatcac cacctgatat    12600
atcctactgc tttatgaaat aatttcatag aaactgagca ccagagggat atacttgtga    12660
gttggcataa tgcacttacc tcacagctca acctcttcct ttggtttcca gatgctacag    12720
tcactcacaa tgtctgtgaa cagaagatgg aaaatgtcca accagcacct gataacgtgt    12780
tgttgactct tcgaccacgg cgtattaata tgacagacac tggtatttca cccatgagta    12840
ccagggatcc atgtaagttt gtttatttgt attactgtcc tacttggttt ccatatgcat    12900
gcatagtgtc aaaaagcata caaggtggtt ttgttgtatt gtcgttcctg gtatttcacc    12960
catgagtacc agggatccat gtaagtttgt ttatttgtat tactgtccta cttggtttcc    13020
atatgcatgc atagtgtcaa aaagcataca aggtggtttt gttgtattgt ctttcctggc    13080
ctcaatttca ggggtctcgt atggcaacct ggtatatcct cctgtttatg agataatttc    13140
ctagaaactg agcatcagag ggatatacct gtggggttac cataatacac ttacctaaca    13200
gctcagcctc ttcatttggt ttccagatgc taccatcact tacaatgtcc ctgaggagaa    13260
gatggaaaag ggccaacccc aacctgataa catcttgtca actgcttcaa cagggcttat    13320
taatgtggca ggagctggta ctccagccat cagcaccaat ggcctgtgta tgtttgcttg    13380
ttaattggat tatcctgctt ggtttccata tacgtgcata ttgtcatgaa ggggagatgg    13440
aggttttgtt gtatcatcta tcttgagctc aatttgaggg gtctcagatc accacctgtc    13500
atgtcctcct gctttatgca ataatttctt agaagctgag catcataggg gtatacctgt    13560
ggggctgaca taatgcactt actcacagct caacctcttc atttgttttc cagattccac    13620
cgtccctcac aatgtctgtg aagagaagat ggaaaatgac caaccgcaac ctaataacgt    13680
attgtcaact gttcaaccag tgattattta tttgacagca actggtattc cgggcatgaa    13740
taccagggat cagtgtatgt ttgtttacta gttgtagtgt cctagttggt ttacatatga    13800
atgcacagtg tcataaaggg aaggaggttg ttttattgga ttctctttca tgagctcaat    13860
ctgaggtgtc tcagatcatc acttgctgta tcctcctgct ttatgagtta atttcctaga    13920
ccctgagcat cagagggata tacctgtagg gctgacataa tacacttagc tcagagctca    13980
agcttttcat ttggtttcca gatgctacca tcactcacaa tgtctgtgaa gagagagtgg    14040
taaataacca accactacct agtaacgcct tgtcaactgt tctaccaggg cttgcttatt    14100
tggcaacagc tgatatgcca gccatgagta ccagggatca gcgtaagttt gtttactagt    14160
tgtggtgtcc tacttggttt ccatatgcat gcatattgtc atcaagggaa gaagacggta    14220
ttgttgtatt atgttttctg gcctcaattt tagggttttc aattgctccc tggtatatcc    14280
tagttcctta ggagataaat tcctagatag tgagcatcag aggggggtatt cctgtgggat    14340 tgacatactg cacttacctc acagctcatc aactacattt ggtttccaga tgctaccatc    14400
attcacaatc tgcgtgaaga gaagaaagat aacagccaac caacccctga taacgtcttg    14460
tcagctgtta caccagagct tattaacttg gcaggagctg gtattccacc catgagtacc    14520
agggatcagt gtatgtttgc ttactagttg tactatccta cttggtttcc atatgaatgc    14580
agtatcataa atggaagaat gtggttttat tatattgtct ttcgtgagtt gaatttgtgg    14640
ggtctcagat cgctgcctgg tatatcctcc tgctttatgt gataaattcc tagaaactga    14700
```

-continued

```
gcatcagagg gatatataca tgtgtgcttg gcataatgca cttaactcac agctcgacct   14760
ctttatttgg tttctagatg ctaccgtcaa tcaccatgtc catgaagcaa ggatggaaaa   14820
tggccaacga aaacaggata acgtcttgtc aaatgttcta tccgggctta ttaatatggc   14880
aggagctagt attccagcaa tgagttccag ggatctgtgt atgtgtgttt tttagttata   14940
ccatcctcct tgatttccat atgcatgcat agtgtcatga agggaagaag gttgttttgt   15000
gaattatctt tcctggcctc aatttgaggg gcctcagatc atcatatgat gtattatcct   15060
gctttatggg ataattttct aaaaattcat catcagtggg atatatcggt ggggttgaca   15120
taatgcacgt acctcacagc ttgacctctc cctttggttt ccagatgcta ccattactca   15180
cagtgttcgt gaagagaaga tggaaagtgg caaacccccaa actgataagg tcatatcaaa   15240
tgatgcacca cagcttggtc atatggctgc aggtggtatt ccatccatga gtaccaagga   15300
tctgtgtatg tctgttaatt agttgtactg tcatacttgg tttacatatg catgcatatt   15360
ttcatgaagg gtagatgtgg ttttgtagta tattctttcc taacctcaat ttgagggatc   15420
tcagttgtcc acatggcata tcctccccag cttttcttaga taatttccta gaaactgggt   15480
atcagaggaa tatatctgca gggctgacat aatgcactta cctcacagct caacctcttc   15540
atgtggtttc cagattttac catcactcac aatgactgtg aagaaaagat taaaaattag   15600
caaagagcac ctgatacatt attgtcaact gttacagcag ggcttatgaa tgtcacaggg   15660
gctggtattc caccctgag taccagggat cagtgtatgt ttgtttacta gtcgtactgt   15720
cctacttgac ttccatacgc atgcagtgtc atgcagggaa gaaggtggtt tttttgcatt   15780
atcgtttctg gactaaattt gaggggtctc agatcaccac ctgttatagc ctcctgtgtt   15840
atggaacaat ttcttacaaa ctgaacatca gagggatata cctgtggtat tgacataatg   15900
cacttacgtc acaagtcaac ctctttattt ggtttccaga tgctaccgtc actcaaaatg   15960
tccatgaaga gaggatggaa aataaccaac cacaacctag ttatgacttg tcaactgttc   16020
taccaggact tacttatttg acagtagctg gtattccggc catgagtacc agggatcagt   16080
gtatgtttgc ttattcagtt gtactgtcct acttggtttt catatgcatg cctagtgtca   16140
tgaataggag aaggtggttt tgttgtatta tctttcatga gttcaatttg agtgttctca   16200
gatcgccatc tggcatatcc tctccggctt tatgatatac ttttctagaa gctgagcatc   16260
aggaagatat acctgtgggg ttgacataat gcacttaact caaaacttaa cctctttatt   16320
tctgttccag atgctaccgt cactcacaat gtccatgaag agaagattaa aaatggccaa   16380
gcagcatccg ataatgtctt ctcgactgtt ccaccagcat ttattaatat ggcagcaact   16440
ggtgtttcat ccatgagtac cagggatcag tgtaagttta ttcacttgtt gtactgtcat   16500
acttggtttc catatgcatg catagtgtca tgagggaaga atgtagtttt gttgtattac   16560
cttttcaggc ctcaatttta gggttctcag attgctacct ggtatatcct ccttcttaat   16620
gagataattt cctagatact gagcatcaga ggggtatgcc tgtgcggttg acataatgca   16680
cttacctcac gcccaacctc ttcttttgtt tccagatgct gcagtcactc acaacatccg   16740
tgaagagaag ataaataaca gccaaccagc acctggtaac atcttgtcaa ctgctcctcc   16800
atggcttcgt catatggcag cagctggaat ttcatccacg attaccaggg atctgtgtat   16860
gtctgcttat tagttgtgct gtcctacttg gtttccctaa gcaggcatat tttcatgaat   16920
ggtagaaggt aattttgttg tatattcttt cctagcctca gtttgagggg tatcatatgt   16980
ccacctggca tatccttgcc ttcttttatt gataacttcc tagaaactga gcatctgaga   17040
```

-continued

```
gatataccta tggggttgac ataatgcact tacctcacgg ctcaatctct tcatttggtt   17100
tccaaatgca accgttactc accatgtccg tggagagaag ataaaaaacg gccaaccagc   17160
atctcataac ttcttgttaa cccttccatc agggcttatt aatatagcag gagctaacat   17220
cccagccatg agtaccaggg atctgtgtat gttttcttat aagttgtact ttcctacttg   17280
atttccatat gcatgcatag tgtcatcaag ggaagaaggt ggttttgcgg tattactttt   17340
gcttgcctca atttcagggt ctctgattgc cacctggtat atcctcctgc tgtatgggat   17400
aacgtcctgg aaactgagca tcagcaggat atccctgtgg ggttgtcatt atgcacttac   17460
ttcacagctc agcctcttca tttttgtttcc agatgtcacc gccactcaca gtgtccatga   17520
ggagaagatg acaaatggcc aacaggcacc tgataactcc ttgtcaacgg ttccacctgg   17580
ttgtattaat ctgtcaggag ctggtatttc atgcagaagt accagggatc tgtgtatgtt   17640
tgtgtattgg ttgtactgtc ctacttggtt tccatatgca tgcatagtgt cctgcaggga   17700
agaaggtggt tttgttgtat tatcttactc aaacttagtt tgaggggtct tggatcacca   17760
cctggtgtat cctcttgctt catgagataa ctccctagaa actgggcatc ggagggatat   17820
actgtggggg tgacataatg cacttatctc acagctcaat tttttcattt ggattccaga   17880
tgctactgtc attcacgata tccaggagga ggagatggaa aatgatcaaa cccctcctga   17940
tggcttcctg tcaaattctg attcaccaga gctgataaat atgacaggac attgtatgcc   18000
acccaatgca ttggattctt tctctcacga cttcacaagt ctcagcaaag atgagctgct   18060
ttacaaacct gatagtaatg aatttgcggt aggcaccaaa aactacagtg tctctgcagg   18120
tgacccacca gttacagtaa tgtctttggt ggaaactgtg ccaaatacac cacaaatatc   18180
tcctgccatg gcaaagaaaa ttaatgatga tataaaatat caattaatga aagaagttcg   18240
aaggtttggg caaagtaagt actgcaagaa tgtctatcaa tgaaagcatg agaagtgtct   18300
cattctatga tttagaacag aattgagctg cctcttgagc tcattgtttg gctgaattgg   18360
atctatatat aatttagcat ggctttactt taatttcact gaaaattgct aatatgtctg   18420
cttaagtgtt ttgtttttcct ttgttagtgt tcacaatagt ttccttagta atatacagat   18480
gtcgtgattt aagcattcaa aacaagcact atgtaacatt gtagcccatg aaaaatgtat   18540
actgtggtag tggatgcact aagattgagg tatatttcat ttttgtaatt gtagaaatac   18600 taattttttaa aatatcttca gattatgaaa gaattttcat tttgcttgaa gaggtacaag   18660
gatctatgaa agtcaagaga caatttgttg aatttaccat caaggaagca gcaaggtgag   18720
tgcaaaaagg aactgtgcta ttgtttttaag cacttgcgcc caatttggga caggggcagg   18780
aaaaaatcat ggtttgttcc tcctaatccc tggccctcaa tcatagttca tgctatttcc   18840
acaggcattt aggttgatac tatcttattc taacactttc ttccaatacc atggaggctt   18900
ccaaatttat caaaatctgg gagtgtatgt gggccctcag ttgactcact ttgtattttt   18960
ctagtttgta tctttcaatg aggatgcatt ttctgtttgc atgtagatgg taaattctat   19020
tttgtatcca ctctacctct tacatctcat agatcctgta ggtatcctct ggtgaatgga   19080
atacctcttt aatttcaggt ttaaaaaagt tgtcttaatt cagcaactcg agaaggcgct   19140
taaagaaata gattcccact gccatctcag aaaagttaag cacatgagaa aaagataatt   19200
gtgttagtgc aaagaccaag gagaaacaag gacatatgct gtaggatgga acaggttatt   19260
gctgaagctc cctataatcc tgaaatgaag agaattccct tccagaagct acgaaaaagg   19320 gagctgtttta aatttaataa atctctgtta gtaaaagctg cac                    19363
```

-continued

```
<210> SEQ ID NO 2
<211> LENGTH: 2946
<212> TYPE: DNA
<213> ORGANISM: Homo sapiens

<400> SEQUENCE: 2
actatcaact gcacagcggg cagaggcaga ggaacacaga accttctcac acagcgggat        60
aaaaggatgc aggcttctcc acttcaaacg agtcaaccaa ctccacctga agaacttcat       120
gctgctgcct atgtgtttac aaatgatggg cagcaaatga ggagtgatga agtaaatctg       180
gttgcaacag ggcatcaaag caaaaagaaa cattccagaa aatccaagag acactcttca       240
tctaagagaa ggaagagtat gtcctcgtgg ttagacaaac aggaagatgc tgcagtcact       300
cacagcattt gtgaagagag gataaataac ggccaaccag tagctgataa tgtcttgtca       360
actgctccac catggcctga tgctaccatc gctcacaata tccgtgaaga gaggatggaa       420
aatggccaat ctcgaactga caaagtcttg tcaactgctc caccacagct tgttcatatg       480
gctgcagctg gtattccatc catgagtacc agggatctgc attctaccgt cactcacaat       540
atccgtgaag agagaatgga aaatggccaa ccccaacctg ataacgtctt gtcaactggt       600
cccacagggc ttattaatat ggcagcaact cctattccag ccatgagtgc cagagatctc       660
tatgctacag tcactcacaa tgtctgtgaa cagaagatgg aaaatgtcca accagcacct       720
gataacgtgt tgttgactct tcgaccacgg cgtattaata tgacagacac tggtatttca       780
cccatgagta ccagggatcc atatgctacc atcacttaca atgtccctga ggagaagatg       840
gaaaagggcc aaccccaacc tgataacatc ttgtcaactg cttcaacagg gcttattaat       900
gtggcaggag ctggtactcc agccatcagc accaatggcc tgtattccac cgtccctcac       960
aatgtctgtg aagagaagat ggaaaatgac caaccgcaac ctaataacgt attgtcaact      1020
gttcaaccag tgattatttta tttgacagca actggtattc cgggcatgaa taccagggat      1080
cagtatgcta ccatcactca caatgtctgt gaagagagag tggtaaataa ccaaccacta      1140
cctagtaacg ccttgtcaac tgttctacca gggcttgctt atttggcaac agctgatatg      1200
ccagccatga gtaccaggga tcagcatgct accatcattc acaatctgcg tgaagagaag      1260
aaagataaca gccaaccaac ccctgataac gtcttgtcag ctgttacacc agagcttatt      1320
aacttggcag gagctggtat tccacccatg agtaccaggg atcagtatgc taccgtcaat      1380
caccatgtcc atgaagcaag gatggaaaat ggccaacgaa acaggataa cgtcttgtca      1440 aatgttctat ccgggcttat taatatggca ggagctagta ttccagcaat gagttccagg      1500
gatctgtatg ctaccattac tcacagtgtt cgtgaagaga gatgggaaag tggcaaaccc      1560
caaactgata aggtcatatc aaatgatgca ccacagcttg gtcatatggc tgcaggtggt      1620
attccatcca tgagtaccaa ggatctgtat gctaccgtca ctcaaaatgt ccatgaagag      1680
aggatggaaa ataaccaacc acaacctagt tatgacttgt caactgttct accaggactt      1740
acttatttga cagtagctgg tattccggcc atgagtacca gggatcagta tgctaccgtc      1800
actcacaatg tccatgaaga gaagattaaa aatggccaag cagcatccga taatgtcttc      1860
tcgactgttc caccagcatt tattaatatg gcagcaactg gtgtttcatc catgagtacc      1920
agggatcagt atgctgcagt cactcacaac atccgtgaag agaagataaa taacagccaa      1980
ccagcacctg gtaacatctt gtcaactgct cctccatggc ttcgtcatat ggcagcagct      2040
ggaatttcat ccacgattac cagggatctg tatgtcaccg ccactcacag tgtccatgag      2100
gagaagatga caaatggcca acaggcacct gataactcct tgtcaacggt tccacctggt      2160
```

-continued

```
tgtattaatc tgtcaggagc tggtatttca tgcagaagta ccagggatct gtatgctact    2220
gtcattcacg atatccagga ggaggagatg gaaaatgatc aaacccctcc tgatggcttc    2280
ctgtcaaatt ctgattcacc agagctgata aatatgacag gacattgtat gccacccaat    2340
gcattggatt ctttctctca cgacttcaca agtctcagca agatgagct gctttacaaa     2400 cctgatagta atgaatttgc ggtaggcacc aaaaactaca gtgtctctgc aggtgaccca    2460
ccagttacag taatgtcttt ggtggaaact gtgccaaata caccacaaat atctcctgcc    2520
atggcaaaga aaattaatga tgatataaaa tatcaattaa tgaaagaagt tcgaaggttt    2580
gggcaaaatt atgaaagaat tttcattttg cttgaagagg tacaaggatc tatgaaagtc    2640
aagagacaat ttgttgaatt taccatcaag gaagcagcaa ggtttaaaaa agttgtctta    2700
attcagcaac tcgagaaggc gcttaaagaa atagattccc actgccatct cagaaaagtt    2760
aagcacatga gaaaaagata attgtgttag tgcaaagacc aaggagaaac aaggacatat    2820
gctgtaggat ggaacaggtt attgctgaag ctccctataa tcctgaaatg aagagaattc    2880
ccttccagaa gctacgaaaa agggagctgt ttaaatttaa taaatctctg ttagtaaaag    2940
ctgcac                                                               2946
```

```
<210> SEQ ID NO 3
<211> LENGTH: 904
<212> TYPE: PRT
<213> ORGANISM: Homo sapiens

<400> SEQUENCE: 3

Met Gln Ala Ser Pro Leu Gln Thr Ser Gln Pro Thr Pro Pro Glu Glu
1               5                   10                  15

Leu His Ala Ala Ala Tyr Val Phe Thr Asn Asp Gly Gln Gln Met Arg
            20                  25                  30

Ser Asp Glu Val Asn Leu Val Ala Thr Gly His Gln Ser Lys Lys Lys
        35                  40                  45

His Ser Arg Lys Ser Lys Arg His Ser Ser Ser Lys Arg Arg Lys Ser
    50                  55                  60

Met Ser Ser Trp Leu Asp Lys Gln Glu Asp Ala Ala Val Thr His Ser
65                  70                  75                  80

Ile Cys Glu Glu Arg Ile Asn Asn Gly Gln Pro Val Ala Asp Asn Val
                85                  90                  95

Leu Ser Thr Ala Pro Pro Trp Pro Asp Ala Thr Ile Ala His Asn Ile
            100                 105                 110

Arg Glu Glu Arg Met Glu Asn Gly Gln Ser Arg Thr Asp Lys Val Leu
        115                 120                 125

Ser Thr Ala Pro Pro Gln Leu Val His Met Ala Ala Ala Gly Ile Pro
    130                 135                 140

Ser Met Ser Thr Arg Asp Leu His Ser Thr Val Thr His Asn Ile Arg
145                 150                 155                 160

Glu Glu Arg Met Glu Asn Gly Gln Pro Gln Pro Asp Asn Val Leu Ser
                165                 170                 175

Thr Gly Pro Thr Gly Leu Ile Asn Met Ala Ala Thr Pro Ile Pro Ala
            180                 185                 190

Met Ser Ala Arg Asp Leu Tyr Ala Thr Val Thr His Asn Val Cys Glu
        195                 200                 205

Gln Lys Met Glu Asn Val Gln Pro Ala Pro Asp Asn Val Leu Leu Thr
    210                 215                 220

Leu Arg Pro Arg Arg Ile Asn Met Thr Asp Thr Gly Ile Ser Pro Met
```

-continued

```
225                 230                 235                 240

Ser Thr Arg Asp Pro Tyr Ala Thr Ile Thr Tyr Asn Val Pro Glu Glu
                245                 250                 255

Lys Met Glu Lys Gly Gln Pro Gln Pro Asp Asn Ile Leu Ser Thr Ala
                260                 265                 270

Ser Thr Gly Leu Ile Asn Val Ala Gly Ala Gly Thr Pro Ala Ile Ser
                275                 280                 285

Thr Asn Gly Leu Tyr Ser Thr Val Pro His Asn Val Cys Glu Glu Lys
        290                 295                 300

Met Glu Asn Asp Gln Pro Gln Pro Asn Asn Val Leu Ser Thr Val Gln
305                 310                 315                 320

Pro Val Ile Ile Tyr Leu Thr Ala Thr Gly Ile Pro Gly Met Asn Thr
                325                 330                 335

Arg Asp Gln Tyr Ala Thr Ile Thr His Asn Val Cys Glu Glu Arg Val
                340                 345                 350

Val Asn Asn Gln Pro Leu Pro Ser Asn Ala Leu Ser Thr Val Leu Pro
                355                 360                 365

Gly Leu Ala Tyr Leu Ala Thr Ala Asp Met Pro Ala Met Ser Thr Arg
        370                 375                 380

Asp Gln His Ala Thr Ile Ile His Asn Leu Arg Glu Glu Lys Lys Asp
385                 390                 395                 400

Asn Ser Gln Pro Thr Pro Asp Asn Val Leu Ser Ala Val Thr Pro Glu
                405                 410                 415

Leu Ile Asn Leu Ala Gly Ala Gly Ile Pro Pro Met Ser Thr Arg Asp
                420                 425                 430

Gln Tyr Ala Thr Val Asn His His Val His Glu Ala Arg Met Glu Asn
        435                 440                 445

Gly Gln Arg Lys Gln Asp Asn Val Leu Ser Asn Val Leu Ser Gly Leu
        450                 455                 460

Ile Asn Met Ala Gly Ala Ser Ile Pro Ala Met Ser Ser Arg Asp Leu
465                 470                 475                 480

Tyr Ala Thr Ile Thr His Ser Val Arg Glu Glu Lys Met Glu Ser Gly
                485                 490                 495

Lys Pro Gln Thr Asp Lys Val Ile Ser Asn Asp Ala Pro Gln Leu Gly
                500                 505                 510

His Met Ala Ala Gly Gly Ile Pro Ser Met Ser Thr Lys Asp Leu Tyr
        515                 520                 525

Ala Thr Val Thr Gln Asn Val His Glu Glu Arg Met Glu Asn Asn Gln
        530                 535                 540

Pro Gln Pro Ser Tyr Asp Leu Ser Thr Val Leu Pro Gly Leu Thr Tyr
545                 550                 555                 560

Leu Thr Val Ala Gly Ile Pro Ala Met Ser Thr Arg Asp Gln Tyr Ala
                565                 570                 575

Thr Val Thr His Asn Val His Glu Glu Lys Ile Lys Asn Gly Gln Ala
        580                 585                 590

Ala Ser Asp Asn Val Phe Ser Thr Val Pro Pro Ala Phe Ile Asn Met
        595                 600                 605

Ala Ala Thr Gly Val Ser Ser Met Ser Thr Arg Asp Gln Tyr Ala Ala
        610                 615                 620

Val Thr His Asn Ile Arg Glu Glu Lys Ile Asn Asn Ser Gln Pro Ala
625                 630                 635                 640

Pro Gly Asn Ile Leu Ser Thr Ala Pro Pro Trp Leu Arg His Met Ala
                645                 650                 655
```

```
Ala Ala Gly Ile Ser Ser Thr Ile Thr Arg Asp Leu Tyr Val Thr Ala
            660                 665                 670

Thr His Ser Val His Glu Glu Lys Met Thr Asn Gly Gln Gln Ala Pro
            675                 680                 685

Asp Asn Ser Leu Ser Thr Val Pro Pro Gly Cys Ile Asn Leu Ser Gly
            690                 695                 700

Ala Gly Ile Ser Cys Arg Ser Thr Arg Asp Leu Tyr Ala Thr Val Ile
705                 710                 715                 720

His Asp Ile Gln Glu Glu Glu Met Glu Asn Asp Gln Thr Pro Pro Asp
                725                 730                 735

Gly Phe Leu Ser Asn Ser Asp Ser Pro Glu Leu Ile Asn Met Thr Gly
            740                 745                 750

His Cys Met Pro Pro Asn Ala Leu Asp Ser Phe Ser His Asp Phe Thr
            755                 760                 765

Ser Leu Ser Lys Asp Glu Leu Leu Tyr Lys Pro Asp Ser Asn Glu Phe
            770                 775                 780

Ala Val Gly Thr Lys Asn Tyr Ser Val Ser Ala Gly Asp Pro Pro Val
785                 790                 795                 800

Thr Val Met Ser Leu Val Glu Thr Val Pro Asn Thr Pro Gln Ile Ser
                805                 810                 815

Pro Ala Met Ala Lys Lys Ile Asn Asp Asp Ile Lys Tyr Gln Leu Met
                820                 825                 830

Lys Glu Val Arg Arg Phe Gly Gln Asn Tyr Glu Arg Ile Phe Ile Leu
                835                 840                 845

Leu Glu Glu Val Gln Gly Ser Met Lys Val Lys Arg Gln Phe Val Glu
            850                 855                 860

Phe Thr Ile Lys Glu Ala Ala Arg Phe Lys Lys Val Val Leu Ile Gln
865                 870                 875                 880

Gln Leu Glu Lys Ala Leu Lys Glu Ile Asp Ser His Cys His Leu Arg
                885                 890                 895

Lys Val Lys His Met Arg Lys Arg
            900
```

```
<210> SEQ ID NO 4
<211> LENGTH: 528
<212> TYPE: PRT
<213> ORGANISM: Homo sapiens

<400> SEQUENCE: 4
```

```
Met Gln Ala Ser Pro Leu Gln Thr Ser Gln Pro Thr Pro Pro Glu Glu
1                   5                   10                  15

Leu His Ala Ala Ala Tyr Val Phe Thr Asn Asp Gly Gln Gln Met Arg
            20                  25                  30

Ser Asp Glu Val Asn Leu Val Ala Thr Gly His Gln Ser Lys Lys Lys
            35                  40                  45

His Ser Arg Lys Ser Lys Arg His Ser Ser Ser Lys Arg Arg Lys Ser
        50                  55                  60

Met Ser Ser Trp Leu Asp Lys Gln Glu Asp Ala Ala Val Thr His Ser
65                  70                  75                  80

Ile Cys Glu Glu Arg Ile Asn Asn Gly Gln Pro Val Ala Asp Asn Val
                85                  90                  95

Leu Ser Thr Ala Pro Pro Trp Pro Asp Ala Thr Ile Ala His Asn Ile
            100                 105                 110

Arg Glu Glu Arg Met Glu Asn Gly Gln Ser Arg Thr Asp Lys Val Leu
```

-continued

```
                    115                 120                 125
Ser Thr Ala Pro Pro Gln Leu Val His Met Ala Ala Ala Gly Ile Pro
    130                 135                 140
Ser Met Ser Thr Lys Asp Leu Tyr Ala Thr Val Thr Gln Asn Val His
145                 150                 155                 160
Glu Glu Arg Met Glu Asn Asn Gln Pro Gln Pro Ser Tyr Asp Leu Ser
                165                 170                 175
Thr Val Leu Pro Gly Leu Thr Tyr Leu Thr Val Ala Gly Ile Pro Ala
            180                 185                 190
Met Ser Thr Arg Asp Gln Tyr Ala Thr Val Thr His Asn Val His Glu
            195                 200                 205
Glu Lys Ile Lys Asn Gly Gln Ala Ala Ser Asp Asn Val Phe Ser Thr
    210                 215                 220
Val Pro Pro Ala Phe Ile Asn Met Ala Ala Thr Gly Val Ser Ser Met
225                 230                 235                 240
Ser Thr Arg Asp Gln Tyr Ala Ala Val Thr His Asn Ile Arg Glu Glu
            245                 250                 255
Lys Ile Asn Asn Ser Gln Pro Ala Pro Gly Asn Ile Leu Ser Thr Ala
            260                 265                 270
Pro Pro Trp Leu Arg His Met Ala Ala Ala Gly Ile Ser Ser Thr Ile
            275                 280                 285
Thr Arg Asp Leu Tyr Val Thr Ala Thr His Ser Val His Glu Glu Lys
    290                 295                 300
Met Thr Asn Gly Gln Gln Ala Pro Asp Asn Ser Leu Ser Thr Val Pro
305                 310                 315                 320
Pro Gly Cys Ile Asn Leu Ser Gly Ala Gly Ile Ser Cys Arg Ser Thr
                325                 330                 335
Arg Asp Leu Tyr Ala Thr Val Ile His Asp Ile Gln Glu Glu Glu Met
            340                 345                 350
Glu Asn Asp Gln Thr Pro Pro Asp Gly Phe Leu Ser Asn Ser Asp Ser
            355                 360                 365
Pro Glu Leu Ile Asn Met Thr Gly His Cys Met Pro Pro Asn Ala Leu
    370                 375                 380
Asp Ser Phe Ser His Asp Phe Thr Ser Leu Ser Lys Asp Glu Leu Leu
385                 390                 395                 400
Tyr Lys Pro Asp Ser Asn Glu Phe Ala Val Gly Thr Lys Asn Tyr Ser
                405                 410                 415
Val Ser Ala Gly Asp Pro Pro Val Thr Val Met Ser Leu Val Glu Thr
                420                 425                 430
Val Pro Asn Thr Pro Gln Ile Ser Pro Ala Met Ala Lys Lys Ile Asn
            435                 440                 445
Asp Asp Ile Lys Tyr Gln Leu Met Lys Glu Val Arg Arg Phe Gly Gln
            450                 455                 460
Asn Tyr Glu Arg Ile Phe Ile Leu Leu Glu Glu Val Gln Gly Ser Met
465                 470                 475                 480
Lys Val Lys Arg Gln Phe Val Glu Phe Thr Ile Lys Glu Ala Ala Arg
                485                 490                 495
Phe Lys Lys Val Val Leu Ile Gln Gln Leu Glu Lys Ala Leu Lys Glu
                500                 505                 510
Ile Asp Ser His Cys His Leu Arg Lys Val Lys His Met Arg Lys Arg
            515                 520                 525
```

<210> SEQ ID NO 5

```
<211> LENGTH: 1042
<212> TYPE: PRT
<213> ORGANISM: Homo sapiens

<400> SEQUENCE: 5

Glu Leu Gln Lys Gly Lys Gly Ala Ala Ala Ala Ala Ala Ser Gly
1               5                   10                  15

Ala Ala Gly Gly Gly Gly Gly Ala Gly Ala Gly Ala Pro Gly Gly
                20                  25                  30

Gly Arg Leu Leu Leu Ser Thr Ser Leu Asp Ala Lys Asp Glu Leu Glu
        35                  40                  45

Glu Arg Leu Glu Arg Cys Met Ser Ile Val Thr Ser Met Thr Ala Gly
    50                  55                  60

Val Ser Glu Arg Glu Ala Asn Asp Ala Leu Asn Ala Tyr Val Cys Lys
65                  70                  75                  80

Gly Leu Pro Gln His Glu Glu Ile Cys Leu Gly Leu Phe Thr Leu Ile
                85                  90                  95

Leu Thr Glu Pro Ala Gln Ala Gln Lys Cys Tyr Arg Asp Leu Ala Leu
            100                 105                 110

Val Ser Arg Asp Gly Met Asn Ile Val Leu Asn Lys Ile Asn Gln Ile
            115                 120                 125

Leu Met Glu Lys Tyr Leu Lys Leu Gln Asp Thr Cys Arg Thr Gln Leu
    130                 135                 140

Val Trp Leu Val Arg Glu Leu Val Lys Ser Gly Val Leu Gly Ala Asp
145                 150                 155                 160

Gly Val Cys Met Thr Phe Met Lys Gln Ile Ala Gly Gly Gly Asp Val
                165                 170                 175

Thr Ala Lys Asn Ile Trp Leu Ala Glu Ser Val Leu Asp Ile Leu Thr
            180                 185                 190

Glu Gln Arg Glu Trp Val Leu Lys Ser Ser Ile Leu Ile Ala Met Ala
            195                 200                 205

Val Tyr Thr Tyr Leu Arg Leu Ile Val Asp His His Gly Thr Ala Gln
    210                 215                 220

Leu Gln Ala Leu Arg Gln Lys Glu Val Asp Phe Cys Ile Ser Leu Leu
225                 230                 235                 240

Arg Glu Arg Phe Met Glu Cys Leu Met Ile Gly Arg Asp Leu Val Arg
                245                 250                 255

Leu Leu Gln Asn Val Ala Arg Ile Pro Glu Phe Glu Leu Leu Trp Lys
            260                 265                 270

Asp Ile Ile His Asn Pro Gln Ala Leu Ser Pro Gln Phe Thr Gly Ile
    275                 280                 285

Leu Gln Leu Leu Gln Ser Arg Thr Ser Arg Lys Phe Leu Ala Cys Arg
    290                 295                 300

Leu Thr Pro Asp Met Glu Thr Lys Leu Leu Phe Met Thr Ser Arg Val
305                 310                 315                 320

Arg Phe Gly Gln Gln Lys Arg Tyr Gln Asp Trp Phe Gln Arg Gln Tyr
                325                 330                 335

Leu Ser Thr Pro Asp Ser Gln Ser Leu Arg Cys Asp Leu Ile Arg Tyr
            340                 345                 350

Ile Cys Gly Val Val His Pro Ser Asn Glu Val Leu Ser Ser Asp Ile
            355                 360                 365

Leu Pro Arg Trp Ala Ile Ile Gly Trp Leu Leu Thr Thr Cys Thr Ser
    370                 375                 380

Asn Val Ala Ala Ser Asn Ala Lys Leu Ala Leu Phe Tyr Asp Trp Leu
```

-continued

```
385                 390                 395                 400
Phe Phe Ser Pro Asp Lys Asp Ser Ile Met Asn Ile Glu Pro Ala Ile
            405                 410                 415
Leu Val Met His His Ser Met Lys Pro His Pro Ala Ile Thr Ala Thr
            420                 425                 430
Leu Leu Asp Phe Met Cys Arg Ile Ile Pro Asn Phe Tyr Pro Pro Leu
            435                 440                 445
Glu Gly His Val Arg Gln Gly Val Phe Ser Ser Leu Asn His Ile Val
    450                 455                 460
Glu Lys Arg Val Leu Ala His Leu Ala Pro Leu Phe Asp Asn Pro Lys
465                 470                 475                 480
Leu Asp Lys Glu Leu Arg Ala Met Leu Arg Glu Lys Phe Pro Glu Phe
            485                 490                 495
Cys Ser Ser Pro Ser Pro Pro Val Glu Val Lys Ile Glu Glu Pro Val
            500                 505                 510
Ser Met Glu Met Asp Asn His Met Ser Asp Lys Asp Glu Ser Cys Tyr
            515                 520                 525
Asp Asn Ala Glu Ala Ala Phe Ser Asp Asp Glu Glu Asp Leu Asn Ser
    530                 535                 540
Lys Gly Lys Lys Arg Glu Phe Arg Phe His Pro Ile Lys Glu Thr Val
545                 550                 555                 560
Val Glu Glu Pro Val Asp Ile Thr Pro Tyr Leu Asp Gln Leu Asp Glu
            565                 570                 575
Ser Leu Arg Asp Lys Val Leu Gln Leu Gln Lys Gly Ser Asp Thr Glu
            580                 585                 590
Ala Gln Cys Glu Val Met Gln Glu Ile Val Asp Gln Val Leu Glu Glu
            595                 600                 605
Asp Phe Asp Ser Glu Gln Leu Ser Val Leu Ala Ser Cys Leu Gln Glu
            610                 615                 620
Leu Phe Lys Ala His Phe Arg Gly Glu Val Leu Pro Glu Glu Ile Thr
625                 630                 635                 640
Glu Glu Ser Leu Glu Glu Ser Val Gly Lys Pro Leu Tyr Leu Ile Phe
            645                 650                 655
Arg Asn Leu Cys Gln Met Gln Glu Asp Asn Ser Ser Phe Ser Leu Leu
            660                 665                 670
Leu Asp Leu Leu Ser Glu Leu Tyr Gln Lys Gln Pro Lys Ile Gly Tyr
            675                 680                 685
His Leu Leu Tyr Tyr Leu Arg Ala Ser Lys Ala Ala Ala Gly Lys Met
    690                 695                 700
Asn Leu Tyr Glu Ser Phe Ala Gln Ala Thr Gln Leu Gly Asp Leu His
705                 710                 715                 720
Thr Cys Leu Met Met Asp Met Lys Ala Cys Gln Glu Asp Asp Val Arg
            725                 730                 735
Leu Leu Cys His Leu Thr Pro Ser Ile Tyr Thr Glu Phe Pro Asp Glu
            740                 745                 750
Thr Leu Arg Ser Gly Glu Leu Leu Asn Met Ile Val Ala Val Ile Asp
            755                 760                 765
Ser Ala Gln Leu Gln Glu Leu Val Cys His Val Met Met Gly Asn Leu
    770                 775                 780
Val Met Phe Arg Lys Asp Ser Val Leu Asn Ile Leu Ile Gln Ser Leu
785                 790                 795                 800
Asp Trp Glu Thr Phe Glu Gln Tyr Cys Ala Trp Gln Leu Phe Leu Ala
            805                 810                 815
```

```
His Asn Ile Pro Leu Glu Thr Ile Ile Pro Ile Leu Gln His Leu Lys
            820                 825                 830

Tyr Lys Glu His Pro Glu Ala Leu Ser Cys Leu Leu Leu Gln Leu Arg
            835                 840                 845

Arg Glu Lys Pro Ser Glu Glu Met Val Lys Met Val Leu Ser Arg Pro
    850                 855                 860

Cys His Pro Asp Asp Gln Phe Thr Thr Ser Ile Leu Arg His Trp Cys
865                 870                 875                 880

Met Lys His Asp Glu Leu Leu Ala Glu His Ile Lys Ser Leu Leu Ile
            885                 890                 895

Lys Asn Asn Ser Leu Pro Arg Lys Arg Gln Ser Leu Arg Ser Ser Ser
            900                 905                 910

Ser Lys Leu Ala Gln Leu Thr Leu Glu Gln Ile Leu Glu His Leu Asp
            915                 920                 925

Asn Leu Arg Leu Asn Leu Thr Asn Thr Lys Gln Asn Phe Phe Ser Gln
    930                 935                 940

Thr Pro Ile Leu Gln Ala Leu Gln His Val Gln Ala Ser Cys Asp Glu
945                 950                 955                 960

Ala His Lys Met Lys Phe Ser Asp Leu Phe Ser Leu Ala Glu Glu Tyr
            965                 970                 975

Glu Asp Ser Ser Thr Lys Pro Pro Lys Ser Arg Arg Lys Ala Ala Leu
            980                 985                 990

Ser Ser Pro Arg Ser Arg Lys Asn  Ala Thr Gln Pro Pro  Asn Ala Glu
            995                 1000                1005

Glu Glu  Ser Gly Ser Ser Ser  Ala Ser Glu Glu Glu  Asp Thr Lys
    1010                1015                1020

Pro Lys  Pro Thr Lys Arg Lys  Arg Lys Gly Ser Ser  Ala Val Gly
    1025                1030                1035

Ser Asp  Ser Asp
    1040
```

```
<210> SEQ ID NO 6
<211> LENGTH: 887
<212> TYPE: PRT
<213> ORGANISM: Homo sapiens

<400> SEQUENCE: 6

Met Pro Ile Leu Leu Phe Leu Ile Asp Thr Ser Ala Ser Met Asn Gln
1               5                   10                  15

Arg Ser His Leu Gly Thr Thr Tyr Leu Asp Thr Ala Lys Gly Ala Val
            20                  25                  30

Glu Thr Phe Met Lys Leu Arg Ala Arg Asp Pro Ala Ser Arg Gly Asp
            35                  40                  45

Arg Tyr Met Leu Val Thr Phe Glu Glu Pro Pro Tyr Ala Ile Lys Ala
    50                  55                  60

Gly Trp Lys Glu Asn His Ala Thr Phe Met Asn Glu Leu Lys Asn Leu
65                  70                  75                  80

Gln Ala Glu Gly Leu Thr Thr Leu Gly Gln Ser Leu Arg Thr Ala Phe
            85                  90                  95

Asp Leu Leu Asn Leu Asn Arg Leu Val Thr Gly Ile Asp Asn Tyr Gly
            100                 105                 110

Gln Gly Arg Asn Pro Phe Phe Leu Glu Pro Ala Ile Ile Ile Thr Ile
            115                 120                 125

Thr Asp Gly Ser Lys Leu Thr Thr Thr Ser Gly Val Gln Asp Glu Leu
```

-continued

```
             130                135                140

His Leu Pro Leu Asn Ser Pro Leu Pro Gly Ser Glu Leu Thr Lys Glu
145                 150                155                160

Pro Phe Arg Trp Asp Gln Arg Leu Phe Ala Leu Val Leu Arg Leu Pro
                165                170                175

Gly Thr Met Ser Val Glu Ser Glu Gln Leu Thr Gly Val Pro Leu Asp
                180                185                190

Asp Ser Ala Ile Thr Pro Met Cys Glu Val Thr Gly Gly Arg Ser Tyr
                195                200                205

Ser Val Cys Ser Pro Arg Met Leu Asn Gln Cys Leu Glu Ser Leu Val
                210                215                220

Gln Lys Val Gln Ser Gly Val Val Ile Asn Phe Glu Lys Ala Gly Pro
225                 230                235                240

Asp Pro Ser Pro Val Glu Asp Gly Gln Pro Asp Ile Ser Arg Pro Phe
                245                250                255

Gly Ser Gln Pro Trp His Ser Cys His Lys Leu Ile Tyr Val Arg Pro
                260                265                270

Asn Pro Lys Thr Gly Val Pro Ile Gly His Trp Pro Val Pro Glu Ser
                275                280                285

Phe Trp Pro Asp Gln Asn Ser Pro Thr Leu Pro Pro Arg Thr Ser His
                290                295                300

Pro Val Val Lys Phe Ser Cys Thr Asp Cys Glu Pro Met Val Ile Asp
305                 310                315                320

Lys Leu Pro Phe Asp Lys Tyr Glu Leu Glu Pro Ser Pro Leu Thr Gln
                325                330                335

Phe Ile Leu Glu Arg Lys Ser Pro Gln Thr Cys Trp Gln Val Tyr Val
                340                345                350

Ser Asn Ser Ala Lys Tyr Ser Glu Leu Gly His Pro Phe Gly Tyr Leu
                355                360                365

Lys Ala Ser Thr Ala Leu Asn Cys Val Asn Leu Phe Val Met Pro Tyr
                370                375                380

Asn Tyr Pro Val Leu Leu Pro Leu Leu Asp Asp Leu Phe Lys Val His
385                 390                395                400

Lys Ala Lys Pro Thr Leu Lys Trp Arg Gln Ser Phe Glu Ser Tyr Leu
                405                410                415

Lys Thr Met Pro Pro Tyr Tyr Leu Gly Pro Leu Lys Lys Ala Val Arg
                420                425                430

Met Met Gly Ala Pro Asn Leu Ile Ala Asp Ser Met Glu Tyr Gly Leu
                435                440                445

Ser Tyr Ser Val Ile Ser Tyr Leu Lys Lys Leu Ser Gln Gln Ala Lys
                450                455                460

Ile Glu Ser Asp Arg Val Ile Gly Ser Val Gly Lys Lys Val Val Gln
465                 470                475                480

Glu Thr Gly Ile Lys Val Arg Ser Arg Ser His Gly Leu Ser Met Ala
                485                490                495

Tyr Arg Lys Asp Phe Gln Gln Leu Leu Gln Gly Ile Ser Glu Asp Val
                500                505                510

Pro His Arg Leu Leu Asp Leu Asn Met Lys Glu Tyr Thr Gly Phe Gln
                515                520                525

Val Ala Leu Leu Asn Lys Asp Leu Lys Pro Gln Thr Phe Arg Asn Ala
                530                535                540

Tyr Asp Ile Pro Arg Arg Asn Leu Leu Asp His Leu Thr Arg Met Arg
545                 550                555                560
```

Ser Asn Leu Leu Lys Ser Thr Arg Arg Phe Leu Lys Gly Gln Asp Glu
            565                 570                 575

Asp Gln Val His Ser Val Pro Ile Ala Gln Met Gly Asn Tyr Gln Glu
            580                 585                 590

Tyr Leu Lys Gln Val Pro Ser Pro Leu Arg Glu Leu Asp Pro Asp Gln
            595                 600                 605

Pro Arg Arg Leu His Thr Phe Gly Asn Pro Phe Lys Leu Asp Lys Lys
        610                 615                 620

Gly Met Met Ile Asp Glu Ala Asp Glu Phe Val Ala Gly Pro Gln Asn
625                 630                 635                 640

Lys His Lys Arg Pro Gly Glu Pro Asn Met Gln Gly Ile Pro Lys Arg
            645                 650                 655

Arg Arg Cys Met Ser Pro Leu Leu Arg Gly Arg Gln Gln Asn Pro Val
            660                 665                 670

Val Asn Asn His Ile Gly Gly Lys Gly Pro Pro Ala Pro Thr Thr Gln
            675                 680                 685

Ala Gln Pro Asp Leu Ile Lys Pro Leu Pro Leu His Lys Ile Ser Glu
        690                 695                 700

Thr Thr Asn Asp Ser Ile Ile His Asp Val Val Glu Asn His Val Ala
705                 710                 715                 720

Asp Gln Leu Ser Ser Asp Ile Thr Pro Asn Ala Met Asp Thr Glu Phe
            725                 730                 735

Ser Ala Ser Ser Pro Ala Ser Leu Leu Glu Arg Pro Thr Asn His Met
            740                 745                 750

Glu Ala Leu Gly His Asp His Leu Gly Thr Asn Asp Leu Thr Val Gly
            755                 760                 765

Gly Phe Leu Glu Asn His Glu Glu Pro Arg Asp Lys Glu Gln Cys Ala
        770                 775                 780

Glu Glu Asn Ile Pro Ala Ser Ser Leu Asn Lys Gly Lys Lys Leu Met
785                 790                 795                 800

His Cys Arg Ser His Glu Glu Val Asn Thr Glu Leu Lys Ala Gln Ile
            805                 810                 815

Met Lys Glu Ile Arg Lys Pro Gly Arg Lys Tyr Glu Arg Ile Phe Thr
            820                 825                 830

Leu Leu Lys His Val Gln Gly Ser Leu Gln Thr Arg Leu Ile Phe Leu
            835                 840                 845

Gln Asn Val Ile Lys Glu Ala Ser Arg Phe Lys Lys Arg Met Leu Ile
        850                 855                 860

Glu Gln Leu Glu Asn Phe Leu Asp Glu Ile His Arg Arg Ala Asn Gln
865                 870                 875                 880

Ile Asn His Ile Asn Ser Asn
                885

<210> SEQ ID NO 7
<211> LENGTH: 861
<212> TYPE: PRT
<213> ORGANISM: Homo sapiens

<400> SEQUENCE: 7

Met Pro Ile Leu Leu Phe Leu Ile Asp Thr Ser Ala Ser Met Asn Gln
1               5                   10                  15

Arg Thr Asp Leu Gly Thr Ser Tyr Leu Asp Ile Ala Lys Gly Ala Val
            20                  25                  30

Glu Leu Phe Leu Lys Leu Arg Ala Arg Asp Pro Ala Ser Arg Gly Asp

-continued

```
            35                    40                    45
Arg Tyr Met Leu Val Thr Tyr Asp Glu Pro Pro Tyr Cys Ile Lys Ala
    50                    55                    60
Gly Trp Lys Glu Asn His Ala Thr Phe Met Ser Glu Leu Lys Asn Leu
65                    70                    75                    80
Gln Ala Ser Gly Leu Thr Thr Leu Gly Gln Ala Leu Arg Ser Ser Phe
                85                    90                    95
Asp Leu Leu Asn Leu Asn Arg Leu Ile Ser Gly Ile Asp Asn Tyr Gly
            100                   105                   110
Gln Gly Arg Asn Pro Phe Phe Leu Glu Pro Ser Ile Leu Ile Thr Ile
            115                   120                   125
Thr Asp Gly Asn Lys Leu Thr Ser Thr Ala Gly Val Gln Glu Glu Leu
    130                   135                   140
His Leu Pro Leu Asn Ser Pro Leu Pro Gly Ser Glu Leu Thr Lys Glu
145                   150                   155                   160
Pro Phe Arg Trp Asp Gln Arg Leu Phe Ala Leu Val Leu Arg Leu Pro
                165                   170                   175
Gly Val Ala Ser Thr Glu Pro Glu Gln Leu Gly Ser Val Pro Thr Asp
                180                   185                   190
Glu Ser Ala Ile Thr Gln Met Cys Glu Val Thr Gly Gly Arg Ser Tyr
                195                   200                   205
Cys Val Arg Thr Gln Arg Met Leu Asn Gln Cys Leu Glu Ser Leu Val
    210                   215                   220
Gln Lys Val Gln Ser Gly Val Val Ile Asn Phe Glu Lys Thr Gly Pro
225                   230                   235                   240
Asp Pro Leu Pro Ile Gly Glu Asp Gly Leu Met Asp Ser Ser Arg Pro
                245                   250                   255
Ser Asn Ser Phe Ala Ala Gln Pro Trp His Ser Cys His Lys Leu Ile
                260                   265                   270
Tyr Val Arg Pro Asn Ser Lys Thr Gly Val Pro Val Gly His Trp Pro
                275                   280                   285
Ile Pro Glu Ser Phe Trp Pro Asp Gln Asn Leu Pro Ser Leu Pro Pro
    290                   295                   300
Arg Thr Ser His Pro Val Val Arg Phe Ser Cys Val Asp Cys Glu Pro
305                   310                   315                   320
Met Val Ile Asp Lys Leu Pro Phe Asp Lys Tyr Glu Leu Glu Pro Ser
                325                   330                   335
Pro Leu Thr Gln Tyr Ile Leu Glu Arg Lys Ser Pro His Thr Cys Trp
                340                   345                   350
Gln Val Phe Val Thr Ser Ser Gly Lys Tyr Asn Glu Leu Gly Tyr Pro
                355                   360                   365
Phe Gly Tyr Leu Lys Ala Ser Thr Thr Leu Thr Cys Val Asn Leu Phe
    370                   375                   380
Val Met Pro Tyr Asn Tyr Pro Val Leu Leu Pro Leu Leu Asp Asp Leu
385                   390                   395                   400
Phe Lys Val His Lys Leu Lys Pro Asn Leu Lys Trp Arg Gln Ala Phe
                405                   410                   415
Asp Ser Tyr Leu Lys Thr Leu Pro Pro Tyr Tyr Leu Leu Thr Lys Leu
            420                   425                   430
Glu Ser Glu Arg Ile Leu Ala Ser Val Gly Lys Lys Pro Pro Gln Glu
            435                   440                   445
Ile Gly Ile Lys Val Lys Asn His Ser Gly Gly Gly Met Ser Leu Thr
    450                   455                   460
```

His Asn Lys Asn Phe Arg Lys Leu Leu Lys Glu Ile Thr Gly Glu Thr
465                 470                 475                 480

Ala Leu Arg Leu Thr Glu Leu Asn Thr Lys Glu Phe Ala Gly Phe Gln
                485                 490                 495

Ile Gly Leu Leu Asn Lys Asp Leu Lys Pro Gln Thr Tyr Arg Asn Ala
            500                 505                 510

Tyr Asp Ile Pro Arg Arg Gly Leu Leu Asp Gln Leu Thr Arg Met Arg
            515                 520                 525

Ser Asn Leu Leu Lys Thr His Lys Phe Ile Val Gly Gln Asp Glu Asp
        530                 535                 540

Ser Leu His Ser Val Pro Val Ala Gln Met Gly Asn Tyr Gln Glu Tyr
545                 550                 555                 560

Leu Lys Thr Leu Ala Ser Pro Leu Arg Glu Ile Asp Pro Asp Gln Pro
                565                 570                 575

Lys Arg Leu His Thr Phe Gly Asn Pro Phe Lys Gln Asp Lys Lys Gly
            580                 585                 590

Met Met Ile Asp Glu Ala Asp Glu Phe Val Ala Gly Pro Gln Asn Lys
            595                 600                 605

Val Lys Arg Pro Gly Glu Pro Asn Ser Pro Met Ser Ser Lys Arg Arg
        610                 615                 620

Arg Ser Met Ser Leu Leu Leu Arg Lys Pro Gln Thr Pro Pro Thr Val
625                 630                 635                 640

Thr Asn His Val Gly Gly Lys Gly Pro Pro Ser Ala Ser Trp Phe Pro
                645                 650                 655

Ser Tyr Pro Asn Leu Ile Lys Pro Thr Leu Val His Thr Asp Ala Thr
            660                 665                 670

Ile Ile His Asp Gly His Glu Glu Lys Met Glu Asn Gly Gln Ile Thr
            675                 680                 685

Pro Asp Gly Phe Leu Ser Lys Ser Ala Pro Ser Glu Leu Ile Asn Met
        690                 695                 700

Thr Gly Asp Leu Met Pro Pro Asn Gln Val Asp Ser Leu Ser Asp Asp
705                 710                 715                 720

Phe Thr Ser Leu Ser Lys Asp Gly Leu Ile Gln Lys Pro Gly Ser Asn
                725                 730                 735

Ala Phe Val Gly Gly Ala Lys Asn Cys Ser Leu Ser Val Asp Asp Gln
            740                 745                 750

Lys Asp Pro Val Ala Ser Thr Leu Gly Ala Met Pro Asn Thr Leu Gln
            755                 760                 765

Ile Thr Pro Ala Met Ala Gln Gly Ile Asn Ala Asp Ile Lys His Gln
        770                 775                 780

Leu Met Lys Glu Val Arg Lys Phe Gly Arg Lys Tyr Glu Arg Ile Phe
785                 790                 795                 800

Ile Leu Leu Glu Glu Val Gln Gly Pro Leu Glu Met Lys Lys Gln Phe
                805                 810                 815

Val Glu Phe Thr Ile Lys Glu Ala Ala Arg Phe Lys Arg Arg Val Leu
                820                 825                 830

Ile Gln Tyr Leu Glu Lys Val Leu Glu Lys Ile Asn Ser His His Leu
            835                 840                 845

His Asn Asn Ile Ser His Ile Asn Ser Arg Ser Ser Cys
        850                 855                 860

<210> SEQ ID NO 8
<211> LENGTH: 87

```
<212> TYPE: PRT
<213> ORGANISM: Homo sapiens

<400> SEQUENCE: 8

Ala Met Ala Lys Lys Ile Asn Asp Asp Ile Lys Tyr Gln Leu Met Lys
1               5                   10                  15

Glu Val Arg Arg Phe Gly Gln Asn Tyr Glu Arg Ile Phe Ile Leu Leu
                20                  25                  30

Glu Glu Val Gln Gly Ser Met Lys Val Lys Arg Gln Phe Val Glu Phe
            35                  40                  45

Thr Ile Lys Glu Ala Ala Arg Phe Lys Lys Val Val Leu Ile Gln Gln
        50                  55                  60

Leu Glu Lys Ala Leu Lys Glu Ile Asp Ser His Cys His Leu Arg Lys
65                  70                  75                  80

Val Lys His Met Arg Lys Arg
                85

<210> SEQ ID NO 9
<211> LENGTH: 407
<212> TYPE: PRT
<213> ORGANISM: Homo sapiens

<400> SEQUENCE: 9

Asp Gln Leu Asp Glu Ser Leu Arg Asp Lys Val Leu Gln Leu Gln Lys
1               5                   10                  15

Gly Ser Asp Thr Glu Ala Gln Cys Glu Val Met Gln Glu Ile Val Asp
                20                  25                  30

Gln Val Leu Glu Glu Asp Phe Asp Ser Glu Gln Leu Ser Val Leu Ala
            35                  40                  45

Ser Cys Leu Gln Glu Leu Phe Lys Ala His Phe Arg Gly Glu Val Leu
        50                  55                  60

Pro Glu Glu Ile Thr Glu Glu Ser Leu Glu Glu Ser Val Gly Lys Pro
65                  70                  75                  80

Leu Tyr Leu Ile Phe Arg Asn Leu Cys Gln Met Gln Glu Asp Asn Ser
                85                  90                  95

Ser Phe Ser Leu Leu Leu Asp Leu Leu Ser Glu Leu Tyr Gln Lys Gln
                100                 105                 110

Pro Lys Ile Gly Tyr His Leu Leu Tyr Tyr Leu Arg Ala Ser Lys Ala
            115                 120                 125

Ala Ala Gly Lys Met Asn Leu Tyr Glu Ser Phe Ala Gln Ala Thr Gln
        130                 135                 140

Leu Gly Asp Leu His Thr Cys Leu Met Met Asp Met Lys Ala Cys Gln
145                 150                 155                 160

Glu Asp Asp Val Arg Leu Leu Cys His Leu Thr Pro Ser Ile Tyr Thr
                165                 170                 175

Glu Phe Pro Asp Glu Thr Leu Arg Ser Gly Glu Leu Leu Asn Met Ile
                180                 185                 190

Val Ala Val Ile Asp Ser Ala Gln Leu Gln Glu Leu Val Cys His Val
            195                 200                 205

Met Met Gly Asn Leu Val Met Phe Arg Lys Asp Ser Val Leu Asn Ile
        210                 215                 220

Leu Ile Gln Ser Leu Asp Trp Glu Thr Phe Glu Gln Tyr Cys Ala Trp
225                 230                 235                 240

Gln Leu Phe Leu Ala His Asn Ile Pro Leu Glu Thr Ile Ile Pro Ile
                245                 250                 255
```

-continued

```
Leu Gln His Leu Lys Tyr Lys Glu His Pro Glu Ala Leu Ser Cys Leu
            260                 265                 270

Leu Leu Gln Leu Arg Arg Glu Lys Pro Ser Glu Glu Met Val Lys Met
        275                 280                 285

Val Leu Ser Arg Pro Cys His Pro Asp Asp Gln Phe Thr Thr Ser Ile
    290                 295                 300

Leu Arg His Trp Cys Met Lys His Asp Glu Leu Leu Ala Glu His Ile
305                 310                 315                 320

Lys Ser Leu Leu Ile Lys Asn Asn Ser Leu Pro Arg Lys Arg Gln Ser
            325                 330                 335

Leu Arg Ser Ser Ser Ser Lys Leu Ala Gln Leu Thr Leu Glu Gln Ile
        340                 345                 350

Leu Glu His Leu Asp Asn Leu Arg Leu Asn Leu Thr Asn Thr Lys Gln
        355                 360                 365

Asn Phe Phe Ser Gln Thr Pro Ile Leu Gln Ala Leu Gln His Val Gln
    370                 375                 380

Ala Ser Cys Asp Glu Ala His Lys Met Lys Phe Ser Asp Leu Phe Ser
385                 390                 395                 400

Leu Ala Glu Glu Tyr Glu Asp
            405
```

```
<210> SEQ ID NO 10
<211> LENGTH: 85
<212> TYPE: PRT
<213> ORGANISM: Homo sapiens

<400> SEQUENCE: 10

Arg Ser His Glu Glu Val Asn Thr Glu Leu Lys Ala Gln Ile Met Lys
1               5                   10                  15

Glu Ile Arg Lys Pro Gly Arg Lys Tyr Glu Arg Ile Phe Thr Leu Leu
            20                  25                  30

Lys His Val Gln Gly Ser Leu Gln Thr Arg Leu Ile Phe Leu Gln Asn
        35                  40                  45

Val Ile Lys Glu Ala Ser Arg Phe Lys Lys Arg Met Leu Ile Glu Gln
    50                  55                  60

Leu Glu Asn Phe Leu Asp Glu Ile His Arg Arg Ala Asn Gln Ile Asn
65                  70                  75                  80

His Ile Asn Ser Asn
            85
```

```
<210> SEQ ID NO 11
<211> LENGTH: 19
<212> TYPE: DNA
<213> ORGANISM: Homo sapiens

<400> SEQUENCE: 11
gcagtcactc acagcattt                                                        19
```

```
<210> SEQ ID NO 12
<211> LENGTH: 19
<212> TYPE: DNA
<213> ORGANISM: Homo sapiens

<400> SEQUENCE: 12
ccaaccagta gctgataat                                                        19
```

```
<210> SEQ ID NO 13
<211> LENGTH: 19
```

<212> TYPE: DNA
<213> ORGANISM: Homo sapiens

<400> SEQUENCE: 13
cctgataacg tcttgtcaa                                               19

<210> SEQ ID NO 14
<211> LENGTH: 19
<212> TYPE: DNA
<213> ORGANISM: Homo sapiens

<400> SEQUENCE: 14
ccacagggct tattaatat                                              19

<210> SEQ ID NO 15
<211> LENGTH: 19
<212> TYPE: DNA
<213> ORGANISM: Homo sapiens

<400> SEQUENCE: 15
gcacctgata acgtgttgt                                              19

<210> SEQ ID NO 16
<211> LENGTH: 19
<212> TYPE: DNA
<213> ORGANISM: Homo sapiens

<400> SEQUENCE: 16
gggatccata tgctaccat                                              19

<210> SEQ ID NO 17
<211> LENGTH: 19
<212> TYPE: DNA
<213> ORGANISM: Homo sapiens

<400> SEQUENCE: 17
cctgataaca tcttgtcaa                                              19

<210> SEQ ID NO 18
<211> LENGTH: 19
<212> TYPE: DNA
<213> ORGANISM: Homo sapiens

<400> SEQUENCE: 18
gcttcaacag ggcttatta                                              19

<210> SEQ ID NO 19
<211> LENGTH: 19
<212> TYPE: DNA
<213> ORGANISM: Homo sapiens

<400> SEQUENCE: 19
ccctcacaat gtctgtgaa                                              19

<210> SEQ ID NO 20
<211> LENGTH: 19
<212> TYPE: DNA
<213> ORGANISM: Homo sapiens

<400> SEQUENCE: 20
ccgcaaccta ataacgtat                                              19

<210> SEQ ID NO 21

-continued

```
<211> LENGTH: 19
<212> TYPE: DNA
<213> ORGANISM: Homo sapiens

<400> SEQUENCE: 21
gggatcagta tgctaccat                                                  19

<210> SEQ ID NO 22
<211> LENGTH: 19
<212> TYPE: DNA
<213> ORGANISM: Homo sapiens

<400> SEQUENCE: 22
cctagtaacg ccttgtcaa                                                  19

<210> SEQ ID NO 23
<211> LENGTH: 19
<212> TYPE: DNA
<213> ORGANISM: Homo sapiens

<400> SEQUENCE: 23
gggcttgctt atttggcaa                                                  19

<210> SEQ ID NO 24
<211> LENGTH: 19
<212> TYPE: DNA
<213> ORGANISM: Homo sapiens

<400> SEQUENCE: 24
gggatcagca tgctaccat                                                  19

<210> SEQ ID NO 25
<211> LENGTH: 19
<212> TYPE: DNA
<213> ORGANISM: Homo sapiens

<400> SEQUENCE: 25
gctgttacac cagagctta                                                  19

<210> SEQ ID NO 26
<211> LENGTH: 19
<212> TYPE: DNA
<213> ORGANISM: Homo sapiens

<400> SEQUENCE: 26
ggataacgtc ttgtcaaat                                                  19

<210> SEQ ID NO 27
<211> LENGTH: 19
<212> TYPE: DNA
<213> ORGANISM: Homo sapiens

<400> SEQUENCE: 27
ggagctagta ttccagcaa                                                  19

<210> SEQ ID NO 28
<211> LENGTH: 19
<212> TYPE: DNA
<213> ORGANISM: Homo sapiens

<400> SEQUENCE: 28
gggatctgta tgctaccat                                                  19
```

-continued

```
<210> SEQ ID NO 29
<211> LENGTH: 19
<212> TYPE: DNA
<213> ORGANISM: Homo sapiens

<400> SEQUENCE: 29
gcaccacagc ttggtcata                                                19

<210> SEQ ID NO 30
<211> LENGTH: 19
<212> TYPE: DNA
<213> ORGANISM: Homo sapiens

<400> SEQUENCE: 30
ggtattccat ccatgagta                                                19

<210> SEQ ID NO 31
<211> LENGTH: 19
<212> TYPE: DNA
<213> ORGANISM: Homo sapiens

<400> SEQUENCE: 31
ccaagcagca tccgataat                                                19

<210> SEQ ID NO 32
<211> LENGTH: 19
<212> TYPE: DNA
<213> ORGANISM: Homo sapiens

<400> SEQUENCE: 32
ggtgtttcat ccatgagta                                                19

<210> SEQ ID NO 33
<211> LENGTH: 19
<212> TYPE: DNA
<213> ORGANISM: Homo sapiens

<400> SEQUENCE: 33
gctgcagtca ctcacaaca                                                19

<210> SEQ ID NO 34
<211> LENGTH: 19
<212> TYPE: DNA
<213> ORGANISM: Homo sapiens

<400> SEQUENCE: 34
cctggtaaca tcttgtcaa                                                19

<210> SEQ ID NO 35
<211> LENGTH: 19
<212> TYPE: DNA
<213> ORGANISM: Homo sapiens

<400> SEQUENCE: 35
ggaatttcat ccacgatta                                                19

<210> SEQ ID NO 36
<211> LENGTH: 19
<212> TYPE: DNA
<213> ORGANISM: Homo sapiens

<400> SEQUENCE: 36
gaagatgaca aatggccaa                                                19
```

-continued

<210> SEQ ID NO 37
<211> LENGTH: 19
<212> TYPE: DNA
<213> ORGANISM: Homo sapiens

<400> SEQUENCE: 37
cctgataact ccttgtcaa                                              19

<210> SEQ ID NO 38
<211> LENGTH: 19
<212> TYPE: DNA
<213> ORGANISM: Homo sapiens

<400> SEQUENCE: 38
ggttccacct ggttgtatt                                              19

<210> SEQ ID NO 39
<211> LENGTH: 19
<212> TYPE: DNA
<213> ORGANISM: Homo sapiens

<400> SEQUENCE: 39
gctggtattt catgcagaa                                              19

<210> SEQ ID NO 40
<211> LENGTH: 19
<212> TYPE: DNA
<213> ORGANISM: Homo sapiens

<400> SEQUENCE: 40
gctactgtca ttcacgata                                              19

<210> SEQ ID NO 41
<211> LENGTH: 19
<212> TYPE: DNA
<213> ORGANISM: Homo sapiens

<400> SEQUENCE: 41
gccacccaat gcattggat                                              19

<210> SEQ ID NO 42
<211> LENGTH: 19
<212> TYPE: DNA
<213> ORGANISM: Homo sapiens

<400> SEQUENCE: 42
gccaaataca ccacaaata                                              19

<210> SEQ ID NO 43
<211> LENGTH: 19
<212> TYPE: DNA
<213> ORGANISM: Homo sapiens

<400> SEQUENCE: 43
cttctcacac agcgggata                                              19

<210> SEQ ID NO 44
<211> LENGTH: 19
<212> TYPE: DNA
<213> ORGANISM: Homo sapiens

<400> SEQUENCE: 44
gagctggtat tccacccat                                              19

-continued

<210> SEQ ID NO 45
<211> LENGTH: 19
<212> TYPE: DNA
<213> ORGANISM: Homo sapiens

<400> SEQUENCE: 45
tcagtatgct accgtcaat                                                   19

<210> SEQ ID NO 46
<211> LENGTH: 19
<212> TYPE: DNA
<213> ORGANISM: Homo sapiens

<400> SEQUENCE: 46
ggagctagta ttccagcaa                                                   19

<210> SEQ ID NO 47
<211> LENGTH: 19
<212> TYPE: DNA
<213> ORGANISM: Homo sapiens

<400> SEQUENCE: 47
cctccatggc ttcgtcata                                                   19

<210> SEQ ID NO 48
<211> LENGTH: 19
<212> TYPE: DNA
<213> ORGANISM: Homo sapiens

<400> SEQUENCE: 48
ccacgattac cagggatct                                                   19

<210> SEQ ID NO 49
<211> LENGTH: 19
<212> TYPE: DNA
<213> ORGANISM: Homo sapiens

<400> SEQUENCE: 49
gagaaggcgc ttaaagaaa                                                   19

<210> SEQ ID NO 50
<211> LENGTH: 19
<212> TYPE: DNA
<213> ORGANISM: Homo sapiens

<400> SEQUENCE: 50
ggaacaggtt attgctgaa                                                   19

<210> SEQ ID NO 51
<211> LENGTH: 19
<212> TYPE: DNA
<213> ORGANISM: Homo sapiens

<400> SEQUENCE: 51
gctgataatg tcttgtcaa                                                   19

<210> SEQ ID NO 52
<211> LENGTH: 19
<212> TYPE: DNA
<213> ORGANISM: Homo sapiens

<400> SEQUENCE: 52

-continued

```
cactcttcat ctaagagaa                                                 19

<210> SEQ ID NO 53
<211> LENGTH: 19
<212> TYPE: DNA
<213> ORGANISM: Homo sapiens

<400> SEQUENCE: 53
cactcacaat gtctgtgaa                                                 19

<210> SEQ ID NO 54
<211> LENGTH: 21
<212> TYPE: DNA
<213> ORGANISM: Homo sapiens

<400> SEQUENCE: 54
ccaaggagaa acaaggacat a                                              21

<210> SEQ ID NO 55
<211> LENGTH: 21
<212> TYPE: DNA
<213> ORGANISM: Homo sapiens

<400> SEQUENCE: 55
gctgcctatg tgtttacaaa t                                              21

<210> SEQ ID NO 56
<211> LENGTH: 21
<212> TYPE: DNA
<213> ORGANISM: Homo sapiens

<400> SEQUENCE: 56
cccaaactga taaggtcata t                                              21

<210> SEQ ID NO 57
<211> LENGTH: 21
<212> TYPE: DNA
<213> ORGANISM: Homo sapiens

<400> SEQUENCE: 57
gctggaattt catccacgat t                                              21

<210> SEQ ID NO 58
<211> LENGTH: 21
<212> TYPE: DNA
<213> ORGANISM: Homo sapiens

<400> SEQUENCE: 58
ctgctgccta tgtgtttaca a                                              21

<210> SEQ ID NO 59
<211> LENGTH: 19
<212> TYPE: DNA
<213> ORGANISM: Homo sapiens

<400> SEQUENCE: 59
gtcccacagg gcttattaa                                                 19

<210> SEQ ID NO 60
<211> LENGTH: 19
<212> TYPE: DNA
<213> ORGANISM: Homo sapiens

<400> SEQUENCE: 60
```
tggtatttca tgcagaagt                                                      19

<210> SEQ ID NO 61
<211> LENGTH: 19
<212> TYPE: DNA
<213> ORGANISM: Homo sapiens

<400> SEQUENCE: 61
gttccacctg gttgtatta                                                     19

<210> SEQ ID NO 62
<211> LENGTH: 21
<212> TYPE: DNA
<213> ORGANISM: Homo sapiens

<400> SEQUENCE: 62
gctggaattt catccacgat t                                                  21

<210> SEQ ID NO 63
<211> LENGTH: 21
<212> TYPE: DNA
<213> ORGANISM: Homo sapiens

<400> SEQUENCE: 63
ctgctgccta tgtgtttaca a                                                  21

<210> SEQ ID NO 64
<211> LENGTH: 21
<212> TYPE: DNA
<213> ORGANISM: Homo sapiens

<400> SEQUENCE: 64
ccaaggagaa acaaggacat a                                                  21

<210> SEQ ID NO 65
<211> LENGTH: 21
<212> TYPE: DNA
<213> ORGANISM: Homo sapiens

<400> SEQUENCE: 65
gctgcctatg tgtttacaaa t                                                  21

<210> SEQ ID NO 66
<211> LENGTH: 21
<212> TYPE: DNA
<213> ORGANISM: Homo sapiens

<400> SEQUENCE: 66
cccagactga taaggtcata t                                                  21

<210> SEQ ID NO 67
<211> LENGTH: 21
<212> TYPE: DNA
<213> ORGANISM: Homo sapiens

<400> SEQUENCE: 67
cccaaactga taaggtcata t                                                  21

<210> SEQ ID NO 68
<211> LENGTH: 19
<212> TYPE: DNA
<213> ORGANISM: Homo sapiens -continued

```
<400> SEQUENCE: 68
aaggaagagt atgtcctcg                                              19

<210> SEQ ID NO 69
<211> LENGTH: 19
<212> TYPE: DNA
<213> ORGANISM: Homo sapiens

<400> SEQUENCE: 69
aagtaaatct ggttgcaac                                             19

<210> SEQ ID NO 70
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 70
gcugauaaug ucuugucaat t                                          21

<210> SEQ ID NO 71
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 71
uugacaagac auuaucagct t                                          21

<210> SEQ ID NO 72
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 72
cacucuucau cuaagagaat t                                          21

<210> SEQ ID NO 73
<211> LENGTH: 21
<212> TYPE: DNA
<213> ORGANISM: Artificial Sequence
```

-continued

```
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 73
uucucuuaga ugaagagugt t                                              21

<210> SEQ ID NO 74
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 74
cacucacaau gucugugaat t                                              21

<210> SEQ ID NO 75
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (1)..(19)
<223> OTHER INFORMATION: deoxyribonucleotides

<400> SEQUENCE: 75
uucacagaca uugugagugt t                                              21

<210> SEQ ID NO 76
<211> LENGTH: 21
<212> TYPE: RNA
<213> ORGANISM: Artificial Sequence
<220> FEATURE:
<223> OTHER INFORMATION: Synthetic

<400> SEQUENCE: 76
ccaaggagaa acaaggacau a                                              21

<210> SEQ ID NO 77
<211> LENGTH: 21
<212> TYPE: RNA
<213> ORGANISM: Artificial Sequence
<220> FEATURE:
<223> OTHER INFORMATION: Synthetic

<400> SEQUENCE: 77
uauguccuug uuucuccuug g                                              21
```

-continued

```
<210> SEQ ID NO 78
<211> LENGTH: 21
<212> TYPE: RNA
<213> ORGANISM: Artificial Sequence
<220> FEATURE:
<223> OTHER INFORMATION: Synthetic

<400> SEQUENCE: 78
cccaaacuga uaaggucaua u                                                21

<210> SEQ ID NO 79
<211> LENGTH: 21
<212> TYPE: DNA
<213> ORGANISM: Artificial Sequence
<220> FEATURE:
<223> OTHER INFORMATION: Synthetic

<400> SEQUENCE: 79
auaugaccuu aucaguuugg g                                                21

<210> SEQ ID NO 80
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 80
gcugcaguca cucacaacat t                                                21

<210> SEQ ID NO 81
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxyribonucleotides

<400> SEQUENCE: 81
uguugugagu gacugcagct t                                                21

<210> SEQ ID NO 82
<211> LENGTH: 58
<212> TYPE: RNA
<213> ORGANISM: Artificial Sequence
<220> FEATURE:
<223> OTHER INFORMATION: Synthetic

<400> SEQUENCE: 82
ccggccaagg agaaacaagg acauacucga guauguccuu guuucuccuu gguuuuug      58

<210> SEQ ID NO 83
<211> LENGTH: 58
```

```
<212> TYPE: RNA
<213> ORGANISM: Artificial Sequence
<220> FEATURE:
<223> OTHER INFORMATION: Synthetic

<400> SEQUENCE: 83
ccgggcugcc uauguguuua caaaucucga gauuuguaaa cacauaggca gcuuuuug          58

<210> SEQ ID NO 84
<211> LENGTH: 58
<212> TYPE: RNA
<213> ORGANISM: Artificial Sequence
<220> FEATURE:
<223> OTHER INFORMATION: Synthetic

<400> SEQUENCE: 84
ccggcccaaa cugauaaggu cauaucucga gauaugaccu uaucagucug gguuuuug          58

<210> SEQ ID NO 85
<211> LENGTH: 58
<212> TYPE: RNA
<213> ORGANISM: Artificial Sequence
<220> FEATURE:
<223> OTHER INFORMATION: Synthetic

<400> SEQUENCE: 85
ccgggcugga auuucaucca cgauucucga gaaucgugga ugaaauucca gcuuuuug          58

<210> SEQ ID NO 86
<211> LENGTH: 58
<212> TYPE: RNA
<213> ORGANISM: Artificial Sequence
<220> FEATURE:
<223> OTHER INFORMATION: Synthetic

<400> SEQUENCE: 86
ccggcugcug ccuauguguu uacaacucga guuguaaaca cauaggcagc aguuuuug          58

<210> SEQ ID NO 87
<211> LENGTH: 97
<212> TYPE: RNA
<213> ORGANISM: Artificial Sequence
<220> FEATURE:
<223> OTHER INFORMATION: Synthetic

<400> SEQUENCE: 87
ugcuguugac agugagcgcg gucccacagg gcuuauuaau uagugaagcc acagauguaa        60
uuaauaagcc cuguggggacc augccuacug ccucgga                                97

<210> SEQ ID NO 88
<211> LENGTH: 97
<212> TYPE: RNA
<213> ORGANISM: Artificial Sequence
<220> FEATURE:
<223> OTHER INFORMATION: Synthetic

<400> SEQUENCE: 88
ugcuguugac agugagcgac ugguauuuca ugcagaagua uagugaagcc acagauguau        60
acuucugcau gaaauaccag cugccuacug ccucgga                                97

<210> SEQ ID NO 89
<211> LENGTH: 97
<212> TYPE: RNA
<213> ORGANISM: Artificial Sequence
<220> FEATURE:
```

-continued

```
<223> OTHER INFORMATION: Synthetic

<400> SEQUENCE: 89
ugcuguugac agugagcgag guuccaccug guuguauuaa uagugaagcc acagauguau        60
uaauacaacc agguggaacc gugccuacug ccucgga                                97

<210> SEQ ID NO 90
<211> LENGTH: 58
<212> TYPE: RNA
<213> ORGANISM: Artificial Sequence
<220> FEATURE:
<223> OTHER INFORMATION: Synthetic

<400> SEQUENCE: 90
ccgggcugga auucaucca cgauucucga gaaucgugga ugaaauucca gcuuuuug         58

<210> SEQ ID NO 91
<211> LENGTH: 58
<212> TYPE: RNA
<213> ORGANISM: Artificial Sequence
<220> FEATURE:
<223> OTHER INFORMATION: Synthetic

<400> SEQUENCE: 91
ccggcugcug ccuauguguu uacaacucga guuguaaaca cauaggcagc aguuuuug         58

<210> SEQ ID NO 92
<211> LENGTH: 58
<212> TYPE: RNA
<213> ORGANISM: Artificial Sequence
<220> FEATURE:
<223> OTHER INFORMATION: Synthetic

<400> SEQUENCE: 92
ccggccaagg agaaacaagg acauacucga guauguccuu guuucuccuu gguuuuug         58

<210> SEQ ID NO 93
<211> LENGTH: 58
<212> TYPE: RNA
<213> ORGANISM: Artificial Sequence
<220> FEATURE:
<223> OTHER INFORMATION: Synthetic

<400> SEQUENCE: 93
ccgggcugcc uauguguuua caaaucucga gauuuguaaa cacauaggca gcuuuuug         58

<210> SEQ ID NO 94
<211> LENGTH: 58
<212> TYPE: RNA
<213> ORGANISM: Artificial Sequence
<220> FEATURE:
<223> OTHER INFORMATION: Synthetic

<400> SEQUENCE: 94
ccggcccaga cugauaaggu cauaucucga gauaugaccu uaucagucug gguuuuug         58

<210> SEQ ID NO 95
<211> LENGTH: 58
<212> TYPE: RNA
<213> ORGANISM: Artificial Sequence
<220> FEATURE:
<223> OTHER INFORMATION: Synthetic

<400> SEQUENCE: 95
ccggcccaaa cugauaaggu cauaucucga gauaugaccu uaucagucug gguuuuug         58
```

-continued

```
<210> SEQ ID NO 96
<211> LENGTH: 23
<212> TYPE: DNA
<213> ORGANISM: Artificial Sequence
<220> FEATURE:
<223> OTHER INFORMATION: Synthetic

<400> SEQUENCE: 96
accgaaggaa gagtatgtcc tcg                                         23

<210> SEQ ID NO 97
<211> LENGTH: 23
<212> TYPE: DNA
<213> ORGANISM: Artificial Sequence
<220> FEATURE:
<223> OTHER INFORMATION: Synthetic

<400> SEQUENCE: 97
accgaagtaa atctggttgc aac                                         23

<210> SEQ ID NO 98
<211> LENGTH: 23
<212> TYPE: DNA
<213> ORGANISM: Artificial Sequence
<220> FEATURE:
<223> OTHER INFORMATION: Synthetic

<400> SEQUENCE: 98
aaaccgagga catactcttc ctt                                         23

<210> SEQ ID NO 99
<211> LENGTH: 23
<212> TYPE: DNA
<213> ORGANISM: Artificial Sequence
<220> FEATURE:
<223> OTHER INFORMATION: Synthetic

<400> SEQUENCE: 99
aaacgttgca accagattta ctt                                         23

<210> SEQ ID NO 100
<211> LENGTH: 22
<212> TYPE: DNA
<213> ORGANISM: Artificial Sequence
<220> FEATURE:
<223> OTHER INFORMATION: Synthetic

<400> SEQUENCE: 100
acttcaaacg agtcaaccaa ct                                          22

<210> SEQ ID NO 101
<211> LENGTH: 23
<212> TYPE: DNA
<213> ORGANISM: Artificial Sequence
<220> FEATURE:
<223> OTHER INFORMATION: Synthetic

<400> SEQUENCE: 101
tctaaccacg aggacatact ctt                                         23

<210> SEQ ID NO 102
<211> LENGTH: 20
<212> TYPE: DNA
<213> ORGANISM: Artificial Sequence
<220> FEATURE:
```

-continued

```
<223> OTHER INFORMATION: Synthetic

<400> SEQUENCE: 102
atcatccctg cctctactgg                                                    20

<210> SEQ ID NO 103
<211> LENGTH: 20
<212> TYPE: DNA
<213> ORGANISM: Artificial Sequence
<220> FEATURE:
<223> OTHER INFORMATION: Synthetic

<400> SEQUENCE: 103
gtcaggtcca ccactgacac                                                    20

<210> SEQ ID NO 104
<211> LENGTH: 102
<212> TYPE: PRT
<213> ORGANISM: Homo sapiens

<400> SEQUENCE: 104

Glu Asn Ile Pro Ala Ser Ser Leu Asn Lys Gly Lys Lys Leu Met His
1               5                   10                  15

Cys Arg Ser His Glu Glu Val Asn Thr Glu Leu Lys Ala Gln Ile Met
                20                  25                  30

Lys Glu Ile Arg Lys Pro Gly Arg Lys Tyr Glu Arg Ile Phe Thr Leu
            35                  40                  45

Leu Lys His Val Gln Gly Ser Leu Gln Thr Arg Leu Ile Phe Leu Gln
        50                  55                  60

Asn Val Ile Lys Glu Ala Ser Arg Phe Lys Lys Arg Met Leu Ile Glu
65                  70                  75                  80

Gln Leu Glu Asn Phe Leu Asp Glu Ile His Arg Arg Ala Asn Gln Ile
                85                  90                  95

Asn His Ile Asn Ser Asn
            100

<210> SEQ ID NO 105
<211> LENGTH: 103
<212> TYPE: PRT
<213> ORGANISM: Homo sapiens

<400> SEQUENCE: 105

Thr Leu Gly Ala Met Pro Asn Thr Leu Gln Ile Thr Pro Ala Met Ala
1               5                   10                  15

Gln Gly Ile Asn Ala Asp Ile Lys His Gln Leu Met Lys Glu Val Arg
                20                  25                  30

Lys Phe Gly Arg Lys Tyr Glu Arg Ile Phe Ile Leu Leu Glu Glu Val
            35                  40                  45

Gln Gly Pro Leu Glu Met Lys Lys Gln Phe Val Glu Phe Thr Ile Lys
        50                  55                  60

Glu Ala Ala Arg Phe Lys Arg Arg Val Leu Ile Gln Tyr Leu Glu Lys
65                  70                  75                  80

Val Leu Glu Lys Ile Asn Ser His His Leu His Asn Asn Ile Ser His
                85                  90                  95

Ile Asn Ser Arg Ser Ser Cys
            100

<210> SEQ ID NO 106
<211> LENGTH: 58
```

-continued

```
<212> TYPE: RNA
<213> ORGANISM: Artificial Sequence
<220> FEATURE:
<223> OTHER INFORMATION: Synthetic

<400> SEQUENCE: 106
ccgggcaguc acucacagca uuuuucaaga gaaaaugcug ugagugacug cuuuuuug        58

<210> SEQ ID NO 107
<211> LENGTH: 58
<212> TYPE: RNA
<213> ORGANISM: Artificial Sequence
<220> FEATURE:
<223> OTHER INFORMATION: Synthetic

<400> SEQUENCE: 107
ccggccaacc aguagcugau aauuucaaga gaauuaucag cuacugguug guuuuuug        58

<210> SEQ ID NO 108
<211> LENGTH: 58
<212> TYPE: RNA
<213> ORGANISM: Artificial Sequence
<220> FEATURE:
<223> OTHER INFORMATION: Synthetic

<400> SEQUENCE: 108
ccggccugau aacgucuugu caauucaaga gauugacaag acguuaucag guuuuuug        58

<210> SEQ ID NO 109
<211> LENGTH: 58
<212> TYPE: RNA
<213> ORGANISM: Artificial Sequence
<220> FEATURE:
<223> OTHER INFORMATION: Synthetic

<400> SEQUENCE: 109
ccggccacag ggcuuauuaa uauuucaaga gaauauuaau aagcccugug guuuuuug        58

<210> SEQ ID NO 110
<211> LENGTH: 58
<212> TYPE: RNA
<213> ORGANISM: Artificial Sequence
<220> FEATURE:
<223> OTHER INFORMATION: Synthetic

<400> SEQUENCE: 110
ccgggcaccu gauaacgugu uguuucaaga gaacaacacg uuaucaggug cuuuuuug        58

<210> SEQ ID NO 111
<211> LENGTH: 58
<212> TYPE: RNA
<213> ORGANISM: Artificial Sequence
<220> FEATURE:
<223> OTHER INFORMATION: Synthetic

<400> SEQUENCE: 111
ccgggggauc cauaugcuac cauuucaaga gaaugguagc auaggaucc cuuuuuug        58

<210> SEQ ID NO 112
<211> LENGTH: 58
<212> TYPE: RNA
<213> ORGANISM: Artificial Sequence
<220> FEATURE:
<223> OTHER INFORMATION: Synthetic

<400> SEQUENCE: 112
```

-continued ccggccugau aacaucuugu caauucaaga gauugacaag auguuaucag guuuuuug          58

<210> SEQ ID NO 113
<211> LENGTH: 58
<212> TYPE: RNA
<213> ORGANISM: Artificial Sequence
<220> FEATURE:
<223> OTHER INFORMATION: Synthetic

<400> SEQUENCE: 113
ccgggcuuca acagggcuua uuauucaaga gauaauaagc ccguugaag cuuuuuug          58

<210> SEQ ID NO 114
<211> LENGTH: 58
<212> TYPE: RNA
<213> ORGANISM: Artificial Sequence
<220> FEATURE:
<223> OTHER INFORMATION: Synthetic

<400> SEQUENCE: 114
ccggcccuca caaugucugu gaauucaaga gauucacaga cauugugagg guuuuuug          58

<210> SEQ ID NO 115
<211> LENGTH: 58
<212> TYPE: RNA
<213> ORGANISM: Artificial Sequence
<220> FEATURE:
<223> OTHER INFORMATION: Synthetic

<400> SEQUENCE: 115
ccggccgcaa ccuaauaacg uauuucaaga gaauacguua uuagguugcg guuuuuug          58

<210> SEQ ID NO 116
<211> LENGTH: 58
<212> TYPE: RNA
<213> ORGANISM: Artificial Sequence
<220> FEATURE:
<223> OTHER INFORMATION: Synthetic

<400> SEQUENCE: 116
ccgggggauc aguaugcuac cauuucaaga gaaugguagc auacugaucc cuuuuuug          58

<210> SEQ ID NO 117
<211> LENGTH: 58
<212> TYPE: RNA
<213> ORGANISM: Artificial Sequence
<220> FEATURE:
<223> OTHER INFORMATION: Synthetic

<400> SEQUENCE: 117
ccggccuagu aacgccuugu caauucaaga gauugacaag gcguuacuag guuuuuug          58

<210> SEQ ID NO 118
<211> LENGTH: 58
<212> TYPE: RNA
<213> ORGANISM: Artificial Sequence
<220> FEATURE:
<223> OTHER INFORMATION: Synthetic

<400> SEQUENCE: 118
ccgggggcuu gcuuauuugg caauucaaga gauugccaaa uaagcaagcc cuuuuuug          58

<210> SEQ ID NO 119
<211> LENGTH: 58
<212> TYPE: RNA
<213> ORGANISM: Artificial Sequence
<220> FEATURE:
<223> OTHER INFORMATION: Synthetic

<400> SEQUENCE: 119
ccgggggauc agcaugcuac cauuucaaga gaauggguagc augcugaucc cuuuuuug        58

<210> SEQ ID NO 120
<211> LENGTH: 58
<212> TYPE: RNA
<213> ORGANISM: Artificial Sequence
<220> FEATURE:
<223> OTHER INFORMATION: Synthetic

<400> SEQUENCE: 120
ccgggcuguu acaccagagc uuauucaaga gauaagcucu gguguaacag cuuuuuug        58

<210> SEQ ID NO 121
<211> LENGTH: 58
<212> TYPE: RNA
<213> ORGANISM: Artificial Sequence
<220> FEATURE:
<223> OTHER INFORMATION: Synthetic

<400> SEQUENCE: 121
ccggggauaa cgucuuguca aauuucaaga gaauuugaca agacguuauc cuuuuuug        58

<210> SEQ ID NO 122
<211> LENGTH: 58
<212> TYPE: RNA
<213> ORGANISM: Artificial Sequence
<220> FEATURE:
<223> OTHER INFORMATION: Synthetic

<400> SEQUENCE: 122
ccggggagcu aguauuccag caauucaaga gauugcugga auacuagcuc cuuuuuug        58

<210> SEQ ID NO 123
<211> LENGTH: 58
<212> TYPE: RNA
<213> ORGANISM: Artificial Sequence
<220> FEATURE:
<223> OTHER INFORMATION: Synthetic

<400> SEQUENCE: 123
ccgggggauc uguaugcuac cauuucaaga gaauggguagc auacagaucc cuuuuuug        58

<210> SEQ ID NO 124
<211> LENGTH: 58
<212> TYPE: RNA
<213> ORGANISM: Artificial Sequence
<220> FEATURE:
<223> OTHER INFORMATION: Synthetic

<400> SEQUENCE: 124
ccgggcacca cagcuugguc auauucaaga gauaugacca agcuggguug cuuuuuug        58

<210> SEQ ID NO 125
<211> LENGTH: 58
<212> TYPE: RNA
<213> ORGANISM: Artificial Sequence
<220> FEATURE:
<223> OTHER INFORMATION: Synthetic

<400> SEQUENCE: 125
ccgggguauu ccauccauga guauucaaga gauacucaug gauggaauac cuuuuuug        58

-continued

```
<210> SEQ ID NO 126
<211> LENGTH: 58
<212> TYPE: RNA
<213> ORGANISM: Artificial Sequence
<220> FEATURE:
<223> OTHER INFORMATION: Synthetic

<400> SEQUENCE: 126
ccggccaagc agcauccgau aauuucaaga gaauuaucgg augcugcuug guuuuuug          58

<210> SEQ ID NO 127
<211> LENGTH: 58
<212> TYPE: RNA
<213> ORGANISM: Artificial Sequence
<220> FEATURE:
<223> OTHER INFORMATION: Synthetic

<400> SEQUENCE: 127
ccgggguguu ucauccauga guauucaaga gauacucaug gaugaaacac cuuuuuug          58

<210> SEQ ID NO 128
<211> LENGTH: 58
<212> TYPE: RNA
<213> ORGANISM: Artificial Sequence
<220> FEATURE:
<223> OTHER INFORMATION: Synthetic

<400> SEQUENCE: 128
ccgggcugca gucacucaca acauucaaga gauguuguga gugacugcag cuuuuuug          58

<210> SEQ ID NO 129
<211> LENGTH: 58
<212> TYPE: RNA
<213> ORGANISM: Artificial Sequence
<220> FEATURE:
<223> OTHER INFORMATION: Synthetic

<400> SEQUENCE: 129
ccggccuggu aacaucuugu caauucaaga gauugacaag auguuaccag guuuuuug          58

<210> SEQ ID NO 130
<211> LENGTH: 58
<212> TYPE: RNA
<213> ORGANISM: Artificial Sequence
<220> FEATURE:
<223> OTHER INFORMATION: Synthetic

<400> SEQUENCE: 130
ccggggaauu ucauccacga uuauucaaga gauaaucgug gaugaaauuc cuuuuuug          58

<210> SEQ ID NO 131
<211> LENGTH: 58
<212> TYPE: RNA
<213> ORGANISM: Artificial Sequence
<220> FEATURE:
<223> OTHER INFORMATION: Synthetic

<400> SEQUENCE: 131
ccgggaagau gacaaauggc caauucaaga gauuggccau uugucaucuu cuuuuuug          58

<210> SEQ ID NO 132
<211> LENGTH: 58
<212> TYPE: RNA
<213> ORGANISM: Artificial Sequence
<220> FEATURE:
<223> OTHER INFORMATION: Synthetic
```

<400> SEQUENCE: 132
ccggccugau aacuccuugu caauucaaga gauugacaag gaguuaucag guuuuuug         58

<210> SEQ ID NO 133
<211> LENGTH: 58
<212> TYPE: RNA
<213> ORGANISM: Artificial Sequence
<220> FEATURE:
<223> OTHER INFORMATION: Synthetic

<400> SEQUENCE: 133
ccgggguucc accugguugu auuuucaaga gaaauacaac cagguggaac cuuuuuug         58

<210> SEQ ID NO 134
<211> LENGTH: 58
<212> TYPE: RNA
<213> ORGANISM: Artificial Sequence
<220> FEATURE:
<223> OTHER INFORMATION: Synthetic

<400> SEQUENCE: 134
ccgggcuggu auuucaugca gaauucaaga gauucugcau gaaauaccag cuuuuuug         58

<210> SEQ ID NO 135
<211> LENGTH: 58
<212> TYPE: RNA
<213> ORGANISM: Artificial Sequence
<220> FEATURE:
<223> OTHER INFORMATION: Synthetic

<400> SEQUENCE: 135
ccgggcuacu gucauucacg auauucaaga gauaucguga augacaguag cuuuuuug         58

<210> SEQ ID NO 136
<211> LENGTH: 58
<212> TYPE: RNA
<213> ORGANISM: Artificial Sequence
<220> FEATURE:
<223> OTHER INFORMATION: Synthetic

<400> SEQUENCE: 136
ccgggccacc caaugcauug gauuucaaga gaauccaaug cauggguggg cuuuuuug         58

<210> SEQ ID NO 137
<211> LENGTH: 58
<212> TYPE: RNA
<213> ORGANISM: Artificial Sequence
<220> FEATURE:
<223> OTHER INFORMATION: Synthetic

<400> SEQUENCE: 137
ccgggccaaa uacaccacaa auauucaaga gauauuugug guguauuugg cuuuuuug         58

<210> SEQ ID NO 138
<211> LENGTH: 58
<212> TYPE: RNA
<213> ORGANISM: Artificial Sequence
<220> FEATURE:
<223> OTHER INFORMATION: Synthetic

<400> SEQUENCE: 138
ccggcuucuc acacagcggg auauucaaga gauaucccgc ugugugagaa guuuuuug         58

<210> SEQ ID NO 139

-continued

```
<211> LENGTH: 58
<212> TYPE: RNA
<213> ORGANISM: Artificial Sequence
<220> FEATURE:
<223> OTHER INFORMATION: Synthetic

<400> SEQUENCE: 139
ccgggagcug guauuccacc cauuucaaga gaaugggugg aauaccagcu cuuuuuug          58

<210> SEQ ID NO 140
<211> LENGTH: 58
<212> TYPE: RNA
<213> ORGANISM: Artificial Sequence
<220> FEATURE:
<223> OTHER INFORMATION: Synthetic

<400> SEQUENCE: 140
ccggucagua ugcuaccguc aauuucaaga gaauugacgg uagcauacug auuuuuug          58

<210> SEQ ID NO 141
<211> LENGTH: 58
<212> TYPE: RNA
<213> ORGANISM: Artificial Sequence
<220> FEATURE:
<223> OTHER INFORMATION: Synthetic

<400> SEQUENCE: 141
ccggggagcu aguauuccag caauucaaga gauugcugga auacuagcuc cuuuuuug          58

<210> SEQ ID NO 142
<211> LENGTH: 58
<212> TYPE: RNA
<213> ORGANISM: Artificial Sequence
<220> FEATURE:
<223> OTHER INFORMATION: Synthetic

<400> SEQUENCE: 142
ccggccucca uggcuucguc auauucaaga gauaugacga agccauggag guuuuuug          58

<210> SEQ ID NO 143
<211> LENGTH: 58
<212> TYPE: RNA
<213> ORGANISM: Artificial Sequence
<220> FEATURE:
<223> OTHER INFORMATION: Synthetic

<400> SEQUENCE: 143
ccggccacga uuaccaggga ucuuucaaga gaagaucccu gguaaucgug guuuuuug          58

<210> SEQ ID NO 144
<211> LENGTH: 58
<212> TYPE: RNA
<213> ORGANISM: Artificial Sequence
<220> FEATURE:
<223> OTHER INFORMATION: Synthetic

<400> SEQUENCE: 144
ccgggagaag gcgcuuaaag aaauucaaga gauuucuuua agcgccuucu cuuuuuug          58

<210> SEQ ID NO 145
<211> LENGTH: 58
<212> TYPE: RNA
<213> ORGANISM: Artificial Sequence
<220> FEATURE:
<223> OTHER INFORMATION: Synthetic

<400> SEQUENCE: 145
```

-continued

```
ccggggaaca gguuauugcu gaauucaaga gauucagcaa uaaccuguuc cuuuuuug        58

<210> SEQ ID NO 146
<211> LENGTH: 23
<212> TYPE: RNA
<213> ORGANISM: Artificial Sequence
<220> FEATURE:
<223> OTHER INFORMATION: Synthetic

<400> SEQUENCE: 146
aaaccgagga cauacucuuc cuu                                               23

<210> SEQ ID NO 147
<211> LENGTH: 23
<212> TYPE: RNA
<213> ORGANISM: Artificial Sequence
<220> FEATURE:
<223> OTHER INFORMATION: Synthetic

<400> SEQUENCE: 147
aaacguugca accagauuua cuu                                               23
```

METHODS AND COMPOSITIONS FOR TREATING AND DIAGNOSING A SAGE1-RELATED CONDITION

FIELD OF THE INVENTION

The present disclosure generally relates to methods for diagnosing and assessing diseases using SAGE1 as a biomarker, and compositions and methods for treating diseases by targeting SAGE1.

BACKGROUND

Cancer-testis antigens (CTAs) are a heterogeneous group of proteins including over 70 families with over 140 members (Fratta E., et al, Mol Oncol (2011) 5:164). Expression of CTAs has been reported in various tumors while their expression in normal tissues is mainly restricted to testis. Due to their restricted expression in tumors and immune-privileged testis, CTAs have been explored as antigens for cancer immunotherapy and vaccine development in recent years. However, CFAs' function in association with tumor cell proliferation are still poorly understood.

Sarcoma antigen 1 (SAGE1) belongs to the CTA family. Although SAGE1 has been discovered as a tumor-specific antigen for almost twenty years, it remains elusive whether, and how, it plays any role in promoting tumor development and progression. As there continues to be a need for developing effective tumor diagnosis and therapy modalities, it is desirable to elucidate SAGE1's role in tumor cell proliferation and explore its potential in acting as a novel diagnostic marker and therapeutic target for tumors.

SUMMARY OF INVENTION

In one aspect, the present disclosure provides a method of diagnosing a SAGE1 positive disorder in a subject, comprising: detecting SAGE1 expression in a biological sample from the subject, and evaluating whether the subject has a SAGE1 positive disorder based on presence or absence or level of the SAGE1 expression detected in the biological sample.

In one aspect, the present disclosure provides a method of diagnosing a SAGE1 positive disorder in a subject, comprising: detecting SAGE1 expression in a biological sample from the subject, wherein the subject is diagnosed as having a SAGE1 positive disorder when the SAGE1 expression is detected in the biological sample.

In some embodiments, the biological sample is of a type of sample that normally has no detectable SAGE1 expression.

In some embodiments, the subject has been determined to have deficiency (e.g. mutation) in TP53.

In some embodiments, the SAGE1 positive disorder is a SAGE1 positive tumor.

In another aspect, the present disclosure provides a method of assessing malignancy or malignancy potential of a tumor in a subject, comprising: detecting SAGE1 expression in a biological sample from the subject, wherein the tumor is assessed to be malignant or as having malignancy potential when the SAGE1 expression is detected in the biological sample.

In another aspect, the present disclosure provides a method of assessing malignancy or malignancy potential of a tumor in a subject, comprising: detecting SAGE1 expression in a biological sample from the subject, and evaluating whether the subject has a malignancy or malignancy potential of a tumor based on presence or absence or level of the SAGE1 expression detected in the biological sample.

In some embodiments, the biological sample is of a type of sample that normally has no detectable SAGE1 expression.

In some embodiments, the malignancy is characterized as having one or more of the following features:
(a) expressing one or more stem cell marker;
(b) capable of metastasis;
(c) capable of uncontrolled cell proliferation;
(d) likely to experience disease progression;
(e) likely to develop resistance to an anti-cancer therapy;
(f) likely to relapse after treatment with an anti-cancer therapy, and
(g) having, or likely to develop, one or more cancer-related driver mutations.

In some embodiments, the subject has not shown any clinical manifestation of malignancy.

In another aspect, the present disclosure provides a method of predicating likelihood of having a SAGE1 positive disorder in a subject, comprising, detecting deficiency in TP53 in a first biological sample from the subject, wherein the subject is predicted as likely to have the SAGE1 positive disorder when deficiency of TP53 is detected.

In another aspect, the present disclosure provides a method of predicating likelihood of having a SAGE1 positive disorder in a subject, comprising, detecting deficiency in TP53 in a first biological sample from the subject, and evaluating whether the subject has likelihood of having a SAGE1 positive disorder based on presence or absence deficiency in the TP53 detected in the first biological sample.

In some embodiments, the method further comprises recommending the subject to test SAGE1 expression when deficiency (e.g. mutation) in TP53 is detected.

In some embodiments, the method further comprises detecting SAGE1 expression in the first biological sample or in a second biological sample from the subject.

In some embodiments, when SAGE1 expression is not detected in the biological sample, the method further comprising monitoring SAGE1 expression in the subject after a course of time.

In some embodiments, the first or the second biological sample is of a type of sample that normally has no detectable SAGE1 expression.

In some embodiments, the method further comprises administering an effective amount of a SAGE1 inhibitor to the subject if SAGE1 expression is detected in the first biological sample or in the second additional biological sample.

In another aspect, the present disclosure provides a method of determining sensitivity of a tumor sample to a SAGE1 inhibitor, comprising: detecting SAGE1 expression in the tumor sample, wherein the tumor sample is determined to be sensitive to a SAGE1 inhibitor when the SAGE1 expression is detected in the tumor sample.

In another aspect, the present disclosure provides a method of determining sensitivity of a tumor sample to a SAGE1 inhibitor, comprising: detecting SAGE1 expression in the tumor sample, and evaluating whether the tumor sample is sensitive to the SAGE1 inhibitor based on presence or absence or level of the SAGE1 expression detected in the tumor sample.

In another aspect, the present disclosure provides a method of identifying a subject having a tumor who is likely to benefit from treatment with a SAGE1 inhibitor, comprising: detecting SAGE1 expression in a biological sample from the subject, wherein the subject is identified as being likely to benefit from treatment with the SAGE1 inhibitor when SAGE1 expression is detected.

In another aspect, the present disclosure provides a method of identifying a subject having a tumor who is likely to benefit from treatment with a SAGE1 inhibitor, comprising: detecting SAGE1 expression in a biological sample from the subject, and evaluating whether the subject is likely to benefit from treatment with a SAGE1 inhibitor based on presence or absence or level of the SAGE1 expression detected in the biological sample.

In some embodiments, the subject has been determined to have a mutation in TP53.

In some embodiments, the method further comprises providing or administering a SAGE1 inhibitor to the subject identified as being likely to benefit from treatment with a SAGE1 inhibitor.

In another aspect, the present disclosure provides a method of monitoring progression of a SAGE1 positive disorder in a subject, comprising: (a) detecting a level of SAGE1 expression in a first biological sample from the subject, (b) detecting a level of SAGE1 expression in a second biological sample from the subject, wherein the second biological sample is obtained after a course of time from the first sample; wherein the tumor is determined as having progressed when the level of SAGE1 expression in the second biological sample is higher than the first.

In another aspect, the present disclosure provides a method of monitoring progression of a SAGE1 positive disorder in a subject, comprising: (a) detecting a level of SAGE1 expression in a first biological sample from the subject, (b) detecting a level of SAGE1 expression in a second biological sample from the subject, wherein the second biological sample is obtained after a course of time from the first sample; and (c) evaluating whether there is progression of the SAGE1 positive disorder in the subject based on the levels of the SAGE1 expression detected in the step (a) and in the step (b), respectively.

In another aspect, the present disclosure provides a method of monitoring responsiveness of a subject having a SAGE1 positive disorder to treatment with a SAGE1 inhibitor within a therapeutic period, the method comprising: (a) detecting a level of SAGE1 expression in a biological sample from the subject after the therapeutic period to obtain a post-treatment level of SAGE1 expression, and (b) comparing the post-treatment level with a baseline level of SAGE1 expression detected in a biological sample obtained from the subject before the therapeutic period, wherein the subject is identified as being responsive to the treatment when the post-treatment level is lower than the baseline level.

In another aspect, the present disclosure provides a method of monitoring responsiveness of a subject having a SAGE1 positive disorder to treatment with a SAGE1 inhibitor within a therapeutic period, the method comprising: (a) detecting a level of SAGE1 expression in a biological sample from the subject after the therapeutic period to obtain a post-treatment level of SAGE1 expression, (b) comparing the post-treatment level with a baseline level of SAGE1 expression detected in a biological sample obtained from the subject before the therapeutic period, and (c) evaluating whether there is responsiveness of the subject to the treatment with the SAGE1 inhibitor based on the levels of the SAGE1 expression detected in the step (a) and in the step (b), respectively.

In some embodiments, the SAGE1 expression is detected at DNA level, RNA level, or protein level.

In some embodiments, the SAGE1 expression is indicated by (a) presence or level of SAGE1 protein;

(b) presence or level of SAGE1 mRNA;

(c) presence or level of a SAGE1 complex;

(d) level of demethylation of in the SAGE1 gene;

(e) presence or level of histone acetylation of the SAGE1 gene;

(f) presence or level of binding of a transcription factor to the SAGE1 gene, or any combination thereof.

In some embodiments, the SAGE1 complex comprises SAGE1 and at least one component selected from INTS3, INIP, NABP1/2, CREBBP, TLE1, TLE2, TLE3, TLE4, TLE5, GGA3, CNOT1, TAX1BP1, SEC16A, CYLD and PAXBP1.

In some embodiments, the SAGE1 complex comprises SAGE1 and INTS3.

In some embodiments, the methylation is detected in a region that is within 3 kb upstream and 3 kb downstream of the transcription start site of SAGE1 gene. (e.g., a CpG-containing part of the SAGE1 gene)

In some embodiments, the histone acetylation is detected near the enhancer region, the promoter region or the expression region of the SAGE1 gene.

In some embodiments, the detection comprises an immunoassay, an amplification assay, a hybridization assay, or a sequencing assay.

In some embodiments, the biological sample is selected from a cell, a tissue, a bodily fluid and any combination thereof.

In some embodiments, the body fluid is selected from blood, serum, plasma, ascites, cyst fluid, pleural fluid, peritoneal fluid, cerebrospinal fluid, tears, urine, saliva, sputum, nipple aspirates, lymph fluid, fluid of the respiratory, intestinal, and genitourinary trances, breast milk, intra-organ system fluid, peritoneal fluid, conditioned media from tissue explant culture, or combinations thereof.

In some embodiments, the tumor is selected from solid tumors or hematological tumors.

In some embodiments, the tumor is selected from adrenal cancer, lymphoepithelial neoplasia, adenoid cell carcinoma, lymphoma, acoustic neuroma, acute lymphocytic leukemia, acral lentiginous melanoma, acute myeloid leukemia, acrospiroma, chronic lymphocytic leukemia, acute eosinophilic leukemia, liver cancer, acute erythrocyte leukemia, small cell lung cancer, acute lymphocytic leukemia, non-small cell lung cancer, acute megakaryoblastic leukemia, MALT lymphoma, acute monocytic leukemia, malignant fibrous histiocytoma, acute promyelocytic leukemia, malignant peripheral schwannomas, mantle cell lymphoma, adenocarcinoma, marginal zone B-cell lymphoma, malignant hippocampal tumor, adenoid cystic carcinoma, gland tumor, adenoma-like odontogenic tumor, mast cell leukemia, adenosquamous carcinoma, mediastinal germ cell tumor, adipose tissue tumor, breast medullary carcinoma, adrenocortical carcinoma, medullary thyroid carcinoma, adult T cell leukemia/lymphoma, Medulloblastoma, invasive NK cell leukemia, melanoma, AIDS-related lymphoma, meningioma, lung rhabdomyosarcoma, Merkel cell carcinoma, alveolar soft tissue sarcoma, mesothelioma, ameloblastoma, metastatic urothelial carcinoma, anaplastic large cell lymphoma, mixed Müllerian tumor, thyroid undifferentiated carcinoma, mucinous neoplasm, angioimmunoblastic T-cell lymphoma, multiple myeloma, angiomyolipoma, muscle tissue tumor, angiosarcoma, mycosis fungoides, astrocytoma, myxoid liposarcoma, atypical deformed rhabdoid tumor, myxoma, B-cell chronic lymphocytic leukemia, mucinous sarcoma, B-cell lymphoblastic leukemia, naso-pharyngeal carcinoma, B-cell lymphoma, schwannomas, basal cell carcinoma, neuroblastoma, biliary tract cancer, neurofibromatosis, bladder cancer, neuroma, blastoma, nodular melanoma, bone cancer, eye cancer, Brenner tumor, oligodendroxoma, brown tumor, oligodendroglioma, Burkitt's lymphoma, eosinophilic breast cancer, brain cancer, optic nerve tumor cancer, oral cancer carcinoma in situ, osteosarcoma, carcinosarcoma, ovarian cancer, cartilage tumor, pulmonary sulcus tumor, papillary thyroid carcinoma, myeloma, paraganglioma, chondroma, pineal blastoma, chordoma, pineal cell tumor, choriocarcinoma, pituitary tumor, choroid plexus papilloma, pituitary adenoma, kidney clear cell sarcoma, pituitary tumor, craniopharyngioma, plasmacytoma, cutaneous T-cell lymphoma, multiple embryonic cell tumor, cervical cancer, precursor T lymphoblastic lymphoma, colorectal cancer, primary central nervous system lymphoma, Degos disease, primary effusion lymphoma, proliferative small round cell tumor, primary preformed peritoneal cancer, diffuse large B-cell lymphoma, prostate cancer, embryonic dysplasia of neuroepithelial neoplasia, pancreatic cancer, anaplastic cell tumor, pharyngeal carcinoma, embryonic carcinoma, peritoneal pseudomyxoma, endocrine gland tumor, renal cell carcinoma, enteropathy-associated T-cell lymphoma, endodermal sinus tumor, renal medullary carcinoma, retinoblastoma, esophageal cancer, rhabdomyosarcoma, endadelphos, rhabdomyosarcoma, fibroids, Richter's transformation, fibrosarcoma, rectal cancer, follicular lymphoma, sarcoma, follicular thyroid cancer, schwannoma, ganglion cell tumor, seminoma, gastrointestinal cancer, Sertoli cell turn, germ cell tumor, sex cord-gonadal stromal tumor, pregnancy choriocarcinoma, signet ring cell carcinoma, giant cell fibroblastoma, skin cancer, bone giant cell tumor of bone, small blue round cell tumor, glioma, small cell carcinoma, glioblastoma multiforme, soft tissue sarcoma, glioma, somatostatin tumor, glioma brain, soot wart, pancreatic high glucagonoma, spinal tumor, Gonadoblastoma, spleen marginal lymphoma, granulosa cell tumor, squamous cell carcinoma, estrogen tumor, synovial sarcoma, gallbladder cancer, Sezary disease, gastric cancer, small intestine cancer, hairy cell leukemia, squamous cell carcinoma, hemangioblastoma, gastric cancer, head and neck cancer, T-cell lymphoma, vascular epithelioma, testicular cancer, hematological malignancies, sarcoma, hepatoblastoma, thyroid cancer, hepatosplenic T-cell lymphoma, transitional cell carcinoma, Hodgkin's lymphoma, laryngeal cancer, non-Hodgkin's lymphoma, urachal cancer, invasive lobular carcinoma, genitourinary cancer, intestinal cancer, urothelial carcinoma, renal cancer, uveal melanoma, laryngeal cancer, uterine cancer, malignant freckle-like sputum, verrucous carcinoma, lethal midline granuloma, visual pathway glioma, leukemia, vulvar cancer, testicular stromal tumor, vaginal cancer, liposarcoma, Waldenstrom's macroglobulinemia Disease, lung cancer, adenolymphoma lymphangioma, nephroblastoma, lymphangisarcoma. colon adenocarcinoma (coad), liver hepatocellular carcinoma (lihc), ovarian serous cystadenocarcinoma (ov), uterine corpus endometrial carcinoma (ucec), thyroid carcinoma (thca), skin cutaneous melanoma (skcm), lung adenocarcinoma (luad), head and neck squamous cell carcinoma (hnsc), glioblastoma multiforme (gbm), prostate adenocarcinoma (prad), thymoma (thym), brain lower grade glioma (lgg), rectum adenocarcinoma (read), pheochromocytoma and paraganglioma (pcpg), esophageal carcinoma (esca), kidney renal clear cell carcinoma (kirc), cervical squamous cell carcinoma and endocervical adenocarcinoma (cesc), bladder urothelial carcinoma (blca), kidney renal papillary cell carcinoma (kirp), pancreatic adenocarcinoma (paad), stomach adenocarcinoma (stad), kidney chromophobe (kich), breast invasive carcinoma (brca), lung squamous cell carcinoma (lusc), sarcoma (sarc), acute myeloid leukemia (laml).

In another aspect, the present disclosure provides a kit for use in any of the method disclosed herein, wherein the kit comprises one or more reagents for detecting SAGE1 expression.

In some embodiment, the one or more reagents for detecting SAGE1 expression is selected from:

(a) a reagent for detecting presence or level of SAGE1 protein;

(b) a reagent for detecting presence or level of SAGE1 mRNA;

(c) a reagent for detecting presence or level of a SAGE1 complex;

(d) a reagent for detecting level of methylation of in the SAGE1 gene;

(e) a reagent for detecting presence or level of histone acetylation of the SAGE1 gene;

(f) a reagent for detecting presence or level of binding of a transcription factor to the SAGE1 gene, or any combination thereof.

In some embodiments, at least one reagent is selected from a SAGE1-specific oligonucleotide primer, a SAGE1-specific oligonucleotide probe, an anti-SAGE1 antibody, and an anti-SAGE1 complex antibody.

In some embodiments, the SAGE1-specific oligonucleotide primer or probe comprises a oligonucleotide comprising, or specifically hybridizable to at least 8 consecutive nucleotides of SEQ ID NO: 2 or at least 8 consecutive nucleotides of SEQ ID NO: 1.

In another aspect, the present disclosure provides a SAGE1 complex inhibitor, wherein the inhibitor reduces the level or activity of SAGE1 complex.

In some embodiments, the SAGE1 complex inhibitor comprises a polypeptide, a compound, an antibody or antigen-binding fragment thereof, or a nucleic acid molecule (e.g. polynucleotide or oligonucleotide).

In some embodiments, the SAGE1 complex comprises SAGE1 in complex with at least one component selected from the group consisting of INTS3, INIP, NABP1/2, CRE-BBP, TLE1, TLE2, TLE3, TLE4, TLE5, GGA3, CNOT1, TAX1BP1, SEC16A, CYLD and PAXBP1.

In some embodiments, the SAGE1 complex comprises SAGE1 in complex with INTS3.

In some embodiments, the SAGE1 complex inhibitor blocks binding of SAGE1 to INTS3.

In some embodiments, the SAGE1 complex inhibitor binds to or prevents INTS3 binding to at least one residue selected from the group consisting of F838, F873, K874, M832, V876, R872, K828, R836 and Q840 of SAGE1 (the residue numbering is according to SEQ ID NO: 3 of SAGE1).

In some embodiments, the SAGE1 complex inhibitor comprises an antibody or antigen-binding fragment thereof that: (a) specifically binds to SAGE1, or (b) specifically binds to the component (e.g. INTS3) in complex with SAGE1, or (c) specifically binds to the SAGE1 complex but not binding to SAGE1 or to the component in complex with SAGE1.

In some embodiments, the SAGE1 complex inhibitor comprises a SAGE1-binding fragment of INTS3 or a variant or derivative thereof or a fusion polypeptide thereof.

In some embodiments, the SAGE1-binding fragment of INTS3 comprises an amino acid sequence of SEQ ID NO:

9 or a variant or a fragment thereof or a fusion polypeptide thereof capable of binding to SAGE1.

In some embodiments, the SAGE1 complex inhibitor comprises an INTS3-binding fragment of SAGE1 or a variant or derivative thereof or a fusion polypeptide thereof.

In some embodiments, the INTS3-binding fragment of SAGE1 comprises an amino acid sequence of SEQ ID NO: 8 or a variant or a fragment thereof or a fusion polypeptide thereof capable of binding to INTS3.

In some embodiments, the SAGE1 complex inhibitor comprises an INTS3-binding fragment of INTS6 or INTS 6L or a variant or derivative thereof or a fusion polypeptide thereof capable of binding to INTS3.

In some embodiments, the INST3-binding fragment of INTS6 or INTS 6L comprises an amino acid sequence of SEQ ID NO: 10, SEQ ID NO: 104, or SEQ ID NO: 105 or a variant or a fragment thereof or a fusion polypeptide thereof capable of binding to INTS3.

In another aspect, the present disclosure provides a SAGE1 inhibitor comprising a first moiety capable of binding to an ubiquitin pathway protein, and a second moiety capable of binding to SAGE1 or SAGE1 complex.

In some embodiments, the first moiety and the second moiety are linked via a linker.

In another aspect, the present disclosure provides a chimeric antigen receptor (CAR) comprising an antigen binding domain, a transmembrane domain, and an intracellular signaling domain, wherein the antigen binding domain specifically binds to an epitope of SAGE1 or an MHC-associated epitope of SAGE1.

In some embodiments, the CAR further comprises a costimulatory domain.

In another aspect, the present disclosure provides a cell genetically modified to express the CAR disclosed herein.

In some embodiments, the cell comprises T cell, tumor infiltrating lymphocyte, NK-T cell, TCR-expressing cell, CD4+ T cell, CD8+ T cell, or NK cell.

In another aspect, the present disclosure provides an ex vivo activated antigen presenting cell by exposure to an epitope of SAGE1 or an WIC-associated epitope of SAGE1, optionally the antigen presenting cell comprises dendritic cell.

In another aspect, the present disclosure provides a pharmaceutical composition comprising the SAGE1 complex inhibitor disclosed herein, the SAGE1 inhibitor disclosed herein, or a cell disclosed herein, and a pharmaceutically acceptable carrier.

In another aspect, the present disclosure provides a pharmaceutical composition comprising a SAGE1 inhibitor, and a pharmaceutically acceptable carrier.

In some embodiments, the SAGE1 inhibitor is capable of reducing the level or activity of SAGE1.

In some embodiments, the SAGE1 inhibitor inhibits SAGE1 mRNA transcription, reduces SAGE1 mRNA level, reduces SAGE1 protein level, or inhibits at least one SAGE1-mediated biological function.

In some embodiments, the SAGE1 inhibitor comprises a polynucleotide or oligonucleotide, a polypeptide, a chemical compound, or an antibody or an antigen-binding fragment thereof.

In some embodiments, the SAGE1 inhibitor specifically binds to SAGE1 protein, and comprises a polypeptide, a chemical compound, an oligonucleotide, or an antibody or an antigen-binding fragment thereof.

In some embodiments, the SAGE1 inhibitor comprises an oligonucleotide targeting SAGE1 nucleic acid (e.g. SAGE1 mRNA or SAGE1 gene), or a polynucleotide encoding the oligonucleotide, or a nucleic acid vector comprising the oligonucleotide or the polynucleotide.

In some embodiment, the oligonucleotide comprises a sequence complementary to at least a portion of SAGE1 mRNA, or complementary to at least a portion of SAGE1 gene.

In some embodiments, the portion of SAGE1 mRNA comprises at least 10 consecutive nucleotides within a sequence spanning from nucleotides 266-366, 866-1116, 1316-1616, 1916-2266, 2466-2666 and 2782-2946 of SEQ ID NO: 2.

In some embodiments, the oligonucleotide comprises a sequence selected from SEQ ID NOs: 82-95 and 106-147.

In some embodiments, the oligonucleotide comprises a pair of sense/antisense sequences selected from SEQ ID NOs: 70/71, 72/73, 74/75, 76/77, 78/79, or 80/81.

In some embodiments, the oligonucleotide is a short interfering RNA, short hairpin RNA, an antisense oligonucleotide, or a guide RNA.

In another aspect, the present disclosure provides a method of preventing or treating a SAGE1 positive disorder in a subject in need thereof, comprising administering to the subject an effective amount of:

(a) the SAGE1 inhibitor disclosed herein, (b) the pharmaceutical composition disclosed herein, (c) the SAGE1 complex inhibitor disclosed herein, (e) the cell disclosed herein, or (f) any combination thereof.

In some embodiments, the SAGE1-positive disorder is SAGE1-positive tumor.

In another aspect, the present disclosure provides a method of preventing or reducing or delaying malignancy of a tumor in a subject having a mutation in TP53, comprising administering to the subject an effective amount of:

(a) the SAGE1 inhibitor disclosed herein, (b) the pharmaceutical composition disclosed herein, (c) the SAGE1 complex inhibitor disclosed herein, (e) the cell disclosed herein, or (f) any combination thereof.

In some embodiments, the SAGE1 inhibitor is capable of reducing the level or activity of SAGE1.

In some embodiments, the SAGE1 inhibitor inhibits SAGE1 mRNA transcription, reduces SAGE1 mRNA level, reduces SAGE1 protein level, or inhibits at least one SAGE1-mediated biological function.

In some embodiments, the SAGE1 inhibitor comprises a polynucleotide or oligonucleotide, a polypeptide, a chemical compound, or an antibody or an antigen-binding fragment thereof.

In some embodiments, the SAGE1 inhibitor comprises an oligonucleotide targeting SAGE1 mRNA or SAGE1 gene, or a polynucleotide encoding the oligonucleotide, or a nucleic acid vector comprising the oligonucleotide or polynucleotide.

In some embodiments, the oligonucleotide comprises a sequence complementary to at least a portion of SAGE1 mRNA, or complementary to at least a portion of SAGE1 gene.

In some embodiments, the SAGE1 inhibitor specifically binds to SAGE1 protein, and comprises a polypeptide, a chemical compound, an oligonucleotide, or an antibody or an antigen-binding fragment thereof.

In some embodiments, the method further comprises administering a second therapeutic agent.

In some embodiments, the second therapeutic agent comprises a chemotherapeutic agent, an anti-cancer drug, radiation therapy, an immunotherapy agent, anti-angiogenesis agent, a targeted therapy agent, a cellular therapy agent, a gene therapy agent, a hormonal therapy agent, or cytokines.

In another aspect the present disclosure provides a method of screening for an agent that is a SAGE1 inhibitor, comprising any one of the following:

(a) contacting SAGE1 protein or a functional equivalent thereof with a test agent, and detecting the binding between the SAGE1 or a functional equivalent thereof with the test agent; or (b) contacting a test agent with a SAGE1-binding fragment of a component of SAGE1 complex, and detecting the binding between the SAGE1-binding fragment with the test agent, or (c) contacting a test agent with SAGE1 and a SAGE1-binding fragment of a component of SAGE1 complex, and detecting the ability of the test agent to block or reduce binding between the SAGE1 and the SAGE1-binding fragment, or reduce the formation of a SAGE1 complex.

In another aspect the present disclosure provides a method of screening an agent that is a SAGE1 inhibitor, comprising contacting a cell expressing SAGE1 or a functional equivalent thereof with a test agent, and determining the ability of the test agent to decrease the amount or activity of SAGE1 or a functional equivalent thereof.

In some embodiments, the cell is a tumor cell.

In another aspect, the present disclosure provides a recombinant cell comprising a first gene encoding SAGE1 and a second gene encoding a reporter, wherein the reporter is configured to generate a detectable signal in response to SAGE1 expression or SAGE1-mediated activity.

In another aspect, the present disclosure provides a set of X-ray crystal structure coordinates of a binding interface of SAGE1 complex, wherein the binding interface comprises one or more amino acid residues of SAGE1 selected from the group consisting of F838, F873, K874, M832, V876, R872, K828, R836 and Q840, or equivalent residues in a fragment, a variant or a derivative thereof, wherein the residue numbering is according to SEQ ID NO: 3.

In some embodiments, the X-ray crystal structure coordinates are set forth in Protein Data Bank (PDB) under code 7C5U.

In another aspect, the present disclosure provides a set of X-ray crystal structure coordinates of a binding interface of INTS3, wherein the binding interface comprises one or more amino acid residues of INTS3 selected from the group consisting of T804, S841, S874, S769, N933, R849, Q773, C777, M781, A816, N818, E838, E850, F871, R848, F805, L845, L815, L844, Y808, C842, Q846, Q870, R877, H878, K882, E732, V766, Q771, D768, A765, Q731, E835, E803, C809 and L772, or equivalent residues in a fragment, a variant or a derivative thereof, wherein the residue numbering is according to SEQ ID NO: 5.

In some embodiments, the X-ray crystal structure coordinates are set forth in Protein Data Bank (PDB) under code 7C5U.

In another aspect, the present disclosure provides a set of X-ray crystal structure coordinates of a binding interface of SAGE1 and INTS3, wherein the binding interface of SAGE1 comprises one or more amino acid residues selected from the group consisting of F838, F873, K874, M832, V876, R872, K828, R836 and Q840 of SAGE1 (the residue numbering is according to SEQ ID NO:3), or equivalent residues in a fragment, a variant or a derivative thereof, and the binding interface of INTS3 comprises one or more amino acid residues selected from the group consisting of T804, S841, S874, S769, N933, R849, Q773, C777, M781, A816, N818, E838, E850, F871, R848, F805, L845, L815, L844, Y808, C842, Q846, Q870, R877, H878, K882, E732, V766, Q771, D768, A765, Q731, E835, E803, C809 and L772 of INTS3 (the residue numbering is according to SEQ ID NO: 5, or equivalent residues in a fragment, a variant or a derivative thereof.

In some embodiments, the X-ray crystal structure coordinates are set forth in Protein Data Bank (PDB) under code 7C5U.

In another aspect, the present disclosure provides a machine readable data storage media having stored thereon the set of X-ray crystal structure coordinates disclosed herein.

In another aspect, the present disclosure provides a method of identifying an agent which is a potential SAGE1 complex inhibitor, comprising the steps of:

(a) generating on a computer a representation of the three dimensional structure of a binding interface based on the set of X-ray crystal structure coordinates disclosed herein, (b) generating on a computer a representation of the agent, (c) fitting the representation of the agent according to step (b) to the computer representation of the three dimensional structure of the binding interface according to step (a), so that the agent interacts with at least one residue of the binding interface; and (d) evaluating the interaction of the step (c) between the agent and at least one residue of the binding interface, wherein the agent is identified as a potential SAGE1 complex inhibitor when the interaction yields a low energy, stable complex comprising the agent and SAGE1 or INTS3, optionally in competition against SAGE1-INTS3 complex.

In another aspect, the present disclosure provides a virtual screening method to identify potential SAGE1 complex inhibitors, comprising the steps of:

(a) generating on a computer a representation of the three dimensional structure of a binding interface based on the X-ray crystal structure coordinates disclosed herein;

(b) generating a representation of an agent or accessing a representation of an agent from a library on a computer;

(c) fitting the representation of the agent according to step (b) to the computer representation of the three dimensional structure of the binding interface according to step a) to provide a configuration of the agent that interacts with at least one residue of the binding interface; and (d) evaluating the interaction of the step (c) between the agent and at least one residue of the binding interface, wherein the agent is identified as a potential SAGE1 complex inhibitor when the interaction yields a low energy, stable complex comprising the agent and SAGE1 or INTS3, optionally in competition against SAGE1 complex.

Throughout the present disclosure, the articles "a," "an," and "the" are used herein to refer to one or to more than one (i.e., to at least one) of the grammatical object of the article. By way of example, "a polypeptide" means one polypeptide or more than one polypeptides.

In all occurrences in this application where there are a series of recited numerical values, it is to be understood that any of the recited numerical values may be the upper limit or lower limit of a numerical range. It is to be further understood that the invention encompasses all such numerical ranges, i.e., a range having a combination of an upper numerical limit and a lower numerical limit, wherein the numerical value for each of the upper limit and the lower limit can be any numerical value recited herein. Ranges provided herein are understood to include all values within the range. For example, 1-10 is understood to include all of the values 1, 2, 3, 4, 5, 6, 7, 8, 9, and 10, and fractional values as appropriate. Similarly, ranges delimited by "at least" are understood to include the lower value provided and all higher numbers.

As used herein, "about" is understood to include within three standard deviations of the mean or within standard ranges of tolerance in the specific art. In certain embodiments, about is understood a variation of no more than 0.5.

The articles "a" and "an" are used herein to refer to one or more than one (i.e. to at least one) of the grammatical object of the article. By way of example, "an element" means one element or more than one element.

The term "including" is used herein to mean, and is used interchangeably with, the phrase "including but not limited to". Similarly, "such as" is used herein to mean, and is used interchangeably, with the phrase "such as but not limited to".

The term "or" is used inclusively herein to mean, and is used interchangeably with, the term "and/or," unless context clearly indicates otherwise.

The term such as "comprising" are to be construed as open-ended terms (i.e., meaning "including, but not limited to,") unless otherwise noted.

BRIEF DESCRIPTION OF THE DRAWINGS

The accompanying drawings, which are incorporated herein, form part of the specification. Together with this written description, the drawings further serve to explain the principles of, and to enable a person skilled in the relevant art(s), to make and use the present disclosure.

FIG. 5B illustrates tumor burden calculation by volume× mean SUV-bw and tumor burden analysis by T test. And the survival time for HCC-P mice were calculated and analyzed by Kaplan-Meier analysis.

FIG. 5C illustrates the evaluations for the presence of metastatic tumors by hematoxylin-eosin and MHC-I staining after euthanasia of mice and dissection of its organ.

FIGS. 7I, 7J, 7K and 7L illustrate re-expression of WT SAGE1 but notSAGE1mut restores cell growth of SAGE1-KD Caco2 (FIG. 7I) and SAGE1-KO HuTu 80 (FIG. 7J) cells, anchorage-independent growth of SAGE1-KO HuTu 80 cells on soft agar (FIG. 7K), and results in dramatic increase of tumor size and weight in xenograft analysis (FIG. 7L).

FIG. 12 illustrates crystal data collection and refinement statistics.

FIG. 13A illustrates residues involved in interaction between $INTS3_{CTD}$ dimer.

FIG. 13B illustrates residues involved in interaction between $INTS3_{CTD}$-$SAGE1_{\beta BD}$.

FIGS. 14A-14D illustrate the spectral counts of the high-confidence SAGE1 interactors in HuTu 80 cells (FIG. 14A), K562 cells (FIG. 14B), U2OS cells (FIG. 14C), and KYSE30 cells (FIG. 14D) identified by IP-MS analysis.

FIG. 15 illustrates prevalence of SAGE1 expression in pan-cancer (estimated by IHC staining).

FIG. 16 illustrates the inhibition of SAGE1 expression by human SAGE1 shRNA.

FIGS. 17A-E illustrate sequences described in the present disclosure.

FIG. 17A is a table showing target sequences within SAGE1 mRNA transcript variant 1 (SEQ ID NO: 2).

FIG. 17B is a table showing target sequences within the SAGE1 genome (SEQ ID NO: 1).

FIG. 17C is a table showing sequences of small interfering RNAs (siRNAs) targeting SAGE1.

FIG. 17D is a table showing sequences of short hairpin RNAs (shRNAs) targeting SAGE1.

FIG. 17E is a table listing sequences of single quide RNAs (sgRNAs) for targeting the SAGE1 gene.

DETAILED DESCRIPTION OF THE INVENTION

Figure 1A:
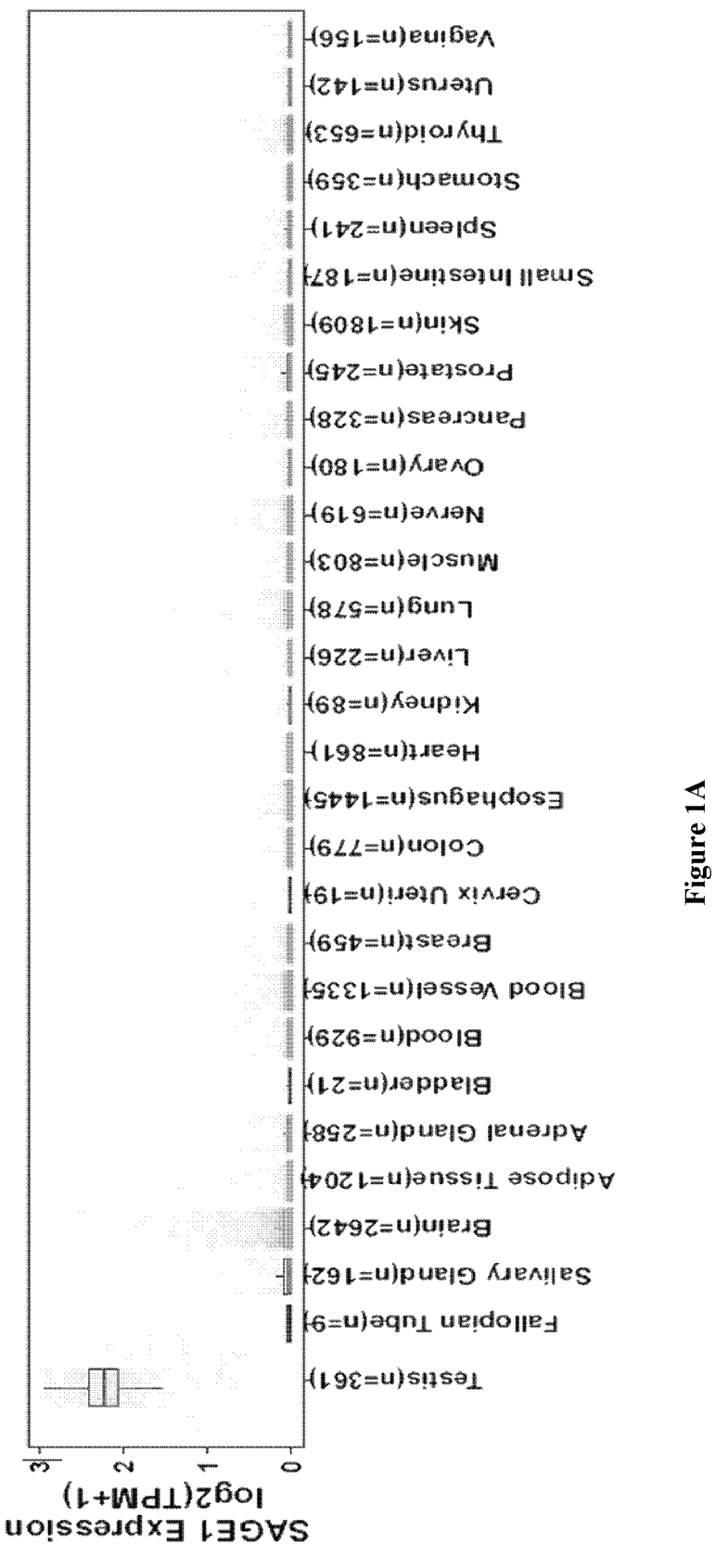
FIG. 1A illustrates expression of SAGE1 in normal tissues according to the GTEx RNA-Seq dataset.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

I. Definition

The following definitions are provided to assist the reader. Unless otherwise defined, all terms of art, notations and other scientific or medical terms or terminology used herein are intended to have the meanings commonly understood by those of skill in the art. In some cases, terms with commonly understood meanings are defined herein for clarity and/or for ready reference, and the inclusion of such definitions herein should not necessarily be construed to represent a substantial difference over the definition of the term as generally understood in the art.

The term "antibody" as used herein includes any immunoglobulin, monoclonal antibody, polyclonal antibody, monovalent antibody, bivalent antibody, multivalent antibody, bispecific antibody, multi-specific antibody that binds to a specific antigen. A native intact antibody comprises two heavy (H) chains and two light (L) chains. Mammalian heavy chains are classified as alpha, delta, epsilon, gamma, and mu, each heavy chain consists of a variable region (VH) and a first, second, third, and optionally fourth constant region (CH1, CH2, CH3, CH4 respectively); mammalian light chains are classified as λ or κ, while each light chain consists of a variable region (VL) and a constant region. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variable regions in both chains generally contain three highly variable loops called the complementarity determining regions (CDRs) (light chain CDRs including LCDR1, LCDR2, and LCDR3, heavy chain CDRs including HCDR1, HCDR2, HCDR3). The three CDRs are interposed between flanking stretches known as framework regions (FRs) (light chain FRs including LFR1, LFR2, LFR3, and LFR4, heavy chain FRs including HFR1, HFR2, HFR3, and HFR4), which are more highly conserved than the CDRs and form a scaffold to support the highly variable loops. The constant regions of the heavy and light chains are not involved in antigen-binding, but exhibit various effector functions. Antibodies are assigned to classes based on the amino acid sequences of the constant regions of their heavy chains. The five major classes or isotypes of antibodies are IgA, IgD, IgE, IgG, and IgM, which are characterized by the presence of alpha, delta, epsilon, gamma, and mu heavy chains, respectively. Several of the major antibody classes are divided into subclasses such as IgG1 (gamma1 heavy chain), IgG2 (gamma2 heavy chain), IgG3 (gamma3 heavy chain), IgG4 (gamma4 heavy chain), IgA1 (alpha1 heavy chain), or IgA2 (alpha2 heavy chain).

The term "antigen-binding fragment" as used herein refers to an antibody fragment formed from a portion of an antibody comprising one or more CDRs, or any other antibody fragment that binds to an antigen but does not comprise an intact native antibody structure. Examples of antigen-binding fragment include, without limitation, a diabody, a Fab, a Fab', a F(ab')$_2$, a Fd, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a bispecific scFv dimer, a single-chain Fv-Fc antibody (scFv-Fc), a camelized single domain antibody, a nanobody, a domain antibody, and a bivalent domain antibody. An antigen-binding fragment is capable of binding to the same antigen to which the parent antibody binds.

The term "biomarker" or "marker" as used here refers to a biological molecule that is a measurable indicator of some biological state or condition. Examples of biomarker provided herein can be a gene (e.g. genomic DNA, cDNA) or a product of the gene such as an mRNA transcribed from the gene, a protein encoded by the gene, and a protein complex. In some embodiments, a biomarker is a tumor marker that is associated with tumors, in particularly malignant tumors. Tumor markers can be quantitatively determined biochemically or immunochemically, and provide information on the diagnosis, prognosis, or therapeutic assays in clinical oncology. Tumor marker is beneficial for tumor patient screening because it can often diagnosis tumor months earlier than clinical and imaging examinations. Tumor makers can also be used for prognosis, monitoring and detecting tumor relapse, and determining treatment efficacy.

The term "complex" as used herein with respect to protein or polypeptide refers to a group of two or more associated polypeptide chains. Different polypeptide chains may have different functions. Typically, polypeptide chains in a protein complex are linked by non-covalent interactions. Different protein complexes may have different degrees of stability over time.

The term "complementary" or "complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds with another nucleic acid sequence (e.g., 5, 6, 7, 8, 9, 10 out of 10 being 50%, 60%, 70%, 80%, 90%, and 100% complementary). Percent complementarity of can be determined routinely using basic local alignment search tools (BLAST programs) (Altschul (1990) J. Mol. Biol. 215, 403-410; Zhang and Madden (1997) Genome Res. 7, 649-656).

The term "derivative" with respect to a polypeptide or a polynucleotide refers to a chemically modified polypeptide or polynucleotide, in which one or more well-defined number of substituent groups have been covalently attached (e.g., by attachment of a heterologous polypeptide, fatty acid or a compound, or by glycosylation, acetylation, phosphorylation) to one or more specific amino acid residues of the polypeptide or one or more specific nucleotides of the polynucleotide. The term "derivative" with respect to a compound refers to a compound that be synthesized from a parent compound by replacement of one atom with another atom or group of atoms.

The term "diagnosing" refers to the use of the methods as described herein to determine the presence or absence of a diseases (e.g., SAGE1 positive disorder) in a subject. The term also includes the use of methods for assessing the level of disease activity in a subject.

The terms "detecting" refers to the act of either quantitatively or semi-quantitatively determining, testing or measuring, which act may be performed by any conventional means. The terms contemplate a transformation of matter, e.g., a transformation of a biological sample, e.g., a blood sample or other tissue sample, from one state to another by means of subjecting that sample to physical testing. The phrase "detecting SAGE1 expression" and the like is used to mean that a sample may be tested (either directly or indirectly) for either the presence or absence of SAGE1 expression or for the level of SAGE1 expression. It will be understood that the presence, the absence or the level of SAGE1 expression may be used to guide a diagnostic or therapeutic decision.

The term "higher" with as used herein respect to a biomarker (e.g. SAGE1) refers to levels of the biomarker as detected in a biological sample is greater than the corresponding reference level of that biomarker. Similarly, "lower" as used herein refer to levels of a biomarker as detected in the sample is less than the corresponding reference level of that biomarker. In some embodiments, the level of SAGE1 expression can be considered "higher" or "lower" than the reference level if the level is 10%, 15%, 20%, 25%, 30%, 35%, 40%, 45%, 50%, 100%, or two, three, four, or five times or more, greater or less, respectively, than the reference level.

The term "effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

The term "fragment" as used herein refers to partial sequence of the reference polypeptide or polynucleotide of any length. A fragment can still retain at least partial biological activities of the reference polypeptide.

The term "inhibitor" as used herein refers to an agent that inhibits (e.g., antagonizes, reduces, decreases, blocks, reverses, or alters) the effect of target molecule(s) (e.g., SAGE1 or SAGE1 complex). The inhibition effects can be exerted through, e.g., reducing the amount of the target molecule or suppressing the activity of the molecule. Such inhibitors can include any compound, protein, or nucleic acid or any derivatives thereof that provides the antagonistic effect.

The term "isolated" as used herein refers to a molecule or a complex thereof that no longer exists in its original natural environment.

The term "Percent (%) sequence identity" is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). In other words, percent (%) sequence identity of an amino acid sequence (or nucleic acid sequence) can be calculated by dividing the number of amino acid residues (or bases) that are identical relative to the reference sequence to which it is being compared by the total number of the amino acid residues (or bases) in the candidate sequence or in the reference sequence, whichever is shorter. Conservative substitution of the amino acid residues is not considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

The term "integrator complex subunit 3" or "INTS3" as used herein refers to INTS3 gene and INTS3 gene products such as mRNA of INTS3 gene and protein encoded by INTS3 gene. It is intended to include fragments, variants and derivatives thereof. The protein encoded by the human INTS3 gene is a putative 1043 amino acid protein with Uniprot accession code Q68E01-1 (the sequence of INTS3 protein where the first methionine is removed is incorporated herein as SEQ ID NO: 5).

The term "integrator complex subunit 6" or "INTS6" as used herein refers to INTS6 gene and INTS6 gene products such as mRNA of INTS6 gene and protein encoded by INTS6 gene. It is intended to include fragments, variants and derivatives thereof. The protein encoded by the human INTS6 gene is a putative 887 amino acid protein with Uniprot accession code Q9UL03-1 (the sequence is incorporated herein as SEQ ID NO: 6).

The term "integrator complex subunit 6-like" or "INTS6L" as used herein refers to INTS6L gene and INTS6L gene products such as mRNA of INTS6L gene and protein encoded by INTS6L gene. It is intended to include fragments, variants and derivatives thereof. The protein encoded by the human INTS6L gene is a putative 861 amino acid protein with Uniprot accession code Q5JSJ4-1 (the sequence is incorporated herein as SEQ ID NO: 7).

The term "kit" as used herein refers to any manufacture (e.g. a package or container) comprising at least one reagent for specifically detecting or modulating the expression of SAGE1 encompassed by the present disclosure. The kit may be promoted, distributed, or sold as a unit for performing the methods disclosed herein.

The term "level" with respect to a biomarker, refers to the amount or quantity of the biomarker of interest present in a sample. Such amount or quantity may be expressed in the absolute terms, i.e., the total quantity of the biomarker in the sample, or in the relative terms, i.e., the concentration or percentage of the biomarker in the sample. Level of a biomarker can be measured at DNA level (for example, as represented by the amount or quantity of epigenetic modification such as DNA methylation or histone acetylation), at RNA level (for example as mRNA amount or quantity), or at protein level (for example as protein or protein complex amount or quantity).

The term "likelihood" and "likely" is a measurement of how probable an event to occur. Likelihood refers to a probability that is more than speculation, but less than certainty when a reasonable person use common sense, training or experience to conclude. In some embodiments, the term "likelihood" and "likely" denotes a chance in percent, for example, at least 50%, at least 60%, at least 80%, at least 90%, at least 95%, at least 99% chance.

The term "near" with respect to histone acetylation on SAGE1 gene refers to the position of the acetylation is close to (e.g., within a distance of 50 bp, 100 bp, 200 bp, 400 bp, 600 bp, 800 bp, or 1 kb upstream or downstream) a specific region or site on SAGE1 gene.

The term "benefit from" or "responsive" as used in the context of cancer therapy (e.g., treatment with a SAGE1 inhibitor) refers to beneficial or favorable response to the therapy, as opposed to unfavorable responses, i.e. adverse events. In a patient, beneficial response can be expressed in terms of a number of clinical parameters, including loss of detectable tumor (complete response), decrease in tumor size and/or tumor cell number (partial response), tumor growth arrest (stable disease), enhancement of anti-tumor immune response, possibly resulting in regression or rejection of the tumor; relief, to some extent, of one or more symptoms associated with the tumor; increase in the length of survival following treatment; and/or decreased mortality at a given point of time following treatment.

The term "TP53" and "p53" are used interchangeably herein, and refer to Tumor Protein p53, and can refer to the p53 protein as well as the DNA (e.g. the cording gene sequence) or the RNA encoding for the p53, including all isoforms and variants. Alternative names for p53 include, e.g., antigen NY-CO-13, phosphorprotein p53, tumor suppressor p53 and cellular tumor antigen p53. Exemplary sequence of human p53 is available in UniProtKB database under the accession number of P04637 (P53-HUMAN).

The term "prognosis" includes a prediction of the probable course and outcome of a disease or the likelihood of recovery from the disease. With used with respect to tumor, the prognosis can be, for example, tendency to benefit or resistant to treatment, development of a clinical subtype, recurrence; metastasis, complete or partial remission. Good prognosis indicates that the expected or likely outcome after treatment of tumor is good and poor prognosis indicates that the expected or likely outcome after treatment of tumor is not good.

The terms "polynucleotide" or "nucleic acid" or "oligonucleotide" are used interchangeably, and refer to a chain of covalently linked nucleotides. The nucleotides may be deoxyribonucleotides or ribonucleotides, and modified or unmodified independent from one another.

The terms "polypeptide" and "protein" are used interchangeably, and refer to a chain of amino acid residues covalently linked by peptide bonds. Proteins or polypeptide may include moieties other than amino acids (e.g., may be glycoproteins) and/or may be otherwise processed or modified. Those of ordinary skill will further appreciate that a protein can sometimes include more than one polypeptide chain, for example linked by one or more disulfide bonds or associated by other means.

The term "subject" refers to a human or any non-human animal (e.g., mouse, rat, rabbit, dog, cat, cattle, swine, sheep, horse or primate). In many embodiments, a subject is a human being. A subject can be a patient who is presented to a medical provider for diagnosis or treatment of a disease. The term "subject" is used herein interchangeably with "individual" or "patient". A subject can be afflicted with or is susceptible to a disease or disorder but may or may not display symptoms of the disease or disorder.

The term "sample" or "biological sample" as used herein refers to a biological sample that is obtained from a subject and contains one or more biomarker(s) of interest to be evaluated by the method of the invention. Samples may contains cells or products that have been secreted from cells, including but not limited to, a sample of isolated cells, a tissue sample or a bodily fluid sample. In some embodiments, a sample comprises tumor cells or products that have been secreted from tumor cells. In some embodiments, a sample is a tumor cell sample.

The term "Sarcoma antigen 1" or "SAGE1" as used herein refers to SAGE1 gene and SAGE1 gene products such as mRNA of SAGE1 gene and protein encoded by SAGE1 gene. It is intended to include fragments, variants and derivatives thereof. Human SAGE1 gene is located in the X chromosome (X:135,893,700-135,913,026, Xq26.3 according to Genome Reference Consortium Human Build 38 patch release 13). It has a Gene ID of 55511 in NCBI database (the sequence is incorporated herein as SEQ ID NO: 1). The human SAGE1 transcript variant 1 is the canonical mRNA sequence of SAGE1 and it has NCBI accession code NM 001381902.1 (GI: 1833303494) (the sequence is incorporated herein as SEQ ID NO: 2). SAGE1 transcription variant 1 encodes at least 2 different SAGE1 proteins. The canonical SAGE1 protein is a putative 904 amino acid protein with Uniprot accession code Q9NXZ1-1 (the sequence is incorporated herein as SEQ ID NO: 3). Unless otherwise indicated, all positional information described with respect to SAGE1 protein are determined from this sequence. An isoform of SAGE1 protein is a putative 528 amino acid protein with NCBI accession code AAI44261.1 (the sequence is incorporated herein as SEQ ID NO: 4), which is also contemplated within the scope of the present disclosure.

The term "structure coordinates" refers to Cartesian coordinates derived from mathematical equations related to the patterns obtained on diffraction of a monochromatic beam of X-rays by the atoms (scattering centers) of a protein or protein complex in crystal form. The diffraction data are used to calculate an electron density map of the repeating unit of the crystal. The electron density maps are then used to establish the positions of the individual atoms of the molecule or molecular complex.

The term "tumor" or "cancer" are used interchangeably and refers to any diseases involving an abnormal cell growth and include all stages and all forms of the disease that affects any tissue, organ or cell in the body. The term includes all known cancers and neoplastic conditions, whether characterized as malignant, benign, soft tissue, solid, or hematologic, or of all stages and grades, including pre- and post-metastatic tumors. In general, tumors can be categorized according to the tissue or organ from which the tumor is located or originated and morphology of cancerous tissues and cells. In some embodiments, types of tumor include, without limitation, adrenal cancer, lymphoepithelial neoplasia, adenoid cell carcinoma, lymphoma, acoustic neuroma, acute lymphocytic leukemia, acral lentiginous melanoma, acute myeloid leukemia, acrospiroma, chronic lymphocytic leukemia, acute eosinophilic leukemia, liver cancer, acute erythrocyte leukemia, small cell lung cancer, acute lymphocytic leukemia, non-small cell lung cancer, acute megakaryoblastic leukemia, MALT lymphoma, acute monocytic leukemia, malignant fibrous histiocytoma, acute promyelocytic leukemia, malignant peripheral schwannomas, mantle cell lymphoma, adenocarcinoma, marginal zone B-cell lymphoma, malignant hippocampal tumor, adenoid cystic carcinoma, gland tumor, adenoma-like odontogenic tumor, mast cell leukemia, adenosquamous carcinoma, mediastinal germ cell tumor, adipose tissue tumor, breast medullary carcinoma, adrenocortical carcinoma, medullary thyroid carcinoma, adult T cell leukemia/lymphoma, Medulloblastoma, invasive NK cell leukemia, melanoma, AIDS-related lymphoma, meningioma, lung rhabdomyosarcoma, Merkel cell carcinoma, alveolar soft tissue sarcoma, mesothelioma, ameloblastoma, metastatic urothelial carcinoma, anaplastic large cell lymphoma, mixed Müllerian tumor, thyroid undifferentiated carcinoma, mucinous neoplasm, angioimmunoblastic T-cell lymphoma, multiple myeloma, angiomyolipoma, muscle tissue tumor, angiosarcoma, mycosis fungoides, astrocytoma, myxoid liposarcoma, atypical deformed rhabdoid tumor, myxoma, B-cell chronic lymphocytic leukemia, mucinous sarcoma, B-cell lymphoblastic leukemia, nasopharyngeal carcinoma, B-cell lymphoma, schwannomas, basal cell carcinoma, neuroblastoma, biliary tract cancer, neurofibromatosis, bladder cancer, neuroma, blastoma, nodular melanoma, bone cancer, eye cancer, Brenner tumor, oligodendroxoma, brown tumor, oligodendroglioma, Burkitt's lymphoma, eosinophilic breast cancer, brain cancer, optic nerve tumor cancer, oral cancer carcinoma in situ, osteosarcoma, carcinosarcoma, ovarian cancer, cartilage tumor, pulmonary sulcus tumor, papillary thyroid carcinoma, myeloma, paraganglioma, chondroma, pineal blastoma, chordoma, pineal cell tumor, choriocarcinoma, pituitary tumor, choroid plexus papilloma, pituitary adenoma, kidney clear cell sarcoma, pituitary tumor, craniopharyngioma, plasmacytoma, cutaneous T-cell lymphoma, multiple embryonic cell tumor, cervical cancer, precursor T lymphoblastic lymphoma, colorectal cancer, primary central nervous system lymphoma, Degos disease, primary effusion lymphoma, proliferative small round cell tumor, primary preformed peritoneal cancer, diffuse large B-cell lymphoma, prostate cancer, embryonic dysplasia of neuroepithelial neoplasia, pancreatic cancer, anaplastic cell tumor, pharyngeal carcinoma, embryonic carcinoma, peritoneal pseudomyxoma, endocrine gland tumor, renal cell carcinoma, enteropathy-associated T-cell lymphoma, endodermal sinus tumor, renal medullary carcinoma, retinoblastoma, esophageal cancer, rhabdomyosarcoma, endadelphos, rhabdomyosarcoma, fibroids, Richter's transformation, fibrosarcoma, rectal cancer, follicular lymphoma, sarcoma, follicular thyroid cancer, schwannoma, ganglion cell tumor, seminoma, gastrointestinal cancer, Sertoli cell turn, germ cell tumor, sex cord-gonadal stromal tumor, pregnancy choriocarcinoma, signet ring cell carcinoma, giant cell fibroblastoma, skin cancer, bone giant cell tumor of bone, small blue round cell tumor, glioma, small cell carcinoma, glioblastoma multiforme, soft tissue sarcoma, glioma, somatostatin tumor, glioma brain, soot wart, pancreatic high glucagonoma, spinal tumor, Gonadoblastoma, spleen marginal lymphoma, granulosa cell tumor, squamous cell carcinoma, estrogen tumor, synovial sarcoma, gallbladder cancer, Sezary disease, gastric cancer, small intestine cancer, hairy cell leukemia, squamous cell carcinoma, hemangioblastoma, gastric cancer, head and neck cancer, T-cell lymphoma, vascular epithelioma, testicular cancer, hematological malignancies, sarcoma, hepatoblastoma, thyroid cancer, hepatosplenic T-cell lymphoma, transitional cell carcinoma, Hodgkin's lymphoma, laryngeal cancer, non-Hodgkin's lymphoma, urachal cancer, invasive lobular carcinoma, genitourinary cancer, intestinal cancer, urothelial carcinoma, renal cancer, uveal melanoma, laryngeal cancer, uterine cancer, malignant freckle-like sputum, verrucous carcinoma, lethal midline granuloma, visual pathway glioma, leukemia, vulvar cancer, testicular stromal tumor, vaginal cancer, liposarcoma, Waldenstrom's macroglobulinemia Disease, lung cancer, adenolymphoma lymphangioma, nephroblastoma, lymphangisarcoma, and the like. In some embodiments, the tumor is selected from colorectal cancer, lung cancer, liver cancer, breast cancer, esophageal cancer, head and neck cancer, skin cancer, kidney cancer, leukemia, colon adenocarcinoma (coad), liver hepatocellular carcinoma (lihc), ovarian serous cystadenocarcinoma (ov), uterine corpus endometrial carcinoma (ucec), thyroid carcinoma (thca), skin cutaneous melanoma (skcm), lung adenocarcinoma (luad), head and neck squamous cell carcinoma (hnsc), glioblastoma multiforme (gbm), prostate adenocarcinoma (prad), thymoma (thym), brain lower grade glioma (lgg), rectum adenocarcinoma (read), pheochromocytoma and paraganglioma (pcpg), esophageal carcinoma (esca), kidney renal clear cell carcinoma (kirc), cervical squamous cell carcinoma and endocervical adenocarcinoma (cesc), bladder urothelial carcinoma (blca), kidney renal papillary cell carcinoma (kirp), pancreatic adenocarcinoma (paad), stomach adenocarcinoma (stad), kidney chromophobe (kich), breast invasive carcinoma (brca), lung squamous cell carcinoma (lusc), sarcoma (sarc), acute myeloid leukemia (laml).

The term "treatment", or "treating" as used herein refers to preventing or alleviating a condition, slowing the onset or rate of development of a condition, preventing or delaying the development of symptoms associated with a condition, reducing or ending symptoms associated with a condition, generating a complete or partial regression of a condition, curing a condition, or some combination thereof. With regard to tumor, "treating" or "treatment" may refer to preventing, inhibiting, delaying or slowing neoplastic or malignant cell development, proliferation, progression or metastasis, or cancer symptoms or some combination thereof. It is understood that treatment does not necessarily refer to a cure or complete ablation of the disease, condition, or symptoms of the disease or condition.

The term "vector" refers to a vehicle into which a polynucleotide may be operably inserted so as to deliver, replicate or express the polynucleotide. A vector may contain a variety of regulatory elements including, without limitation, origin of replication, promoter, transcription initiation sequences, enhancer, selectable marker genes, and reporter genes. A vector may also include materials to aid in its entry into a host cell, including but not limited to a viral particle, a liposome, or ionic or amphiphilic compounds.

It is noted that in this disclosure, terms such as "comprises", "comprised", "comprising", "contains", "containing" and the like have the meaning attributed in United States Patent law; they are inclusive or open-ended and do not exclude additional, un-recited elements or method steps. Terms such as "consisting essentially of" and "consists essentially of" have the meaning attributed in United States Patent law; they allow for the inclusion of additional ingredients or steps that do not materially affect the basic and novel characteristics of the claimed invention. The terms "consists of" and "consisting of" have the meaning ascribed to them in United States Patent law; namely that these terms are close ended.

II. SAGE1 as a Novel Diagnostic Biomarker and Therapy Target

Sarcoma antigen 1 (SAGE1) belongs to a large and heterogeneous group of cancer testis antigens (CTA). Although SAGE1 has been identified as a tumor-specific antigen for almost twenty years, its role in tumor development and progression remains poorly understood.

The present disclosure finds, in a large number of studies, that SAGE1 is expressed in various tumor tissues and cells, such as intestinal cancer, lung cancer, liver cancer, breast cancer, skin cancer, head and neck cancer, leukemia, etc., and that SAGE1 is not detected in normal cells except testis tissues.

The present disclosure unexpectedly reveals SAGE1 drives oncogenic transcription and up-regulates many pro-cancerous pathways. Such enhanced proliferative capacity could be a major driving force for abnormal proliferation, neoplasm, tumor progression, rendering SAGE1 expression a valuable biomarker for SAGE1-positive disease diagnosis, prognosis, monitoring of SAGE1-positive disease progression, prediction of therapeutic efficacy and selection of treatment plans.

The present disclosure further, for the first time, validates SAGE1 as a tumor-agnostic therapeutic target. Down-regulation of SAGE1 in patient-derived xenograft (PDX) models of different tumors effectively suppresses tumor growth and even achieves pathological complete response. The present disclosure finds that expression of SAGE1, which could lead to an oncogene addiction regardless of tissue origin or genomic landscape diversity, defines a new diagnostic entity as SAGE1-positive disorder (e.g., SAGE1-positive tumor) and inhibition of SAGE1 level or activity could be an effective therapeutic approach for SAGE1-positive disorder.

As used herein, the term "SAGE1-positive" means presence of SAGE1 expression in a cell or tissue. The term SAGE1-positive disorder means that the disorder is characterized in having a SAGE1-positive cell or SAGE1-positive tissue that normally does not have SAGE1 expression. SAGE1-positive disorder is characterized by the aberrant or unwanted expression of SAGE1 that deviates from its normal expression pattern. SAGE1 is not expressed in normal tissues except for spermatogenic cells and, for some instances, placenta and brain.

In certain embodiments, the SAGE1-positive disorder is characterized in having a SAGE1-positive cell which is not a spermatogonial stem cell (SSC or SPG). In certain embodiments, the SAGE1-positive disorder is characterized in having a SAGE1-positive cell which is a cell found in fallopian tube, salivary gland, adipose tissue, adrenal gland, blood, bladder, blood vessel, breast, cervix uteri, colon, esophagus, heart, kidney, liver, lung, muscle, nerve, ovary, pancreas, prostate, skin, small intestine, spleen, stomach, thyroid, uterus or vagina.

In certain embodiments, the SAGE1-positive disorder is characterized in having a SAGE1-positive abnormal cell. The term "abnormal cell" as used herein means a cell that differs from a corresponding normal cell in one or more biological or physiological or pathological aspects. An abnormal cell can differ from a corresponding normal cell in, for example, cell growth, gene mutation, aberrant activation of certain biological pathways, aberrant expression of certain genes, aberrant ability to migrate or aberrant ability to differentiate, among others.

In some embodiments, the SAGE1-positive disorder comprises tumor (i.e., SAGE1-positive tumor).

In some embodiments, the SAGE1-positive disorder is selected from solid tumors or hematological tumors.

In some embodiments, the SAGE1-positive disorder is selected from adrenal cancer, lymphoepithelial neoplasia, adenoid cell carcinoma, lymphoma, acoustic neuroma, acute lymphocytic leukemia, acral lentiginous melanoma, acute myeloid leukemia, acrospiroma, chronic lymphocytic leukemia, acute eosinophilic leukemia, liver cancer, acute erythrocyte leukemia, small cell lung cancer, acute lymphocytic leukemia, non-small cell lung cancer, acute megakaryoblastic leukemia, MALT lymphoma, acute monocytic leukemia, malignant fibrous histiocytoma, acute promyelocytic leukemia, malignant peripheral schwannomas, mantle cell lymphoma, adenocarcinoma, marginal zone B-cell lymphoma, malignant hippocampal tumor, adenoid cystic carcinoma, gland tumor, adenoma-like odontogenic tumor, mast cell leukemia, adenosquamous carcinoma, mediastinal germ cell tumor, adipose tissue tumor, breast medullary carcinoma, adrenocortical carcinoma, medullary thyroid carcinoma, adult T cell leukemia/lymphoma, Medulloblastoma, invasive NK cell leukemia, melanoma, AIDS-related lymphoma, meningioma, lung rhabdomyosarcoma, Merkel cell carcinoma, alveolar soft tissue sarcoma, mesothelioma, ameloblastoma, metastatic urothelial carcinoma, anaplastic large cell lymphoma, mixed Müllerian tumor, thyroid undifferentiated carcinoma, mucinous neoplasm, angioimmunoblastic T-cell lymphoma, multiple myeloma, angiomyolipoma, muscle tissue tumor, angiosarcoma, mycosis fungoides, astrocytoma, myxoid liposarcoma, atypical deformed rhabdoid tumor, myxoma, B-cell chronic lymphocytic leukemia, mucinous sarcoma, B-cell lymphoblastic leukemia, nasopharyngeal carcinoma, B-cell lymphoma, schwannomas, basal cell carcinoma, neuroblastoma, biliary tract cancer, neurofibromatosis, bladder cancer, neuroma, blastoma, nodular melanoma, bone cancer, eye cancer, Brenner tumor, oligodendroxoma, brown tumor, oligodendroglioma, Burkitt's lymphoma, eosinophilic breast cancer, brain cancer, optic nerve tumor cancer, oral cancer carcinoma in situ, osteosarcoma, carcinosarcoma, ovarian cancer, cartilage tumor, pulmonary sulcus tumor, papillary thyroid carcinoma, myeloma, paraganglioma, chondroma, pineal blastoma, chordoma, pineal cell tumor, choriocarcinoma, pituitary tumor, choroid plexus papilloma, pituitary adenoma, kidney clear cell sarcoma, pituitary tumor, craniopharyngioma, plasmacytoma, cutaneous T-cell lymphoma, multiple embryonic cell tumor, cervical cancer, precursor T lymphoblastic lymphoma, colorectal cancer, primary central nervous system lymphoma, Degos disease, primary effusion lymphoma, proliferative small round cell tumor, primary preformed peritoneal cancer, diffuse large B-cell lymphoma, prostate cancer, embryonic dysplasia of neuroepithelial neoplasia, pancreatic cancer, anaplastic cell tumor, pharyngeal carcinoma, embryonic carcinoma, peritoneal pseudomyxoma, endocrine gland tumor, renal cell carcinoma, enteropathy-associated T-cell lymphoma, endodermal sinus tumor, renal medullary carcinoma, retinoblastoma, esophageal cancer, rhabdomyosarcoma, endadelphos, rhabdomyosarcoma, fibroids, Richter's transformation, fibrosarcoma, rectal cancer, follicular lymphoma, sarcoma, follicular thyroid cancer, schwannoma, ganglion cell tumor, seminoma, gastrointestinal cancer, Sertoli cell turn, germ cell tumor, sex cord-gonadal stromal tumor, pregnancy choriocarcinoma, signet ring cell carcinoma, giant cell fibroblastoma, skin cancer, bone giant cell tumor of bone, small blue round cell tumor, glioma, small cell carcinoma, glioblastoma multiforme, soft tissue sarcoma, glioma, somatostatin tumor, glioma brain, soot wart, pancreatic high glucagonoma, spinal tumor, Gonadoblastoma, spleen marginal lymphoma, granulosa cell tumor, squamous cell carcinoma, estrogen tumor, synovial sarcoma, gallbladder cancer, Sezary disease, gastric cancer, small intestine cancer, hairy cell leukemia, squamous cell carcinoma, hemangioblastoma, gastric cancer, head and neck cancer, T-cell lymphoma, vascular epithelioma, testicular cancer, hematological malignancies, sarcoma, hepatoblastoma, thyroid cancer, hepatosplenic T-cell lymphoma, transitional cell carcinoma, Hodgkin's lymphoma, laryngeal cancer, non-Hodgkin's lymphoma, urachal cancer, invasive lobular carcinoma, genitourinary cancer, intestinal cancer, urothelial carcinoma, renal cancer, uveal melanoma, laryngeal cancer, uterine cancer, malignant freckle-like sputum, verrucous carcinoma, lethal midline granuloma, visual pathway glioma, leukemia, vulvar cancer, testicular stromal tumor, vaginal cancer, liposarcoma, Waldenstrom's macroglobulinemia Disease, lung cancer, adenolymphoma lymphangioma, nephroblastoma, lymphangisarcoma. colon adenocarcinoma (coad), liver hepatocellular carcinoma (lihc), ovarian serous cystadenocarcinoma (ov), uterine corpus endometrial carcinoma (ucec), thyroid carcinoma (thca), skin cutaneous melanoma (skcm), lung adenocarcinoma (luad), head and neck squamous cell carcinoma (hnsc), glioblastoma multiforme (gbm), prostate adenocarcinoma (prad), thymoma (thym), brain lower grade glioma (lgg), rectum adenocarcinoma (read), pheochromocytoma and paraganglioma (pcpg), esophageal carcinoma (esca), kidney renal clear cell carcinoma (kirc), cervical squamous cell carcinoma and endocervical adenocarcinoma (cesc), bladder urothelial carcinoma (blca), kidney renal papillary cell carcinoma (kirp), pancreatic adenocarcinoma (paad), stomach adenocarcinoma (stad), kidney chromophobe (kich), breast invasive carcinoma (brca), lung squamous cell carcinoma (lusc), sarcoma (sarc), or acute myeloid leukemia (laml).

III. Detection of SAGE1 Expression for Diagnosis, Prognosis and Monitoring of Diseases i. Diagnosis of SAGE1 Positive Disorder In one aspect, the present disclosure provides a method of diagnosing a SAGE1 positive disorder in a subject, comprising: detecting SAGE1 expression in a biological sample from the subject, and evaluating whether the subject has a SAGE1 positive disorder based on presence or absence or level of the SAGE1 expression detected in the biological sample.

In one aspect, the present disclosure provides a method of diagnosing a SAGE1 positive disorder in a subject, comprising detecting SAGE1 expression in a biological sample from the subject, wherein the subject is diagnosed as having SAGE1 positive disorder when SAGE1 expression is detected in the biological sample.

In some embodiments, the SAGE1 positive disorder is a SAGE1 positive tumor. In some embodiments, the subject has been determined to have deficiency (e.g. mutation) in p53. Details of this embodiments are provided in below sections.

In some embodiments, the method further comprises recommending, prescribing, or administering a SAGE1 inhibitor to the subject diagnosed as having a SAGE1 positive disorder.

ii. Assessing Malignancy

In another aspect, the present disclosure provides a method of assessing malignancy or malignancy potential of a tumor in a subject, comprising: detecting SAGE1 expression in a biological sample from the subject, and evaluating whether the subject has a malignancy or malignancy potential of a tumor based on presence or absence or level of the SAGE1 expression detected in the biological sample.

In one aspect, the present disclosure provides a method of assessing malignancy or malignancy potential of a tumor in a subject, comprising detecting SAGE1 expression in a biological sample from the subject, wherein the tumor is assessed to be malignant or as having malignancy potential when the SAGE1 expression is detected in the biological sample.

The term "malignancy", as opposed to benign, refers to the presence of malignant tumor cells that have the ability to invade nearby (locally) and destroy tissues or even spread to other sites in the body (metastasize). Malignant cells tend to have fast, uncontrolled growth, do not die normally due to changes in their genetic makeup. Some malignant cells may exhibit a stem cell-like phenotype ("stemness") that presumably causes relapse and metastasis by giving rise to new tumors. Accordingly, malignant tumors may be resistant to treatment and may return after all detectable traces of them have been removed or destroyed during treatment. The term "malignancy potential" means the likelihood of disease progression to malignancy. A subject may not yet demonstrate any signs of malignancy but may have malignancy potential if the subject later develops malignancy or has disease progression to malignancy.

In some embodiments, the malignancy is characterized as having one or more of the following features: a) expressing one or more stem cell marker; b) capable of metastasis; c) capable of uncontrolled cell proliferation; d) likely to experience disease progression; e) likely to develop resistance to an anti-cancer therapy; f) likely to relapse after treatment with an anti-cancer therapy, and g) having, or likely to develop, one or more cancer-related driver mutations. Tumor progression can be manifested as shorter survival time of a patient, increased metastasis, increased cellular proliferation, or increased tumor burden. In some embodiments, the subject has not shown any clinical manifestation of malignancy (e.g. any of the above-mentioned features).

"Cancer-related Driver mutations" as used herein refers to mutations that provide a selective growth advantage, and thus promote cancer development. Cancer-related driver mutations can affect the function of genes by, e.g, copy number alterations, mutations in coding or noncoding regions, dysregulation of microRNA, epigenetic changes, and mutation in chromatin modifiers, among others. Cancer-related driver mutations have been frequently observed in genes, such as the tumor suppressor p53, the CDKN2A gene, the KMT2D gene, the SMARCA4 gene, the NFE2L2 gene, the FAT1 gene, the SPTA1 gene, the ARID1A gene (see, e.g.

Figure 10A:
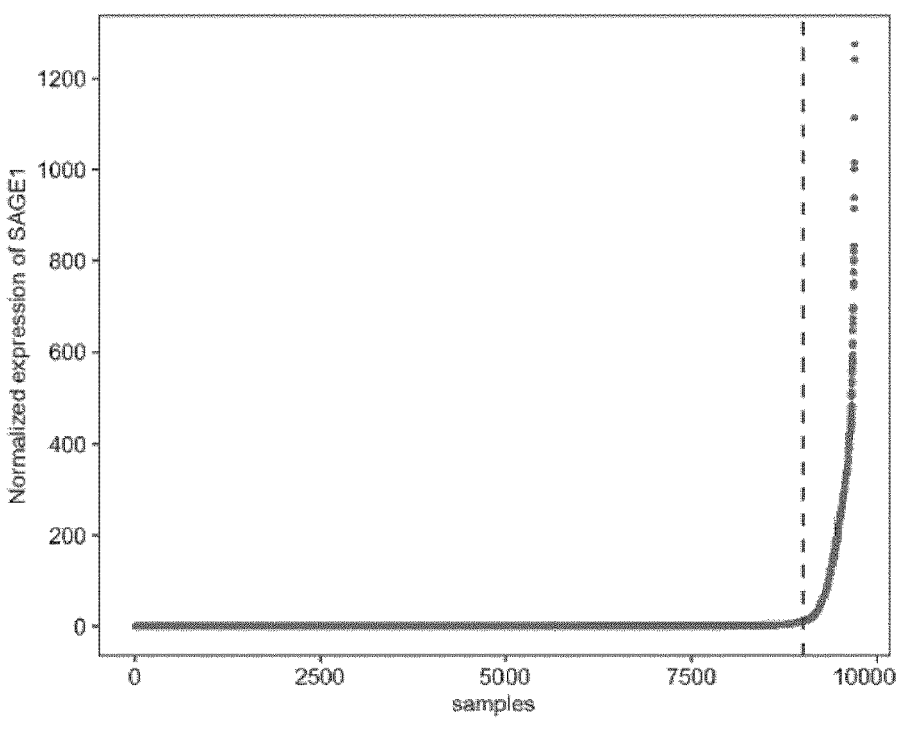
FIG. 10A illustrates the distribution of SAGE1 expression across primary tumors, and the dot line indicated the threshold for SAGE1 high (top 6% of SAGE1 expression in TCGA patients) and SAGE1 low patients (the other 94% TCGA patients).
Figure 10B:
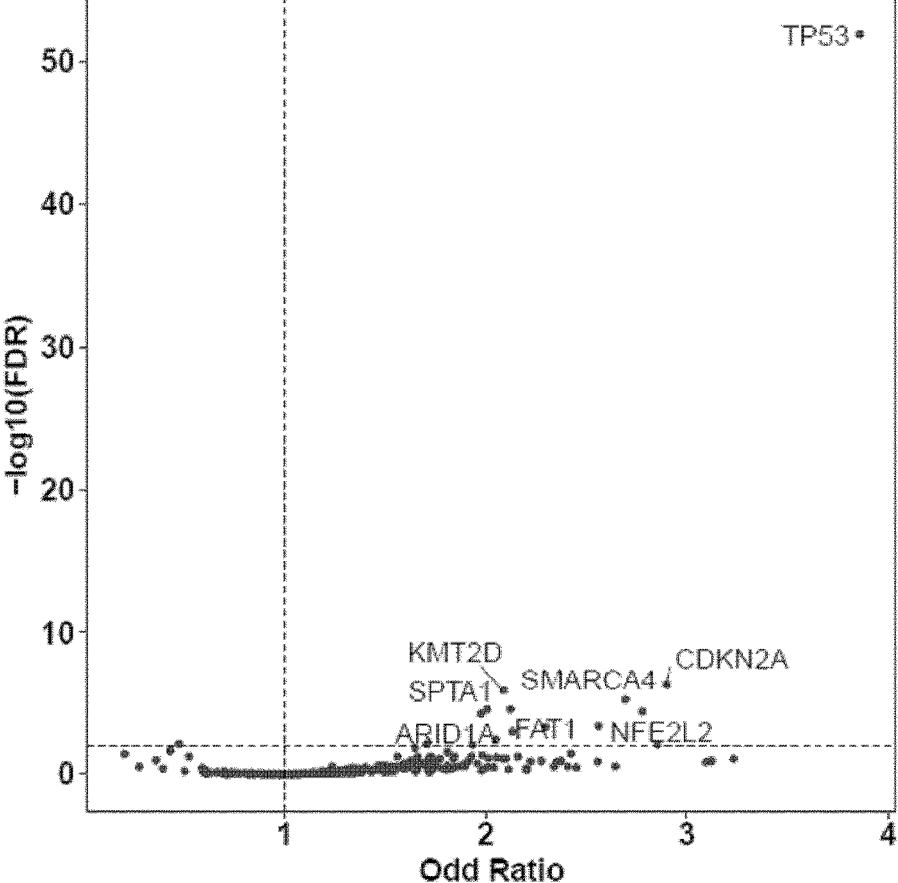
FIG. 10B illustrates enrichment of genomic alterations between SAGE1 high (top 6% of SAGE1 expression in TCGA patients) and SAGE1 low patients (the other 94% TCGA patients). The odd ratio was estimated with Fisher exact test, and the FDR method was applied to adjust p-value. Somatic mutations in TP53, and only protein coding mutations retained in SAGE1 high patient (Frame_Shift_Del, Frame_Shift_Ins, In_Frame_Del, In_Frame_Ins, Missense_Mutation, Nonsense_Mutation, Nonstop_Mutation, Splice_Site, and Translation_Start_Site).

FIG. 10B), the MYC oncogene, the BRAF oncogene in tumor patient (see, for example, Pon, Julia R and Marra, Marco A, Annu. Rev. Pathol. Mech. Dis. 2015. 10:25-50).

In some embodiments, the SAGE1-positive tumor is likely to be malignant or having malignancy potential.

In some embodiments, the method further comprising recommending a treatment option suitable for malignancy for the subject whose tumor is assessed as being malignant or as having malignancy potential.

In some embodiments, the subject has been determined to have a mutation in p53. Details of this embodiments are provided in below sections.

In some embodiments, the method further comprises recommending, prescribing, or administering a SAGE1 inhibitor to the subject when SAGE1 expression is detected in the biological sample.

iii. TP53 Deficiency (or Mutation)

In another aspect, the present disclosure provides a method of predicating likelihood of having a SAGE1 positive disorder in a subject, comprising, detecting deficiency in TP53 in a first biological sample from the subject, and evaluating whether the subject has likelihood of having a SAGE1 positive disorder based on presence or absence deficiency in the TP53 detected in the first biological sample.

In another aspect, the present disclosure provides a method of predicating likelihood of having a SAGE1 positive disorder in a subject, comprising, detecting deficiency in TP53 in a first biological sample from the subject, wherein the subject is predicted as likely to have the SAGE1 positive disorder when TP53 deficiency is detected.

In certain embodiments, the subject has been determined to have deficiency (e.g. mutation) in TP53.

As used herein, "deficiency" or "deficient" refers to insufficiency in activity or level, and can include, for example, being less than normal activity or level, or being absent or null in activity or level. For example, deficiency in activity or level of TP53 can result in TP53 having no or less than normal function, or an absence of or reduced expression level of TP53 in a biological sample.

Loss of TP53 is a common genetic aberration occurring in a variety of cancers. In certain embodiments, the deficiency in activity or level of TP53 can be indicated by the presence of the inactivating mutation in TP53. The term "inactivating mutation," as used herein with respect to TP53, refers to a mutation that results in at least partial (or complete) loss of function or activity of the gene or of the gene product of TP53, or results in a nonfunctional gene or gene product. For example, the activity of the affected gene or gene product of TP53 would be significantly lower than wild-type counterpart or even be eliminated. In certain embodiments, an inactivating mutation in TP53 may be a translocation, deletion, insertion, substitution or any combination thereof, which reduces the biological activity of TP53.

The term TP53 provided herein are intended to encompass different forms including mRNA, protein and also DNA (e.g. genomic DNA). Therefore, the level and/or activity and/or mutation status of TP53 can be measured with RNA (e.g. mRNA), protein or DNA (e.g. genomic DNA).

Mutation status or expression level of TP53 at DNA or RNA level can be measured by any methods known in the art, for example, without limitation, an amplification assay, a hybridization assay, or a sequencing assay. Mutation status or expression level of TP53 at protein level can be measured by any methods known in the art, for example, without limitation, immunoassays.

In some embodiments, the method further comprises recommending the subject to test SAGE1 expression when deficiency in TP53 is detected, for example, when an inactivating mutation in TP53 is detected.

In some embodiments, the method further comprises detecting SAGE1 expression in the first biological sample or in a second biological sample from the subject. SAGE1 expression can be detected in the first biological sample, i.e. the same sample for which TP53 is detected, or alternatively can be detected a second biological sample obtained from the subject, which can be of the same tissue type as the first biological sample or of a different tissue type. The biological sample for detection of SAGE1 expression is of a type of sample that normally has no detectable SAGE1 expression.

In some embodiments, when SAGE1 expression is not detected in the biological sample, the method further comprising monitoring SAGE1 expression in the subject after a course of time, for example, after a month, after two months, after three months, and so on.

iv. Determining Sensitivity to a SAGE1 Inhibitor

In another aspect, the present disclosure provides a method of determining sensitivity of a tumor sample to a SAGE1 inhibitor, comprising: detecting SAGE1 expression in the tumor sample, and evaluating whether the tumor sample is sensitive to the SAGE1 inhibitor based on presence or absence or level of the SAGE1 expression detected in the tumor sample.

In another aspect, the present disclosure provides a method of determining sensitivity of a tumor sample to a SAGE1 inhibitor, comprising detecting SAGE1 expression in a sample tumor cell, wherein the SAGE1 expression detected indicates that the tumor cell is sensitive to a SAGE1 inhibitor.

The term "sensitivity" with regard to tumor cells refers to the ability of tumor cell to respond to a tumor treatment (e.g., treatment with SAGE1 inhibitor). Sensitivity of tumor cells can be measured in terms of, e.g., inhibition of tumor cell proliferation or tumor cell death.

In some embodiments, the tumor sample is obtained from a subject. In some embodiments, the method further comprises recommending the subject to be treated with a SAGE1 inhibitor when the tumor sample is determined as sensitive to a SAGE1 inhibitor. In some embodiments, the method further comprises providing or administering a SAGE1 inhibitor to the subject from whom the tumor sample is obtained and determined as sensitive to a SAGE1 inhibitor.

v. Identifying a Subject Responsive to a SAGE1 Inhibitor

In another aspect, the present disclosure provides a method of identifying a subject having a tumor who is likely to benefit from treatment with a SAGE1 inhibitor, comprising: detecting SAGE1 expression in a biological sample from the subject, and evaluating whether the subject is likely to benefit from treatment with a SAGE1 inhibitor based on presence or absence or level of the SAGE1 expression detected in the biological sample.

In another aspect, the present disclosure provides a method identifying a subject having a tumor who is likely to benefit from treatment with a SAGE1 inhibitor, comprising detecting SAGE1 expression in a sample from the subject, wherein the subject is identified as being likely to benefit from treatment with the SAGE1 inhibitor when SAGE1 expression is detected.

In some embodiments, the subject has been determined to have a mutation in TP53.

In some embodiments, the method further comprises recommending, prescribing, or administering a SAGE1 inhibitor to the subject identified as likely to benefit from treatment with a SAGE1 inhibitor.

In some embodiments, the method further comprises detecting SAGE1 expression in the biological sample or in an additional biological sample from the subject.

In some embodiments, when SAGE1 expression is not detected in the biological sample, the method further comprises monitoring SAGE1 expression in the subject after a course of time.

vi. Monitoring Progression of a SAGE1 Positive Disorder

In another aspect, the present disclosure provides a method of monitoring progression of a SAGE1 positive disorder in a subject, comprising: (a) detecting a level of SAGE1 expression in a first biological sample from the subject, (b) detecting a level of SAGE1 expression in a second biological sample from the subject, wherein the second biological sample is obtained after a course of time from the first sample; and (c) evaluating whether there is progression of the SAGE1 positive disorder in the subject based on the levels of the SAGE1 expression detected in the step (a) and in the step (b), respectively.

In another aspect, the present disclosure provides a method of monitoring progression of a tumor in a subject, comprising: a) detecting a level of SAGE1 expression in a first biological sample from the subject, b) detecting a level of SAGE1 expression in a second biological sample from the subject, wherein the second biological sample is obtained after a course of time from the first sample. In some embodiments, the method further comprises: c) comparing the level of SAGE1 expression in the second sample to the level in the first sample to determine the progression of tumor. In some embodiments, wherein the tumor is determined as having progressed when the level of SAGE1 expression in the second biological sample is higher than the first.

In some embodiments, the tumor is determined as having regressed when the level of SAGE1 expression in the second biological sample is lower than the first. In some embodiments, treatment for tumor is present or absent during the course of time between the first and second biological sample. In some embodiment, the method further comprises recommending, prescribing, or administering a SAGE1 inhibitor to the subject when the tumor is determined as having progressed.

vii. Monitoring Responsiveness of a Subject to a SAGE1 Inhibitor

In another aspect, the present disclosure provides a method of monitoring responsiveness of a subject having a SAGE1 positive disorder to treatment with a SAGE1 inhibitor within a therapeutic period, the method comprising: (a) detecting a level of SAGE1 expression in a biological sample from the subject after the therapeutic period to obtain a post-treatment level of SAGE1 expression, (b) comparing the post-treatment level with a baseline level of SAGE1 expression detected in a biological sample obtained from the subject before the therapeutic period, and (c) evaluating whether there is responsiveness of the subject to the treatment with the SAGE1 inhibitor based on the levels of the SAGE1 expression detected in the step (a) and in the step (b), respectively.

In another aspect, the present disclosure provides a method of monitoring responsiveness of a subject having a tumor to treatment with a SAGE1 inhibitor, comprising: a) detecting a level of SAGE1 expression in a biological sample from the subject after the therapeutic period to obtain a post-treatment level of SAGE1 expression, and b) comparing the post-treatment level with a baseline level of SAGE1 expression detected in a biological sample obtained from the subject before the therapeutic period.

In some embodiments, the subject is determined as responsive to the treatment when the post-treatment level is lower than the baseline level.

In some embodiments, the subject is determined as not responsive to the treatment when the post-treatment level is higher than the baseline level.

viii. Detection of SAGE1 Expression

In any of the methods and embodiments provided herein, SAGE1 expression can be detected using any suitable methods known in the art. In some embodiments, the method provided herein involves contacting the biological sample with an agent capable of detecting the presence or level of SAGE1 expression in the biological sample.

The detection of SAGE1 expression can be based on the presence or absence of SAGE1 expression, wherein the presence of SAGE1 expression indicates SAGE1 positivity.

Alternatively, the detection can be based on the level of SAGE1 expression, wherein the detected level that is higher than a reference level indicates SAGE1-positivity. A reference level can be obtained from one or more reference samples (e.g., samples obtained from healthy subjects, from healthy tissues or even paracancerous tissues of a tumor patients). The detection of SAGE1 expression can be conducted in parallel in the reference sample and the biological sample of interest. A reference level can also be obtained from a database, which includes a collection of data, standard, or level from one or more reference samples. In some embodiments, such collection of data, standard or level are normalized. It should be understood that the reference level encompasses a level (or noise level) which is indicative of absence of SAGE1 expression, as SAGE1 is normally not found in most of the healthy cell or tissues.

SAGE1 provided herein are intended to encompass different forms including mRNA, protein (and the complex thereof) and also DNA (e.g. genomic DNA). Therefore, the SAGE1 expression can be detected at DNA transcription level, mRNA level, or protein level.

In some embodiments, the SAGE1 expression is indicated by: a) presence or level of SAGE1 protein; b) presence or level of SAGE1 mRNA; c) presence or level of a SAGE1 complex; d) level of methylation of in the SAGE1 gene; e) presence or level of histone acetylation of the SAGE1 gene; f) presence or level of binding of a transcription factor to the SAGE1 gene, or g) any combination thereof.

In some embodiments, the SAGE1 expression is indicated by (a) the presence, or relative to a reference level, a higher level of transcription of SAGE1 gene; (b) the presence, or relative to a reference level, a higher level of SAGE1 mRNA; (c) the presence, or relative to a reference level, a higher level SAGE1 protein; (d) the presence, or relative to a reference level, a higher level of SAGE1 complex, or (e) any combination thereof.

The presence or level of SAGE1 mRNA can be detected by any suitable nucleic acid assays known in the art, for example, a nucleic acid amplification assay, a nucleic acid hybridization assay, a nucleic acid sequencing assay, and other methods such as high performance liquid chromatography (HPLC) fragment analysis, capillary electrophoresis, and the like. The nucleic acid amplification assays, hybridization assays, and sequencing assays are described in below sections. In order to detect the presence and level of target RNA molecules by amplification assays or sequencing assays, RNA may need to be reverse transcribed into cDNA before the analysis.

The presence or level of SAGE1 protein can be detected by any suitable assays for detecting or quantifying polypeptide that are well known in the art. These may include analytic biochemical methods such as electrophoresis, capillary electrophoresis, high performance liquid chromatography (HPLC), thin layer chromatography (TLC), hyperdiffusion chromatography, mass spectrometry and the like, or various immunoassays. A skilled artisan can readily adapt known protein detection methods for use in determining the presence or level of SAGE1 protein expression.

The presence or level of SAGE1 can also be indicated by the presence or level of SAGE1 complex. "SAGE1 complex", "SAGE1-containing complex" and "complex containing SAGE1" are herein used interchangeably and refer to a protein complex comprises one or more proteins or polypeptides in addition to SAGE1 protein or fragment thereof. The present disclosure unexpectedly discovered that SAGE1 can form complexes with other proteins or polypeptides and exert biological functions via these complexes. For example, SAGE1 interacts with INTS3 to displace INTS6 from Integrator. Integrator is a large protein complex consists of at least 14 different subunits (INTS1 to INTS14) that plays a pivotal role in the regulation of most RNAPII dependent genes, including 3'-end processing of noncoding small nuclear RNAs, biogenesis of enhancer RNAs, transcription pause-release and processivity, and premature termination of Integrator target genes and enhancers. In some embodiments, the SAGE1 complex comprises SAGE1 and INTS3. In some embodiments, the SAGE1 complex is SAGE1-INTS3 complex. The SAGE1-INTS3 complex is capable of binding to the promotor proximal regions of genes engaged by Integrator and thereafter activate the transcription of such genes. The present disclosure found that the expression of SAGE1 evidently stimulates the expression of genes that are enriched in pathways essential for cell proliferation and cancer phenotype. In some embodiments, the SAGE1 complex further comprises one or more molecules selected from INIP, NABP1/2, CREBBP, TLE1, TLE2, TLE3, TLE4, TLE5, GGA3, CNOT1, TAX1BP1, SEC16A, CYLD and PAXBP1.

The presence or level of SAGE1 complex can be detected by any suitable methods for measuring protein-protein interaction. In certain embodiments, the protein-protein interaction assay is based on immunoassay or proximity assays, such as meso scale discovery (MSD) advanced enzyme-linked immunosorbent assay (MSD-ELISA), standard complex ELSIA, proximity ligation assay (PLA), co-immunoprecipitation, or immunoblotting assay. Immunoassays for detecting SAGE1 complex typically involves using antibodies that specifically bind to the components in the complex, or to an epitope unique to the complex, to detect or measure the presence or level of the complex. While most protein-protein interactions are transient and may dissociate during sample preparation, chemical or physical cross-linking can be used to stabilize or permanently adjoin the components of interaction of protein complexes. Once the components of a protein complex are covalently crosslinked, other steps (e.g., cell lysis, affinity purification, electrophoresis or mass spectrometry) can be used to analyze the protein-protein interaction while maintaining the original interacting complex.

The transcription of SAGE1 gene can be determined by measuring DNA methylation or DNA demethylation of SAGE1 gene. DNA methylation is a biological process by which methyl groups are added (for example, by the action of a DNA methyl transferase enzyme) to the DNA molecule (for example, to a cytosine base or bases of the DNA molecule). In mammals, DNA methylation is generally found at the 5' position of a cytosine-phosphate-guanine (CpG) dinucleotides (i.e. "CpG site"), which tend to be near transcription start sites, and can lead to epigenetic inactivation of genes. Conversely, in a DNA demethylation process the methyl groups can be removed from the methylated DNA molecule (e.g., change of a methlycytosine base into a cytosine) and lead to epigenetic activation of genes. In some embodiment, the presence, or relative to a reference level, a higher level of transcription of SAGE1 gene in indicated by a lower level of DNA methylation (or a higher level of DNA demethylation) of the SAGE1 gene relative to a reference level.

Human SAGE1 gene is located in the X chromosome (ChrX:135,893,700-135,913,026, Xq26.3 according to Genome Reference Consortium Human Build 38 patch release 13) with Gene ID of 55511 in NCBI database (the sequence is incorporated herein as SEQ ID NO: 1). DNA methylation in SAGE1 gene may occur either in the expression region (ChrX: 135,893,716-135,913,062), which is transcribed in SAGE1 mRNA, or the in non-expression region (e.g, ChrX: 135,890,700-135,893,715) 5' upstream the expression region. The expression region contains a stretch of DNA enriched in CpG (ChrX: 135,893,450-135, 893,866), which is designed as CpG-containing region. In some embodiments, the DNA methylation of SAGE1 gene is detected in the CpG-containing region of the SAGE1 gene. Cap Analysis of Gene Expression (CAGE) analysis of gene expression of SAGE1 gene shows that the transcription start site is located near ChrX: 135893700, and whole genome bisulfite sequencing (WGBS) further shows differential DNA methylation within a region that is 1 kb upstream or downstream of the transcription start site of SAGE1 gene across the cell lines having various levels of SAGE1 expression (based on WGBS date of K562: ENCSR765JPC, ENCSR481JIW (A549), ENCSR550RTN (HeLa-S3), retrieved from www.encodeproject.org). In some embodiments, the DNA methylation is detected in a region that is within 1 kb upstream and 1 kb downstream of the transcription start site of SAGE1 gene (i.e., a region spanning ChrX: 135,892,700-135,894,700). In some embodiments, the DNA methylation is detected in a region that is within 3 kb upstream and 3 kb downstream of the transcription start site of SAGE1 gene (i.e., a region spanning ChrX: 135,890,700-135,896,700).

DNA methylation can be determined by any suitable methods in the art. In some embodiments, a biological sample is treated with a reagent capable of distinguishing between unmethylated and methylated cytosine in the DNA contained in the biological sample to obtain treated DNA. Such reagents include, for example, bisulfites and methylation sensitive restriction enzyme. Bisulfites can selectively modify unmethylated cytosine and convert it into uracils while leaving the methylated cytosine intact. Following the conversion, DNA methylation at specific loci or gene(s) can be detected and measured by nucleic acid amplification assays, sequencing assays or hybridization assays as described below. In some embodiments, the DNA contained in the biological sample is amplified before the detection of DNA methylation.

The presence or level of transcription of SAGE1 gene can also be determined by measuring histone acetylation of SAGE1 gene. Histone acetylation is a biological process by which acetyl groups are added (for example, by the action of a histone acetyltransferase) to the N-terminus of histone proteins. Histone acetylation transforms condensed chromatin into a more relaxed structure that is associated with greater levels of gene transcription. In mammals, histone acetylation is generally found at $9^{th}$ or $27^{th}$ lysine residues of the histone H3 protein, or $16^{th}$ lysine residues of the histone H4 protein (H3K9ac, H3K27ac, H4K16ac). In some embodiment, the presence, or relative to a reference level, a higher level of transcription of SAGE1 gene in indicated by a higher level of histone acetylation of the SAGE1 gene relative to a reference level. In some embodiments, histone acetylation is detected in the non-expression region or the expression region of SAGE1 gene. In some embodiments, histone acetylation is detected near the enhancer or promoter region of SAGE1 gene. In some embodiments, the histone acetylation or binding of a transcription factor to SAGE1 gene is detected in a region that is within 1 kb upstream and 1 kb downstream of the transcription start site of SAGE1 gene (chrX:135,892,700-135,894,700). In some embodiments, the histone acetylation or binding of a transcription factor to SAGE1 gene is detected in a region that is within 3 kb upstream and 3 kb downstream of the transcription start site of SAGE1 gene (chrX:135,890,700-135,896,700).

The presence or level of transcription of SAGE1 gene can also be determined by measuring the binding of transcription factors to SAGE1 gene, such as the promoter region or enhancer region of SAGE1 gene. In some embodiments, the binding of a transcription factor to SAGE1 gene is detected in a region spanning from ChrX: 135,892,756-135,894,140. The transcription of SAGE1 gene is regulated by the transcription factors such as Myc and CTCF. In some embodiment, the presence, or relative to a reference level, a higher level of transcription of SAGE1 gene in indicated by the presence of or, relative to a reference level, a higher level of binding transcription factors to SAGE1 gene.

The histone acetylation and binding of transcription factors to SAGE1 gene can both be analyzed by chromatin immunoprecipitation assays (ChIP). ChIP can detect and relatively quantify specific protein-DNA interaction at a single locus or multiple loci. ChIP involves chemically or physically cross-linking proteins to DNA sequences, which is followed by shearing of DNA sequences into fragments, immunoprecipitation of the cross-linked complexes by antibodies specific to proteins of interest, reversal of the cross-linking to release the associated DNA fragments, and analysis of the resultant DNA fragments by nucleic acid amplification assays (e.g., endpoint or quantitative polymerase chain reaction), hybridization assays (e.g., ChIP-chip)), or sequencing assays (ChIP-seq). The nucleic acid amplification assays, hybridization assays, and sequencing assays have been described above. For detection of histone acetylation, useful antibodies include those specific for acetylated histones, such as anti-H3K9ac, anti-H3K27ac, anti-H4K16ac antibodies, and for detection of binding of transcription factors to SAGE1 gene, useful antibodies include anti-Myc antibody. ChIP-seq analysis of multiple tumor cell lines has revealed that the regions close to transcription start site of SAGE1 gene is enriched for H3K27ac modification and binding of an array of transcription factors.

Any suitable methods can be used for the detection of SAGE1 expression, for example, an immunoassay, an amplification assay, a hybridization assay, or a sequencing assay.

Amplification Assays

A nucleic acid amplification assay involves copying a target nucleic acid (e.g. DNA or RNA), thereby increasing the number of copies of the amplified nucleic acid sequence. Amplification may be exponential or linear. Exemplary nucleic acid amplification methods include, but are not limited to, amplification using the polymerase chain reaction ("PCR", see U.S. Pat. Nos. 4,683,195 and 4,683,202; *PCR Protocols: A Guide To Methods And Applications* (Innis et al., eds, 1990)), reverse transcriptase polymerase chain reaction (RT-PCR), quantitative real-time PCR (qRT-PCR); quantitative PCR, such as TaqMan®, nested PCR, ligase chain reaction (See Abravaya, K., et al., *Nucleic Acids Research,* 23:675-682, (1995), branched DNA signal amplification (see, Urdea, M. S., et al., AIDS, 7 (suppl 2):S11-S14, (1993), amplifiable RNA reporters, Q-beta replication (see Lizardi et al., *Biotechnology* (1988) 6: 1197), transcription-based amplification (see, Kwoh et al., *Proc. Natl. Acad. Sci. USA* (1989) 86: 1173-1177), boomerang DNA amplification, strand displacement activation, cycling probe technology, self-sustained sequence replication (Guatelli et al., *Proc. Natl. Acad. Sci. USA* (1990) 87:1874-1878), rolling circle replication (U.S. Pat. No. 5,854,033), isothermal nucleic acid sequence based amplification (NASBA), and serial analysis of gene expression (SAGE).

The level of nucleic acid can be quantified during the amplification assay, which is also known as real-time amplification or quantitative amplification. Methods of quantitative amplification are disclosed in, e.g., Gibson et al., *Genome Research* (1996) 6:995-1001; DeGraves, et al., *Biotechniques* (2003) 34(1): 106-10, 112-5; Deiman B, et al., *Mol Biotechnol.* (2002) 20(2): 163-79. Quantification is usually based on the monitoring of the detectable signal representing copies of the template in cycles of an amplification (e.g., PCR) reaction. Detectable signals can be generated by intercalating agents or labeled primer or labeled probes used during the amplification. Levels of the detected biomarker can be quantified using methods known in the art. As a quality control measure, level of an internal control biomarker may be measured. The skilled artisan will understand that an internal control biomarker can be inherently present in the sample and its level can be used to normalize the measured level of SAGE1 to offset any difference in the absolute amount of the sample. Alternatively, the level of nucleic acid can be quantified after the amplification assay Hybridization Assay Nucleic acid hybridization assays use probes to hybridize to the target nucleic, thereby allowing detection of the target nucleic acid. In certain embodiments, the probes for hybridization assay are detectably labeled. In certain embodiments, the nucleic acid-based probes for hybridization assay are unlabeled. Such unlabeled probes can be immobilized on a solid support such as a microarray, and can hybridize to the target nucleic acid molecules which are detectably labeled.

In certain embodiments, hybridization assays can be performed by isolating the nucleic acids (e.g. RNA or DNA), separating the nucleic acids (e.g. by gel electrophoresis) followed by transfer of the separated nucleic acid on suitable membrane filters (e.g. nitrocellulose filters), where the probes hybridize to the target nucleic acids and allows detection. See, for example, Molecular Cloning: A Laboratory Manual, J. Sambrook et al., eds., 2nd edition, *Cold Spring Harbor Laboratory Press,* 1989, Chapter 7. The hybridization of the probe and the target nucleic acid can be detected or measured by methods known in the art. For example, autoradiographic detection of hybridization can be performed by exposing hybridized filters to photographic film. Densitometric scanning of the photographic films exposed by the hybridized filters provides an accurate measurement of the target nucleic acid levels. Computer imaging systems can also be used to quantify the level of the biomarker.

Sequencing Assays

Sequencing assays (e.g., next-generation sequencing methods or third-generation sequencing methods) are useful in the detection of the presence and level of target DNA molecules, which involves sequencing of the target DNA and enumeration of the sequenced target DNA molecules. These sequencing methods are based on principals such as, sequencing-by-synthesis, sequencing-by-ligation, ultra-deep sequencing, or single molecule sequencing. For example, sequence-by-synthesis may involve synthesizing a complementary strand of the target nucleic acid by incorporating labeled nucleotide or nucleotide analog in a polymerase amplification. Immediately after or upon successful incorporation of a label nucleotide, a signal of the label is measured and the identity of the nucleotide is recorded. The detectable label on the incorporated nucleotide is removed before the incorporation, detection and identification steps are repeated. Sequencing-by-synthesis may be performed on a solid surface (or a microarray or a chip) using fold-back PCR and anchored primers. Target DNA fragments can be attached to the solid surface by hybridizing to the anchored primers, and bridge amplified. Examples of sequencing methods include, without limitation, Illumina® sequencing, pyrosequencing, supported oligonucleotide ligation and detection (SoLiD), Ion torrent technology, single-molecular real time (SMRT) sequencing, Helicos sequencing, Nanopore sequencing.

Immunoassays

Immunoassays typically involves using antibodies that specifically bind to the protein of interest. Such antibodies can be obtained using methods known in the art (see, e.g., Huse et al., *Science* (1989) 246:1275-1281; Ward et al, *Nature* (1989) 341: 544-546), or can be obtained from commercial sources. Examples of immunoassays include, without limitation, Western blotting, enzyme-linked immunosorbent assay (ELISA), enzyme immunoassay (EIA), radioimmunoassay (RIA), immunoprecipitations, sandwich assays, competitive assays, immunofluorescent staining and imaging, immunohistochemistry, and fluorescent activating cell sorting (FACS). For a review of immunological and immunoassay procedures, see *Basic and Clinical Immunology* (Stites & Terr eds., 7th ed. 1991). Moreover, the immunoassays can be performed in any of several configurations, which are reviewed extensively in *Enzyme Immunoassay* (Maggio, ed., 1980); and Harlow & Lane, supra. For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991).

Any of the assays and methods provided herein for the detection of SAGE1 expression can be adapted or optimized for use in automated and semi-automated systems, or point of care assay systems. When determining the level of SAGE1 expression, the level of SAGE1 expression detected by the assays as described herein can be normalized using a proper method known in the art. For example, the level of can be normalized to an internal control which can be an internal marker, or an average level or a total level of a plurality of internal markers.

In some embodiments, SAGE1 is a single biomarker to be detected in the method provided herein. In some embodiments, the detection of SAGE1 expression in the method provided herein comprises providing a biological sample obtained from a subject.

ix. Evaluation Based on SAGE1 Expression

SAGE1 is found to be expressed in cells with high sternness such as in totipotent human stem cells during embryonic development, but not expressed in most normal tissues. In contrast, SAGE1 is found expressed in various abnormal tissues, indicating that SAGE1 can be used as a biomarker for diagnosing SAGE1-positive disorders.

Based on detection of SAGE1 expression, methods are provided for diagnosing tumors that traditionally lack effective early detection, for evaluating tumor malignancy, progression, metastasis, relapse, prognosis and effects of tumor treatment, and for selecting targeted therapy. Compared with the existing traditional biomarkers, SAGE1 has higher specificity and has an accuracy close to 100% in distinguishing tumor from normal tissues.

In some embodiments, presence of SAGE1 expression in a biological sample that normally does not express SAGE1 indicates that the subject from whom the biological sample is derived has a SAGE1-positive disorder. In contrast, absence of the SAGE1 expression is indicative of absence of such a SAGE1-positive disorder.

Similarly, presence of SAGE1 expression in a tumor biological sample indicates that the tumor is likely to be malignant or has malignancy potential, or that the tumor is sensitive to treatment of a SAGE1 inhibitor, or that a subject is likely to be responsive to a SAGE1 inhibitor.

In some embodiments, level of SAGE1 expression can be determined and compared with a threshold level. The threshold level can be determined based on a positive reference sample which is known to express SAGE1 and a negative reference sample which is known to be absent for SAGE1 expression, and the threshold level can be a level that is sufficient to distinguish a positive reference sample from a negative reference sample.

In some embodiments, change in level of SAGE1 expression in a subject can indicate progression of the SAGE1 positive disorder, or responsiveness of the subject to a SAGE1 inhibitor. For example, increase in level of SAGE1 expression can indicate that the SAGE1 positive disorder has progressed, or the subject receiving SAGE1 inhibitor is likely not responding to the treatment or has developed resistance to the treatment.

x. Biological Sample

Any suitable biological samples can be used for detection of SAGE1 expression. In some embodiments, the biological sample is suspected of containing a SAGE1 positive cell, or a SAGE1 expression product, or a SAGE1 gene, or fragments thereof, among others.

In some embodiments, the biological sample contains an abnormal cell suspected of containing a SAGE1 expression product, or a SAGE1 gene, or fragments thereof, among others. In certain embodiments, the biological sample is of a type of sample that normally has no detectable SAGE1 expression. In certain embodiments, the biological sample does not contain a spermatogonial stem cell (SSC). In certain embodiments, the biological sample is derived from fallopian tube, salivary gland, adipose tissue, adrenal glad, blood, bladder, blood vessel, breast, cervix uteri, colon, esophagus, heart, kidney, liver, lung, muscle, nerve, ovary, pancreas, prostate, skin, small intestine, spleen, stomach, thyroid, uterus or vagina.

In some embodiments, the biological sample is selected from a cell, a tissue, a bodily fluid and any combination thereof. Suitable methods of obtaining a biological sample from a subject are known to a person of skill in the art. In general, the sample type (i.e., cell, tissue or bodily fluid) is selected based upon the accessibility and structure of the organ or tissue to be evaluated for tumor cell growth or upon what type of cancer is to be evaluated. A biological sample can include any bodily fluid or tissue from a subject that may contain tumor cells or contents (e.g., DNA, RNA, protein, subcellular organelles) of tumor cells. In some embodiments, the biological sample is selected from the group consisting of a tissue section, biopsy, a paraffin-embedded tissue, a bodily fluid, a surgical resection sample, and any combination thereof.

A bodily fluid can include intracellular fluid, extracellular fluid, or any mixture of the two. In some embodiments, the bodily fluid is selected from the group consisting of blood, serum, plasma, ascites, cyst fluid, pleural fluid, peritoneal fluid, cerebrospinal fluid, tears, urine, saliva, sputum, nipple aspirates, lymph fluid, fluid of the respiratory, intestinal, and genitourinary trances, breast milk, intra-organ system fluid, peritoneal fluid, conditioned media from tissue explant culture, or combinations thereof.

The biological sample can be used fresh, frozen, fixed or otherwise preserved. The biological sample can be prepared by any suitable method for the detection technique utilized. For example, the preparation involves isolating or extracting tumor cells (e.g., circulating tumor cells) from a bodily fluid sample. For another example, the preparation involves immobilizing a tissue sample in paraffin. The immobilized tissue is subsequently sectioned and contacted with an antibody for detection of binding of the antibody to a target (e.g., SAGE1 protein or SAGE1 complex). In certain embodiments, the biological sample is processed to isolate proteins, DNAs (e.g. genome DNAs or cell free DNAs), mRNAs or subcellular organelles for detection of SAGE1 expression.

xi. Kit for Detection of SAGE1 Expression

In another aspect, the present disclosure provides a kit for use in any of the methods disclosed herein, wherein the kit comprises one or more reagents for detecting SAGE1 expression.

In some embodiment, the one or more reagents for detecting SAGE1 expression is selected from: a reagent for detecting presence or level of SAGE1 protein; a reagent for detecting presence or level of SAGE1 mRNA; a reagent for detecting presence or level of a SAGE1 complex; a reagent for detecting level of methylation of in the SAGE1 gene; a reagent for detecting presence or level of histone acetylation of the SAGE1 gene; a reagent for detecting presence or level of binding of a transcription factor to the SAGE1 gene, or any combination thereof.

In certain embodiments, the kit comprises one or more of agents, such as primers, probes, and/or antibodies. The agents can be specific for detection of SAGE1 genomic DNA, SAGE1 mRNA, SAGE1 protein, SAGE1 complex, methylated or unmethylated cytosine or the converted nucleotide thereof, or can be specific for detection of acetylated histones, or transcription factors, which are bound to the SAGE1 genomic DNA.

In some embodiments, the kit contains at least one agent selected from a SAGE1-specific oligonucleotide primer, a SAGE1-specific oligonucleotide probe, an anti-SAGE1 antibody, and an anti-SAGE1 complex antibody.

The term "primer" and "probe" with respect to nucleic acid as used herein refer to oligonucleotides that can specifically hybridize to a target polynucleotide sequence, due to the sequence complementarity of at least part of the primer within a sequence of the target polynucleotide sequence. Primers are useful in nucleic acid amplification and sequencing assays in which the primer is extended to produce a new strand of the polynucleotide. Probes are useful for identification of target nucleic acid in a sample by hybridizing to such target nucleic acid. Primers and probes can be readily designed by a skilled artisan using common knowledge known in the art, such that they can specifically anneal to the nucleotide sequence of the target nucleotide sequence of provided herein. A primer or probe can have a length of at least 8 nucleotides, typically 8 to 70 nucleotides, usually of 18 to 26 nucleotides. For proper hybridization to the target sequence, a primer can have at least 75%, at least 80%, at least 85%, at least 90%, or at least 95% sequence complementarity to the hybridized portion of the target polynucleotide sequence.

In certain embodiments, the primers or probes provided herein comprise a polynucleotide sequence hybridizable to a portion (e.g. at least 6, 7, 8, 9, 10, 11, 12, 13, 14, 15, 16, 17, 18, 19, 20 or more consecutive nucleotides) within the sequence of SAGE1 genomic DNA (SEQ ID NO: 1) or mRNA (SEQ ID NO: 2). In certain embodiments, the primes or probes provided herein comprise a polynucleotide sequence having at least 60%, 65%, 70%, 75%, 80%, 85%, 90%, 95%, 97%, 98%, 99% or 100% complementarity to a portion (e.g. at least 66, 7, 8, 9, 10, 11, 12, 13, 14, 15, 16, 17, 18, 19, 20 or more consecutive nucleotides) within the sequence of SAGE1 genomic DNA (SEQ ID NO: 1) or mRNA (SEQ ID NO: 2).

In certain embodiments, the antibody provided herein comprise an antigen-binding region capable of specifically binding to an epitope within SAGE1 protein having the sequence of SEQ ID NO: 3.

The primers, the probes, and/or the antibodies provided herein may or may not be detectably labeled. The term "detectable label" as used herein refers to a molecule or moiety that allows detection. The term "detectably labeled" with respect to a reagent means that the reagent comprises a detectable label or can be bound by a detectable label. In certain embodiments, the primers, the probes and the antibodies provided herein can specifically bind to a ligand which is detectably labeled. Examples of the detectable label suitable for labeling primers, probes and antibodies include, for example, chromophores, radioisotopes, fluorophores, chemiluminescent moieties, particles (visible or fluorescent), nucleic acids, ligand, or catalysts such as enzymes. It should be understood that it is not necessary for a detectable label to produce a detectable signal by itself, for example, in some embodiments, it may can react with a detectable partner or react with one or more additional compounds to generate a detectable signal. For another example, enzymes are useful a detectable label due to their catalytic activity to catalyze chromo-, fluoro-, or lumo-genic substrate which results in generation of a detectable signal.

In certain embodiments, the kits may further comprise other agents to perform the methods described herein. In such applications the kits may include any or all of the following: suitable buffers, reagents for isolating nucleic acid, reagents for amplifying the nucleic acid (e.g. polymerase, dNTP mix), reagents for sequencing the nucleic acid, reagents for quantifying the nucleic acid (e.g. intercalating agents, detection probes), reagents for isolating the protein, and reagents for detecting the protein (e.g. secondary antibody).

In some embodiments, the kits may include agents for detection of methylation. In such applications the kits include a conversion reagent capable of distinguishing between unmethylated and methylated CpG site(s) in the DNA for treating a DNA. In some embodiments, the reagent is bisulfite reagent. The bisulfite reagent can be selected from, e.g., the group consisting of ammonium bisulfite, sodium bisulfite, potassium bisulfite, calcium bisulfite, magnesium bisulfite, aluminum bisulfite, hydrogen sulfite and any combination thereof. Alternatively, the bisulfite reagent is commercially available, for example, MethylCode™ Bisulfite Conversion Kit, EpiMark™ Bisulfite Conversion Kit, EpiJET™ Bisulfite Conversion Kit, EZ DNA Methylation-Gold™ Kit, etc. In some embodiments, the reagent is a methylation sensitive restriction enzyme (MSRE). In some embodiments, the MSRE is selected from the group consisting of HpaII, SalI, SalI-HF®, ScrFI, BbeI, NotI, SmaI, XmaI, MboI, BstBI, ClaI, MluI, NaeI, NarI, PvuI, SacII, HhaI and any combination thereof.

Typically, the reagents useful in any of the methods provided herein are contained in a carrier or compartmentalized container. The carrier can be a container or support, in the form of, e.g., bag, box, tube, rack, and is optionally compartmentalized.

In certain embodiments, the kits can further comprise a standard negative control, and/or a standard positive control.

In addition, the kits may include instructional materials containing directions (i.e., protocols) for the practice of the methods provided herein. While the instructional materials typically comprise written or printed materials they are not limited to such.

In another aspect, the present disclosure provides use of a substance for detecting SAGE1 gene or an active fragment thereof in the preparation of a kit for diagnosing a tumor. The kit can detect the expression level of the SAGE1 gene or an active fragment to diagnose tumor or determine whether SAGE1-targeted therapy is suitable for a subject. The inventor finds that the expression of SAGE1 gene or active fragment thereof is closely related to whether a subject has tumor and that SAGE1-targeted therapy is more suitable for a tumor patient having positive expression or high expression of SAGE1. The present disclosure demonstrates that inhibition of SAGE1 can significantly inhibit the proliferation, migration and anchorage-independent growth of tumor cell while colonogenic capacity of tumor cells can be restored if the disrupted expression of SAGE1 is restored.

In some embodiments, SAGE1 is a single biomarker in the kit. The kit does not include substances for detecting other biomarkers in addition to the substance for detecting SAGE1 gene or active fragments thereof.

IV. Targeting SAGE1 and SAGE1 Complex for Disease Treatment

In another aspect, the present disclosure provides a SAGE1 inhibitor, and its use in treating a SAGE1-positive disorder.

The present disclosure surprisingly found that inhibiting the expression and/or function of SAGE1 could significantly inhibit proliferation, migration, anchorage-independent growth and the like of in a variety of tumor cells that express SAGE1, while restoration of SAGE1 expression could restore the tumorigenicity of the cells, thereby demonstrating that SAGE1 inhibitors could be used as for treating tumors. Further, SAGE1 is specifically expressed in various tumor tissues and but not in normal tissues except testis. Although SAGE1 protein is typically located in nucleus, peptide fragments of the protein are presented on the surface of tumor cells by major histocompatibility complex (WIC), which can be utilized for target recognition and/or immune activation in tumor therapy. Hence, SAGE1-targeted therapy provides high specificity, not affecting normal tissues with SAGE1 expression.

The term "SAGE1 inhibitor" as used herein refers to an agent that reduces SAGE1 level or SAGE1 mediated biological activity. For example, the SAGE1 inhibitor can partially inhibit, i.e., reduce the expression and/or activity of SAGE1, or completely inhibit, i.e., completely eliminate the expression and/or activity of SAGE1, which includes the ability of SAGE1 binding to INTS3 to form SAGE1-INTS3 complex. Reduction of SAGE1 level can be achieved by inhibiting transcription of SAGE1 gene, reducing SAGE1 mRNA level or reducing SAGE1 protein level. Inhibition of SAGE1 biological activity can be achieved by inhibition of SAGE1 from binding to or activating one or more of its binding partners.

SAGE1 inhibitor can be any suitable type of inhibitors. In some embodiments, the SAGE1 inhibitor comprises a nucleic acid molecule (e.g. polynucleotide or oligonucleotide,), a polypeptide, a compound (e.g. chemical compound,), or an antibody or an antigen-binding fragment thereof. In some embodiments, the SAGE1 inhibitor provided herein is not a chimeric receptor or a T cell receptor. In some embodiments, the SAGE1 inhibitor provided herein is not a chimeric receptor or a T cell receptor that binds to an SAGE1 epitope or binds to an MHC-associated epitope of SAGE1.

i. Nucleic Acid

In some embodiments, the SAGE1 inhibitor comprises a nucleic acid molecule. In some embodiments, the SAGE1 inhibitor comprises an oligonucleotide targeting SAGE1 nucleic acid such as SAGE1 mRNA or SAGE1 gene, or a polynucleotide encoding the oligonucleotide, or a nucleic acid vector comprising the oligonucleotide or the polynucleotide.

The oligonucleotide targeting SAGE1 nucleic acid can include both single stranded and double-stranded oligonucleotides. Examples include, without limitation, antisense oligonucleotides, small interfering RNAs (siRNA), micro RNAs (miRNA), small hairpin RNA (shRNA), CRISPR/Cas9-guide RNAs, and other oligomeric compounds or oligonucleotide mimetics.

The oligonucleotide can target any suitable portion of SAGE1 nucleic acid. The term "portion" as used herein refer to a defined number of contiguous nucleotides of an oligonucleotide or nucleic acid. A suitable target portion of SAGE1 can be determined by a skilled person in the art, for example, to have a sufficiently unique sequence so as to minimize undesirable off-target binding, and/or to be sufficiently accessible to oligonucleotide binding despite of the secondary or tertiary structure of the SAGE1 nucleic acid. A variety of tools are available to this end. For example, the BLAST algorithm can be used to compare the sequence of SAGE1 nucleic acid to other sequences throughout the genome, to prevent selection of target portions that may hybridize in a non-specific manner to sequences other than a selected target nucleic acid (i.e., non-target or off target sequences). In some embodiment, the target portion of SAGE1 nucleic acid is of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more nucleotides in length, or is between a range defined by any two of the above lengths.

In some embodiments, the SAGE1 nucleic acid is SAGE1 mRNA. The target portions in SAGE1 mRNA may be located in a structurally defined region of SAGE1 mRNA, such as a 3' UTR, a 5' UTR, an intron, an exon/intron junction, a coding region, a translation initiation region, or a translation termination region. In some embodiments, the target portion of SAGE1 mRNA comprises at least 6 (e.g., 7, 8, 9, 10, 11, 12, 13, 14, 15, 16, 17, 18, 19, 20, 21, 22, 23, 24, 25, 26, 27, 28, 29, 30) consecutive nucleotides within a sequence spanning from nucleotides 266-366, 866-1116. 1316-1616, 1916-2266, 2466-2666, 2782-2946 of SEQ ID NO: 2. In some embodiments, the target portion of SAGE1 mRNA can be selected from the group consisted of the sequences spanning from nucleotides 282-310, 333-351, 1076-1094, 880-898, 1933-1951, 2148-2166, 1471-1489, 2493-2511, 1331-1349, 2215-2233, 1559-1579, 2799-2819 of SEQ ID NO: 2. In some embodiments, the target portion of SAGE1 mRNA comprises the sequences selected from a group consisting of SEQ ID NOs: 11-67.

In some embodiments, the SAGE1 nucleic acid is SAGE1 genomic DNA. The target portions in SAGE1 genomic DNA may be located in the non-coding region or coding region of SAGE1 genomic DNA. In some embodiments, the target portion of SAGE1 genomic comprises the sequences selected from SEQ ID NOs: 68 and 69.

In some embodiments, the SAGE1 inhibitor comprises a sequence complementary to a target portion in SAGE1 nucleic acids (e.g. genomic DNA or mRNA) and inhibit its expression or function. 100% complementarity between the sequence of the oligonucleotide and the targeted portion of SAGE1 nucleic acids may not be required. In certain embodiments, the SAGE1 inhibitor comprises a sequence at least, 70%, 75%, 80%, 85%, 86%, 87%, 88%, 89%, 90%, 91%, 92%, 93%, 94%, 95%, 96%, 97%, 98%, 99%, or 100% complementary to the targeted portion of SAGE1 nucleic acid. The level of complementarity is considered sufficient when the hybridization between an oligonucleotide and the SAGE1 target nucleic acid can lead to a desired effect. The desired effects include, without limitation, a reduction in mRNA levels of the target nucleic acid, a reduction in the levels of protein encoded by the target nucleic acid or a phenotypic change associated with the target nucleic acid.

In some embodiments, the oligonucleotide targeting SAGE1 nucleic acid is at least 8 to 80, 10 to 80, 12 to 50, 15 to 30, 18 to 24, 19 to 22, or 20 nucleotides or base pairs in length. In some embodiments, the oligonucleotide is 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides or base pairs in length, or is between a range defined by any two of the above lengths.

In some embodiments, the oligonucleotides can be chemically modified. The modifications encompass substitutions or changes to internucleoside linkage, sugar moiety of a nucleotide or nucleobase of a nucleotide. Modified oligonucleotides can have desirable properties such as, for example, enhanced cellular uptake, enhanced affinity for nucleic acid target, increased stability in the presence of nucleases, or increased inhibitory activity. Chemically modified nucleotides can also be employed to increase the binding affinity of a shortened or truncated oligonucleotide for its target nucleic acid.

The naturally occurring internucleoside linkage of RNA and DNA is a 3' to 5' phosphodiester linkage. Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Representative non-phosphorus containing internucleoside linkages include, but are not limited to, amide backbones, morpholino backbones, and peptide nucleic acid (PNA) backbone. Methods of preparation of phosphorous-containing and non-phosphorouscontaining linkages are well known. In certain embodiments, oligonucletodies targeted to an SAGE1 nucleic acid comprise one or more modified internucleoside linkages.

The oligonucleotides of the present disclosure can contain one or more nucleosides wherein the sugar group has been modified. In certain embodiments, nucleosides comprise chemically modified ribofuranose ring moieties. Examples of chemically modified ribofuranose rings include without limitation, addition of substitutent groups (including 2', 3' and 5' substituent groups), bridging of non-geminal ring atoms to form bicyclic nucleic acids (BNA), replacement of the ribosyl ring oxygen atom with S, N(R), or C(R1)(R2) (R, R1 and R2 are each independently H, C1-C2 alkyl or a protecting group) and combinations thereof. Oligonucleotides may also have sugar mimetics such as cyclobutyls in place of the pentofuranosyl group.

Nucleobase (or base) modifications or substitutions are structurally distinguishable from, yet functionally interchangeable with, naturally occurring nucleobases. As used herein, "natural" nucleobases include adenine (A), guanine (G), thymine (T), cytosine (C) and uracil (U). Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, inosine, hypoxanthine, 6-methyladenine, 5-Me pyrimidines (e.g, 5-methylcytosine (5-me-C)), 5-hydroxymethylcytosine (HMC), glycosyl HMC, gentobiosyl HMC., as well as synthetic nucleobases, e.g., 2-aminoadenine, 2-(methylamino)adenine, 2-(imidazolylalkyl) adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N 6 (6-aminohexyl)adenine, 2,6-diaminopurine; 5-ribosyluracil (Carlile (2014) Nature 5 15(7525): 143-6).

It is not necessary for all positions in a given oligonucleotide to be uniformly modified, and in fact more than one of the aforementioned modifications may be incorporated in a single oligonucleotide or even at within a single nucleoside within an oligonucleotide. In some embodiments, both the nucleobase and backbone may be modified. In some embodiments, both a sugar and an internucleoside linkage. In some embodiments, the oligonucleotides are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Such chimeric oligonucleotides have also been referred to in the art as hybrids or gapmers.

The oligonucleotides may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

The oligonucleotides can also be modified to have one or more stabilizing groups that are generally attached to one or both termini of the oligonucleotides to enhance properties such as, for example, nuclease stability. These terminal modifications protect the oliogonucleotides from exonuclease degradation, and can help in delivery and/or localization within a cell. Included in stabilizing groups are cap structures. The cap can be present at the 5'-terminus (5-cap), or at the 3'-terminus (3'-cap), or can be present on both termini.

ii. Antisense Oligonucleotides

In some embodiments, the SAGE1 inhibitor provided herein are oligonucleotides. In some embodiments, the oligonucleotides are antisense oligonucleotides. Antisense oligonucleotides are typically designed to block expression of a DNA or RNA target by binding to the target and halting expression at the level of transcription, translation, or splicing. Antisense oligonucleotides of the present disclosure are antisense nucleic acid sequences designed to hybridize under stringent conditions to an SAGE1 nucleic acid. "Stringent condition" as used herein refers to a condition under which a sequence will hybridize to its target sequence but will not hybridize to other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the melting temperature (Tm) for the specific sequence at a defined ionic strength and pH. Thus, oligonucleotides are chosen that are sufficiently complementary to the target, i.e., that hybridize sufficiently well and with sufficient specificity, to give the desired effect, while striving to avoid significant off-target effects i.e. must not directly bind to, or directly significantly affect expression levels of, transcripts other than the intended target.

The optimal length of the antisense oligonucleotide may very (e.g., 12-18 nucleotides in length) while ensuring that its target sequence is unique in the transcriptome (Seth (2009) J Med Chem 52: 10-13). In some embodiments, the antisense oligonucleotides include one or more modifications as described herein. For example, the modified internucleoside linkage of the antisense oligonucleotide is a phosphorothioate internucleoside linkage, the modified sugar is a bicyclic sugar or 2'-O-methyoxyethyl and the modified nucleobase is a 5-methylcytosine. For another example, the antisense oligonucleotide is a gamper, comprising a gap segment consisting of linked deoxynucleosides, a 5' wing segment consisting of linked nucleosides and a 3' wing segment consisting linked nucleosides, and wherein the gap segment is positioned immediately adjacent to and between the 5' wing segment and the 3' wing segment and wherein each nucleoside of each wing segment comprises a modified sugar.

iii. Interfering Oligonucleotides

In some embodiments, the oligonucleotide is a double-stranded interfering oligonucleotides, including but not limited to a small interfering RNA ("siRNA") or a small hairpin RNA ("shRNA"). The double-stranded interfering oligonucleotides is capable of cause translational repression or degradation of target mRNAs.

The interfering RNA (e.g., siRNA) can be assembled from two separate oligonucleotides, where one strand is the sense strand and the other is the antisense strand, wherein the antisense and sense strands are self-complementary and form a duplex or double stranded structure; the antisense strand comprises nucleotide sequence that is complementary to at least a portion of a target nucleic acid molecule and the sense strand comprises nucleotide sequence corresponding to at least a portion of the target nucleic acid sequence. In some embodiments, the double-stranded structure is about 15 to about 30, e.g., about 15, 16, 17, 18, 19, 20, 21, 22, 23, 24, 25, 26, 27, 28, 29 or 30 base pairs. In some embodiments, the siRNA has a 3' overhangs (e.g., a doublet such as dTdT) on each strand. In some embodiments, the siRNA comprises a pair of sense RNA strand/antisense RNA strand with or without 3' dTdT overhangs selected from the group consisting of SEQ ID NOs: 70/71, 72/73, 74/75, 76/77, 78/79, 80/81.

Alternatively, interfering RNA (e.g., shRNA) can be a single oligonucleotide, where the self-complementary sense and antisense regions are linked by means of nucleic acid based or non-nucleic acid-based linker(s). In some embodiments, the interfering RNA is a shRNA having a sense region, an antisense region and a loop region. The loop region is generally between about 2 and about 10 nucleotides in length. In some embodiments, the loop region is from about 6 to about 9 nucleotides in length. In some embodiments, the sense region and the antisense region are between about 15 to about 30 nucleotides (e.g., about 15, 16, 17, 18, 19, 20, 21, 22, 23, 24, 25, 26, 27, 28, 29 or 30 nucleotides) in length. Following post-transcriptional processing, the shRNA can be converted into a siRNA by a cleavage event mediated by the enzyme Dicer.

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition.

In some embodiments, the shRNA useful in the present disclosure comprises the sequences selected from the group consisting of SEQ ID NOs: 82-95 and 106-145.

In some embodiments, the double-stranded interfering oligonucleotides include one or more modifications as described herein. In some embodiments, the double-stranded interfering oligonucleotides need not be limited to those molecules containing only RNA, but further encompasses chemically modified nucleotides. For example, both strands consist entirely of ribonucleotides, one strand consists entirely of ribonucleotides and one strand consists entirely of deoxyribonucleotides, or one or both strands contain a mixture of ribonucleotides and deoxyribonucleotides.

iv. CRISPR/Cas

CRISPR-Cas genome editing system, typically comprising a non-specific CRISPR-associated endonuclease (endonuclease (Cas, e.g. Cas9) and a guide RNA, enable efficient genome editing in a wide variety of organisms and cell types (Doudna & Charpentier, Science 346, 1258096 (2014)). The CRISPR/Cas genome editing system can also be used to inhibit expression of SAGE1. In some embodiments, the oligonucleotide is a guide RNA. Terms "sgRNA" and "guide RNA" are herein used interchangeably and refer to a short RNA comprising a "scaffold" sequence necessary for Cas9-binding and a user-defined nucleotide "spacer" or "targeting" or "guide" sequence which is complementary to at least a portion of a target genomic DNA. The term "guide sequence" herein also includes the corresponding DNA or DNA encoding the RNA guide sequence. The target site recognition by Cas9 is programmed by both the guide sequence of the guide RNA and the recognition of a short neighboring PAM. Guide RNAs can be designed using standard tools well known in the art.

The genomic target of Cas9 can be changed by changing the guide sequence present in the guide RNA. The guide sequence of the guide RNA sequence may be within or outside a loci of a gene. In general, a guide sequence can be any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence is about or more than about 50%, 60%, 75%, 80%, 85%, 90%, 95%, 97.5%, 99%, or more. In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length.

In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfoid, developed at Institute for Theoretical Chemistry at the University of Vienna, using the centroid structure prediction algorithm (see e.g. A. R. Gruber et al, 2008, Cell 106(1): 23-24; and P A Carr and GM Church, 2009, Nature Biotechnology 27(12): 1151-62).

In some embodiments, the guide sequence is complementary to a portion of SAGE1 genomic comprises the sequences selected from a group consisting of SEQ ID NO: 68 and 69. In some embodiments, the guide RNA comprises the sequence selected from the group consisting of SEQ ID NOs: 146 and 147.

v. SAGE1 Complex Inhibitor

In some embodiments, the SAGE1 inhibitor provided herein comprises a SAGE1 complex inhibitor.

The term "SAGE1 complex inhibitor" as used herein refers to an agent that is capable of reducing the level or activity of SAGE1 complex. For example, a SAGE1 complex inhibitor may inhibit formation of a SAGE1 complex or render the SAGE1 complex inactive or reduce biological activity of the SAGE1 complex. The biological activities of SAGE1 complex (e.g., SAGE1-INTS3 complex) including, without limitation, binding of SAGE1 complex to DNA (e.g., promotor proximal regions of genes that are typically engaged by Integrator) and regulating the transcription of genes.

In some embodiments, the SAGE1 complex inhibitor inhibit formation of a SAGE1 complex. In some embodiments, the SAGE1 complex inhibitor inactivates a SAGE1 complex. In some embodiments, the SAGE1 complex inhibitor reduce biological activity of a SAGE1 complex.

The present disclosure has provided a variety of SAGE1 complexes. Protein-protein interactions between SAGE1 and other binding partners can be identified and examined using, for example, immunoprecipitation techniques (see, e.g., Hamilton B. J., et al. Biochem. Biophys. Res. Commun.

1999, 261:646-51). SAGE1 can be immunoprecipitated from SAGE1-expressing cell lines using anti-SAGE1 antibodies. Alternatively, antibodies against His-tag can be used in a cell line engineered to express fusions of SAGE1 and a His-tag. The immunoprecipitated complex can be examined for protein association by procedures such, as Western blotting, $^{35S}$-methionine labeling of proteins, protein microsequencing, silver staining and two-dimensional gel electrophoresis.

In some embodiments, the SAGE1 complex comprises SAGE1 in complex with at least one component selected from the group consisting of INTS3, INIP (UniProt Accession: Q9NRY2), NABP1/2 (UniProt Accession: Q96AH0, Q9BQ15), CREBBP (UniProt Accession: Q92793), TLE1 (UniProt Accession: Q04724), TLE2 (UniProt Accession: Q04725), TLE3 (UniProt Accession: Q04726), TLE4 (UniProt Accession: Q04727), TLE5 (UniProt Accession: Q08117), GGA3 (UniProt Accession: Q9NZ52), CNOT1 (UniProt Accession: A5YKK6), TAX1BP1 (UniProt Accession: Q86VP1), SEC16A (UniProt Accession: 015027), CYLD (UniProt Accession: Q9NQC7) and PAXBP1 (UniProt Accession: Q9Y5B6), or any combination thereof. Any inhibitor that inhibits a complex formed by SAGE1 and the at least one component is contemplated herein.

In some embodiments, the SAGE1 complex comprises SAGE1 in complex with INTS3. In some embodiments, the SAGE1-complex inhibitor inhibits the interaction between SAGE1 and INTS3 to reduce the level of SAGE1 complex. In some embodiments, the SAGE1-complex inhibitor blocks binding of SAGE1 to INTS3.

The present disclosure surprisingly found that inhibition of SAGE1 complex in tumor cells can inhibit tumor growth, and tumor cell proliferation could be restored by expression of exogenous wild type SAGE1 but not by expression of mutant SAGE1 in which residues putatively responsible for interaction with INTS3 are mutated. The present disclosure also found that the differential expression of genes in response to reduction of SAGE1 expression is consistent with the reduction of INTS3. These findings indicated that SAGE1 can form a complex with INTS3 to function, and demonstrated that disruption of SAGE1 and INTS3 interaction or reduction of the amount of SAGE1-INTS3 complex in a SAGE1-positive cell can be useful in treatment of SAGE1-positive tumors.

In some embodiments, the SAGE1 complex inhibitor disrupts interaction between SAGE1 and the component (e.g. INTS3) in complex with SAGE1. In some embodiments, the SAGE1 complex inhibitor disrupts interaction between SAGE1 and INTS3. The disruption can be mediated by blocking the amino acid residues in SAGE1 protein that are involved in interaction with INTS3. As used herein, SAGE1-INTS3 complex generally refers to the complex formed between SAGE1 (or a fragment thereof) and INTS3 (or a fragment thereof) by protein-protein interaction. The INTS3 may typically form a dimer, and the formed dimer may further form SAGE1-INTS3 complex with SAGE1. According to a crystal structure of a complex comprising a C-terminal fragment of SAGE1 (residues 818-904 of SEQ ID NO: 3) and a C-terminal fragment of INTS3 (residues 572-978 of SEQ ID NO: 5), the amino acid residues of SAGE1 at the binding interface with INTS3 can include at least one or more residue selected from the group consisting of F838, F873, K874, M832, V876, R872, K828, R836 and Q840 (residue numbered according to SEQ ID NO: 3). In some embodiments, the SAGE1-complex inhibitor binds to or prevents INTS3 binding to at least one or more of the residues selected from F838, F873, K874, M832, V876, R872, K828, R836 and Q840 on SAGE1. For example, the SAGE1-complex inhibitor may compete against INTS3 for binding to at least one or more of the binding interface residues on SAGE1, or may bind to SAGE1 or INTS3 in a way that allosterically changes conformation of SAGE1 or INTS3 to reduce or abolish binding between SAGE1 and INTS3.

SAGE1-complex inhibitor can be any suitable type of inhibitors, for example, a nucleic acid molecule (e.g. polynucleotide or oligonucleotide,), a polypeptide, a compound (e.g. chemical compound,), or an antibody or an antigen-binding fragment thereof.

a) Compound

In some embodiment, the SAGE1 complex inhibitor comprises a compound which can inhibit the formation of SAGE1 complex (e.g., SAGE1-INTS3 complex). The compounds can be obtained using any of the numerous approaches in combinatorial library methods known in the art, including: spatially addressable parallel solid phase or solution phase libraries; synthetic library methods requiring deconvolution; the "one-bead one-compound' library method; and synthetic library methods using affinity chromatography selection. (Lam, K. S. (1997) Anticancer Drug Des. 12: 145).

The compound suitable for the purpose of the present disclosure can bind either to an active binding site or allosteric binding site of SAGE1. Active binding site refers to a region of SAGE1, as a result of its shape and charge potential, favorably interactive with another component (e.g., INTS3) of SAGE1 complex via various covalent and/or non-covalent binding force. Allosteric binding site refers to a region of SAGE1 other than the active binding site, binding to which by a modulator causes conformational change of SAGE1 and affects the activity of SAGE1. In some embodiments, the compound competes with INTS3 for binding to an active binding site of SAGE1. For example, the compound can displace an INTS3 protein or a fragment thereof bound to SAGE1 and leads to the disassembly of a SAGE1 complex and inhibition of its activity. In some embodiments, the compound binds to an allosteric binding site of SAGE1 and does not compete with INTS3.

Compounds can be screened in cell based or non-cell based assays disclosed here. Compounds can be also be virtually screened by the method disclosed herein. In some embodiment, a lead compound is initially identified and the pharmacophore thereof that is necessary for binding to SAGE1 is subsequently determined Computer modeling may be followed to generate to design and select a series of candidate compounds that share the same pharmacophore with the lead compound but show improved pharmacological properties. Compounds can be screened in pools (e.g. multiple compounds in each testing sample) or as individual compounds.

b) Anti-SAGE1 Antibodies

In some embodiment, the SAGE1 complex inhibitor comprises an antibody or a fragment thereof.

In some embodiment, the SAGE1 complex inhibitor comprises an antibody or a fragment thereof that: (a) specifically binds to SAGE1, or (b) specifically binds to the component (e.g. INTS3 and any components disclosed herein) in complex with SAGE1, or (c) specifically binds to the SAGE1 complex but not binding to SAGE1 or to the component in complex with SAGE1.

In some embodiment, SAGE1 complex inhibitor comprises antibodies or fragments thereof can bind specifically to SAGE1 or a fragment of SAGE1 that may interact with INTS3, thereby blocking the interaction between SAGE1 and INTS3.

The SAGE1 protein or a fragment of SAGE1 (e.g., residues 818-904 of SEQ ID NO: 3) that interacts with INTS3 can be used as an immunogen to generate antibodies that bind to said immunogen, using standard techniques for polyclonal and monoclonal antibody preparation according to well-known methods in the art. An antigenic peptide typically comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues. In one embodiment such epitopes can be specific for a given polypeptide molecule from one species, such as mouse or human.

Additionally, recombinant polypeptide antibodies, such as chimeric and humanized monoclonal antibodies, comprising both human and non-human portions, which can be made using standard recombinant DNA techniques, are within the scope of the invention. Fully human antibodies that is made against SAGE1 protein or a fragment thereof is also within the scope of the invention. The fully human antibody can be prepared by using mice of which a constant region of human immunoglobulin gene have been transferred, and a target antibody can be mass-produced by making the antibody production lymphocytes separated from mice to hybridomas. It also can be prepared by phage display method, by using phages that incorporates the human antibody gene and display the human antibody on the surface of the phage as a form fused with coat protein of the phages.

In some embodiments, the antibody or antigen binding fragment of the present disclosure is a monoclonal antibody, a bispecific antibody, a multi-specific antibody, a recombinant antibody, a labeled antibody, a bivalent antibody, an anti-idiotypic antibody, a dimerized, polymerized antibody, or a modified antibody (e.g. glycosylated antibody). In some embodiments, the antibody or antigen binding fragment of the present disclosure is a diabody, a Fab, a Fab', a F(ab')2, a Fd, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), an scFv dimer (bivalent diabody), a bispecific scFv dimer, a multispecific antibody, a heavy chain antibody, a camelized single domain antibody, a nanobody, a domain antibody, or a bivalent domain antibody.

c) Inhibitory Polypeptide

In some embodiment, the SAGE1 complex inhibitor comprises a polypeptide. Polypeptide useful in the present disclosure include polypeptides which may be a fragment, or variant, or derivative of SAGE1 that retain the ability to bind to a component (e.g. INTS3) in complex with SAGE1, or may be a fragment, or variant, or derivative of such a component (e.g. INTS3) in complex with SAGE1 that retain the ability to bind SAGE1, but the resultant complexes lack the activity of the SAGE1 complex (e.g. SAGE1-INTS3 complex) in regulating gene transcription.

In some embodiments, the SAGE1 complex inhibitor comprises a SAGE1-binding fragment of INTS3, or a variant or derivative thereof. The polypeptide fragment of INTS3 bind to SAGE1 and interferes with the binding of SAGE1 to INTS3. The terms "variant" refers to a polypeptide having one or more amino acid residue changes or modification relative to a naturally occurring polypeptide. Variant polypeptide may have an amino acid sequence having at least 50%, 60%, 70%, 80%, 85%, 90%, 95%, 98% or 100% identity to the amino acid sequences of INTS3 or a fragment of INTS3. Exemplary amino acid sequence of INTS3 is shown in SEQ ID NO: 5. In some embodiments, the polypeptide fragment of INTS3 comprises a C-terminal fragment of INTS3. The C-terminal fragment of INTS3 may comprise the last 500, 400, 300, 250, 200 or 150 residues from the C-terminus, or the 500-100, 400-100, 300-100, 200-100, 500-50, 400-50, 300-50, or 200-50 residues from the C-terminus. In some embodiments, the C-terminal SAGE1-binding fragment of INTS3 comprises an amino acid sequence of SEQ ID NO: 9 (i.e., residues 572-978 of SEQ ID NO: 5), or a variant or a fragment thereof capable of binding to SAGE1.

In some embodiments, the SAGE1 complex inhibitor comprises a INTS3-binding fragment of SAGE1, or a variant or derivative thereof. The polypeptide fragment of SAGE1 bind to INTS3 and interferes the binding of SAGE1 to INTS3. In some embodiments, the INTS3-binding fragment of SAGE1 comprises a C-terminal fragment of SAGE1. The C-terminal fragment of SAGE1 may comprises the last 100, 90, 80, 70, 60 or 50 residues from the C-terminus. In some embodiments, the C-terminal fragment of SAGE1 comprises residues 818-904 of SEQ ID NO: 3. In some embodiments, the SAGE1 complex inhibitor comprises a polypeptide having the sequence of SEQ ID NO: 8 (i.e., residues 818-904 of SEQ ID NO: 3), or a variant or a fragment thereof capable of binding to SAGE1.

Polypeptide useful in the present in the present disclosure also include an INTS3-binding fragment of INTS6 or INTS 6L or a variant or derivative. The INTS3-binding fragment of INTS6 or INTS6L are capable of competing with SAGE1 to bind INTS3, thereby blocking binding of SAGE1 to INTS3. In some embodiments, the SAGE1-binding fragment of INTS6 or INTS 6L comprises an amino acid sequence of SEQ ID NO: 10 (e.g., residues 803-887 of SEQ ID NO: 6 of INTS6), SEQ ID NO: 104 (e.g., residues 786-887 of SEQ ID NO: 6 of INTS6) or SEQ ID NO: 105 (e.g., residues 759-861 of SEQ ID NO: 7 of INTS6L), or a variant (e.g. having at least 50% sequence identity) or a fragment thereof capable of binding to INTS3.

In some embodiments, the polypeptide fragments described herein that are capable of disrupting or competitively inhibiting interaction between SAGE1 and INTS3 is fused to a second polypeptide that is heterologous to the fragments described herein to form a fusion polypeptide. The second polypeptide, for example, an immunoglobulin constant region or a human serum albumin binding moiety, may alter the solubility, affinity, stability or valency of the first polypeptide, or facilitate the expression, secretion or purification of the fusion polypeptide.

vi. Proteolysis Targeting Chimeras (Protac)

The present disclosure also contemplates SAGE1 inhibitor (and SAGE1 complex inhibitor) comprising a bi-functional molecule comprising a first moiety capable of binding to an ubiquitin pathway protein, and a second moiety capable of binding to SAGE1 or SAGE1 complex. The bi-functional molecule is capable of placing SAGE1 or SAGE1 complex in proximity to the ubiquitin pathway to effect degradation of SAGE1 or SAGE1 complex.

In some embodiments, the bi-functional molecule comprises a proteolysis targeting chimeras (PROTAC) that promotes the degradation of the SAGE1 protein or SAGE1 complex through ubiquitin pathway. PROTACs mediate the degradation of proteins of interest by hijacking the activity of E3 ubiquitin ligases for ubiquitination of the protein of interest for subsequent degradation by the 26S proteasome (more details can be found at, for example, Wang Y, Acta Pharmaceutica Sinica B 2020; 10(2):207-238).

The ubiquitin pathway protein binding moiety may include any molecule that binds E3 ligase. Examples of E3 ligases suitable for development of the bi-functional molecules such as PROTAC include, without limitation, Von Hippel-lindau (VHL), cereblon, Mouse double minute 2 (MDM2), beta-TrCP1, inhibitor of apoptosis protein (IAP) E3 ligase, TRIM21 (UniProtKB—P19474 (RO52_HUMAN)), Anaphase-promoting complex (APC); UBR5 (EDD1); SOCS/BC-box/eloBC/CUL5/RING; LNXp80; CBX4; CBLL1; HACE1; HECTD1; HECTD2; HECTD3; HECW1; HECW2; HERC1; HERC2; HERC3; HERC4; HUWE1; ITCH; NEDD4; NEDD4L; PPIL2; PRPF19; PIAS1; PIAS2; PIAS3; PIAS4; RANBP2; RNF4; RBX1; SMURF1; SMURF2; STUB1; TOPORS; TRIP12; UBE3A; UBE3B; UBE3C; UBE4A; UBE4B; UBOX5; UBR5; WWP1; WWP2; Parkin; A20/TNFAIP3; AMFR/gp78; ARA54; beta-TrCP1/BTRC; BRCA1; CBL; CHIP/STUB1; E6; E6AP/UBE3A; F-box protein 15/FBXO15; FBXW7/Cdc4; GRAIL/RNF128; HOIP/RNF31; cIAP-1/HIAP-2; cIAP-2/HIAP-1; cIAP (pan); ITCH/AIP4; KAP1; MARCH8; Mind Bomb 1/MIB1; Mind Bomb 2/MIB2; MuRF1/TRIM63; NDFIP1; NEDD4; NleL; Parkin; RNF2; RNF4; RNF8; RNF168; RNF43; SART1; Skp2; SMURF2; TRAF-1; TRAF-2; TRAF-3; TRAF-4; TRAF-5; TRAF-6; TRIMS; TRIM21; TRIM32; UBR5; and ZNRF3.

As an example, VHL is one of the E3 ligases with exciting therapeutic potential. VHL is the substrate recognition subunit of the E3 ligase complex VCB, which also consists of elongins B and C, Cul2 and Rbx1.

As another example, cereblon is a protein that in humans is encoded by the CRBN gene. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins.

The two moieties of the compound can be connected directly or via a chemical linker. The linker can be a cleavable linker or a non-cleavable linker. The linker preferably has a certain flexibility, thus varying lengths of PEG and (un)saturated alkane chains are commonly used. In some embodiments, the linker is independently covalently bonded to the two moieties through e.g., an amide, ester, thioester, keto, carbamate (urethane), carbon or ether group, each of which groups may be inserted anywhere on the two moieties to provide maximum binding of the ubiquitin pathway protein binding moiety on the ubiquitin ligase and the SAGE1 or SAGE1 complex binding moiety on SAGE1 or SAGE1 complex to be degraded.

In certain embodiments, the compounds as described herein comprise multiple ubiquitin pathway protein binding moieties, multiple SAGE1 or SAGE1 complex binding moieties, multiple linkers, or any combinations thereof.

Methods of designing and making the bi-functional molecules are known in the art, and details can be found in, for example, PCT patent application WO2017201449A1, U.S. Pat. Nos. 10,584,101, 10,071,164; US patent application US20180147202, Ishida T, Ciulli A. E3 Ligase Ligands for PROTACs: How They Were Found and How to Discover New Ones. SLAS DISCOVERY: Advancing the Science of Drug Discovery. November 2020. doi:10.1177/2472555220965528, Wang, Y. et al, Degradation of proteins by PROTACs and other strategies, Acta Pharmaceutica Sinica B, Volume 10, Issue 2, 2020, Pages 207-238, which are incorporated herein to the entirety.

V. Pharmaceutical Composition and Combination

In another aspect, the present disclosure provides a pharmaceutical composition comprising a SAGE1 inhibitor as described herein. In some embodiments, the SAGE1 inhibitor is a SAGE1 complex inhibitor. The term "pharmaceutical composition" refers to a formulation containing the SAGE1 inhibitor of the present disclosure in a form suitable for administration to a subject. The composition can be used for treating tumors, and/or modulating the expression level of SAGE1-INTS3.

In some embodiments, the pharmaceutical composition further comprises a pharmaceutically acceptable excipient. The term "pharmaceutically acceptable excipient" means an excipient that is useful in preparing a pharmaceutical composition that is generally safe, non-toxic and neither biologically nor otherwise undesirable to a subject. In some embodiment, the pharmaceutically acceptable excipient comprises a pharmaceutically acceptable carrier and/or a pharmaceutically acceptable diluent. Suitable excipient may include, for example, antioxidants, fillers, binders, disintegrants, buffers, preservatives, lubricants, flavorings, thickeners, coloring agents, emulsifiers, stabilizers and the like.

Pharmaceutical compositions are typically formulated to be compatible with its intended route of administration. The particular excipient used will depend upon the means and purpose for which the compounds of the present disclosure is being applied. Solvents are generally selected based on solvents recognized by persons skilled in the art as safe to be administered to a mammal including humans. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof.

In some embodiments, suitable excipients may include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In some embodiments, suitable excipients may include one or more stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present disclosure or pharmaceutical composition thereof) or aid in the manufacturing of the pharmaceutical product (i.e., medicament). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). A "liposome" is a small vesicle composed of various types of lipids, phospholipids and/or surfactant which is useful for delivery of a drug (such as the compounds disclosed herein and, optionally, a chemotherapeutic agent) to a mammal including humans. The components of the liposome are commonly arranged in a bilayer formation, similar to the lipid arrangement of biological membranes.

The pharmaceutical compositions provided herein can be in any form that allows for the composition to be administered to a subject, including, but not limited to a human, and formulated to be compatible with an intended route of administration. Examples of routes of administration include parenteral (including subcutaneous, intravenous, intramuscular and intraperitoneal), oral, rectal, dermal, transdermal, intrathoracic, intrapulmonary and intranasal (respiratory) routes. The pharmaceutical composition can be, for example, a liquid solution, suspension, emulsion, pill, capsule, tablet, sustained release formulation, or powder.

A variety of routes are contemplated for the pharmaceutical compositions provided herein, and accordingly the pharmaceutical composition provided herein may be supplied in bulk or in unit dosage form depending on the intended administration route. For example, for oral, buccal, and sublingual administration, powders, suspensions, granules, tablets, pills, capsules, gelcaps, and caplets may be acceptable as solid dosage forms, and emulsions, syrups, elixirs, suspensions, and solutions may be acceptable as liquid dosage forms. For injection administration, emulsions and suspensions may be acceptable as liquid dosage forms, and a powder suitable for reconstitution with an appropriate solution as solid dosage forms. For inhalation administration, solutions, sprays, dry powders, and aerosols may be acceptable dosage form. For topical (including buccal and sublingual) or transdermal administration, powders, sprays, ointments, pastes, creams, lotions, gels, solutions, and patches may be acceptable dosage form. For vaginal administration, pessaries, tampons, creams, gels, pastes, foams and spray may be acceptable dosage form. Methods of formulating suitable pharmaceutical compositions are known in the art, see, e.g., Remington: The Science and Practice of Pharmacy, 21st ed., 2005).

In embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art. In certain embodiments, a sterile, lyophilized powder is prepared by dissolving the polypeptide conjugate as disclosed herein in a suitable solvent. Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

In some embodiments, the pharmaceutical compositions of the present disclosure can be formulated as short-acting, fast-releasing, long-acting, and sustained-releasing. Accordingly, the pharmaceutical formulations of the present disclosure may also be formulated for controlled release or for slow release. In some embodiments, the pharmaceutical composition comprising a SAGE1 inhibitor that is or comprises a nucleic acid can be administered by any method suitable for administration of nucleic acid agents. These methods include, for example, gene guns, bio injectors, and skin patches.

The pharmaceutical compositions can be included in a container, pack, or dispenser together with instructions for administration.

In certain embodiments, the SAGE1 inhibitor provided herein may be administered in combination with any other therapeutic agent for use in the treatment tumors. The term "administered in combination" as used herein includes administration simultaneously as part of the same pharmaceutical composition, simultaneously as separate compositions, or at different timings as separate compositions. A pharmaceutical composition administered prior to or after another agent is considered to be administered "in combination" with that agent as the phrase is used herein, even if the composition and the second agent are administered via different routes. The SAGE1 inhibitor provided herein and other therapeutic agent can be administered either punctually or at different time points, as long as they exert effects in the subject during an overlapped timeframe. Where possible, additional therapeutic agents administered in combination with the SAGE1 inhibitor provided herein are administered according to the schedule listed in the product information sheet of the additional therapeutic agent, or according to the Physicians' Desk Reference (Physicians' Desk Reference, 70th Ed (2016)) or protocols well known in the art.

VI. Cell Therapy i. Engineered Immune Cells

The present disclosure also contemplated immune cells engineered to express a chimeric receptor that redirect them against SAGE1-positive tumors. The specificity to the tumor cells derives from an antibody binding domain of the receptors that confers binding specificity to an epitope of SAGE1 or an MHC-associated epitope of SAGE1.

"MHC" as used herein refers to major histocompatibility complex molecule that are found on cell surface to display fragments of proteins from within the cell to immune cells (such as T cells). In some embodiments, the MHC molecule is MHC class I protein that present peptides derived from cytosolic proteins. In some embodiments, the MHC class I protein is HLA-A, HLA-B, HLA-C, HLA-E, HLA-F, or HLA-G. In some embodiments, the HLA-A is HLA-A02.

In some embodiments, the epitope of SAGE1 is an MHC class I-restricted peptide. In some embodiments, the epitope is from about 8 to about 12 (such as about any of 8, 9, 10, 11, or 12) amino acids in length. Suitable MHC class I-restricted peptide of SAGE1 can be determined, for example, based on the presence of certain MHC (e.g., HLA-A*02:01)-binding motifs and cleavage sites for proteasomes and immune-proteasomes using computer prediction models known to those of skill in the art.

In some embodiments, the antibody binding domain is an Fv-like antigen-binding module. In some embodiments, the antibody binding domain is a Fab-like antigen-binding module, comprising a first and a second polypeptide chain.

In some embodiments, the engineered receptor is a chimeric antigen receptor (CAR) comprising an antigen binding domain, a transmembrane domain, and an intracellular signaling domain, wherein the antigen binding domain specifically binds to an epitope of SAGE1 or an MHC-associated epitope of SAGE1.

The transmembrane domain of the CAR may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the α, β, δ, γ, or ζ chain of the T-cell receptor, CD28, CD3s, CD3 CD45, CD4, CD5, CD8, CD9, CD16, CD22, CD33, CD37, CD64, CD80, CD86, CD134, CD137, or CD154. In some embodiments, the transmembrane domain may be synthetic, in which case it may comprise predominantly hydrophobic residues such as leucine and valine. In some embodiments, a triplet of phenylalanine, tryptophan and valine may be found at each end of a synthetic transmembrane domain. In some embodiments, a short polypeptide linker, having a length of, for example, between about 2 and about 10 (such as about any of 2, 3, 4, 5, 6, 7, 8, 9, or 10) amino acids in length may form the linkage between the transmembrane domain and the intracellular signaling domain of the CAR. In some embodiments, the linker is a glycine-serine doublet.

The intracellular signaling domain of the CAR is responsible for activation of at least one of the normal effector functions of the immune cell in which the CAR has been placed in. Effector function of a T cell, for example, may be cytolytic activity or helper activity including the secretion of cytokines. Thus the intracellular signaling domain can comprises an intracellular signaling sequence that is derived from a full length or a truncated portion of the intracellular signaling domain of a protein which transduces the effector function signal and directs the cell to perform a specialized function. Examples of intracellular signaling domains include the cytoplasmic sequences of the T cell receptor (TCR) and co-receptors that act in concert to initiate signal transduction following antigen receptor engagement, as well as any derivative or variant of these sequences and any synthetic sequence that has the same functional capability. Examples of intracellular signaling sequence that are of particular use in the disclosure include those derived from CD3 gamma, CD3 delta, CD3 epsilon, CD3 zeta, CD5, CD22, CD79a, CD79b, CD66d, FcR gamma, FcR beta, and TCR zeta.

In some embodiments, the intracellular signaling domain of the CAR further comprising a costimulatory domain. It is known that the full activation of a T-cell requires signals generated through the T-cell receptor (TCR) and a secondary or co-stimulatory signal. The co-stimulatory domain useful for the present disclosure can be derived from an intracellular domain of a co-stimulatory molecule. Examples of co-stimulatory molecules include for example, CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, and the like.

In some embodiments, the intracellular signaling domain of the CAR comprises a CD3ζ intracellular signaling sequence and a CD28 and/or a 4-IBB intracellular signaling sequence.

In some embodiments, the engineered receptor is a engineered T cell receptor (TCR) comprising an antigen binding domain and a T cell receptor module (TCRM) comprising TCR transmembrane domains, wherein the antigen binding domain specifically binds to an WIC-associated epitope of SAGE1.

In some embodiments, the engineered TCR is a heterodimer, comprising a first polypeptide chain and a second polypeptide chain. The first and second polypeptide chains can be linked, such as by a covalent linkage (e.g., peptide or other chemical linkage) or non-covalent linkage (e.g., disulfide bond).

In some embodiments, the TCRM is capable of recruiting at least one TCR-associated signaling module. In some embodiments, the TCR-associated signaling module is selected from the group consisting of CD3δ ε, CD3γε, and ζ ζ.

In some embodiments, the TCRM comprises the transmembrane module of a TCR (such as an αβTCR or a γδTCR). In some embodiments, the TCRM further comprises one or both of the connecting peptides or fragments thereof of a TCR. In some embodiments, the engineered TCR further comprises at least one intracellular domain. For example, one or more of the at least one intracellular domain of the engineered TCR comprises a sequence from the intracellular domain of a TCR or from a T cell costimulatory signaling sequence. The costimulatory signaling sequence can be a portion of the intracellular domain of a costimulatory molecule including, for example, CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like. In some embodiments, the engineered TCR further comprises one or more peptide linkers between the antigen binding domain and the TCRM to optimize the length of the extracellular domain.

Nucleic acid(s) encoding the CAR or engineered TCR and vectors in which such nucleic acid(s) are contemplated within the disclosure. The vectors may include a sequence that encodes a signal peptide such that the expression of the receptor is targeted to cell surface.

The present disclosure also provides a cell genetically modified to express the CAR or the engineered TCR. Such cells can be generated by introducing a vector comprising the nucleic acid(s) encoding the CAR or engineered TCR into the cells. In some embodiments, the cell comprises a dendritic cell, a T cell, or a Natural Killer.

ii. Engineered Antigen Presenting Cells

In another aspect, the present disclosure provides an ex vivo activated antigen presenting cell (APC) that is loaded with SAGE1 or a fragment thereof for boosting immune response (e.g., inducing antigen specific T cell response) to a SAGE1-positive disorder.

APCs are cells that display antigens complexed with major histocompatibility complex (MHC) proteins on their surfaces. Examples of APCs include dendritic cells (DCs), macrophages, B cells, and certain activated epithelial cells. In some embodiments, APCs are dendritic cells. The APCs loaded with SAGE1 presents SAGE1 specific peptides in complex with MHC-I and/or MHC-II molecules to immune cells (e.g., T cells) in the patients, thereby initiating a strong, tumor specific immune response.

In general, the preparation of ex vivo activated APCs involves isolating APC cells (e.g., DCs) from patients. The isolated cells are activated and matured ex vivo to present the antigen of interest before injected back into the patients. Specific tumor antigens (e.g., SAGE1), tumor lysates and the like can be used for activating the APCs. The APCs can also be activated by electroporation, transfection or transduction with expression vectors (e.g., viral vectors or mRNA) that encode the specific tumor antigens (e.g. epitope of SAGE1 or MHC-associated epitope of SAGE1), total tumor cell-mRNA, tumor derived exosomes (TDEs), or a cell (e.g. fibroblast cell) modified to express the epitope of SAGE1 or MHC-associated epitope of SAGE1, and the like.

APCs, suitable for administration to subjects (e.g., cancer patients), can be isolated or obtained from any tissue in which such cells are found, or can be otherwise cultured and provided. APCs (e.g., DCs) can be found, by way of example, in the bone marrow or PBMCs of a mammal, in the spleen of a mammal, or in the skin of a mammal. For example, bone marrow can be harvested from a mammal and cultured in a medium that promotes the growth of DC. GM-CSF, IL-4 and/or other cytokines (e.g., TNF-α), growth factors and supplements can be included in this medium. DCs occur in low numbers in all tissues in which they reside, making isolation and enrichment of DCs a requirement. Any of a number of procedures entailing repetitive density gradient separation, fluorescence activated cell sorting techniques, positive selection, negative selection, or a combination thereof, are routinely used to obtain enriched populations of isolated DCs.

After a suitable amount of time in culture in medium containing appropriate cytokines (e.g., suitable to expand and differentiate the DCs into mature DCs, e.g., 4, 6, 8, 10, 12, or 14 days), clusters of DC can be cultured in the presence of one or more epitopes of SAGE1 or transfected/transduced with an expression vector that encodes one or more epitopes of SAGE1, and harvested for use in a cancer vaccine using standard techniques. In some embodiments, the APCs can also be fused with the cell expressing the epitope of SAGE1 or the MHC-associated epitope of SAGE1. In some embodiments, the epitopes of SAGE1 are MHC class I-restricted epitope or MHC class II-restricted epitope.

In another aspect, the present disclosure provides a vaccine composition comprising the ex vivo activated APCs provided herein. In another aspect, the present disclosure provides a method of preventing or treating a SAGE1 positive disorder, comprising administering an effective amount of the activated APCs provided herein.

The APC-based vaccine can be delivered to a subject by any suitable delivery route, which can include injection, infusion, inoculation, direct surgical delivery, or any combination thereof. In other embodiments, the vaccine is administered intravenously.

VII. Methods of Treatment of SAGE1-Positive Disorder

In another aspect, the present disclosure provides a method of treating a SAGE1 positive disorder in a subject in need thereof, comprising administering to the subject an effective amount of: a) a SAGE1 inhibitor; b) the pharmaceutical composition provided herein, c) the SAGE1 complex inhibitor provided herein; d) the cell provided herein; and e) any combination thereof. In certain embodiments, SAGE1 expression is detected in a biological sample from the subject prior to the administration. Detection of SAGE1 expression can use any of the methods disclosed herein.

In some embodiments, the SAGE1 positive disorder is tumor. Any tumor disclosed herein may be treated using the methods provided herein, as long as the tumor is SAGE1 positive. In some embodiments, the treatment prevents, delays or reduces the development, progression metastasis, or relapse of the tumor.

In another aspect, the present disclosure provides a method of preventing or reducing or delaying malignancy of a tumor in a subject having a mutation in TP53, comprising administering to the subject an effective amount of: a) a SAGE1 inhibitor; b) the pharmaceutical composition provided herein, c) the SAGE1 complex inhibitor provided herein; d) the cell provided herein; and e) any combination thereof. In certain embodiments, SAGE1 expression is detected in a biological sample from the subject prior to the administration. Any SAGE1 inhibitors, SAGE1 complex inhibitors, and cells provided herein can be used.

In certain embodiments, the effective amount is a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art. The therapeutically effective amount is varied according to the particular treatment involved for a subject and depend upon various factors known in the art, such as the subject's body weight, size, and health; the nature and extent of the condition; the rate of administration; the therapeutic or combination of therapeutics selected for administration; and the discretion of the prescribing physician. Therapeutically effective amounts for a given situation can be determined by routine experimentation that is within the skill and judgment of the clinician. For example, the initial administration dosage may be higher than subsequent administration dosages. For another example, the administration dosage may vary over the course of treatment depending on the reaction of the subject.

In certain embodiments, the effective amount is a prophylactically effective amount. The prophylactically effective amount can be an amount that produces a desired prophylactic effect in a subject, such as preventing a condition (e.g. SAGE1-positive disorder) or alleviating symptoms associated with the condition (e.g. SAGE1-positive disorder). Whether a symptom has been ameliorated can be assessed by any clinical measurement typically used by physicians or other skilled healthcare providers to assess the severity or progression status of that symptom or in certain instances will ameliorate the need for hospitalization.

Methods of introducing oligonucleotides or nucleic acids into a cell include physical, biological and chemical methods. Physical methods for introducing a polynucleotide into a cell include transfection, transformation, transduction, calcium phosphate precipitation, lipofection, particle bombardment, microinjection, electroporation, and the like.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Biological methods for introducing a polynucleotide of interest into a cell include the use of a nucleic acid vectors. Oligonucleotides disclosed herein can be inserted into vectors and expressed from transcription units within the vectors. In some embodiments, the oligonucleotides are comprised or encoded by a nucleic acid vector. As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation.

Viral vectors are the most widely used method for inserting genes into mammalian, e.g., human cells. The viral vectors to be used are suitable for replication and, optionally, integration in eukaryotic cells. Typical vectors contain transcription and translation terminators, initiation sequences, and promoters useful for regulation of the expression of the desired nucleic acid sequence, as well as an origin of replication functional in at least one organism and one or more selectable markers (4th Edition, Molecular Cloning: A Laboratory Manual, Cold Spring Harbor Laboratory, New York, 2012). Viral vectors, including DNA and RNA viruses, can be derived from retrovirus, lentivirus, poxviruses, herpes simplex virus I, adenoviruses and adeno-associated viruses, and the like.

In certain embodiments, one or more vectors driving expression of one or more elements of a CRISPR system are introduced into a host cell, such that expression of the elements of the CRISPR system direct formation of a CRISPR complex at one or more target sites. For example, a CAS enzyme and a guide sequence could be operably linked to the same or separate regulatory elements on a single vector, or each linked to separate regulatory elements on separate vectors.

Non-viral vector such as plasmids can also be used to introduce nucleic acids or polynucleotides into a cell. In certain embodiments plasmids encoding shRNA or guide RNAs are transfected into a cell.

VIII. Methods of Screening SAGE1 Inhibitors

In another aspect, the present disclosure provides method of identifying or screening agents that are SAGE1 inhibitors (e.g., agents inhibiting SAGE1 level or SAGE1 mediated biological activities). The agents can be, for example, a polynucleotide, a polypeptide, a compound, an antibody or antigen-binding fragment thereof, or a derivative of any one of the foregoing.

In some embodiment, the method comprises: contacting SAGE1 protein or a functional equivalent thereof with the agent to be screened, and detecting the binding between the SAGE1 or a functional equivalent thereof with and the agent. Presence of binding indicates that the agent can be a SAGE1 inhibitor. "Functional equivalent" as used herein refers to a fragment, variant, derivative or a fusion polypeptide of a naturally-occurring polypeptide (e.g., SAGE1) that despite of having differences in their chemical structures retains at least partially biological functions of naturally-occurring polypeptide. In some embodiments, a functional equivalent retains at least 80%, 85%, 90%, 91%, 92%, 93%, 94%, 95%, 96%, 97%, 98%, 99% or 100% biological activity of naturally-occurring polypeptide. The biological function of SAGE1, without limitation, include binding with INTS3 and promoting tumorigenesis by e.g., up-regulating transcription of pro-proliferative genes.

In some embodiment, the method comprises: contacting a test agent with a SAGE1-binding fragment of a component of SAGE1 complex, and detecting the binding between the SAGE1-binding fragment with the test agent. Presence of binding indicates that the agent can be a SAGE1 complex inhibitor.

In some embodiment, the method comprises: contacting a test agent with SAGE1 and a SAGE1-binding fragment of a component of SAGE1 complex, and detecting the ability of the agent to block or reduce binding between the SAGE1 and the SAGE1-binding fragment. Alternatively, the method may comprise detecting the ability of the agent to reduce formation of SAGE1 complex. If the test agent blocks or reduces binding of SAGE1 to the SAGE1-binding fragment of the component of the SAGE1 complex, or reduces formation of the SAGE1 complex, then the test agent can be a SAGE1 complex inhibitor. In some embodiment, the component of SAGE1 complex comprises one or more components selected from the group consisting of INTS3, NABP1/2, CREBBP, TLE1, TLE2, TLE3, TLE4, TLE5, GGA3, CNOT1, TAX1BP1, SEC16A, CYLD and PAXBP1. In some embodiment, the component of SAGE1 complex comprises INTS3. In some embodiment, the SAGE1-binding fragment of INTS3 comprises an amino acid sequence of SEQ ID NO: 9, or a variant or fragment thereof capable of SAGE1-binding, or a fusion protein of any of the foregoing.

In some embodiments, the method comprise contacting SAGE1 with INTS3 in the presence of an agent and detecting the formation of SAGE1-INTS3 complex, wherein the agent is identified as a SAGE1 inhibitor when it inhibits the formation of SAGE1-INTS3 complex. In some embodiment, the cell-free screening assay comprises contacting a SAGE1-INTS3 complex with an agent, and detecting the amount of the complex, wherein the agent is identified as a SAGE1 inhibitor when it decreases the amount of the complex.

The binding between the agent and the SAGE1 or a functional equivalent thereof can be determined by various methods. For example, SDS-PAGE and/or mass spectrometry can be used to analyze the presence and/or amount of the binding. For another example, SAGE1, SAGE1-binding fragment of a component of SAGE1 complex (e.g., INTS3) can be coupled with a radioisotope or enzymatic label such that binding of the agent to SAGE1 or to the SAGE1 binding fragment can be determined by detecting the labeled molecule in the association. The binding can also be determined in real time without labeling any of the components by methods such as surface plasmon resonance (SPR). In some embodiments, it may be desirable to immobilize either SAGE1 or the SAGE1-binding fragment of a component of SAGE1 complex (e.g., INTS3) to facilitate separation/detection of the binding or bound molecules, as well as to accommodate automation of the assay. For example, SAGE1 and/or a SAGE1-binding fragment of a component of SAGE1 complex (e.g., INTS3) can be provided in the forms of fusion proteins (e.g., a glutathione-S-transferase-base fusion protein) that contain additional domain allowing the proteins to be bound to a matrix.

For example, one can screen peptide libraries to identify molecules that interact with or bind to SAGE1 or a functional equivalent thereof, or a SAGE1-binding fragment of INTS3, or molecules that interferes with or blocks the binding of SAGE1 to its binding partner such as INTS3. Useful peptide libraries include those that encode a random or controlled collection of amino acids, which can be expressed as fusion proteins of bacteriophage coat proteins, and subsequently screened against the SAGE1 or a functional equivalent thereof. Typical peptide libraries include those based on HSP90 or fibronectin (Anders Olson C. et al, Protein Sci., 2007; 16:476, Wahlberg E. et al, Proc. Natl.

Acad. Sci. (2003); 100:3185). Screening methods that can be used to identify molecules that interact with SAGE1 protein sequences are disclosed for example in U.S. Pat. Nos. 5,723,286, and 5,733,731.

In some embodiment, the method comprises contacting a cell expressing SAGE1 or a functional equivalent thereof with the agent to be screened, and determining the ability of the agent to decrease the amount or activity of SAGE1 or a functional equivalent thereof. In some embodiments, the cell is a tumor cell.

For example, small molecules can be identified that interfere with SAGE1 function, including molecules that interfere with SAGE1's ability to mediate RNAPII-dependent transcription regulation, ability to activate transcription of oncogenes, or transcription misregulation leading to tumorigenesis. Ligands that regulate SAGE1 function can be identified based on their ability to bind SAGE1 complex or interfere with their function.

The activity of SAGE1 can be determined, for example, by detecting the expression of genes regulated by SAGE1 complex. For example, the activity of SAGE1 can be indicated by detecting the induction of a reporter gene that is operatively linked to a responsive regulatory element targeted by the SAGE1 complex.

In some embodiment, the method comprises contacting the SAGE1 complex (e.g. SAGE1-INTS3 complex) with an agent, and detecting the activation of a reporter gene under the control of SAGE1 complex, wherein the agent is identified as a SAGE1 inhibitor when it reduces or prevents activation of the reporter gene.

In some embodiment, the present disclosure provides a recombinant cell comprising a first gene encoding SAGE1 and a second gene encoding a reporter, wherein the reporter is configured to generate a detectable signal in response to SAGE1 expression or SAGE1-mediated activity.

Typical methods are discussed for example in U.S. Pat. No. 5,928,868 issued 27 Jul. 1999, and include methods for forming hybrid ligands in which at least one ligand is a small molecule. In an illustrative embodiment, cells engineered to express a fusion protein of SAGE1 and a DNA-binding protein are used to co-express a fusion protein of a hybrid ligand/small molecule and a cDNA library transcriptional activator protein. The cells further contain a reporter gene, the expression of which is conditioned on the proximity of the first and second fusion proteins to each other, an event that occurs only if the hybrid ligand binds to target sites on both hybrid proteins. Those cells that express the reporter gene are selected and the unknown small molecule or the unknown ligand is identified. This method provides a means of identifying modulators, which activate or inhibit SAGE1.

In some embodiment, the screening assay for agents that are SAGE1 inhibitors is a cell-based assay, comprising contacting a cell that expresses SAGE1-expressing cell with a test agent, and determining the ability of the test agent to decrease the amount or activity of SAGE1 or SAGE1 complex. In some embodiments, the cell is a tumor cell. The tumor cell can be derived from an animal model or a human patient afflicted with the tumor. In some embodiments, the step of contacting occurs in vivo, ex vivo, or in vitro.

The amount of SAGE1 can be indicated by the level of expression of SAGE1 mRNA or protein or fragments thereof. The expression level of SAGE1 mRNA or protein or fragments thereof in the cells can be determined by methods described herein for detecting SAGE1 mRNA or protein. When amount of SAGE1 mRNA is reduced (statistically significantly less) in the presence of the agent than in its absence, the agent is identified as a SAGE inhibitor.

The activity of SAGE1 can be indicated by the amount or activity of SAGE1 complex, which can be determined as described above. The activity of SAGE1 or SAGE1 complex can be further indicated by a cellular response regulated by SAGE1, such as reduced viability or proliferation of the tumor cell relative to a control. The control can be a tumor cell not contacted with the agent or contacted with an anti-cancer agent. For example, cellular proliferation or invasion can be determined by monitoring cell number count, cellular movement, matrigel assays, induction of proliferation- and/or invasion-related gene expression, and the like, as described herein. Further, the in vivo activity of SAGE1 or SAGE1 complex can be indicated by tumor shrinkage by imaging if it is solid tumor, by a PET scan for example.

This disclosure further pertains to agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of agents identified by the above-described screening assays for treatments as described herein.

IX. Structural-Based Discovery of SAGE1-INTS3 Complex Inhibitor

In another aspect, the present disclosure provides an isolated SAGE1-INST3 complex comprising SAGE1 or a fragment thereof, and INST3 or a fragment thereof. In some embodiments, the fragment of SAGE1 is capable of binding to INTS3. In some embodiments, the fragment of INTS3 is capable of binding to SAGE1.

In some embodiments, the fragment of INTS3 comprises a C-terminal fragment of INTS3, e.g., the 500, 400, 300, 250, 200 or 150 residues from the C-terminus, or the 500-100, 400-100, 300-100, 200-100, 500-50, 400-50, 300-50, or 200-50 residues from the C-terminus. In some embodiments, the fragment of SAGE1 comprises a C-terminal fragment of SAGE1, e.g., the last 100, 90, 80, 70, 60 or 50 residues from the C-terminus. In some embodiments, SAGE1 having an amino acid sequence of SEQ ID NO: 3 or a sequence having at least 70% identity thereto. In some embodiments, INTS3 having an amino acid sequence of SEQ ID NO: 5 or a sequence having at least 70% identity thereto. In some embodiments, the SAGE1-INTS3 complex comprising the C-terminal fragment of INTS3 comprising residues 572-978 of SEQ ID NO: 5, the C-terminal fragment of SAGE1 comprising residues 818-904 of SEQ ID NO: 3.

In some embodiments, the SAGE1-INTS3 complex is crystallized. The crystallized SAGE1-INTS3 complex may provide means to obtain atomic modeling information of the specific amino acids and their atoms that are engaged in the interface of SAGE1 and INTS3.

In some embodiments, the crystallized SAGE1-INTS3 complex of the present disclosure is capable of diffracting X-rays to a resolution of better than 5 Å, 4 Å, 3 Å, 2 Å or 1.5 Å, and are useful for determining the three-dimensional structure of the molecules.

i. X-Ray Crystal Structure Coordinates

In another aspect, the present disclosure provides a set of X-ray crystal structure coordinates of the SAGE1-INTS3 complex. The set of X-ray crystal structure coordinates is deposited in Protein Date Bank (PDB) under code 7C5U (Deposition ID D_1300015303) (Bernstein, F. C, T. F. Koetzle, et al. (1977) J Mol Biol 112(3): 535-42), which shows the X-ray crystal structure coordinates of SAGE1-INTS3 complex comprising the SAGE1 polypeptide comprising an amino acid sequence of residues 818-904 of SEQ ID NO: 3 and the INTS3 polypeptide having an amino acid sequence of residues 572-978 of SEQ ID NO: 5. In some embodiments, the crystal provided herein has approximately the following dimensions: a 260.112±0.1 Å, 1)=46.240±0.1 Å, c=103.101±0.1 Å, $\alpha$=90±0.1°, $\beta$=113.280±0.1°, $\gamma$=90±0.1°, and a symmetry, or space group, of C2.

The three dimensional structure of SAGE1-INTS3 complex, in particular the interface between SAGE1 and INTS3, permits design and identification of SAGE1 inhibitors, including SAGE1-INTS3 complex inhibitors, that interfere the interaction between SAGE1 and INTS3. For example, the knowledge of the three dimensional structure allows one to design molecules, preferably pharmaceutical agents, capable of binding to either SAGE1 or INTS3, thereby disrupting SAGE1-INTS3 complex and preventing the complex from exerting its biological functions such as up-regulating the expression of genes involved in cell proliferation and cancer phenotype. When referring to the interface, it may refer to a portion of the interface (e.g. all or part of the structure coordinates of the SAGE1 portion in the deposited coordinate file (PDB code: 7C5U), or all or part of the structure coordinates of the INTS3 portion in the deposited coordinate file (PDB code: 7C5U)), or both of SAGE1 portion and of INTS3 portion in the deposited coordinate file (PDB code: 7C5U). The structure coordinates have been deposited on May 20, 2020 with RCSB PDB, with an accession number of 7C5U. The deposited information will be released to public after publication of the invention disclosed herein.

In some embodiments, the present disclosure provides a set of X-ray crystal structure coordinates of a SAGE1 complex, wherein the binding interface comprises one or more amino acid residues of SAGE1 selected from the group consisting of F838, F873, K874, M832, V876, R872, K828, R836 and Q840 (the numbering is according to SEQ ID NO: 3), or equivalent residues in a fragment, a variant or a derivative thereof.

In some embodiments, the present disclosure provides a set of X-ray crystal structure coordinates of a binding (e.g. SAGE1-binding) interface of INTS3, wherein the binding interface comprises one or more amino acid residues of INTS3 selected from the group consisting of: T804, S841, S874, S769, N933, R849, Q773, C777, M781, A816, N818, E838, E850, F871, R848, F805, L845, L815, L844, Y808, C842, Q846, Q870, R877, H878, K882, E732, V766, Q771, D768, A765, Q731, E835, E803, C809 and L772 (the numbering is according to SEQ ID NO: 5) or equivalent residues in a fragment, a variant or a derivative thereof.

In some embodiments, the present disclosure provides a set of X-ray crystal structure coordinates of a binding interface of SAGE1 and INTS3, wherein the binding interface of SAGE1 comprises one or more amino acid residues selected from the group consisting of F838, F873, K874, M832, V876, R872, K828, R836 and Q840 of SAGE1 (the residue numbering is according to SEQ ID NO: 3), or equivalent residues in a fragment, a variant or a derivative thereof; and the binding interface of INTS3 comprises one or more amino acid residues selected from the group consisting of T804, S841, S874, S769, N933, R849, Q773, C777, M781, A816, N818, E838, E850, F871, R848, F805, L845, L815, L844, Y808, C842, Q846, Q870, R877, H878, K882, E732, V766, Q771, D768, A765, Q731, E835, E803, C809 and L772 of INTS3 (the numbering is according to SEQ ID NO: 5) or equivalent residues in a fragment, a variant or a derivative thereof.

A person skilled in the art will understand that, a set of structure coordinates for protein complex or a portion thereof, is a relative set of points that define a shape in three dimensions. Thus, it is possible that an entirely different set of coordinates could define a similar or identical shape, and thus be within the scope of the present invention. Moreover, slight variations in the individual coordinates will have little effect on overall shape. In terms of binding interface, these variations would not be expected to significantly alter the atoms or residues engaged in the interface.

It is also noteworthy that modifications in the crystal structure due to mutations, additions, substitutions, and/or deletions of amino acids, or other changes in any of the components that make up the crystal could also account for variations in structure coordinates. If such variations are within an acceptable standard of error such as a root mean square deviation (rmsd) not more than about 2 Å from the conserved backbone atoms as compared to the original coordinates, the resulting three dimensional shape is considered to be the same. In some embodiments, the root mean square deviation is not more than about 1.5 Å, 1.0 Å, or 0.5 Å. The term "root mean square deviation" as used herein refers to the square root of the arithmetic mean of the square of the deviations from the mean. In the context of atomic objects, the numbers are given in angstroms (Å).

The modifications discussed above may be generated because of mathematical manipulations of the SAGE1-INTS3 complex structure coordinates. For example, the structure coordinates set forth in the deposited coordinate file (PDB code: 7C5U) could be manipulated by crystallographic permutations of the raw structure coordinates, fractionalization of the raw structure coordinates, integer additions or subtractions to sets of the raw structure coordinates, inversion of the raw structure coordinates or any combination of the above. For example, the SAGE1-INTS3 complex of the present disclosure preferably comprise a binding interface characterized by the amino acid residues as set forth in deposited coordinate file (PDB code: 7C5U)±a root mean square deviation from the conserved backbone atoms of said amino acids of not more than 2 Å (or more preferably, not more than 1.5 Å, or more preferably, not more than 1 Å, and most preferably, not more than 0.5 Å).

Therefore, the present disclosure further provides the X-ray crystal structure coordinates comprising a binding interface of SAGE1-INTS3 complex as provided herein (e.g., the deposited coordinate file (PDB code: 7C5U)) within a root mean square deviation from the backbone atoms of the amino acids making up the binding interface of not more than about 2 Å, not more than about 1.5 Å, not more than about 1 Å, or not more than about 0.5 Å.

ii. Computer-Readable Storage Medium

It is noted that in order to use the structural coordinates generated from the SAGE1-INTS3 complex described herein, it may be necessary to display the relevant coordinates as, or convert them to, a three-dimensional shape or graphical representation, or to otherwise manipulate them. In general, such a three-dimensional representation of the structural coordinates will find use in rational drug design, molecular replacement analysis, homology modeling, and mutation analysis. This is typically accomplished using any of a wide variety of commercially available software programs capable of generating three-dimensional graphical representations of molecules or portions thereof from a set of structural coordinates. The scientific art is replete with conventional software programs, which are incorporated by reference herein in their entireties. Refer to, for example, GRID (Oxford University, Oxford, UK); AUTODOCK (Scripps Research Institute, La Jolla, Calif.); Flo99 (Thistlesoft, Morris Township, NJ.) etc.

Therefore, in another aspect, the present disclosure provides a computer-readable storage medium having stored thereon the crystal structure coordinates in accordance with the present disclosure, such as that set out in deposited coordinate file (PDB code: 7C5U).

For storing, transferring and using such programs, a machine, such as a computer, is also contemplated, which produces a three-dimensional representation of the SAGE1-INTS3 complex comprising the bind interface. The machine would comprise a machine-readable data storage medium having stored thereon the crystal structure coordinates in accordance with the present disclosure. Computer-readable storage mediums are well-known to those skilled in the art and include, for example, hard-disk, CD-ROM, diskette, DVD, thumb drive, etc. and other magnetic, magneto-optical, optical, floptical and other media which may be adapted for use with a computer. The machine further comprises a working memory for storing instructions for processing the machine-readable data, as well as a central processing unit (CPU) coupled to the working memory and to the machine-readable data storage medium for the purpose of processing the machine-readable data into the desired three-dimensional representation. As well, the machine of the present invention further comprises a display connected to the CPU so that the three-dimensional representation may be visualized by the user. Accordingly, when used with a machine programmed with instructions for using said data, e.g., a computer loaded with one or more programs of the sort identified above, the machine provided for herein is capable of displaying a graphical three-dimensional representation of the SAGE1-INTS3 complex described herein.

iii. Method of Identifying and Screening Potential SAGE1 Complex Inhibitors

In another aspect, the present disclosure provides a method of identifying an agent that is a potential SAGE1 complex inhibitor, comprising the steps of:

(a) generating on a computer a representation of the three dimensional structure of a binding interface based on the set of X-ray crystal structure coordinates as disclosed herein, (b) generating on a computer a representation of the agent, (c) fitting the representation of the agent according to step (b) to the computer representation of the three dimensional structure of the binding interface according to step a), so that the agent interacts with at least one residue of the binding interface; and (d) evaluating the interaction of the step (c) between the agent and at least one residue of the binding interface, wherein the agent is identified as a potential SAGE1 complex inhibitor when the interaction a low energy, stable complex comprising the agent and SAGE1 or INTS3, optionally in competition against the SAGE1-INTS3 complex.

In another aspect, the present disclosure provides a virtual screening method to identify a potential SAGE1 complex inhibitors, comprising the steps of:

(a) generating on a computer a representation of the three dimensional structure of a binding interface based on the X-ray crystal structure coordinates as disclosed herein;

(b) generating a representation of an agent or accessing a representation of an agent from a library on a computer;

(c) fitting the representation of the agent according to step (b) to the computer representation of the three dimensional structure of the binding interface according to step a) so that the agent interacts with at least one residue of the binding interface; and (d) evaluating the interaction of the step (c) between the agent and at least one residue of the binding interface, wherein the agent is identified as a potential SAGE1 complex inhibitor when the interaction yields a low energy, stable complex comprising the agent and SAGE1 or INTS3, optionally in competition against the SAGE1 complex.

The representation on a computer of a binding interface can a graphical representation, or a plot of the amino acid residue coordinates in a three dimensional space. Softwares for generating the three-dimensional graphical representations of the binding interface in step (a) and/or an agent in step (b) are known and commercially available. Examples include Quanta and WebLite Viewer, Schrödinger Suite, AUTODOCK, DOCK, and the like.

The fitting (or docketing) in step (c) above is a process to assess the complementarity between the representation of the agent according to step (b) and the representation of the three dimensional structure of the binding interface according to step (a). The fitting can be performed by well-known methods in the art, for example, by various computational techniques that evaluate the "fit" between the binding interface and the agent, such as the extra-precision glide docking (Glide XP).

The interaction of an agent with at least one residue of the binding interface of the SAGE1-INTS3 complex of the present disclosure may be tested and optimized by computational evaluation. For example, it may be evaluated by shape, size and electrostatic complementarity as determined qualitatively by visual inspection or as determined quantitatively by the use of scoring functions such as LUDI, PLP, PMF, SCORE, GOLD, FlexX, Emodel score and Glide XP score. These methods of qualitative and quantitative evaluation may be employed individually or in combination, for example, as in a consensus scoring manner.

Alternatively, interaction of an agent with at least one residue of the binding interface can be evaluated based on the interaction energy of a complex formed by the binding or association of an agent with the SAGE1 molecule or the INTS3 molecule alone. The term "low energy, stable complex" as used herein refers to a complex in which the energy of interactions, including the hydrophobic enclosure, the hydrogen bond interaction, the internal energy (such as van de Waals interaction), between the agent and SAGE1 or INTS3, is less than a predetermined threshold, which can be set by a computer program. The energy of interactions can be determined using known softwares in the art, for example, the extra-precision glide docking (Glide XP) by Glide program.

The comparison of the energy to a predetermined threshold may be carried out manually or computer assisted. For a computer assisted comparison, the value of the energy of interaction may be compared to the predetermined threshold which is stored in a database by a computer program, and the computer program may further evaluate the result of the comparison, and automatically provide the desired assessment in a suitable output format. Based on the comparison a person skilled in the art can readily identify a potential SAGE1-INTS3 complex inhibitor. In some embodiments, the predetermined threshold is a Glide XP score, which is dependent on the hydrophobic enclosure, the hydrogen bond interaction, the internal energy (such as van de Waals interaction), the electrostatic interaction and two XP penalties (i.e., the desolvation penalty and the ligand-strain penalty). In some embodiments, the predetermined threshold is a Glide XP score of $-10$ with a reference Glide XP score of $-12$.

The effect of the potential SAGE1 complex inhibitor identified as described above may be further evaluated computationally, or experimentally (e.g., by competitive binding experiments or by measuring the effect of the agent on the biological activity of SAGE1-INTS3 complex).

In some embodiments, the method of identifying or screening potential SAGE1-INTS3 complex inhibitors further comprises step (e) modifying the agent based on the result obtained in step (d). Modifications can be made to the agent in order to improve or modify its selectivity and binding properties—that is its affinity for SAGE1 or INTS3. Generally, initial modification are conservative, i.e., the replacement group will have approximately the same size, shape, hydrophobicity and charge as the original group. Such modified agent may then be analyzed for interaction with at least one residue of the binding interface of SAGE1-INTS3 complex by the same computer methods described in detail above. In some embodiments, the method further comprises repeating steps (b) to (e) in the method of identifying or screening potential SAGE1-INTS3 complex inhibitors Various molecular analysis and rational drug design techniques are further disclosed in U.S. Pat. Nos. 5,834,228, 5,939,528 and 7,930,109, as well as in PCT Application WO 99/09148, the contents of which are hereby incorporated by reference.

In some embodiments, the agent is a polynucleotide, a polypeptide, a compound, an antibody or antigen-binding fragment thereof, or a derivative of any one of the foregoing.

X. Incorporation of Embodiments Disclosed in Priority Applications i. Use of SAGE1 as a Biomarker for Tumors In another aspect, the present disclosure provides use of a substance for detecting SAGE1 gene or an active fragment thereof in the manufacture of a kit for evaluating the therapeutic effect of treatment for tumor and/or determining the prognosis of tumor.

In some embodiments, the substance is for detecting SAGE1 gene or the active fragment thereof in a cell, a tissue, or a body fluid, preferably the body fluid being selected from the group consisting of intracellular fluids, extracellular fluids, interstitial fluids, plasma, lymph fluids and a combination thereof; and/or, the substance is for detecting the protein expression level of SAGE1 gene or the molecular expression level of SAGE1 gene; and/or, the substance for detecting SAGE1 gene or active fragment thereof comprises a specific probe for detecting SAGE1 gene or the active fragment thereof; and/or the substance for detecting SAGE1 gene or the active fragment thereof comprises a primer for specifically amplifying SAGE1 gene.

In some embodiments, the tumor is a solid tumor or hematological tumor, preferably selected from intestinal cancer, lung cancer, liver cancer, breast cancer, esophageal cancer, head and neck cancer, skin cancer, kidney cancer, leukemia, colon adenocarcinoma (coad), liver hepatocellular carcinoma (lihc), ovarian serous cystadenocarcinoma (ov), uterine corpus endometrial carcinoma (ucec), thyroid carcinoma (thca), skin cutaneous melanoma (skcm), lung adenocarcinoma (luad), head and neck squamous cell carcinoma (hnsc), glioblastoma multiforme (gbm), prostate adenocarcinoma (prad), thymoma (thym), brain lower grade glioma (lgg), rectum adenocarcinoma (read), pheochromocytoma and paraganglioma (pcpg), esophageal carcinoma (esca), kidney renal clear cell carcinoma (kirc), cervical squamous cell carcinoma and endocervical adenocarcinoma (cesc), bladder urothelial carcinoma (blca), kidney renal papillary cell carcinoma (kirp), pancreatic adenocarcinoma (paad), stomach adenocarcinoma (stad), kidney chromophobe (kich), breast invasive carcinoma (brca), lung squamous cell carcinoma (lusc), sarcoma (sarc), acute myeloid leukemia (laml).

In some embodiments, the kit for evaluating the therapeutic effect of treatment for tumor and/or determining the prognosis of tumor based is on the expression level of SAGE1 gene in a sample.

In some embodiments, the SAGE1 gene is a single biomarker in the kit.

In another aspect, the present disclosure provides use of a substance for detecting SAGE1 gene or an active fragment thereof in the manufacture of a kit for diagnosing a tumor.

In some embodiments, the substance is for detecting SAGE1 gene or the active fragment thereof in a cell, a tissue, or a body fluid, preferably the body fluid being selected from the group consisting of intracellular fluids, extracellular fluids, interstitial fluids, plasm, lymph fluids and a combination thereof; and/or, the substance is for detecting the protein expression level of SAGE1 gene or the molecular expression level of SAGE1 gene; and/or, the substance for detecting SAGE1 gene or active fragment thereof comprises a specific probe for detecting SAGE1 gene or the active fragment thereof; and/or the substance for detecting SAGE1 gene or the active fragment thereof comprises a primer for specifically amplifying SAGE1 gene.

In some embodiments, the tumor is a solid tumor or hematological tumor, preferably selected from intestinal cancer, lung cancer, liver cancer, breast cancer, esophageal cancer, head and neck cancer, skin cancer, kidney cancer, leukemia, colon adenocarcinoma (coad), liver hepatocellular carcinoma (lihc), ovarian serous cystadenocarcinoma (ov), uterine corpus endometrial carcinoma (ucec), thyroid carcinoma (thca), skin cutaneous melanoma (skcm), lung adenocarcinoma (luad), head and neck squamous cell carcinoma (hnsc), glioblastoma multiforme (gbm), prostate adenocarcinoma (prad), thymoma (thym), brain lower grade glioma (lgg), rectum adenocarcinoma (read), pheochromocytoma and paraganglioma (pcpg), esophageal carcinoma (esca), kidney renal clear cell carcinoma (kirc), cervical squamous cell carcinoma and endocervical adenocarcinoma (cesc), bladder urothelial carcinoma (blca), kidney renal papillary cell carcinoma (kirp), pancreatic adenocarcinoma (paad), stomach adenocarcinoma (stad), kidney chromophobe (kich), breast invasive carcinoma (brca), lung squamous cell carcinoma (lusc), sarcoma (sarc), acute myeloid leukemia (laml).

In some embodiments, the diagnosis of tumor or whether the subject is suitable for targeted therapy of SAGE1 is based on the expression level of SAGE1 gene in a sample.

In some embodiments, SAGE1 gene is a single biomarker in the kit.

Cancer-testis antigen, a tumor-associated antigen, which mainly expressed in cells of testis and embryonic tissues, has low or no expression in other normal tissues. However, it has high expression in different proportions of malignant tumor cells of different tissue types, and is a potential antigen target for early detection and immunotherapy of tumor. Recent studies have evaluated their roles in tumorigenesis, which may involve the regulation of important cellular processes during development, stem cell differentiation and carcinogenesis. However, whether and how these reactivated testicular proteins play a role in supporting tumorigenicity remains largely unexplained. The present disclosure have unexpectedly discovered in a large amount of studies that SAGE1, a CT-X cancer testicular antigen located on the X chromosome (X: 135895410-135913726, Xq26.3), is expressed in various tumor tissues and cells, such as intestinal cancer, lung cancer, liver cancer, breast cancer, skin cancer, head and neck cancer, leukemia, etc., and the expression of SAGE1 is not detected in other normal cells except for testicular tissue. SAGE1 (e.g. SAGE1 gene or its expression products) is thereby contemplated for use in for assessing whether a subject is susceptible to a tumor, diagnosing whether a subject has a tumor, or assessing the therapeutic effect of a tumor treatment and/or determining the prognosis of a tumor.

In one aspect, the present disclosure provides use of a substance for detecting SAGE1 gene or an active fragment thereof in the preparation of a kit for evaluating the therapeutic effect of treatment for tumor and/or determining the prognosis of tumor. The kit can generally detect the expression amount of SAGE1 gene or an active fragment thereof in a sample by a substance for detecting the SAGE1 gene or the active fragment thereof, so that the expression amount of the SAGE1 gene or the active fragment thereof in the sample can be used to evaluate the malignancy of tumor, evaluate the therapeutic effect of treatment for tumor and/or determine the prognosis of tumor. The present disclosure discovered that the expression of SAGE1 gene or an active fragment thereof is closely related to the malignancy of tumor in patients, the therapeutic effect of treatment in patients after receiving the treatment and/or prognosis of tumor.

In particular, for solid tumor or hematological tumor, SAGE1-positive tumors generally show higher level of malignancy, and patients with SAGE1-positive tumors generally show relatively poor response after receiving tumor treatment, have relatively poor prognosis and have new tumor(s) developed in a relatively shorter period of time. For example, patients with SAGE1-positive tumor have relatively shorter overall survival and/or progression-free survival. As another example, positive SAGE1 expression is associated with lymph node metastasis and patients with SAGE1 positive tumor are more likely to have lymph node metastasis or develop new tumor. The SAGE1 expression can refer to the expression level of SAGE1 mRNA, or the expression level of SAGE1 protein. Positive SAGE1 expression (or SAGE1 positivity) generally refers to the presence of SAGE1 expression, or a higher level of SAGE1 expression relative to a reference. In one embodiment, positive SAGE1 expression is indicated by the detectable expression of SAGE1 mRNA in a tumor tissue. In one embodiment, positive SAGE1 expression is indicated by the detectable expression of SAGE1 protein in a tumor tissue. In one embodiment, positive SAGE1 expression is indicated by the detection of a higher expression of SAGE1 mRNA in a sample relative to the surrounding healthy tissues. In one embodiment, positive SAGE1 expression is indicated by the detection of a higher expression of SAGE1 protein in a sample relative to the surrounding healthy tissues.

For patient with solid tumor or hematological tumor, those with higher level of SAGE1 expression usually have tumors with higher level of malignancy, and generally show relatively poor response after receiving tumor treatment, have relatively poor prognosis and have new tumor(s) developed in a relatively shorter period of time. For example, the higher the level of SAGE1 expression, the shorter the overall survival and/or progression survival of the patient. For another example, high level of SAGE1 expression is associated with lymph node metastasis; the higher the level of SAGE1 expression, the more likely the patients to have lymph node metastasis or develop new tumor(s).

The therapeutic effect of tumor treatment or the prognosis of tumor can be evaluated by evaluating the overall survival and/or progression-free survival in tumor patients. The Overall Survival (OS) usually refers to the time period between a certain time point (e.g., when the tumor is evaluated or when the tumor is removed surgically, etc.) to the death of the patient due to any cause. The progression-free survival (PFS) generally refers to the time period from a certain time point (e.g., when the tumor is evaluated, when the tumor is removed surgically, etc.) to another time point when local or regional regression of tumor is detected or distant metastasis is detected, or to the death of the patient.

In another aspect, the present disclosure provides use of a substance for detecting SAGE1 gene or an active fragment thereof in the preparation of a kit for diagnosing a tumor. The kit can detect the expression level of the SAGE1 gene or an active fragment to diagnose tumor or determine whether SAGE1-targeted therapy is suitable for a subject. The present disclosure found that the expression of SAGE1 gene or an active fragment thereof is closely related to whether a subject has tumor and that SAGE1-targeted therapy is more suitable for a tumor patient having positive SAGE1 expression or a high level of SAGE1 expression.

Specifically, among patients with solid tumor and/or hematologic tumor, SAGE1 gene is specifically and positively expressed in tumor tissues. Therefore, whether a patient has a tumor can be determined by the expression amount of the SAGE1 gene. For example, patients with positive SAGE1 expression usually are more likely to have tumor. Alternatively, the expression amount of the SAGE1 gene can be used to determine whether a subject is suitable for targeted therapy for SAGE1. The present disclosure demonstrates that inhibition of SAGE1 can significantly inhibit the proliferation, migration and anchorage-independent growth of tumor cell while colonogenic capacity of tumor cells can be restored if the disrupted expression of SAGE1 is restored, indicating that patients with positive SAGE1 expression and/or high level of SAGE1 expression are generally suitable for targeted therapy for SAGE 1.

In the present disclosure, the substance for detecting SAGE1 gene or its active fragment are well known to those skilled in the art, so are the method for preparing the substance. Specifically, the substance may detect the expression of SAGE1 gene or an active fragment thereof in general, and specifically may detect the protein expression level of SAGE1 gene, or the molecule (e.g., SAGE1 mRNA) expression level of SAGE1 gene. For example, the substance may be a substance capable of specifically binding to a target molecule (e.g., SAGE1 mRNA, SAGE1 protein, etc.), and the binding of the substance is detected. In one embodiment, the substance can be a probe capable of specifically binding to SAGE1 gene; in another embodiment, the substance can be an antibody capable of specifically targeting SAGE1 protein. As another example, the substance may be a substance capable of specifically amplifying the SAGE1 gene, and the expression of the SAGE1 gene or an active fragment thereof can be detected by detecting the gene fragment obtained from the specific amplification. In one embodiment, the substance may be a primer capable of specifically amplifying the SAGE1 gene and/or a label (e.g., a dye) suitable for detecting the product resulting from amplification, or the like.

In the present disclosure, the method of using the kit generally depends on the substance for detecting SAGE1 gene or an active fragment thereof. The kit can be in general used for detection carried out on cells, tissues and body fluids from a patient. Specifically, the substance for detecting the SAGE1 gene or the active fragment thereof can be used for detecting the SAGE1 gene or the active fragment thereof in the cells, the tissues and the body fluids from a subject. The body fluid can be, for example, one or a combination of more fluids selected from intracellular fluid (including nuclei), extracellular fluid and the like. The extracellular fluid can specifically be, for example, one or a combination of more of the body fluids selected from interstitial fluid, plasma, lymph fluid and the like. In one embodiment, the sample to be detected by the kit is selected from a cell, a blood sample (e.g., a plasma sample and/or a whole blood sample, etc.), and a tissue (e.g., a tumor tissue or a paracancerous tissue, etc.) or a pathological section thereof.

In some embodiments, the tumor is a solid tumor or hematological tumor, selected from e.g., intestinal cancer, lung cancer, liver cancer, breast cancer, esophageal cancer, head and neck cancer, skin cancer, kidney cancer, leukemia, colon adenocarcinoma (coad), liver hepatocellular carcinoma (lihc), ovarian serous cystadenocarcinoma (ov), uterine corpus endometrial carcinoma (ucec), thyroid carcinoma (thca), skin cutaneous melanoma (skcm), lung adenocarcinoma (luad), head and neck squamous cell carcinoma (hnsc), glioblastoma multiforme (gbm), prostate adenocarcinoma (prad), thymoma (thym), brain lower grade glioma (lgg), rectum adenocarcinoma (read), pheochromocytoma and paraganglioma (pcpg), esophageal carcinoma (esca), kidney renal clear cell carcinoma (kirc), cervical squamous cell carcinoma and endocervical adenocarcinoma (cesc), bladder urothelial carcinoma (blca), kidney renal papillary cell carcinoma (kirp), pancreatic adenocarcinoma (paad), stomach adenocarcinoma (stad), kidney chromophobe (kich), breast invasive carcinoma (brca), lung squamous cell carcinoma (lusc), sarcoma (sarc), acute myeloid leukemia (laml) and the like.

The SAGE1 gene may be a single biomarker in the kit, that is, the kit does not include any substances for detecting other biomarkers in addition to the substances for detecting the SAGE1 gene or an active fragments thereof. The SAGE1 gene can be used as a single biomarker in the kit to evaluate the therapeutic effect of the tumor treatment and/or determine the prognosis of tumor or diagnose tumor.

The present disclosure provides SAGE1 gene or an active fragment thereof act as a biomarker for evaluating tumor malignancy, metastasis, relapse, prognosis and for selecting targeted therapy. Compared with the existing traditional biomarkers, SAGE1 has a higher specificity (SAGE1 expresses in tumor tissues but not normal tissues) and an accuracy close to 100% in distinguishing tumor from normal tissues, and it can also serve as a therapeutic target for tumor treatment and be used for tumor-immune imaging. In addition, the expression profile of SAGE1 can provide basis for evaluating the therapeutic effect of tumor treatment, monitoring relapse and metastasis, and determining the malignancy level of a tumor.

ii. Use of SAGE1 Inhibitor in Preparation of Medicine or Kit

In another aspect, the present disclosure provides use of a SAGE1 inhibitor in the manufacture of a medicament or kit for: 1) treating tumor; and/or 2) modulating the expression level of a SAGE1-INTS3 complex.

In some embodiments, the SAGE1 inhibitor inhibits the expression and/or function of SAGE 1.

In some embodiments, the SAGE1 inhibitor is a single active ingredient.

In some embodiments, the SAGE1 inhibitor is selected from a nucleic acid molecule, a protein molecule, or a compound.

In some embodiments, the nucleic acid molecule is selected from the group consisting of an interfering RNA for SAGE1, an antisense oligonucleotide for SAGE1 and an agent for knocking-out or knocking-down SAGE1 expression; and/or, the protein molecule is an anti-SAGE 1 antibody, preferably a monoclonal antibody.

In some embodiments, the nucleic acid molecule targets a target sequence comprising a sequence as set forth in any one of SEQ ID Nos. 59-67, the polynucleotide sequence of the nucleic acid molecule comprises a sequence as set forth in any one of SEQ ID Nos. 87-95 and 96-99.

In some embodiments, the SAGE1 inhibitor competes with SAGE1 for binding to INTS3, preferably the SAGE1 inhibitor is INTS6, INTS6L, or the combination thereof.

In some embodiments, the tumor is a SAGE1 positive tumor.

In some embodiments, the tumor is a solid tumor or hematological tumor, preferably selected from intestinal cancer, lung cancer, liver cancer, breast cancer, esophageal cancer, head and neck cancer, skin cancer, kidney cancer, leukemia, colon adenocarcinoma (coad), liver hepatocellular carcinoma (lihc), ovarian serous cystadenocarcinoma (ov), uterine corpus endometrial carcinoma (ucec), thyroid carcinoma (thca), skin cutaneous melanoma (skcm), lung adenocarcinoma (luad), head and neck squamous cell carcinoma (hnsc), glioblastoma multiforme (gbm), prostate adenocarcinoma (prad), thymoma (thym), brain lower grade glioma (lgg), rectum adenocarcinoma (read), pheochromocytoma and paraganglioma (pcpg), esophageal carcinoma (esca), kidney renal clear cell carcinoma (kirc), cervical squamous cell carcinoma and endocervical adenocarcinoma (cesc), bladder urothelial carcinoma (blca), kidney renal papillary cell carcinoma (kirp), pancreatic adenocarcinoma (paad), stomach adenocarcinoma (stad), kidney chromophobe (kich), breast invasive carcinoma (brca), lung squamous cell carcinoma (lusc), sarcoma (sarc), acute myeloid leukemia (laml).

In another aspect, the present disclosure provides a composition comprising the SAGE1 inhibitor as disclosed herein, wherein the composition is for use in:

treating tumor; and/or modulating the expression level of SAGE1-INTS3 complex.

Genes of cancer/testis (cancer-testis antigen or CTA) family are normally expressed only in the testis of adult animals with low or no expression in other normal tissues, but they are also expressed in almost all types of malignancies and hematological tumors. These CTAs are considered as key biomarkers of cancer and are also excellent antigen targets for cancer immunotherapy. Several cancer testis antigens, such as NY-ESO-1, have been developed for cancer vaccines that have entered third-phase clinics. Recent studies have assessed their role in tumorigenesis, which may involve the regulation of important cellular processes during development, stem cell differentiation and carcinogenesis. It has been demonstrated that a large number of cancer testis antigens are selectively expressed in cancer stem cells (CSCs) or cancer-initiating cells (CICs); however, whether and how these reactivated testis proteins play a role in supporting tumorigenicity remains largely unexplained. The present disclosure has discovered unexpectedly in a large number of studies that SAGE1, the CT-X cancer testis antigen located on the X chromosome (X: 135895410-135913726, Xq26.3), is abnormally activated in various types of human tumors as a tumor-specific antigen outside normal testis tissues. SAGE1 can form a functional complex with INTS3; SAGE1-INTS3 complex are found specifically in various tumor cells and tumor tissues. The present disclosure further demonstrates that specifically targeting SAGE1 genes/proteins or SAGE1-INTS3 complex genes/proteins can significantly inhibits the proliferation and anchorage-independent growth of SAGE1 positive cancer cells as well as the growth of xenografts in-vivo, thereby providing a new effective target for the treatment of tumors.

In one aspect, the invention provides the use of a SAGE1 inhibitor in the manufacture of a medicament or kit for use in the treatment of tumors. It is found that SAGE1 is not only positively expressed across different types of tumors, but patients with positive SAGE1 expression also show relatively poor prognosis. SAGE1 is specifically and positively expressed in tumor tissues but not healthy tissues (e.g., paracancerous tissues). The present disclosure found that inhibition of SAGE1 can significantly inhibit the proliferation, migration and anchorage-independent growth of tumor cell while colonogenic capacity of tumor cells can be restored if the disrupted expression of SAGE1 is restored, demonstrating that the SAGE1 inhibitor can be used for the treatment of tumors.

The term "treatment" as used herein refers to prophylactic, curative or palliative treatment that can lead to a desired pharmaceutical and/or physiological effect. Preferably, such effect refers to medically reducing one or more symptoms of the disease or completely eliminating the disease, or blocking or delaying the occurrence of the disease and/or reducing of the risk of disease progression or deterioration.

In another aspect, the disclosure provides use of a SAGE1 inhibitor in the manufacture of a medicament or kit for use in modulating the expression level of a SAGE1-INTS3 complex. The present disclosure discovered that SAGE1 as a tumor specific antigen can form a complex with INTS3 after abnormal activation. The SAGE1-INTS3 complex are specifically found in various tumor cells and tumor tissues. When SAGE1 is inhibited, expression of wild type SAGE1 could promote tumor cell proliferation but expression of mutant SAGE1 carrying point mutations in key residues ((F838A, F873A, K874A, R872A, M832A, Q840A) that interact with INTS3 could not. These findings indicated that SAGE1 needs to form a complex with INTS3 to function, and that reducing the amount of SAGE1-INTS3 complex in the cell by disrupting SAGE1 and INTS3 interaction can be used to inhibit the growth of tumor cells.

The SAGE1-INTS3 complex generally refers to a complex of SAGE1 and INTS3 that is formed by protein-protein interaction. Typically, the INTS3 can form a dimer (e.g., in solution), which can further form a complex with SAGE1 through interactions such as hydrogen bond, salt bridge and the like. The crystal structure of the SAGE1-INTS3 complex can have the unit cell parameters shown below: a=260.112±0.1 Å, b=46.240±0.1 Å, c=103.101±0.1 Å, α=90±0.1 Å, β=113.280±0.1 Å, γ=90±0.1 Å. In the SAGE1-INTS3 complex, the key amino acid residues for the formation of the SAGE1 and INTS3 complex typically include F838, F873, K874, R872, M832, Q840, and the like.

The SAGE1 inhibitor as disclosed herein can inhibit the expression and/or function of SAGE1. For example, the SAGE1 inhibitor can either partially inhibit, i.e., reducing, the expression and/or function of SAGE1, or completely inhibit, i.e., eliminating, the expression and/or function of SAGE1, which function includes the ability of SAGE1 to bind to INTS3 to form SAGE1-INTS3 complex. The types of agents capable of acting as SAGE1 inhibitors are known to those skilled in the art. For example, the inhibitors can be antagonists, blockers and the like. For another example, the inhibitors can inhibit SAGE1 expression at the nucleic acid (e.g., mRNA) level or protein level. For further examples, the inhibitors can be an agent that competes with SAGE1 for binding to INTS3. In some embodiments, the SAGE1 inhibitor is a nucleic acid molecule, a protein molecule, a compound or the like. The nucleic acid molecule may be selected from an interfering RNA against SAGE1, an antisense oligonucleotide against SAGE1, an agent for knocking out or knocking down expression of SAGE. Specifically, the SAGE1 inhibitor can be siRNA, miRNA, shRNA, a gene knock-out vector or a gene expression vector that is capable of expressing siRNA, shRNA, interfering RNA or the like. The protein molecule may be selected from anti-SAGE 1 antibodies, which may be monoclonal antibodies or polyclonal antibodies. As one example. the agent capable of competing with SAGE1 for binding to INTS3 can be INTS6 (DDX26, Accession: NP 036273.1) or INTS6L (DDX26b, Accession: Q8BND4.1) or a combination thereof. In some embodiments, the nucleic acid molecule targets a target sequence comprising a sequence as set forth in any one of SEQ ID Nos. 59 to 67. In one embodiment, the polynucleotide sequence of the nucleic acid molecule comprises a sequence as set forth in any one of SEQ ID Nos. 87-95. In one embodiment, the polynucleotide sequence of the nucleic acid molecule comprises a sequence as set forth in any one of SEQ ID Nos. 96-99.

In the medicament or kit disclosed herein, the SAGE1 inhibitor can be used as a single active ingredient, or in combination with other active ingredient(s) for the treatment of tumors.

The tumors to be treated by the medicament or kit disclosed herein are generally SAGE1 positive tumor. SAGE1 positivity or positive SAGE1 expression generally refers to the presence of SAGE1 expression, or a higher level of SAGE1 expression relative to a reference. In one embodiment, positive SAGE1 expression is indicated by the detectable expression of SAGE1 mRNA in a tumor tissue. In one embodiment, positive SAGE1 expression is indicated by the detectable expression of SAGE1 protein in a tumor tissue. In one embodiment, positive SAGE1 expression is indicated by the detection of a higher expression of SAGE1 mRNA in a tumor tissue relative to its surrounding healthy tissues. In one embodiment, positive SAGE1 expression is indicated by the detection of a higher expression of SAGE1 protein in a tumor tissue relative to its surrounding healthy tissues. In some embodiments, the tumor is a solid tumor or hematological tumor, selected from e.g., intestinal cancer, lung cancer, liver cancer, breast cancer, esophageal cancer, head and neck cancer, skin cancer, kidney cancer, leukemia, colon adenocarcinoma (coad), liver hepatocellular carcinoma (lihc), ovarian serous cystadenocarcinoma (ov), uterine corpus endometrial carcinoma (ucec), thyroid carcinoma (thca), skin cutaneous melanoma (skcm), lung adenocarcinoma (luad), head and neck squamous cell carcinoma (hnsc), glioblastoma multiforme (gbm), prostate adenocarcinoma (prad), thymoma (thym), brain lower grade glioma (lgg), rectum adenocarcinoma (read), pheochromocytoma and paraganglioma (pcpg), esophageal carcinoma (esca), kidney renal clear cell carcinoma (kirc), cervical squamous cell carcinoma and endocervical adenocarcinoma (cesc), bladder urothelial carcinoma (blca), kidney renal papillary cell carcinoma (kirp), pancreatic adenocarcinoma (paad), stomach adenocarcinoma (stad), kidney chromophobe (kich), breast invasive carcinoma (brca), lung squamous cell carcinoma (lusc), sarcoma (sarc), acute myeloid leukemia (laml) and the like.

In another aspect, the present disclosure provides a composition comprising the SAGE1 inhibitor as disclosed herein, wherein the composition is for use in: treating tumor; and/or modulating the expression level of SAGE1-INTS3 complex.

In another aspect, the present disclosure provides a modulating method, which can be used to modulate the expression level of the SAGE1-INTS3 complex, e.g., in an individual, a cell, and the like. For example, the method can comprise administering an effective amount of SAGE1 inhibitor or composition in a subject as disclosed herein.

In another aspect, the present disclosure provides a treatment method, comprising administering an effective amount of SAGE1 inhibitor or composition as disclosed herein in a subject. The method can be used for the treatment of diseases including, without limitation, tumors. In some embodiments, the tumor is a solid tumor or hematological tumor, selected from, e.g., intestinal cancer, lung cancer, liver cancer, breast cancer, esophageal cancer, head and neck cancer, skin cancer, kidney cancer, leukemia, colon adenocarcinoma (coad), liver hepatocellular carcinoma (lihc), ovarian serous cystadenocarcinoma (ov), uterine corpus endometrial carcinoma (ucec), thyroid carcinoma (thca), skin cutaneous melanoma (skcm), lung adenocarcinoma (luad), head and neck squamous cell carcinoma (hnsc), glioblastoma multiforme (gbm), prostate adenocarcinoma (prad), thymoma (thym), brain lower grade glioma (lgg), rectum adenocarcinoma (read), pheochromocytoma and paraganglioma (pcpg), esophageal carcinoma (esca), kidney renal clear cell carcinoma (kirc), cervical squamous cell carcinoma and endocervical adenocarcinoma (cesc), bladder urothelial carcinoma (blca), kidney renal papillary cell carcinoma (kirp), pancreatic adenocarcinoma (paad), stomach adenocarcinoma (stad), kidney chromophobe (kich), breast invasive carcinoma (brca), lung squamous cell carcinoma (lusc), sarcoma (sarc), acute myeloid leukemia (laml) and the like.

"Subject" as used herein generally refers to humans, non-human primates such as mammals, dogs, cats, horses, sheep, pigs, cows, etc., which would benefit from treatment with the agents, kits, or combinations described herein.

"Therapeutically effective amount" as used herein generally refers to an amount that is effective, after an appropriate period of administration, for treating a disease disclosed herein.

The SAGE1 gene provided herein can be used as a target for anti-tumor medicament. The present disclosure found that silencing the expression of SAGE1 gene could significantly inhibit proliferation, migration, the like of in a variety of tumor cells (e.g., melanoma cell A375, duodenum adenocarcinoma cell HUTO80, colorectal adenocarcinoma cell Caco-2, esophageal cancer cells TE1) that show positive SAGE1 expression, indicating that SAGE1 act as a tumor-promoting factor across different types of tumors. In addition, silencing the expression of SAGE1 gene can significantly inhibit the growth of human-derived solid tumors and promote tumor cell death in solid tumors, indicating that this target has significant physiological functions. Further, SAGE1 is specifically expressed in various tumor tissues and but not in normal tissues except for testis. Although SAGE1 protein is typically located in a nucleus, peptide fragments of the protein are presented on the surface of tumor cells by major histocompatibility complex (WIC), which can be utilized for target recognition in targeted therapy and/or immune activation in cancer immunotherapy. Hence, SAGE1-targeted gene interference therapy provides high specificity and does not affect normal tissues without SAGE1 expression, thereby not affecting normal physiological functions or health. SAGE1 inhibitor, which inhibits the expression and/or function of SAGE1, has great potential in tumor treatment in the clinic.

iii. Use of Substances for Modulating the Expression and/or Function of the SAGE1-INTS3 Complex In another aspect, the present disclosure provides use of a substance for modulating the expression and/or function of SAGE1-INTS3 complex in the manufacture of a medicament or kit for treating tumor.

In some embodiment, the substance for modulating the expression and/or function of SAGE1-INTS3 complex is a single active ingredient.

In some embodiment, the substance is for use in modulating the expression and/or function of SAGE1-INTS3 complex.

In some embodiments, the substance for modulating the expression and/or function of SAGE1-INTS3 complex is selected from a nucleic acid molecule, a protein molecule and a compound.

In some embodiment, the substance for modulating the expression and/or function of SAGE1-INTS3 complex is a SAGE1 inhibitor.

In some embodiment, the SAGE1 inhibitor is selected from the group consisting of an interfering RNA for SAGE1, an antisense oligonucleotide for SAGE1 and an agent for knocking-out or knocking-down SAGE1 expression;

In some embodiment, the SAGE1 inhibitor is a substance that competes with SAGE1 for binding to INTS3, and/or the SAGE1 inhibitor is selected from INTS6 and INTS6L.

In some embodiments, the tumor is a SAGE1 positive tumor.

In some embodiments, the tumor is a solid tumor or hematological tumor, preferably selected from intestinal cancer, lung cancer, liver cancer, breast cancer, esophageal cancer, head and neck cancer, skin cancer, kidney cancer, leukemia, colon adenocarcinoma (coad), liver hepatocellular carcinoma (lihc), ovarian serous cystadenocarcinoma (ov), uterine corpus endometrial carcinoma (ucec), thyroid carcinoma (thca), skin cutaneous melanoma (skcm), lung adenocarcinoma (luad), head and neck squamous cell carcinoma (hnsc), glioblastoma multiforme (gbm), prostate adenocarcinoma (prad), thymoma (thym), brain lower grade glioma (lgg), rectum adenocarcinoma (read), pheochromocytoma and paraganglioma (pcpg), esophageal carcinoma (esca), kidney renal clear cell carcinoma (kirc), cervical squamous cell carcinoma and endocervical adenocarcinoma (cesc), bladder urothelial carcinoma (blca), kidney renal papillary cell carcinoma (kirp), pancreatic adenocarcinoma (paad), stomach adenocarcinoma (stad), kidney chromophobe (kich), breast invasive carcinoma (brca), lung squamous cell carcinoma (lusc), sarcoma (sarc), acute myeloid leukemia (laml).

In another aspect, the present disclosure provides a composition for use in the treatment of tumor, wherein the composition comprise a substance for use in modulating the expression and/or function of SAGE1-INTS3 complex.

The present disclosure have unexpectedly discovered in a large amount of studies that SAGE1, a CT-X cancer testicular antigen located on the X chromosome (X: 135895410-135913726, Xq26.3), is expressed as a tumor specific antigen in various tumor tissues and cells, such as intestinal cancer, lung cancer, liver cancer, breast cancer, skin cancer, head and neck cancer, leukemia, etc., and, after abnormal activation, forms a novel functional complex with INTS3 in various types of human tumors. The present disclosure found that specifically targeting SAGE1 genes/proteins or SAGE1-INTS3 complex genes/proteins can significantly inhibits the proliferation and anchorage-independent growth of SAGE1 positive cancer cells as well as the growth of xenografts in-vivo, thereby providing a new effective target for the treatment of tumors.

In one aspect, the present disclosure provides use of a substance for modulating the expression and/or function of SAGE1-INTS3 complex in the manufacture of a medicament or kit for treating tumor. The present disclosure found that SAGE-INTS3 complex only present in cells where SAGE1 are expressed and binds INTS3, but does not present in cells that is negative in SAGE1 expression. The major differential gene expression resulted from reduction of SAGE1 expression is consistent with that resulted from reduction of INTS3 expression., i.e., the genes that are up-regulated in response to reduction of SAGE1 expression is also up-regulated in response to reduction of INTS3 expression, and vice versa, suggesting that SAGE1 regulates and alters the expression of tumor-associated genes by forming a complex with INTS3. INTS3 and SAGE1 are synergistic and function as one complex unit. Furthermore, the disruption of the interaction between INTS3-SAGE1 can completely abrogate the ability of SAGE1 to promote tumor cell growth and significantly inhibit the growth of xenografts. The present disclosure demonstrates that SAGE1-INTS3 complex can act as the target for inhibiting tumor growth.

The SAGE1-INTS3 complex generally refers to a complex of SAGE1 and INTS3 that is formed by protein-protein interaction. Typically, the INTS3 can form a dimer (e.g., in solution), which can further form a complex with SAGE1 through interactions such as hydrogen bond, salt bridge and the like. The crystal structure of the SAGE1-INTS3 complex can have the unit cell parameters shown below: a=260.112±0.1 Å, b=46.240±0.1 Å, c=103.101±0.1 Å, α=90±0.1 Å, β=113.280±0.1 Å, γ=90±0.1 Å. In the SAGE1-INTS3 complex, the key amino acid residues for the formation of the SAGE1 and INTS3 complex typically include F838, F873, K874, R872, M832, Q840, and the like.

The term "treatment" as used herein refers to prophylactic, curative or palliative treatment that can lead to a desired pharmaceutical and/or physiological effect. Preferably, such effect refers to medically reducing one or more symptoms of the disease or completely eliminating the disease, or blocking or delaying the occurrence of the disease and/or reducing of the risk of disease progression or deterioration.

The substance for modulating the expression and/or function of SAGE1-INTS3 complex can be a substance that inhibit the expression and/or function of SAGE1-INTS3 complex. For example, the substance for inhibiting the expression and/or function of SAGE1-INTS3 complex may partially inhibit, i.e., reduce the expression and/or function of SAGE1-INTS3, or completely inhibit, i.e., completely eliminate the expression and/or function of SAGE1-INTS3. The substance for inhibiting the expression and/or function of the SAGE1-INTS3 complex may be any substances (e.g., a nucleic acid molecule, a protein molecule, or a compound, and the like) capable of performing the above mentioned function.

The substance for modulating the expression and/or function of SAGE1-INTS3 complex can be a SAGE1 inhibitor. The SAGE1 inhibitor can either partially inhibit, i.e., reducing, the expression and/or function of SAGE1, or completely inhibit, i.e., eliminating, the expression and/or function of SAGE1, which function includes the ability of SAGE1 to bind to INTS3 to form SAGE1-INTS3 complex. The types of agents capable of acting as SAGE1 inhibitors are known to those skilled in the art. For example, the inhibitors can be antagonists, blockers and the like. For another example, the inhibitors can inhibit SAGE1 expression at the nucleic acid (e.g., mRNA) level or protein level. For further examples, the inhibitors can be an agent that competes with SAGE1 for binding to INTS3. In some embodiments, the SAGE1 inhibitor is a nucleic acid molecule, a protein molecule, a compound or the like. The nucleic acid molecule may be selected from an interfering RNA against SAGE1, an antisense oligonucleotide against SAGE1, an agent for knocking out or knocking down expression of SAGE. Specifically, the SAGE1 inhibitor can be siRNA, miRNA, shRNA, a gene knock-out vector or a gene expression vector that is capable of expressing siRNA, shRNA, interfering RNA or the like. The protein molecule may be selected from anti-SAGE 1 antibodies, which may be monoclonal antibodies or polyclonal antibodies. As one example. the agent capable of competing with SAGE1 for binding to INTS3 can be INTS6 (DDX26, Accession: NP_036273.1) or INTS6L (DDX26b, Accession: Q8BND4.1) or a combination thereof. In one embodiment, In some embodiments, the nucleic acid molecule targets a target sequence comprising a sequence as set forth in any one of SEQ ID Nos. 59-67. In one embodiment, the polynucleotide sequence of the nucleic acid molecule comprises a sequence as set forth in any one of SEQ ID Nos. 87-95. In one embodiment, the polynucleotide sequence of the nucleic acid molecule comprises a sequence as set forth in any one of SEQ ID Nos. 96-99.

In the medicament or kit disclosed herein, the SAGE1 inhibitor can be used as a single active ingredient, or in combination with other active ingredient(s) for the treatment of tumors.

The tumors to be treated by the medicament or kit disclosed herein are generally SAGE1 positive tumor. SAGE1 positivity or positive SAGE1 expression generally refers to the presence of SAGE1 expression, or a higher level of SAGE1 expression relative to a reference. In one embodiment, positive SAGE1 expression is indicated by the detectable expression of SAGE1 mRNA in a tumor tissue. In one embodiment, positive SAGE1 expression is indicated by the detectable expression of SAGE1 protein in a tumor tissue. In one embodiment, positive SAGE1 expression is indicated by the detection of a higher expression of SAGE1 mRNA in a tumor tissue relative to its surrounding healthy tissues. In one embodiment, positive SAGE1 expression is indicated by the detection of a higher expression of SAGE1 protein in a tumor tissue relative to its surrounding healthy tissues. In some embodiments, the tumor is a solid tumor or hematological tumor, selected from e.g., intestinal cancer, lung cancer, liver cancer, breast cancer, esophageal cancer, head and neck cancer, skin cancer, kidney cancer, leukemia, colon adenocarcinoma (coad), liver hepatocellular carcinoma (lihc), ovarian serous cystadenocarcinoma (ov), uterine corpus endometrial carcinoma (ucec), thyroid carcinoma (thca), skin cutaneous melanoma (skcm), lung adenocarcinoma (luad), head and neck squamous cell carcinoma (hnsc), glioblastoma multiforme (gbm), prostate adenocarcinoma (prad), thymoma (thym), brain lower grade glioma (lgg), rectum adenocarcinoma (read), pheochromocytoma and paraganglioma (pcpg), esophageal carcinoma (esca), kidney renal clear cell carcinoma (kirc), cervical squamous cell carcinoma and endocervical adenocarcinoma (cesc), bladder urothelial carcinoma (blca), kidney renal papillary cell carcinoma (kirp), pancreatic adenocarcinoma (paad), stomach adenocarcinoma (stad), kidney chromophobe (kich), breast invasive carcinoma (brca), lung squamous cell carcinoma (lusc), sarcoma (sarc), acute myeloid leukemia (laml) and the like.

In another aspect, the present disclosure provides a composition for use in the treatment of tumor, wherein the composition comprise a substance as disclosed herein for use in modulating the expression and/or function of SAGE1-INTS3 complex.

In another aspect, the present disclosure provides a treatment method, comprising administering an effective amount of a substance that is capable of modulating the expression and/function of SAGE1-INTS3 complex or a complex as disclosed herein in a subject. The method can be used for the treatment of diseases including, without limitation, tumors. In some embodiments, the tumor is a solid tumor or hematological tumor, selected from, e.g., intestinal cancer, lung cancer, liver cancer, breast cancer, esophageal cancer, head and neck cancer, skin cancer, kidney cancer, leukemia, colon adenocarcinoma (coad), liver hepatocellular carcinoma (lihc), ovarian serous cystadenocarcinoma (ov), uterine corpus endometrial carcinoma (ucec), thyroid carcinoma (thca), skin cutaneous melanoma (skcm), lung adenocarcinoma (luad), head and neck squamous cell carcinoma (hnsc), glioblastoma multiforme (gbm), prostate adenocarcinoma (prad), thymoma (thym), brain lower grade glioma (lgg), rectum adenocarcinoma (read), pheochromocytoma and paraganglioma (pcpg), esophageal carcinoma (esca), kidney renal clear cell carcinoma (kirc), cervical squamous cell carcinoma and endocervical adenocarcinoma (cesc), bladder urothelial carcinoma (blca), kidney renal papillary cell carcinoma (kirp), pancreatic adenocarcinoma (paad), stomach adenocarcinoma (stad), kidney chromophobe (kich), breast invasive carcinoma (brca), lung squamous cell carcinoma (lusc), sarcoma (sarc), acute myeloid leukemia (laml) and the like.

In the present invention, "subject" generally includes humans, non-human primates, such as mammals, dogs, cats, horses, sheep, pigs, cows, etc., which would benefit from treatment with the formulation, kit or combined formulation.

In the present invention, a "therapeutically effective amount" generally refers to an amount which, after an appropriate period of administration, is capable of achieving the effect of treating the diseases as listed above.

The SAGE1-INTS3 complex provided herein can be used as a target for anti-tumor medicament. SAGE1 is expressed on the cell surface of a variety of tumors such as melanoma, bladder cancer, liver cancer, epidermoid cancer, non-small cell lung cancer, squamous cell cancer and the like, but typically not expressed in normal tissues except for testis. SAGE1-INTS3 complex can effectively serves as a therapeutic target for any types of tumors that are positive in SAGE1 expression, and the fraction of tumors that are positive in SAGE1 expression is relatively high. The SAGE1-INTS3 complex is different from other targets that have been used for targeted therapy: the interaction of SAGE1 and INTS3 in the novel complex, rather than a gene mutation, provides the basis for the mechanism of action in the targeted therapy, which also relies on the fact that SAGE1 expression is normally only found in the reproductive system, such as testis, or in the brain at a low level but not other tissues under physiological condition whereas SAGE1 is specifically expressed with different frequency in various tumor tissues. The barriers in testis and brain prevent the specific targeting on SAGE1/SAGE1-INTS3 gene/protein from affecting the normal tissues.

EXAMPLE

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

Materials and methods used in the examples are provided at the end of this section.

Example 1: SAGE1 Expression Distribution Among Normal and Cancerous Tissues

Figure 1B:
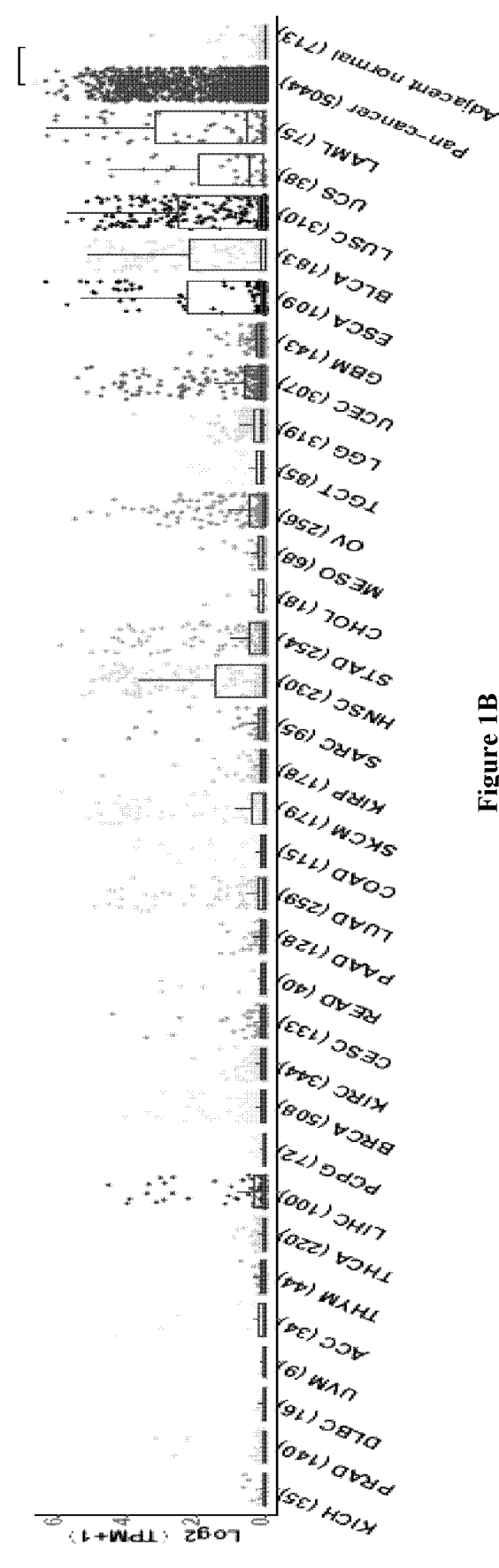
FIG. 1B illustrates expression of SAGE1 in myriad of TCGA cancer types.

SAGE1 expression is restricted in the testis with little or no expression in most somatic tissues (FIGS. 1A and 1B). TPM values for each gene that are used for visualization at the GTEx website (https://gtexportal.org/home/gene/) were downloaded from the GTEx website (https://gtexportal.org/home/datasets).

For cancerous tissues, SAGE1 aberrantly expressed in almost all types of malignancies (FIG. 1B). FPKM values for each gene in TCGA projects were obtained from the GDC website (https://portal.gdc.cancer.gov) and were converted to TPMs using this formula: $\exp(\log(FPKM)-\log(sum(FPKM))+\log(10^6))$.

Figure 1C:
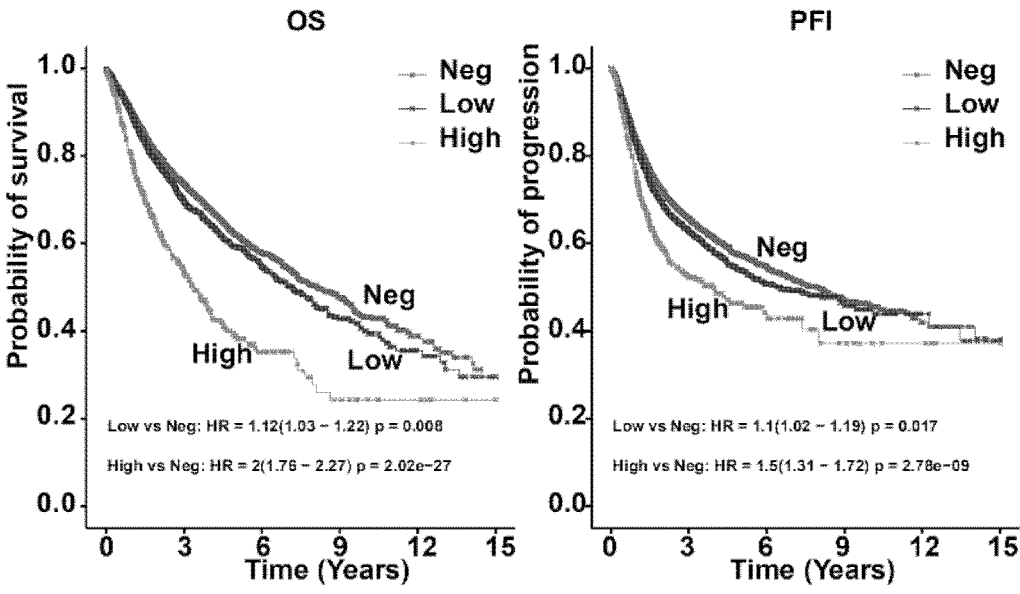
FIG. 1C illustrates overall survival (OS) and progression free interval (PFI) in patients from TCGA stratified by SAGE1 mRNA expression level.

Example 2: Overall Survival Analyses and Pattern of SAGE1 Expression Levels in Different Cancer Types in TCGA We identify SAGE1 as a pro-cancerous gene whose expression promotes cancer cell proliferation and is associated with poor prognosis of cancer patients (FIG. 1C). To understand the biological implication of SAGE1 expression in cancers, survival curve analysis was performed using TCGA datasets. The presence of SAGE1 in pan-cancers was related to poor prognosis. We further identified that a higher level of SAGE1 expression in pan-cancers was related to overall shorter survival, suggesting that expression of SAGE1 is likely associated with the advanced stage of diseases and poor prognosis.

Figure 2A:
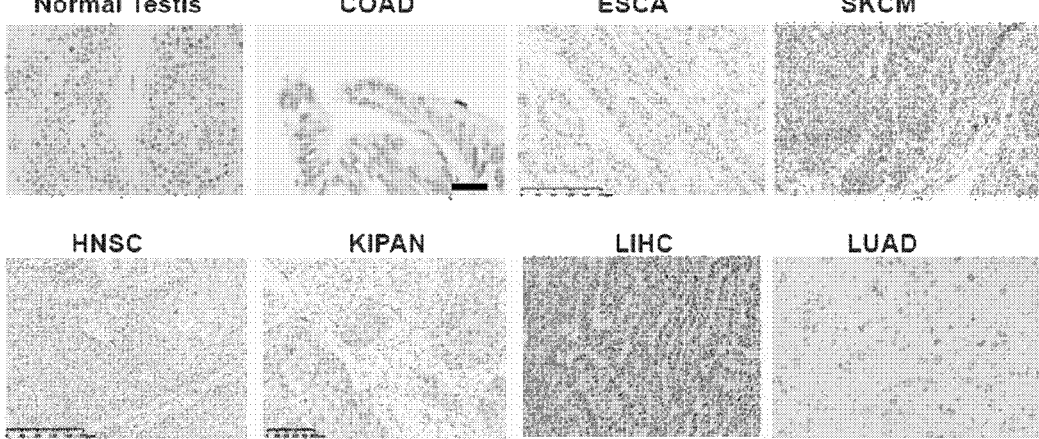
FIG. 2A illustrates IHC staining showing that SAGE1 is expressed in human testis and some tumor tissues.

We analyses SAGE1 expression levels in different cancer types in TCGA, and divided into three group according to normalized count: Negative (0 RESM), Low expression (0.1857-11.2969RESM), High expression (>11.30RESM) (FIG. 2E).

Example 3: SAGE1 Expression Levels in Many Different Tumor Tissues and PDX Mouse Treatment Effect Experiments Through IHC Staining In sharp to the restricted expression in normal tissue, we identified high expression of SAGE1 in a myriad of cancer types and a number of cancer cell lines except for testicular cancer compared to healthy tissues or paracancerous regions (FIG. 2A).

Figure 4A:
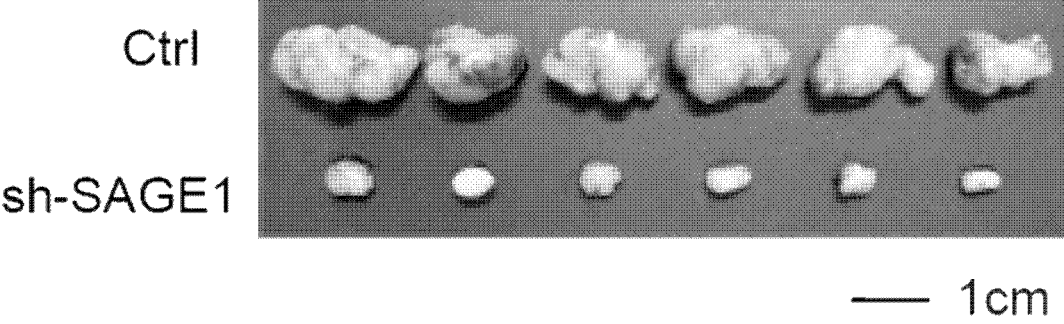
FIGS. 4A, 4B and 4C illustrate knockdown of SAGE1 in human hepatocellular carcinoma (HCC-P). Representative images of HCC-PDX tumors treated with (n=9) or without (n=9) shSAGE1 adenoviruses (FIG. 4A), and statistical analysis of tumor volumes (FIG. 4B) and weights (FIG. 4C), ***P<0.01 by nonparametric Mann-Whitney test.
Figure 4B:
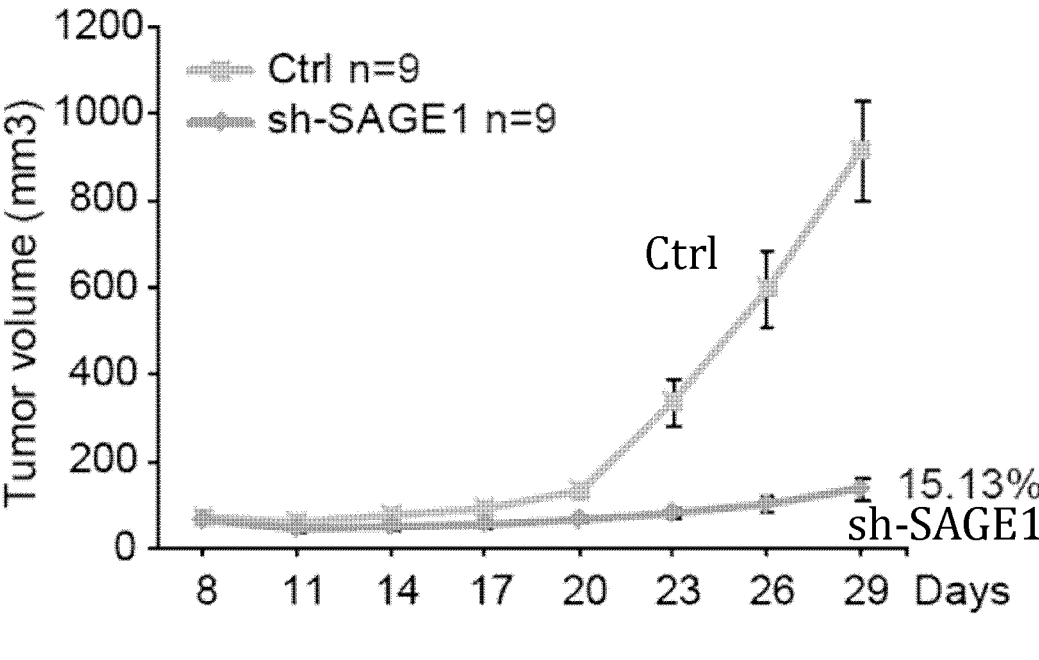
Figures 4C, 4D:
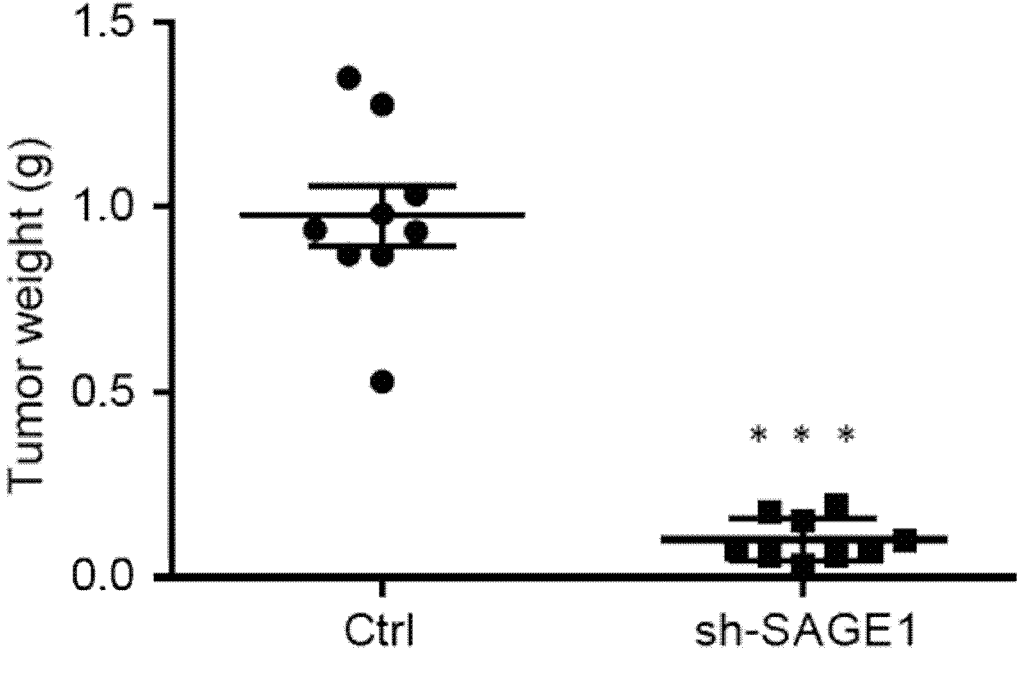
FIGS. 4D, 4E and 4F illustrate knockdown of SAGE1 in human colorectal cancer (CRC-P). Representative images of CRC-PDX tumors treated with (n=6) or without (n=9) shSAGE1 adenoviruses (FIG. 4D), and statistical analysis of tumor volumes (FIG. 4E) and weights (FIG. 4F), ***P<0.01 by nonparametric Mann-Whitney test.
Figure 4E:
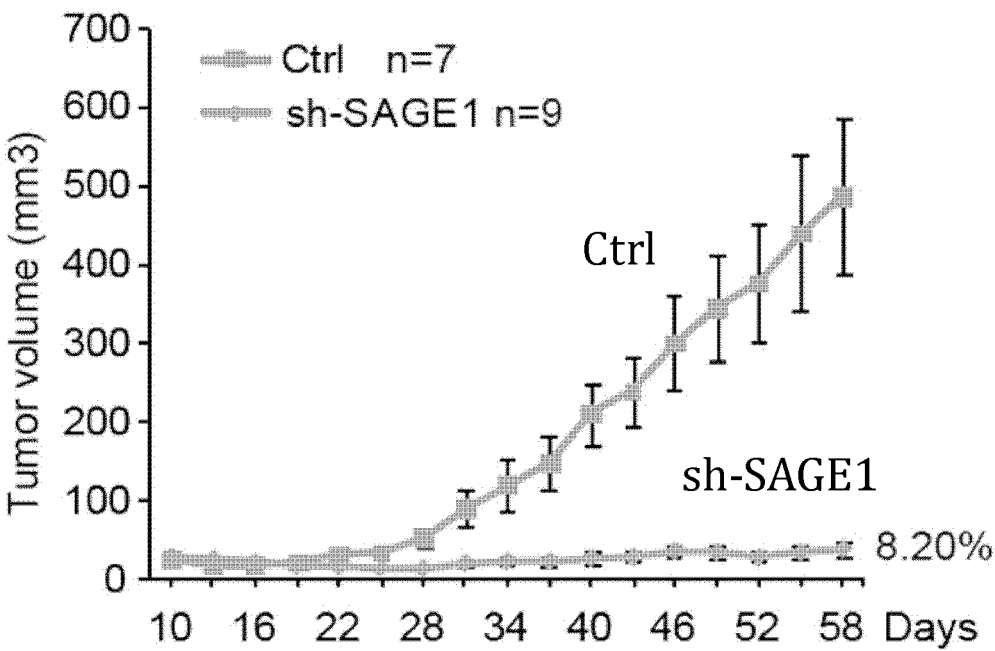
Figure 4F:
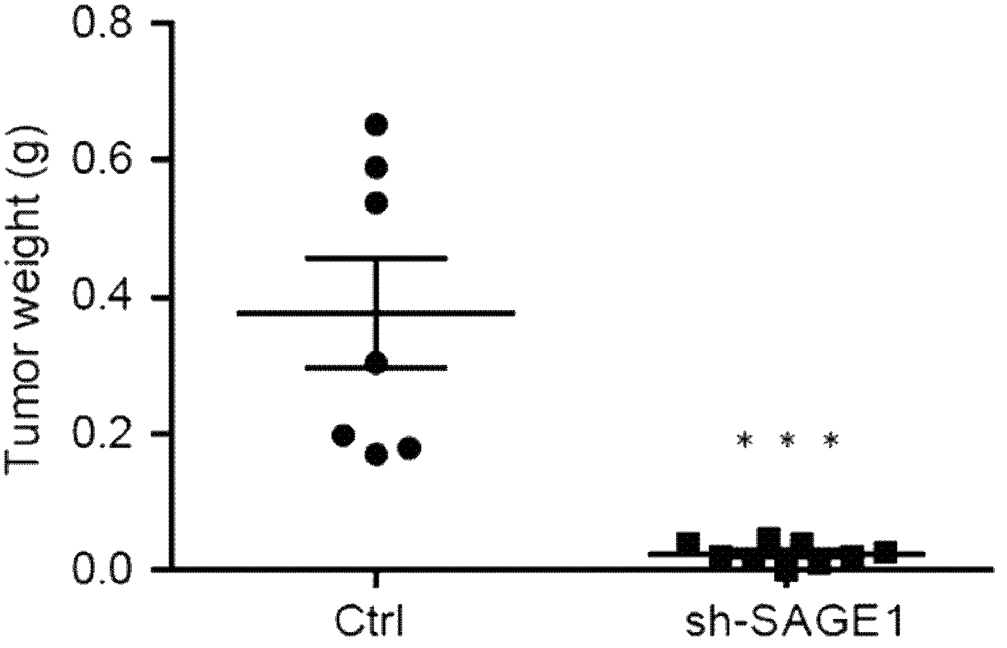
Figure 4G:
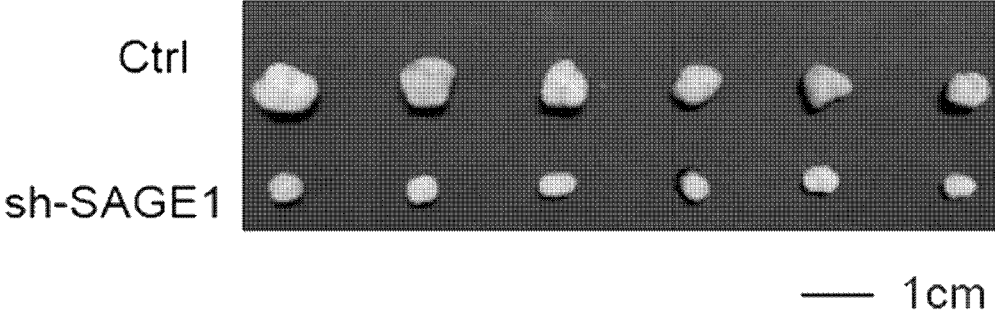
FIGS. 4G, 4H, and 4I illustrate knockdown of SAGE1 in human lung ademocarcinoma (LUAD-P). Representative images of LUAD-PDX tumors treated with (n=6) or without (n=9) shSAGE1 adenoviruses (FIG. 4G), and statistical analysis of tumor volumes (FIG. 4H) and weights (FIG. 4I), ***P<0.01 by nonparametric Mann-Whitney test.
Figure 4H:
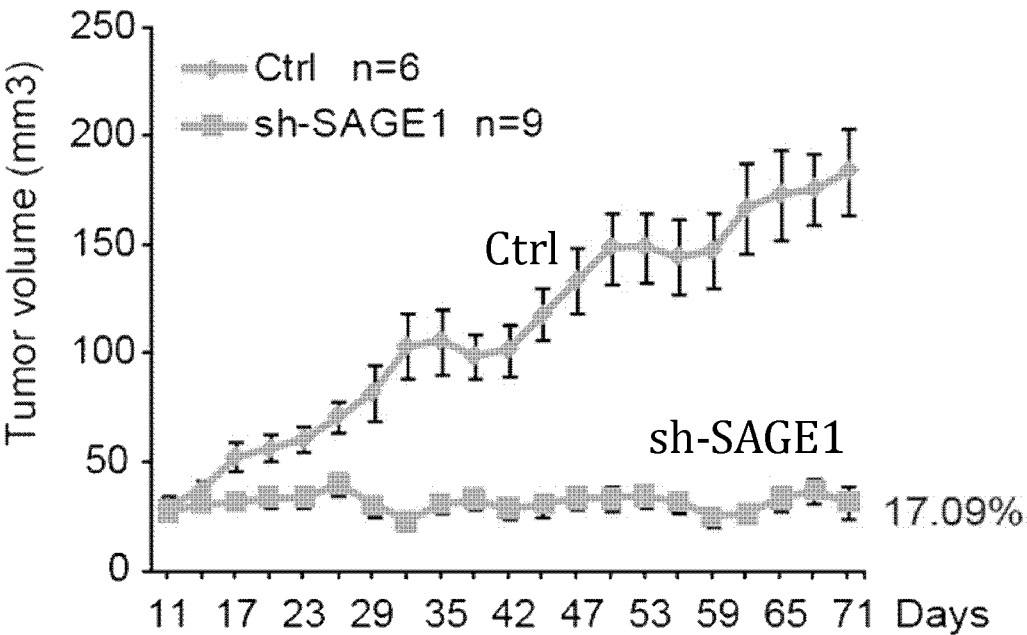
Figure 4I:
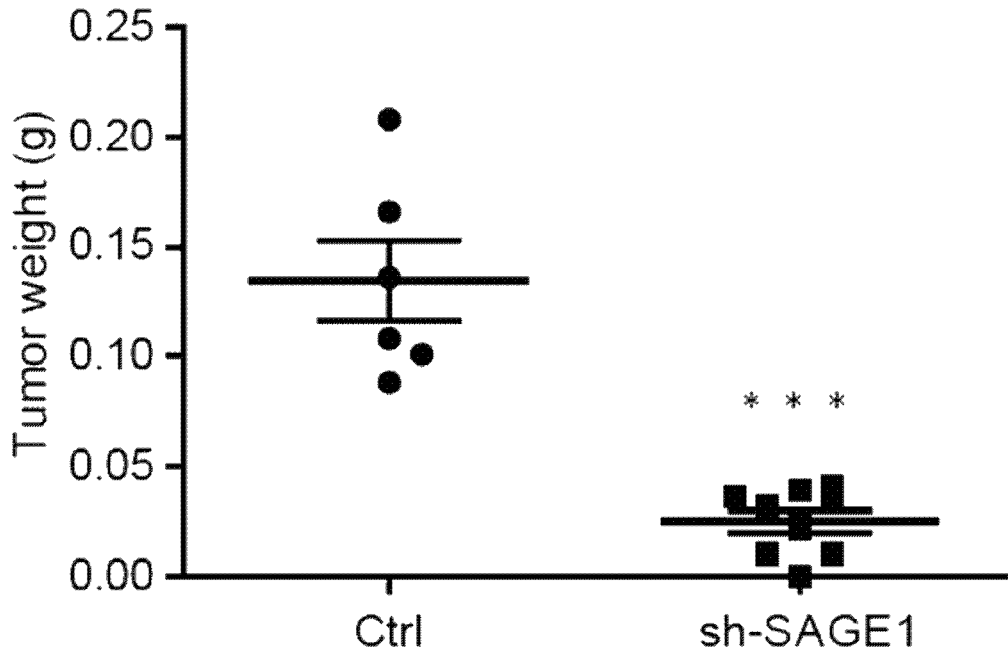
Figure 4J:
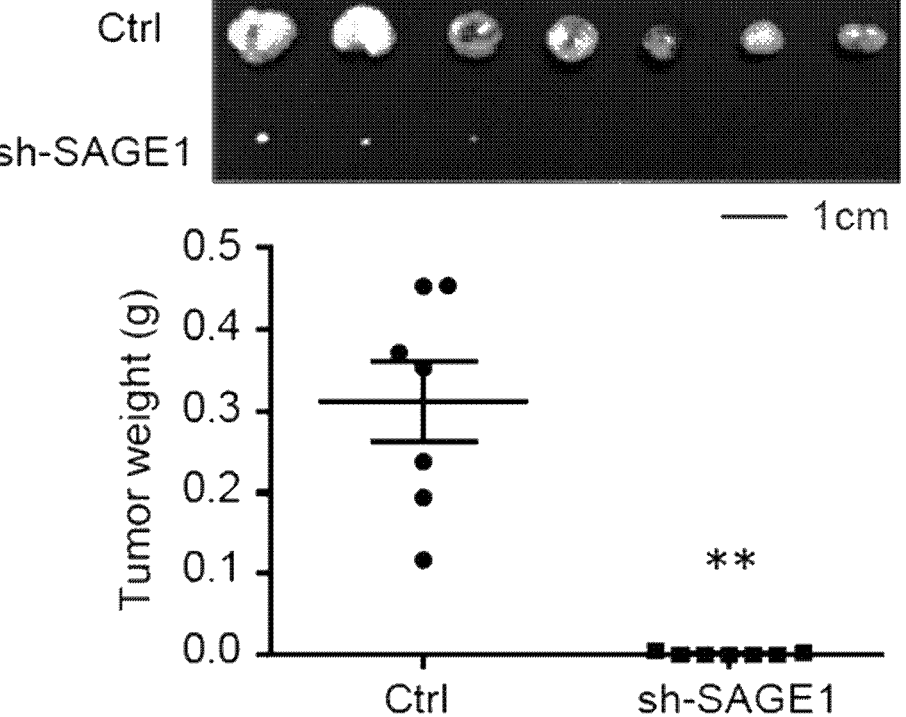
FIGS. 4J, 4K, and 4L illustrate knockdown of SAGE1 in human lung squamous carcinoma (LUSC-P). Representative images of LUSC-PDX tumors treated with (n=7) or without (n=9) shSAGE1 adenoviruses, and statistical analysis of tumor weight (FIG. 4J), ***P<0.01 by nonparametric Mann-Whitney test, and volumes (FIG. 4K). Hematoxylin and eosin (H&E) staining of xenograft tumor tissues and IHC staining for pan-Cytokeratin, a marker to identify carcinoma cells from surrounding nonepithelial cells (FIG. 4L).
Figure 4K:
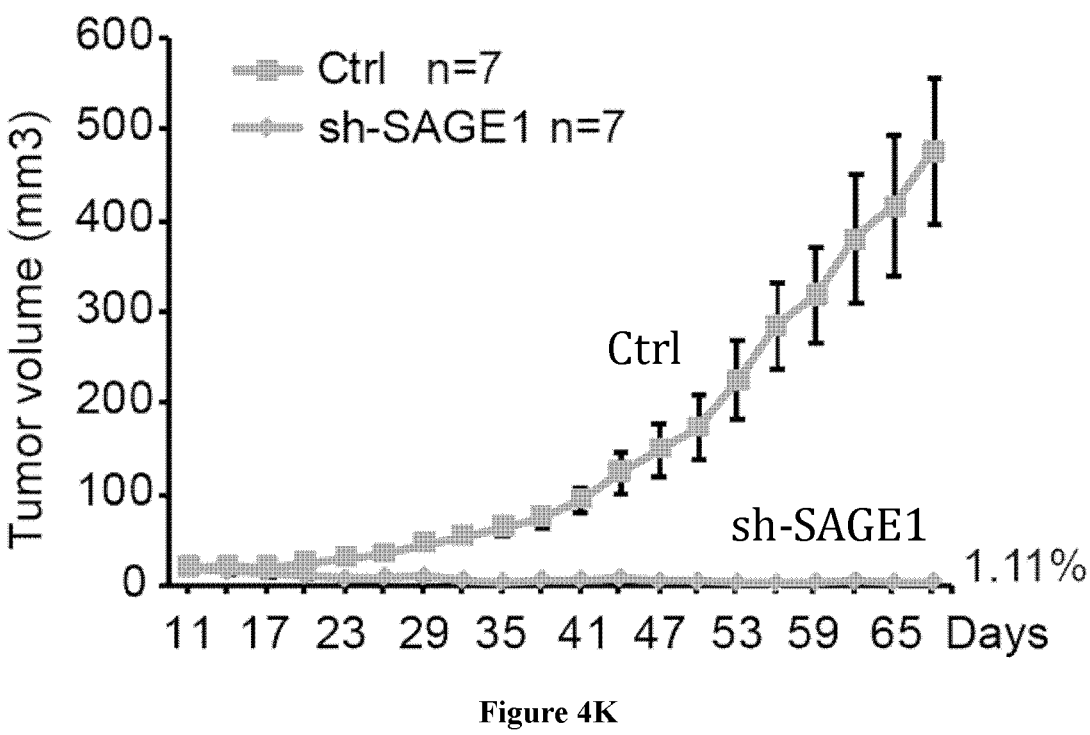
Figure 4L:
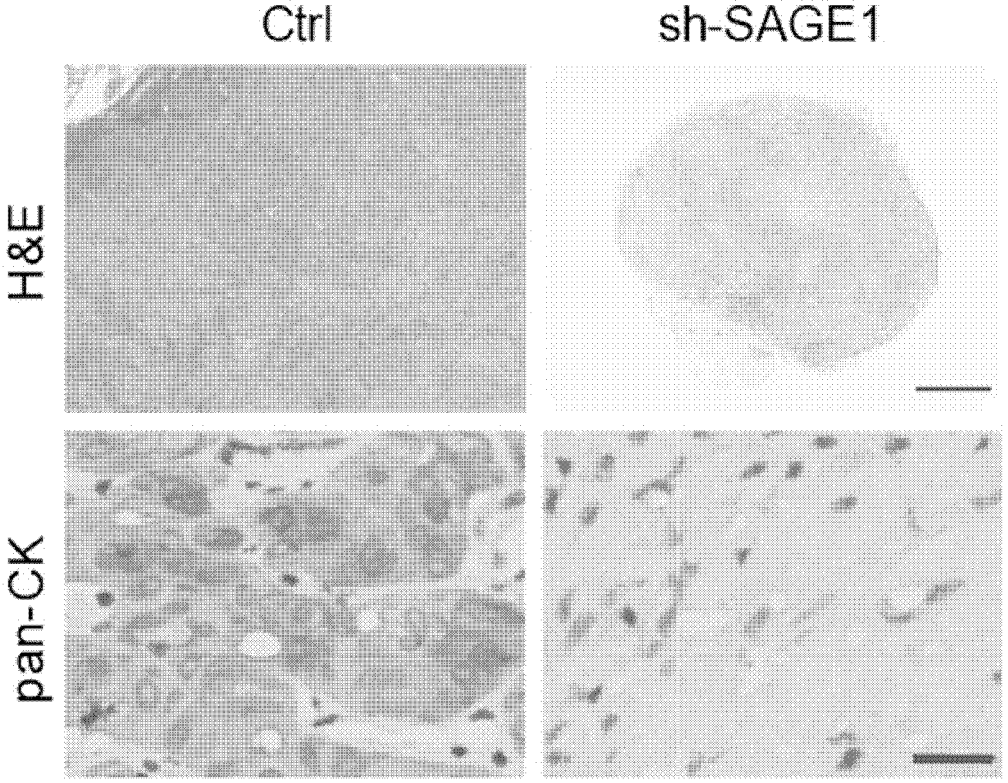

Histologically, both SAGE1 expression and cell proliferation levels were substantially suppressed in SAGE1 knockdown tumors as shown by IHC staining (FIG. 4L). Strikingly, four of the seven tumors in shSAGE1 treated LUS-P were not detectable at the endpoint, and the other three residual masses presented fibro-inflammation with no evidence of cancer remnant confirmed by pathological and IHC examinations.

Example 4: SAGE1 Positive Cancer Cells are Addictive to SAGE1

Figure 2B:
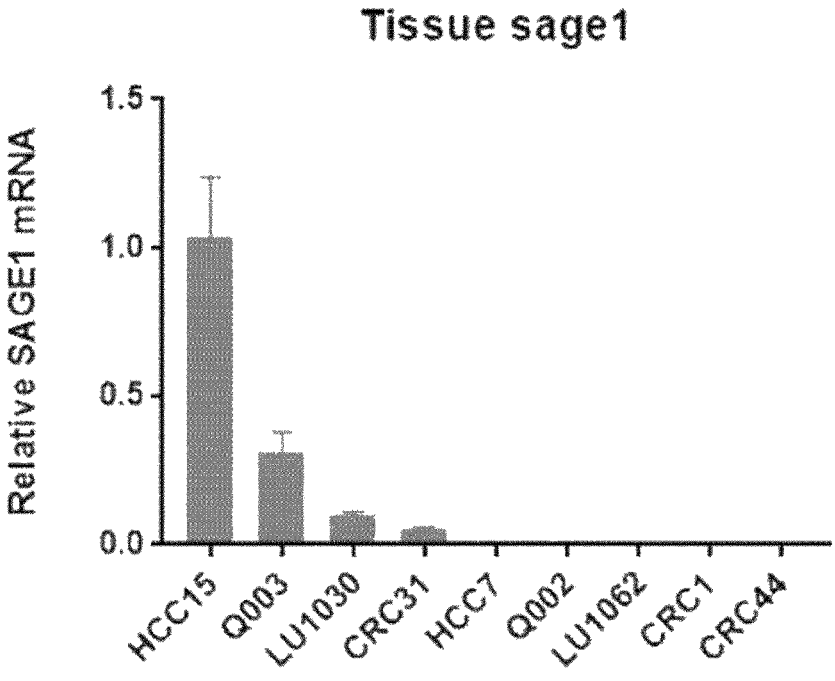
FIG. 2B illustrates real-time qPCR analysis of SAGE1 expression levels in different tumor tissues

To investigate the function of SAGE1 in cancers, we first identified SAGE1 positive cancer cell lines (FIG. 2C) by Western blotting and qPCR analyses of tumor tissue (FIG. 2B). SAGE1 was knocked down by lentivirus carrying short hairpin RNA (shRNA Y12682 (SEQ ID NO: 128) targeting the sequence set forth in SEQ ID NO: 33 GCTGCAGT-CACTCACAACA) against SAGE1 (SAGE1-KD) in five cancer cell lines (FIG. 3A), which blunted cell growth in both real-time cell analysis (RTCA) and anchorage-independent growth assay (FIG. 3B). To further investigate the in vivo function of SAGE1, we examined xenograft growth in nude mice via subcutaneous injection of HuTu 80 parental and SAGE1-KO cells parallelly. Compared to parental xenografts, SAGE1-KO HuTu 80 xenografts exhibited a significant growth reduction (FIG. 3C). In addition, in a SAGE1 positive uveal melanoma cell line (MUM2B) derived orthotropic model, knockdown of SAGE1 significantly decreased the luminance signal compared to the control group (P<0.001, FIG. 3D), while the baseline imaging at 5 days after intraocular seeding showed an equal luminance intensity (FIG. 3D). Moreover, substantially better survival for SAGE1-KD group was observed (FIG. 3E). Taken together, these results demonstrate that SAGE1 is critical for the oncogenic growth of SAGE1 positive cancer cells. We test the efficiency of SAGE1 KD in KYSE30 using different siRNAs (SEQ ID NOs: 70-81) through QPCR (FIG. 3F).

Figure 9A:
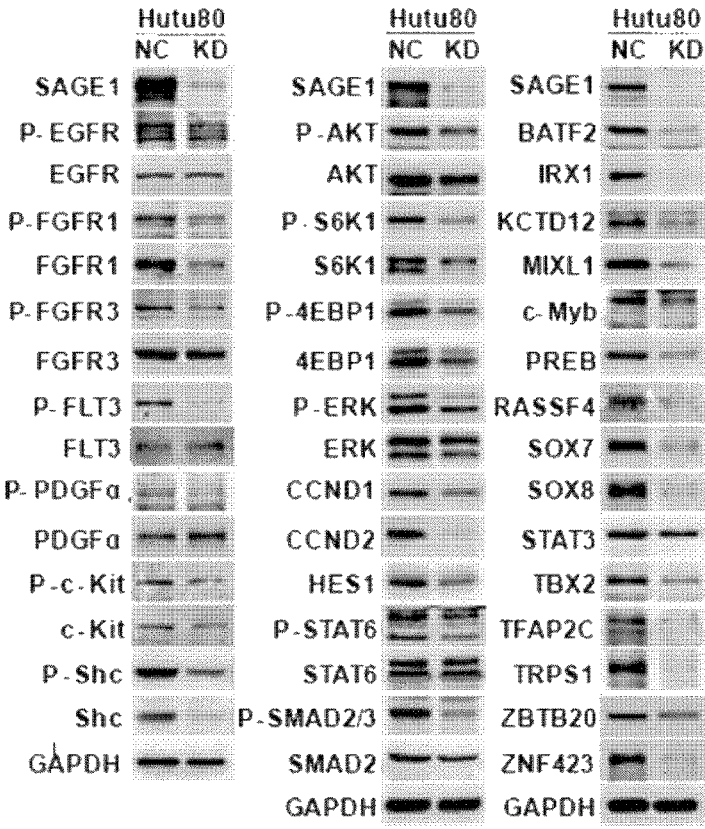
FIG. 9A illustrates depletion of SAGE1 in HuTu 80 cells affects a panel of cell signaling pathway, transcription factors and membrane proteins in western blot assay.

Example 5: SAGE1 Regulates Multiple Pathways for Cancer Cell Proliferation and Cell Cycle To further investigate the function of SAGE1 in cancer cells at the protein level, we monitored the protein products of receptor tyrosine kinases (RTKs) that are activated by these growth factors should exhibit lower levels of phosphorylation in SAGE1 depleted cancer cells. Indeed, the phosphorylations of EGFR, FGFR1, FGFR3, Met, Kit, FLT3, and PDGFα were clearly suppressed in SAGE1-KD HuTu80 cells, strongly suggesting that SAGE1 plays a key role in regulating RTK-mediated pathways. We also observed marked phosphorylation reductions of key signal molecules in Wnt, TGF-β, JAK-STAT, and Notch pathways, confirming that these pathways are also regulated by SAGE1. Western blotting analysis also revealed clear protein reductions of SAGE1-regulated transcription factors in SAGE1-KD cells (FIG. 9A).

Figure 9B:
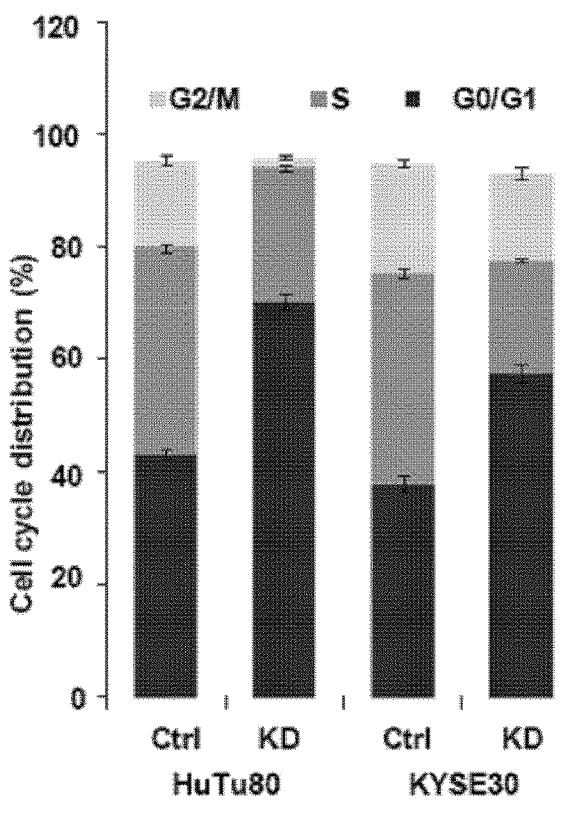
FIG. 9B illustrates depletion of SAGE1 in HuTu 80, KYSE30 cells resulted in G0/G1 blockage in flow cytometry assay.

The major downstream effect of all these SAGE1-regulated pathways is cell proliferation. To directly evaluate the effect of SAGE1 on cancer cell proliferation, we performed fluorescence-activated cell sorting (FACS) analysis of multiple SAGE1 positive cancer cell lines in both WT and SAGE1-KD states. The quantitative measurement revealed that knockdown of SAGE1 induces an arrest in the Go/G1 phase and blockage of the entry into the G2/M phase of the cell cycle (FIG. 9B), suggesting that SAGE1 plays a key role in cell proliferation in SAGE1 positive cancer cells.

Figure 9C:
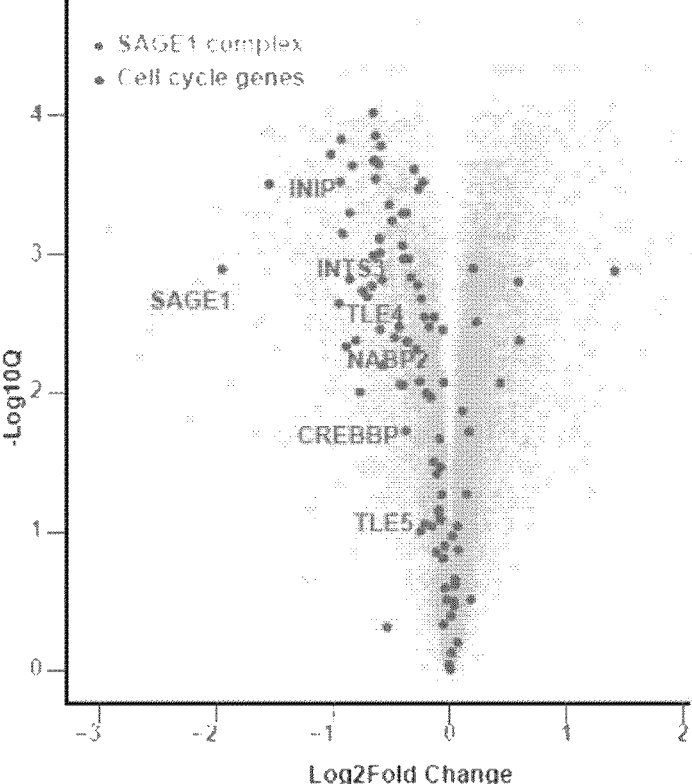
FIG. 9C illustrate MS analysis which revealed decreased expressions of most cell cycle genes in SAGE1-KD HCC-P cells. These results suggested that SAGE1 is also essential for cell cycle regulation in primary liver cancer cells
Figure 9D:
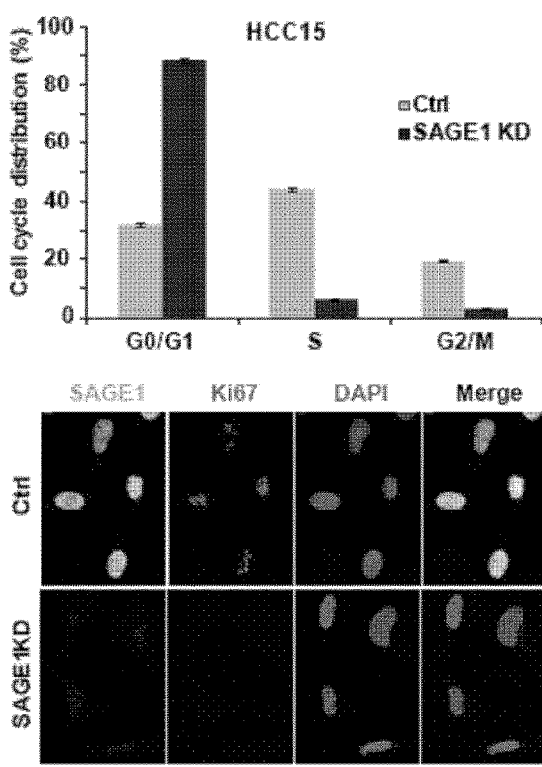
FIG. 9D illustrates depletion of SAGE1 in HCC15 cells resulted in G0/G1 blockage in flow cytometry assay. Depletion of SAGE1 in HCC15 cells abolished ki67 expression in IF staining, indicating G0 phase arrested.
Figure 9E:
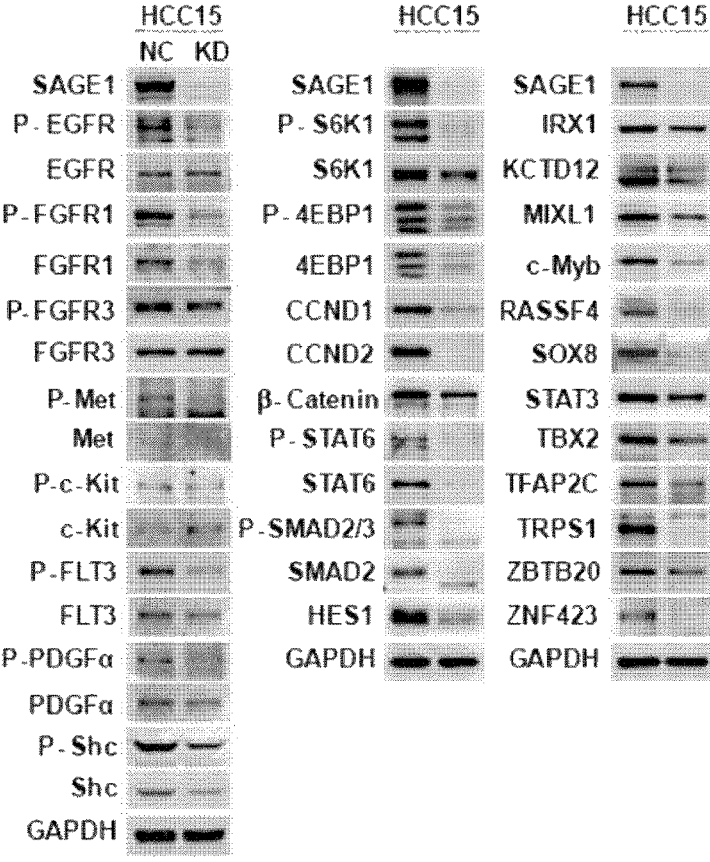
FIG. 9E illustrates depletion of SAGE1 in HCC15 primary cancer cells affects a panel of cell signaling pathway, transcription factors and membrane proteins in western blot assay.

To further investigate the function of SAGE1 in patient-derived primary tumor cells, we performed WB and TMT labeled MS-bac towards HCC-P control and SAGE1-KD in primary HCC-P cells (FIGS. 9C and 9E). The results showed that the expression of RTKs, cell cycle-related proteins and transcription factors is dependent on SAGE 1, indicating that the gene expression program in HCC-P cells is regulated by SAGE1 in similar manner as in HuTu 80 cells. Consistently, FACS and Ki67 staining data also displayed a clear arrest at the Go/G1-phase (FIG. 9D), and MS analysis revealed decreased expressions of most cell cycle genes in SAGE1-KD HCC-P cells. These results suggested that SAGE1 is also essential for cell cycle regulation in primary liver cancer cells. Taken together, our analyses demonstrated that SAGE1 is a pan-cancer master regulator for tumor cell proliferation by activating multiple cancer pathways.

Example 6

Figure 2C:
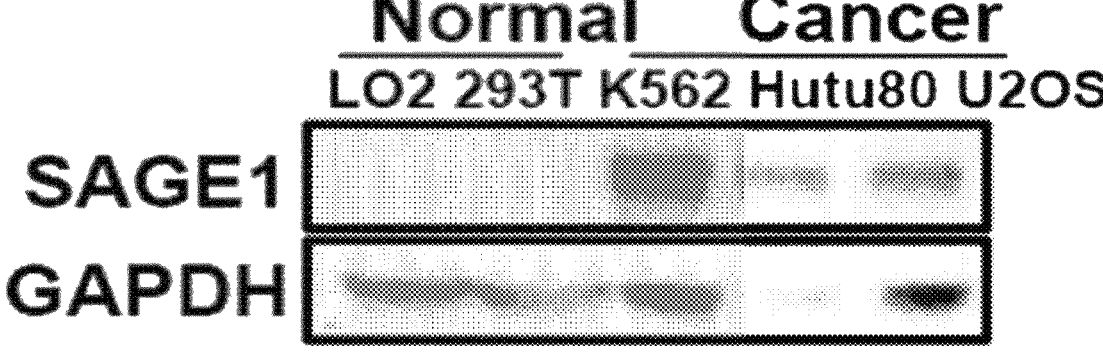
FIG. 2C illustrates Western blot analysis of SAGE1 expression levels in different cancer cell lines as well as SAGE1 negative non-cancer cell lines.
Figure 2D:
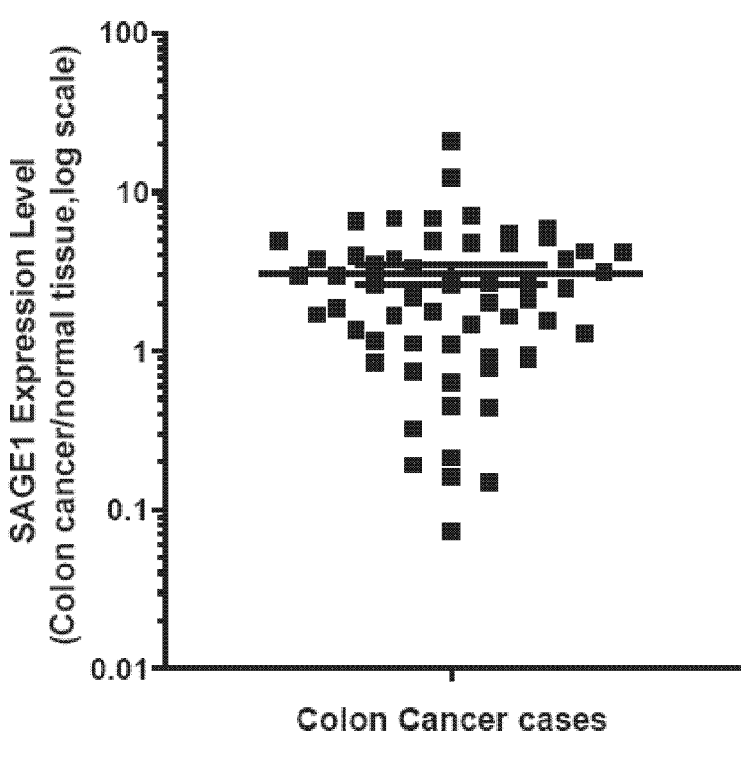
FIG. 2D illustrates real-time qPCR analysis of SAGE1 expression levels of 60 colorectal cancer tissues and corresponding paracancerous regions.
Figure 2E:
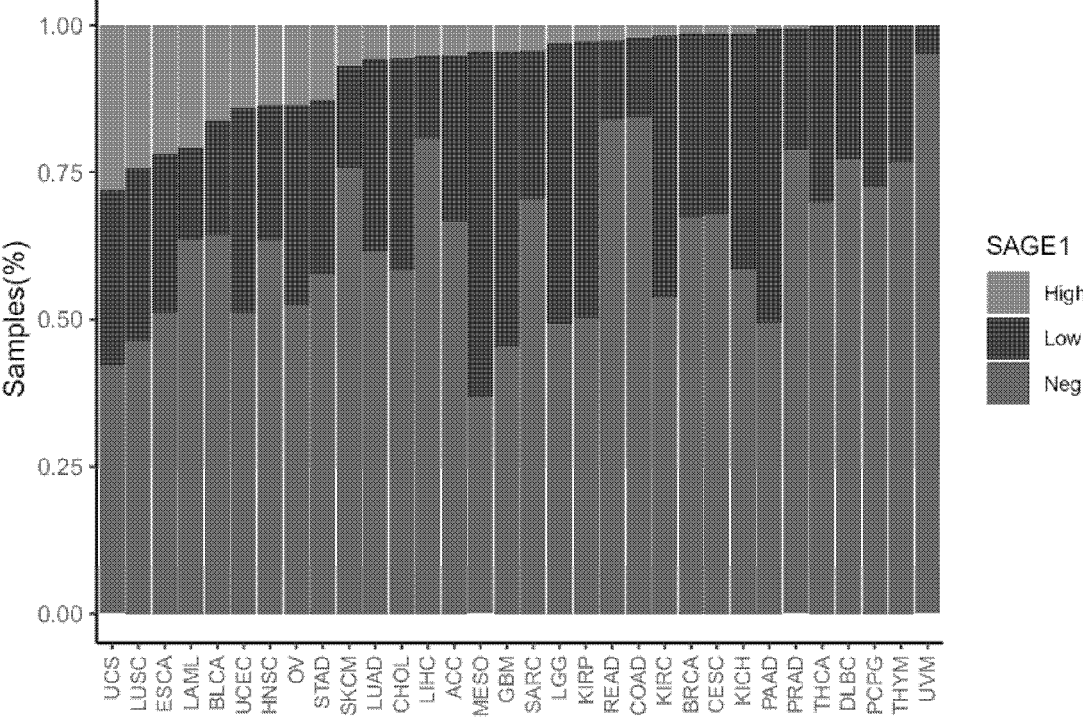
FIG. 2E illustrates pattern of SAGE1 expression levels in different cancer types in TCGA.
Figure 3A:
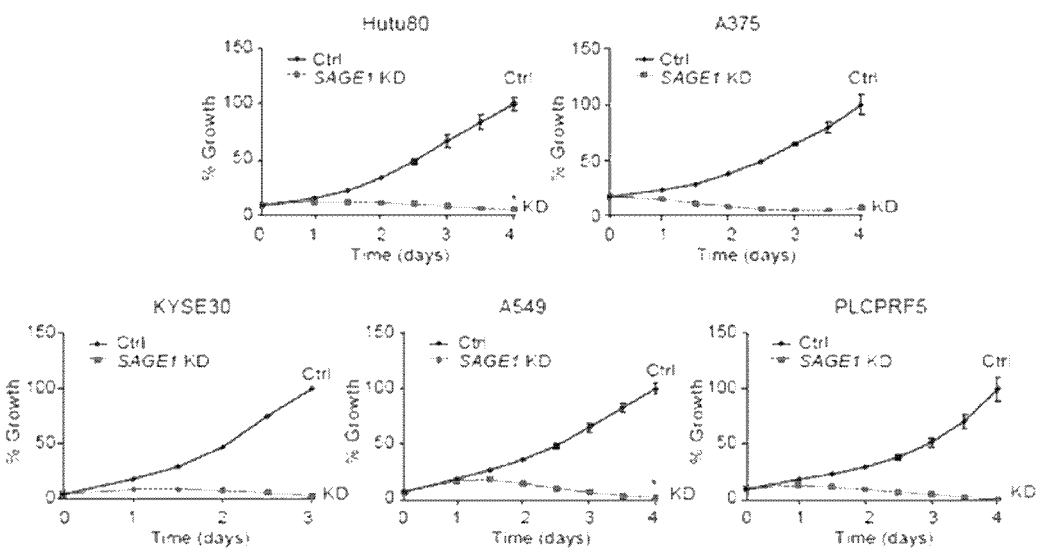
FIG. 3A illustrates depletion of SAGE1 suppresses cell growth of HuTu 80, A375, KYSE30, A549 and PLCPRF5 cells in RTCA assay.
Figure 3B:
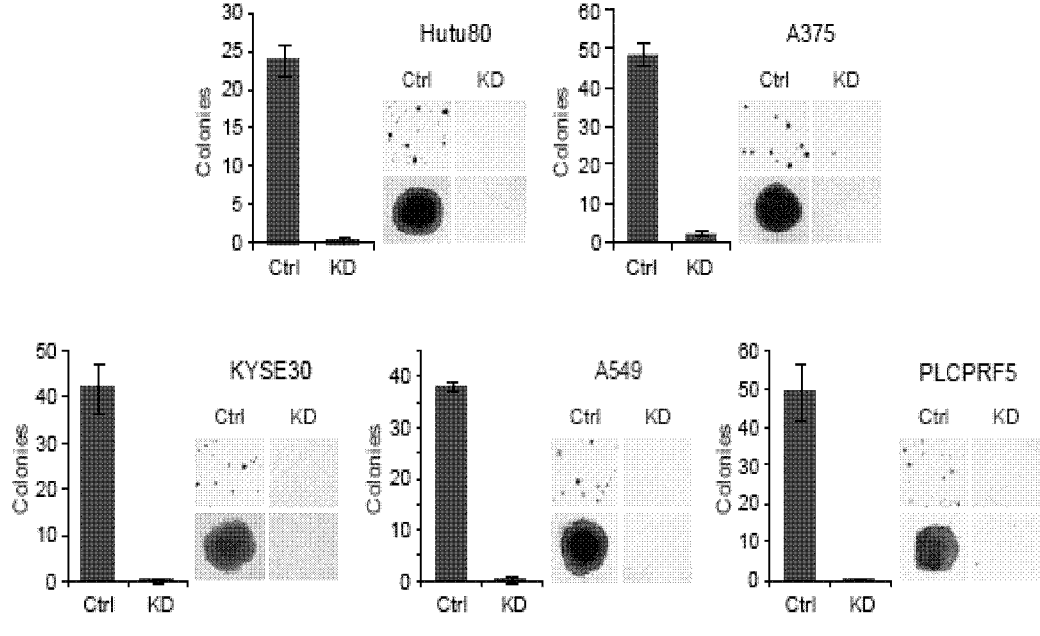
FIG. 3B illustrates depletion of SAGE1 suppresses anchorage-independent growth of HuTu 80, A375, KYSE30, A549 and PLCPRF5 cells on soft agar.
Figure 3C:
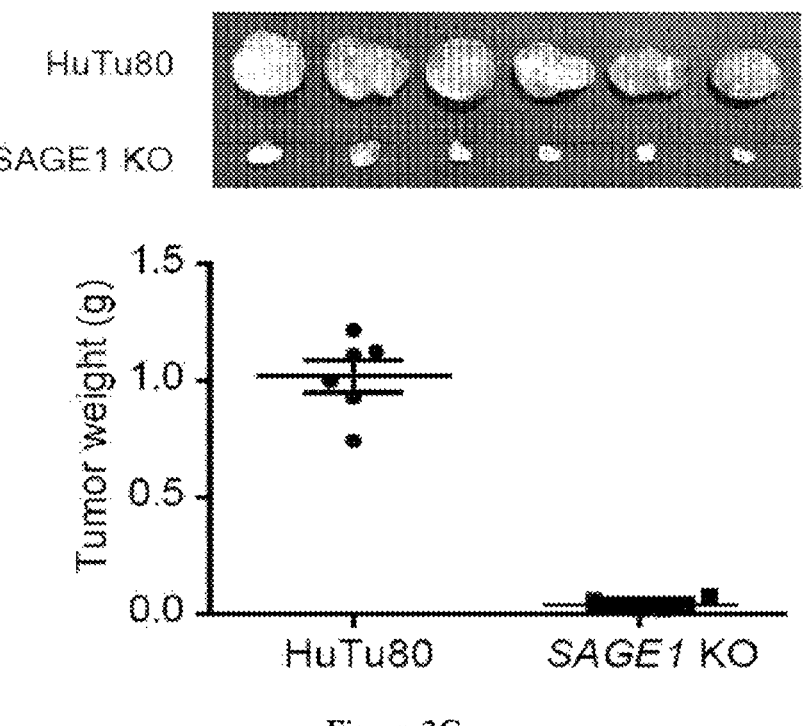
FIG. 3C illustrates depletion of SAGE1 in HuTu 80 cells impedes xenograft growth in nude mice.
Figure 3D:
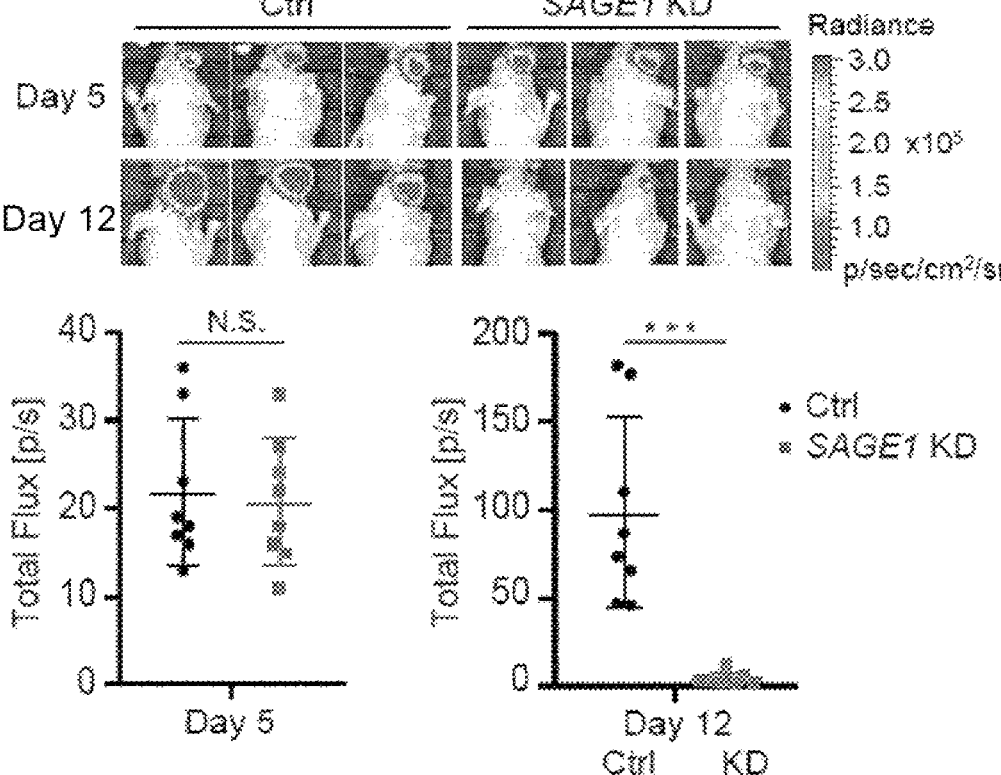
FIGS. 3D and 3E illustrate the shSAGE1 treatment decreased the luminance signal of uveal melanoma cell line MUM2B derived orthotropic model (FIG. 3D), and prolonged survival (FIG. 3E).
Figure 3E:
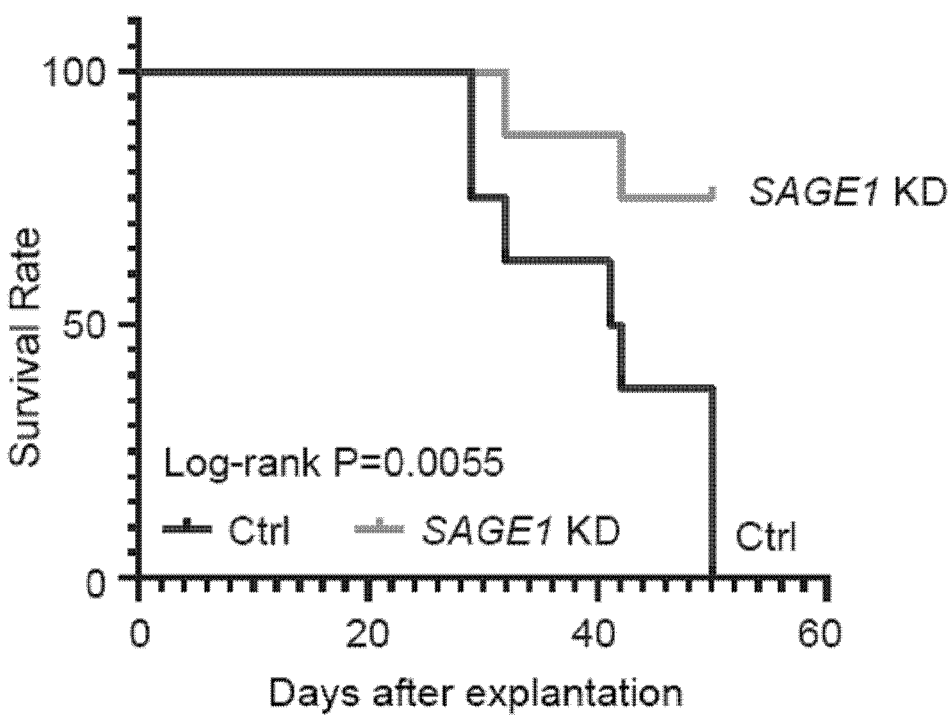
Figure 3F:
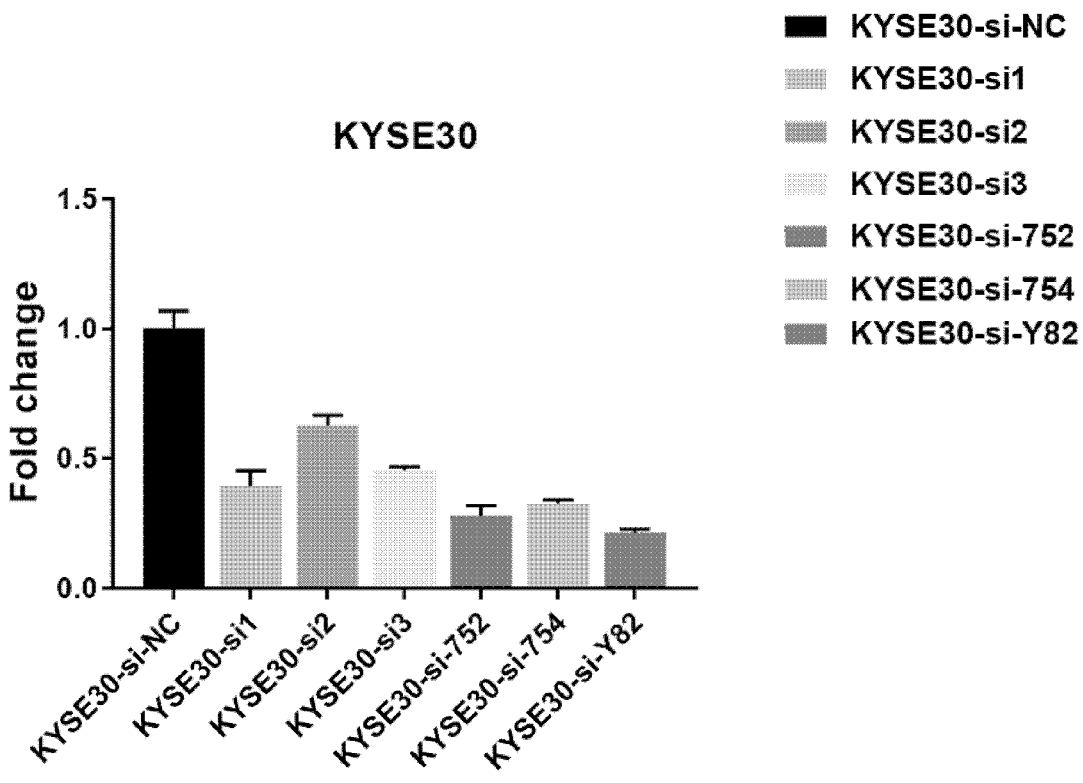
FIG. 3F illustrates the efficiency of SAGE1 KD in KYSE30 using different siRNAs through QPCR.

To further investigate the function of SAGE1 in patient-derived tissue and primary tumor cells, we carried out qPCR and Western blotting analyses for SAGE1 (FIGS. 2B and 2C). In sharp to the restricted expression in normal tissue, we identified high expression of SAGE1 in a number of cancer cell lines and tumor tissues compared to healthy tissues or paracancerous regions. This cancer-specific expression profile of SAGE1 was further corroborated by qPCR analysis of 60 colorectal cancer (CRC) tissues and corresponding paracancerous regions (FIG. 2D).

Figure 4M:
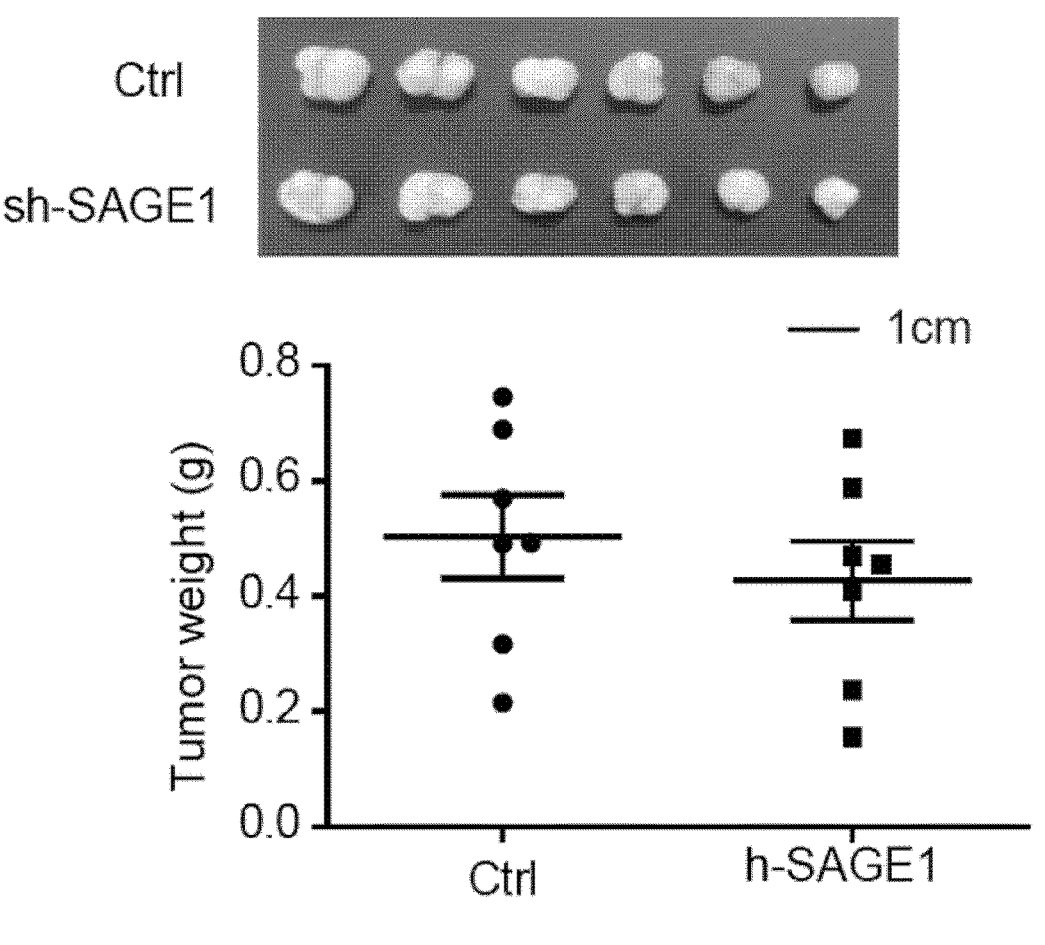
FIGS. 4M, 4N, and 4O illustrates delivery of shSAGE1 adenoviruses to SAGE1 negative HCC fails to suppress tumor growth. Representative images of PDX tumors treated with or without shSAGE1 adenoviruses, and statistical analysis of tumor weight (FIG. 4M) and volume (FIG. 4N), n=7/group, ***P<0.01 by nonparametric Mann-Whitney test. Representative histopathological pictures from heart, liver, spleen, kidney and lung of the nude mice in both control and shSAGE1-treated groups (H&E stain, Scale bar, 200 μm) (FIG. 4O).
Figure 4N:
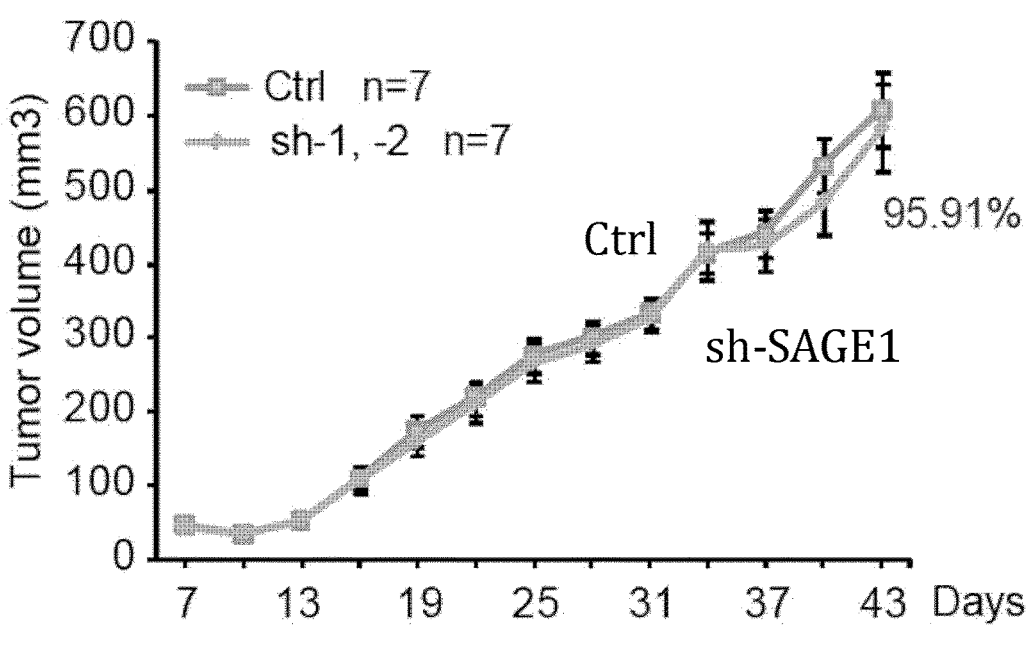
Figure 4O:
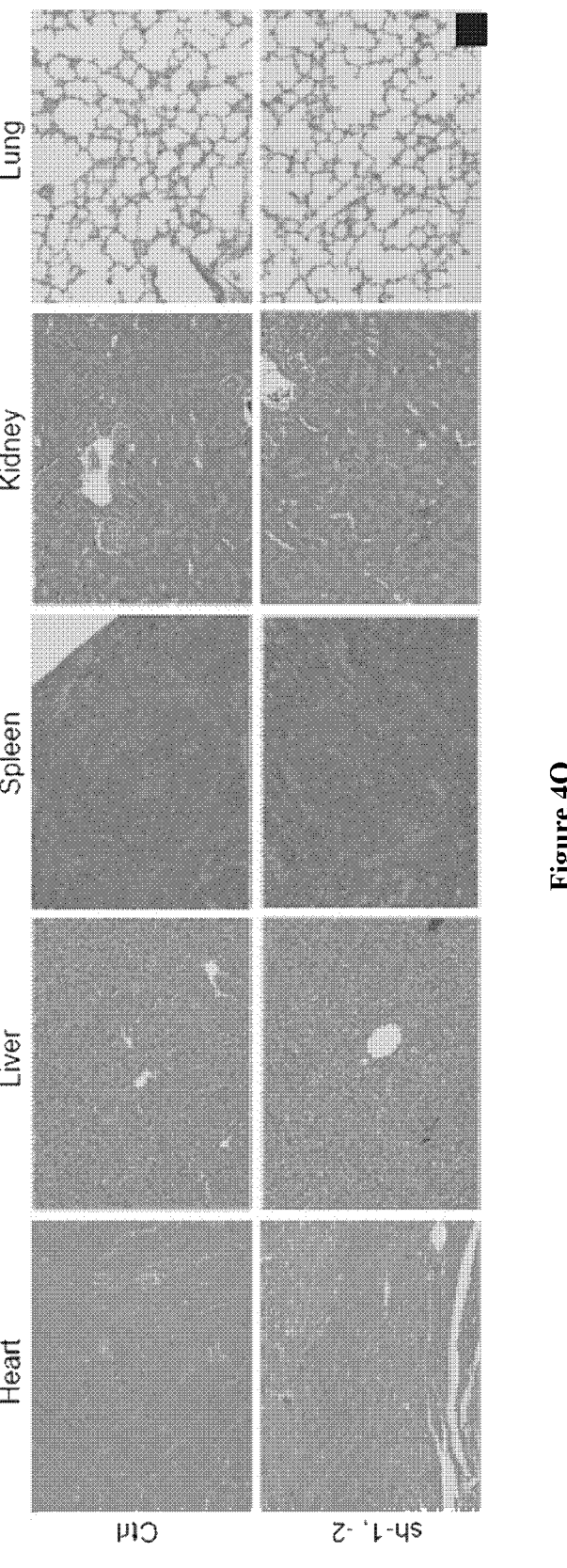

Example 7. Targeting SAGE1 Potentiates a Novel Approach to Intercept Cancer Progression Given that SAGE1 is required for SAGE1 positive cancer cell proliferation, we next evaluated directly whether targeting SAGE1 could be an effective anti-cancer strategy. A large panel of early passage patient derived xenografts (PDXs) were screened for SAGE1 positive tumors by immunohistochemistry (IHC) staining (FIG. 15). Seven SAGE1 positive PDXs derived from different cancer types were recruited for in vivo SAGE1-KD therapeutics, including hepatocellular carcinoma (HCC-P), lung squamous carcinoma (LUS-P), lung adenocarcinoma (LUA-P), colon cancer (CRC-P), oropharyngeal squamous cell carcinoma (OSC-P), gallbladder cancer (GBC-P), and esophageal squamous cell carcinoma (ESC-P). Two SAGE1 negative PDXs, HCC-N and LUS-N, were employed as control.

shRNA 82 (SEQ ID NO: 80) were packed into adenoviruses and dosed PDX mice. The treatment dramatically decreased tumor volume and weight, with an average growth inhibition rate over 85% (P<0.001), supporting a critical role of SAGE1 in tumor growth (FIGS. 4A-4L). Strikingly, four of the seven tumors in shSAGE1 treated LUS-P were not detectable at the endpoint, and the other three residual masses presented fibro-inflammation with no evidence of cancer remnant confirmed by pathological and IHC examinations (FIGS. 4J-4L). In sharp contrast, the same adenoviruses treatment in two SAGE1 negative tumors, HCC-N and LUS-N, generated no significant effect on tumor growth throughout the dosing period with an average growth inhibition rate of 3.08%, strongly suggesting that the tumor suppression observed for SAGE1 positive PDXs was SAGE1 specific (FIGS. 4M-4O). It is noteworthy that no significant changes in body weight, the appearance and behavioral pattern, or sign of organ damage in shSAGE1 treated animals were observed (FIG. 4O), indicating that shSAGE1 administration has no detectable off-target effect at both organ and intravital levels. Collectively, our pre-clinical data indicate that SAGE1 is crucial for oncogenic growth in multiple cancer types. The fact that SAGE1 knockdown blunted tumor growth suggests such tumors have become addictive to SAGE1, and that targeting SAGE1 could serve as a novel therapeutic strategy against SAGE1 positive tumors.

Example 8. SAGE1 Competes with INTS6 for INTS3 Binding in Cancer Cells

Figure 6A:
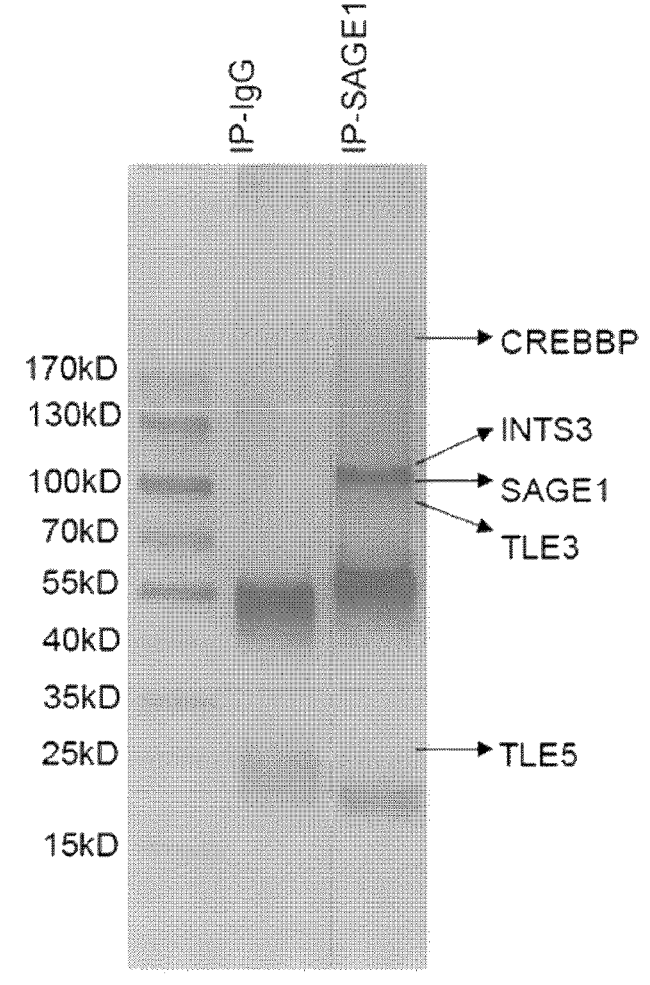
FIG. 6A illustrates SDS-PAGE and silver staining analysis of immunoprecipitated SAGE1-interacting proteins in HuTu 80 cells.
Figure 6B:
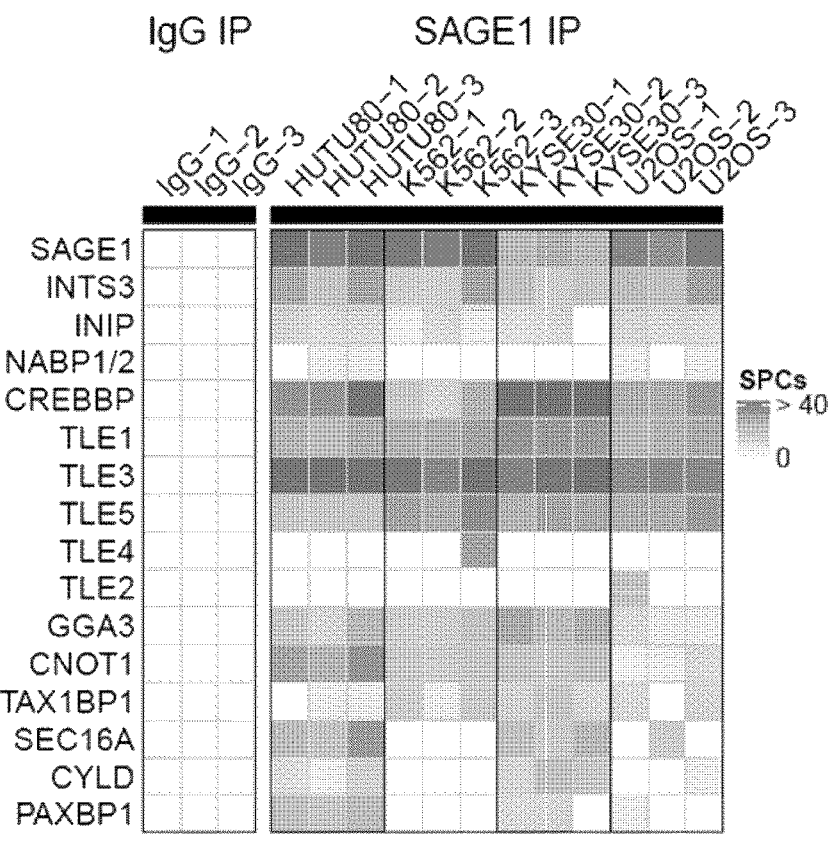
FIG. 6B illustrates MS analysis of the immunoprecipitated SAGE1 complex composition from four different cancer cell lines.
Figure 6C:
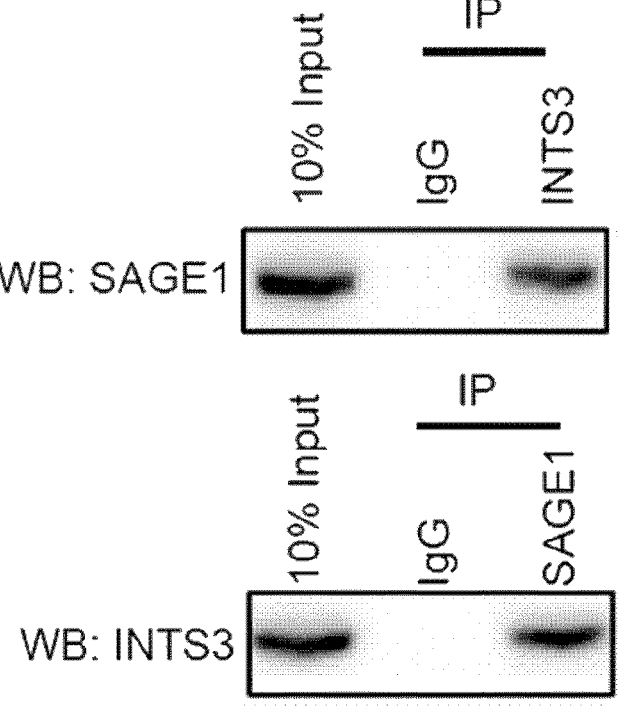
FIGS. 6C and 6D illustrate Co-IP analysis of the interactions of SAGE1 with INTS3 (FIG. 6C), and TLE3 and CBP (FIG. 6D).
Figures 6D, 6E:
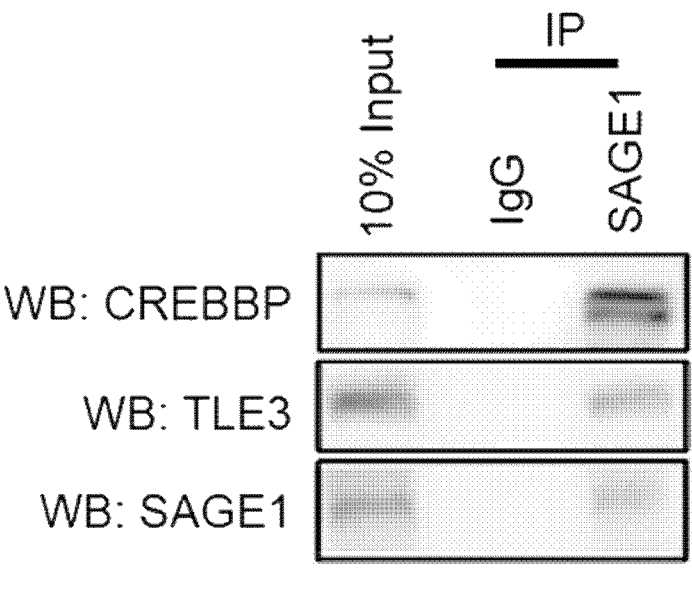
FIG. 6E illustrates domain organization of SAGE1, INTS3, and INTS6.

To gain mechanistic insight into SAGE1 function in tumorigenesis, we performed a proteomic analysis of the endogenous SAGE1 complex pulled down in HuTu 80 cells by an anti-SAGE1 antibody. The complex was resolved by SDS-PAGE, visualized by silver staining, and subjected to MS analysis (FIG. 6A and FIGS. 14A-14D). A number of proteins previously linked to transcriptional regulation were reproducibly identified as high-confidence SAGE1 interactors, including CBP (CRBP-binding protein), TLE (Groucho/Transducin-Like Enhancer of Split) proteins, INTS3 (a component of the Integrator complex) and INTS3-binding partners NABP (Nucleic Acid Binding Protein) and INIP (INTS3 and NABP interacting protein) (FIG. 6B). Notably, proteomic analysis of the SAGE1 complex in other SAGE1-expressing cancer cell lines also identified the same group of proteins, strongly suggesting that these proteins are the bona fide SAGE1-interacting factors in cancer cells (FIG. 6B). The interactions between SAGE1 and these proteins were further confirmed by co-immunoprecipitation (co-IP) analysis (FIG. 6C and FIG. 6D).

Figure 6F:
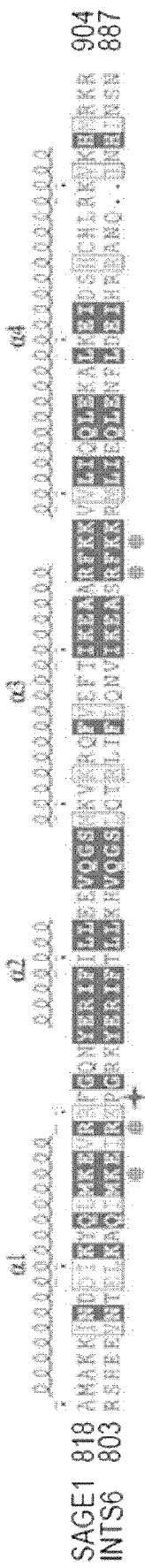
FIG. 6F illustrates structure-based sequence alignment of $SAGE1_{I3BD}$ and INTS6I3BD.
Figure 6G:
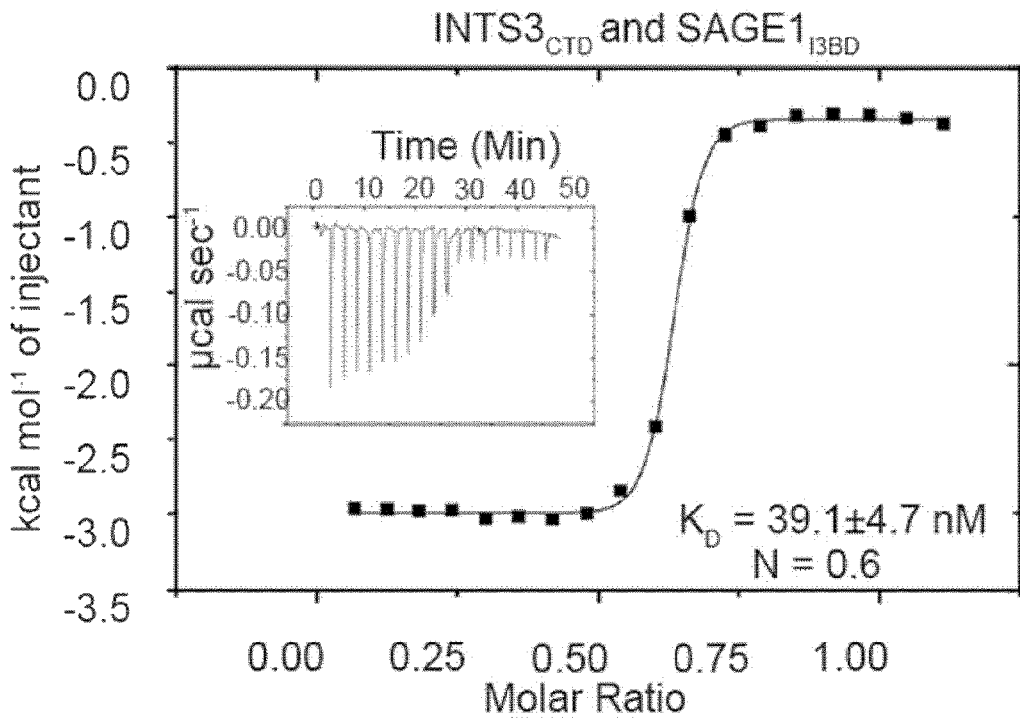
FIG. 6G illustrates ITC measurement of the interaction between $SAGE1_{\beta BD}$ and $INTS3_{CTD}$. Inset: ITC titration data.
Figure 8A:
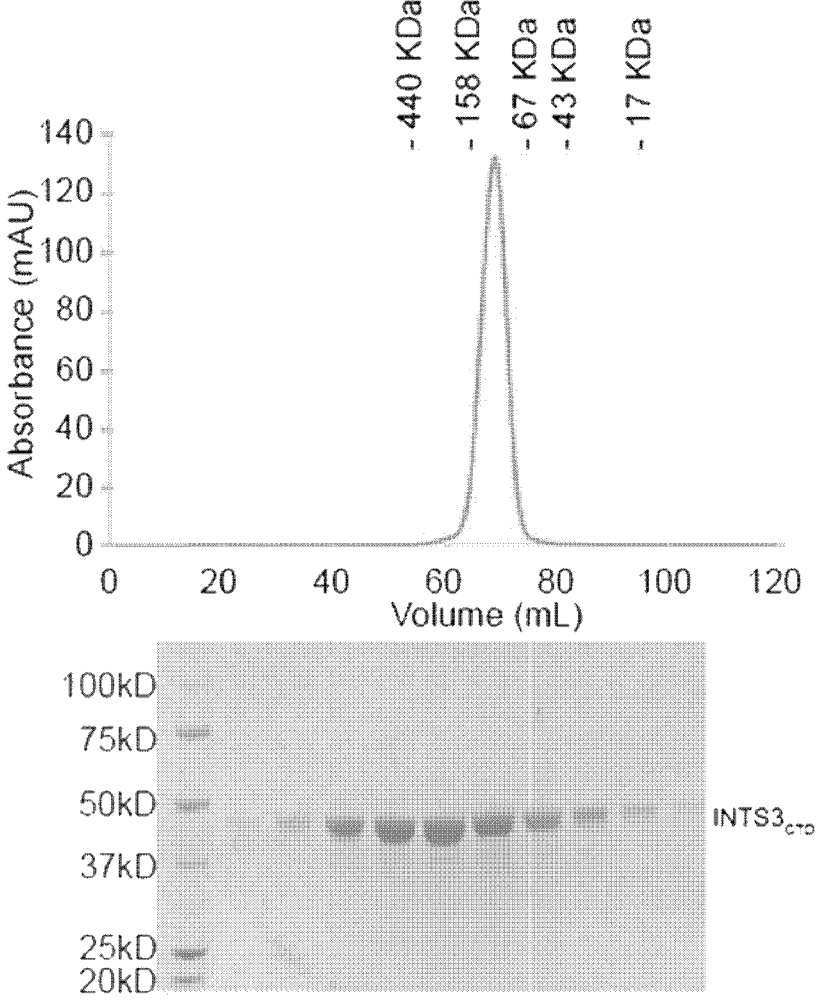
FIGS. 8A and 8B illustrate size-exclusion chromatography profile of the $INTS3_{CTD}$ (FIG. 8A) and $INTS3_{CTD}$-$INTS6_{\beta BD}$ (FIG. 8B) complex on a Superdex 200 column, and illustrate the peak fractions of the purified complex were resolved by SDS-PAGE and stained with Coomassie brilliant blue.
Figure 8B:
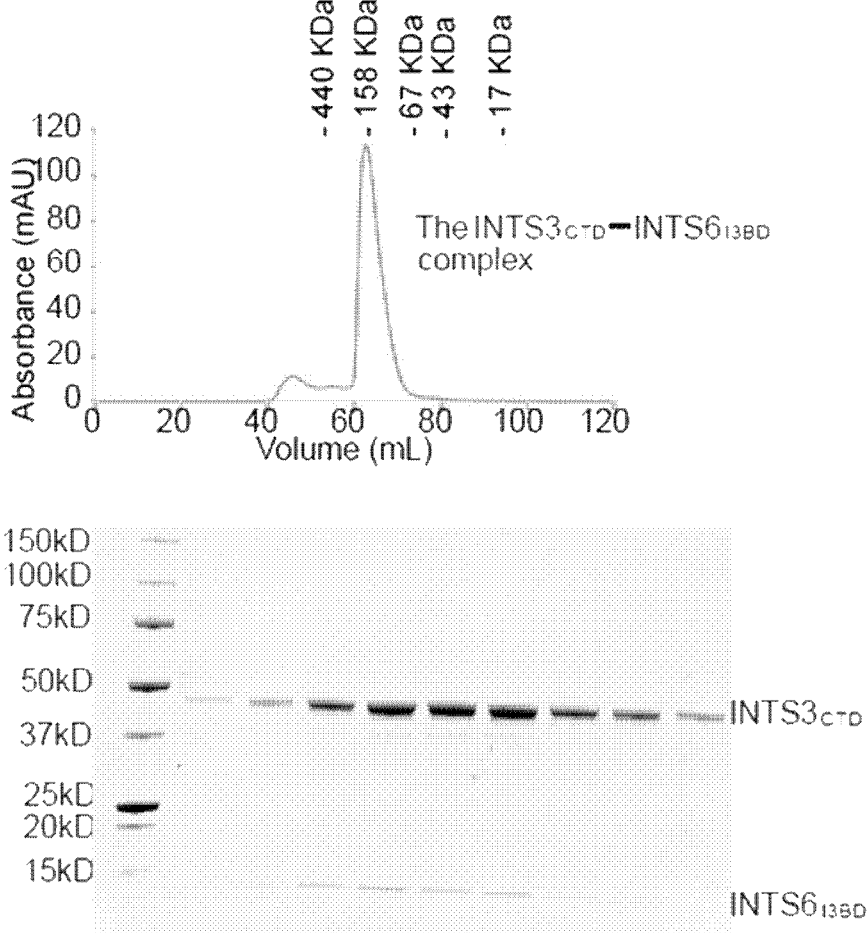

A previous study suggested that the C-terminal domain of INTS3 (INTS3$_{CTD}$, residues 572-978, SEQ ID NO: 9) mediates a direct interaction with a small domain at the C-terminus of INTS6 (residues 803-887, SEQ ID NO: 10). Consistent with this data, we co-purified INTS3$_{CTD}$ and INTS6$_{803-887}$ and found that they formed a stable binary complex that could survive size-exclusion chromatography analysis (FIG. 8A and FIG. 8B). Interestingly, a small C-terminal region of SAGE1 (residues 818-904, SEQ ID NO: 8) shares a high sequence similarity to INTS6$_{803-887}$ (43% identity and 82% similarity) (FIG. 6E and FIG. 6F), indicating that SAGE1$_{818-904}$ very likely has a similar three-dimensional structure as INTS6$_{803-887}$ and may mediate the interaction with INTS3$_{CTD}$ as well. Indeed, isothermal calorimetry (ITC) measurement showed that SAGE1$_{818-904}$ could bind to INTS3$_{CTD}$ with an equilibrium disassociation constant of ~39 nM (FIG. 6G). Thus, hereafter we refer SAGE1$_{818-904}$ and INTS6$_{803-887}$ as to SAGE1$_{I3BD}$ and INTS6$_{I3BD}$ (the INTS3-binding domains of SAGE1 and INTS6), respectively (FIG. 6E).

Figure 6H:
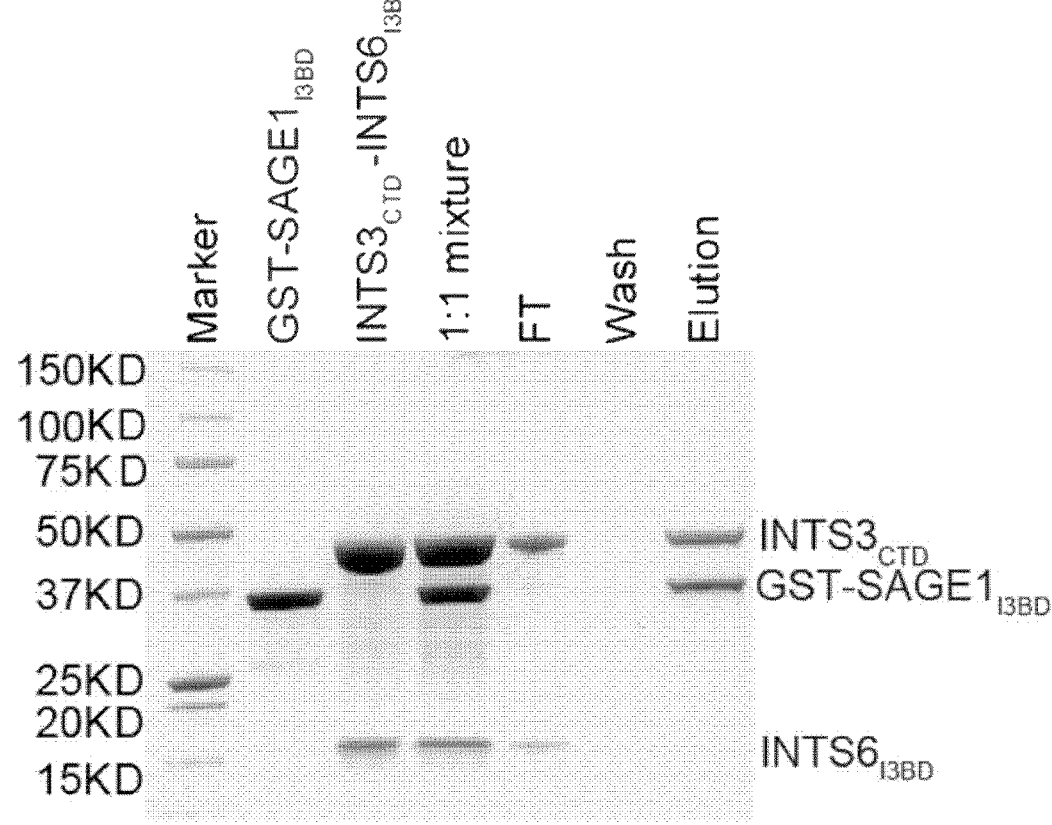
FIG. 6H illustrates GST-pull-down analysis of the mixture of the purified $INTS3_{CTD}$-$INTS6_{\beta BD}$ complex and GST-tagged $SAGE1_{\beta BD}$.
Figure 6I:
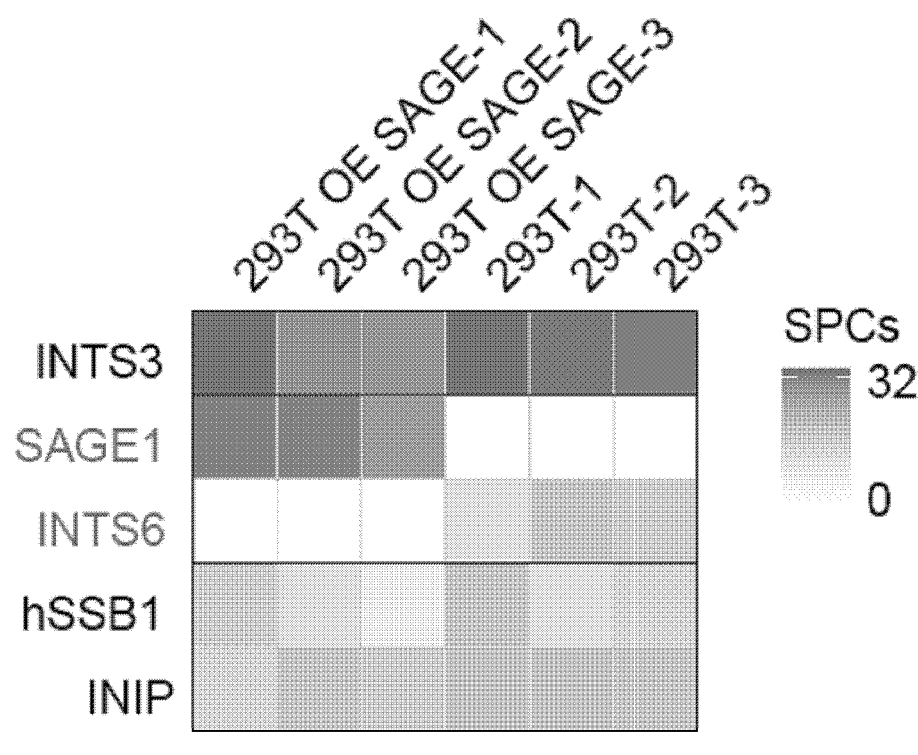
FIG. 6I illustrates quantitative MS analysis of the immunoprecipitated complexes using anti-INTS3 antibody from 293T cells (293 T-1, 293 T-2, 293 T-3) or SAGE1-overexpressing 293T cells (293 OE SAGE-1, 293 OE SAGE-2, 293 OE SAGE-3).

Given that SAGE1$_{I3BD}$ highly resembles INTS6$_{I3BD}$, it is likely that they interact with INTS3$_{CTD}$ in a mutually exclusive manner. To test this idea, we mixed purified INTS3$_{CTD}$-INTS6$_{I3BD}$ complex with GST-tagged SAGE1$_{I3BD}$ and conducted a GST-pull-down analysis. This in vitro competition assay clearly revealed that SAGE1$_{I3BD}$ indeed competed with INTS6$_{I3BD}$ for INTS3$_{CTD}$ binding with a higher affinity (FIG. 6H). To further test this competition in vivo, we examined the INTS3-interacting proteins in SAGE1 negative 293T cells by IP-MS analysis. The anti-INTS3 antibody can successfully pull down INTS6 and all other components of Integrator, suggesting that INTS3 exists as a subunit of Integrator in 293T cells (FIG. 6I). In contrast, the same approach failed to pull down INTS6 in SAGE1-overexpressing 293T cells (FIG. 6I). Instead, SAGE1 can be reliably detected by the pull-down assay (FIG. 6I), indicating that ectopically expressed SAGE1 in 293T cells can disrupt the INTS3-INTS6 interaction and snatch INTS3 from Integrator to form a new SAGE1-INTS3 complex.

Example 9. Crystal Structure of the INTS3$_{CTD}$-SAGE1$_{I3BD}$ Complex

Figure 7A:
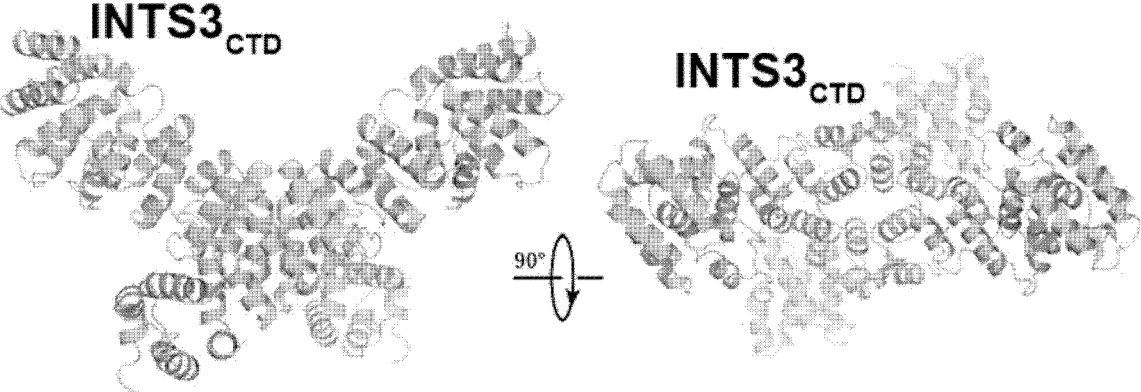
FIGS. 7A and 7B illustrate Ribbon diagrams of two orthogonal views of $INTS3_{CTD}$ dimer (FIG. 7A) and the $SAGE1_{\beta BD}$-$INTS3_{CTD}$ complex crystal structures (FIG. 7B).
Figure 8C:
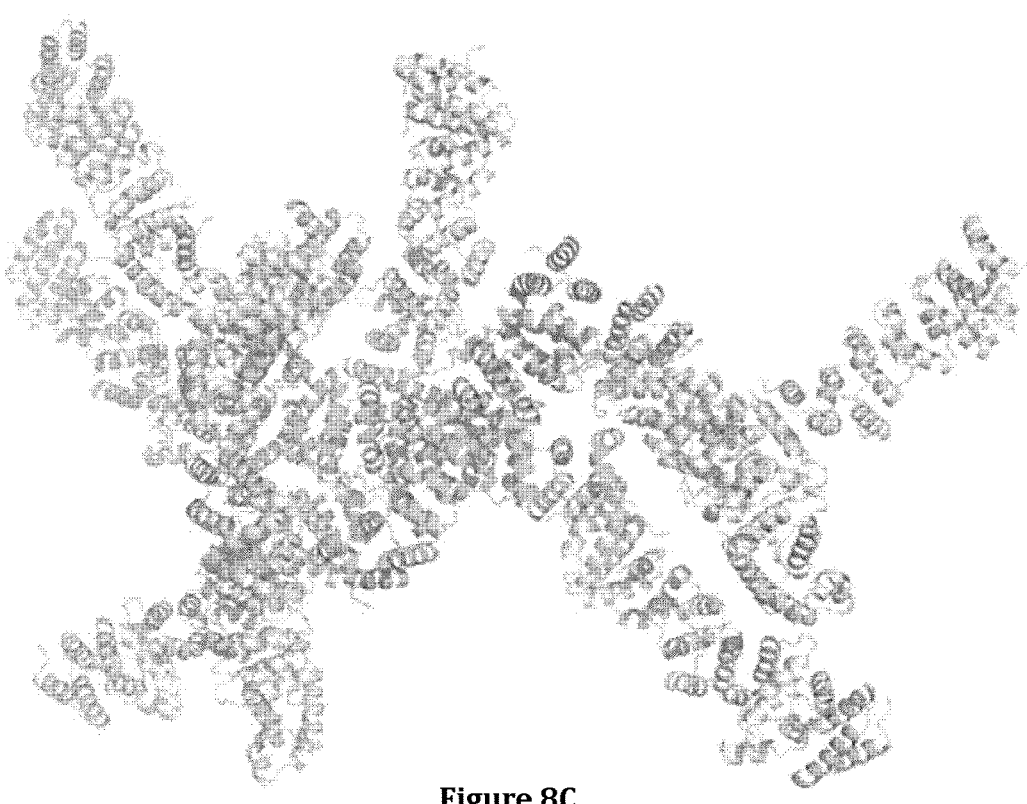
FIG. 8C illustrates crystal lattice analysis showing that two crystallographic symmetry-related $INTS3_{CTD}$ molecules mediate an extensive interaction.
Figure 8D:
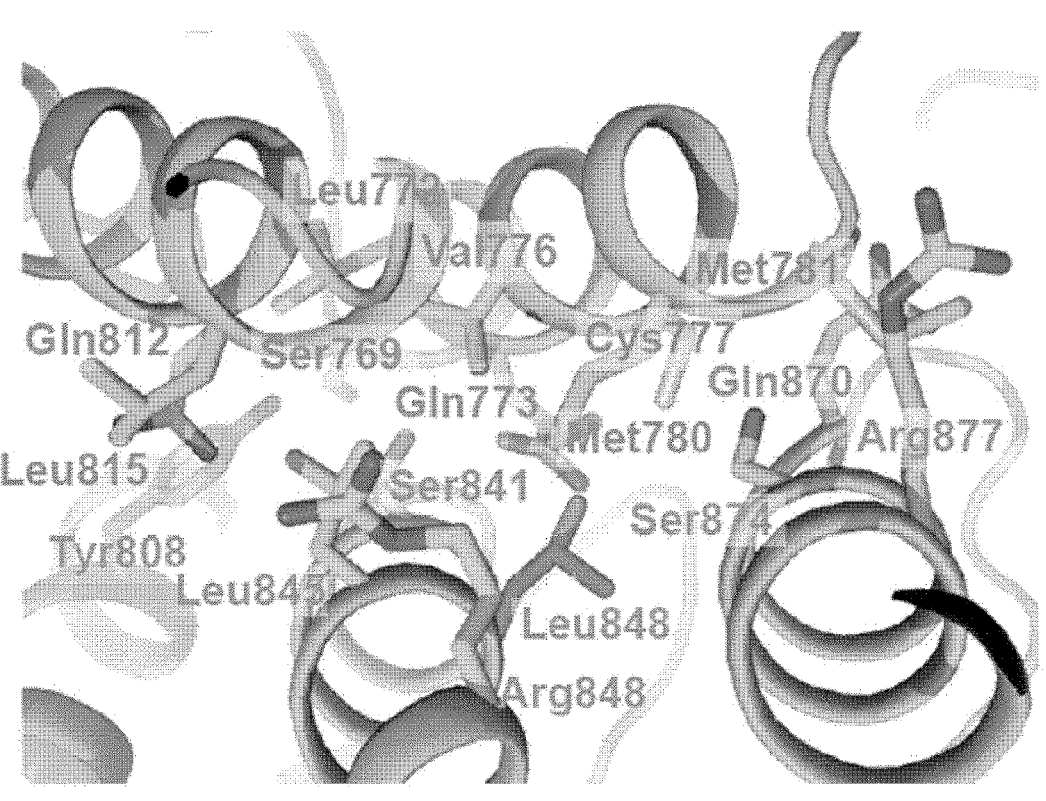
FIG. 8D illustrates details of the $INTS3_{CTD}$ dimeric interface. Sidechains of residues important for the interactions are shown in stick models.
Figure 8E:
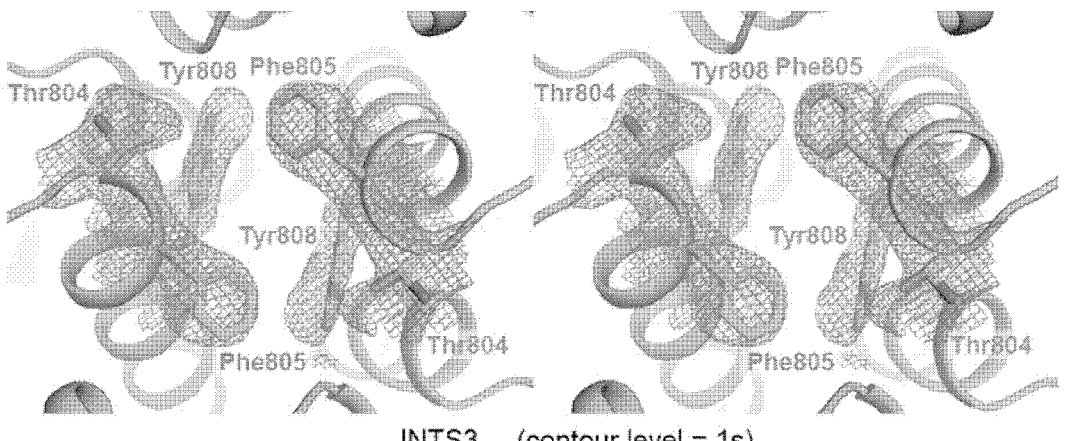
FIGS. 8E and 8F illustrate stereo views of the electron density maps of $Phe805^{INTS3}$ and $Tyr808^{INTS3}$ in apo $INTS3_{CTD}$ dimer (FIG. 8E) and the $SAGE1_{\beta BD}$-$INTS3_{CTD}$ complex structures (FIG. 8F).

To understand how SAGE1 competes with INTS6 for the interaction with INTS3, we first determined the crystal structure of INTS3$_{CTD}$ at a resolution of 2.3 Å using the single wavelength dispersion (SAD) method (FIG. 7A, the coordinates deposited in PDB under code: 7C5T). INTS3$_{CTD}$ is composed of 23 tightly packed helices and adopts an elongated rod-shaped conformation (FIG. 7A). Notably, INTS3$_{CTD}$ adopts a dimeric conformation in the crystal and the dimer interface involves both hydrophobic and electrostatic interactions and buries a total of ~1,620 Å$^2$ solvent-accessible surface area (FIGS. 8C, 8D and 8E). experiments using calibrated size exclusion chromatography showed that the elution peak of INTS3$_{CTD}$ corresponded to a molecular weight of ~95 kDa (FIG. 8A), confirming that INTS3$_{CTD}$ also exists as a dimer in solution. We also purified the INTS3-INTS6 protein complex (FIG. 8B).

Figure 7B:
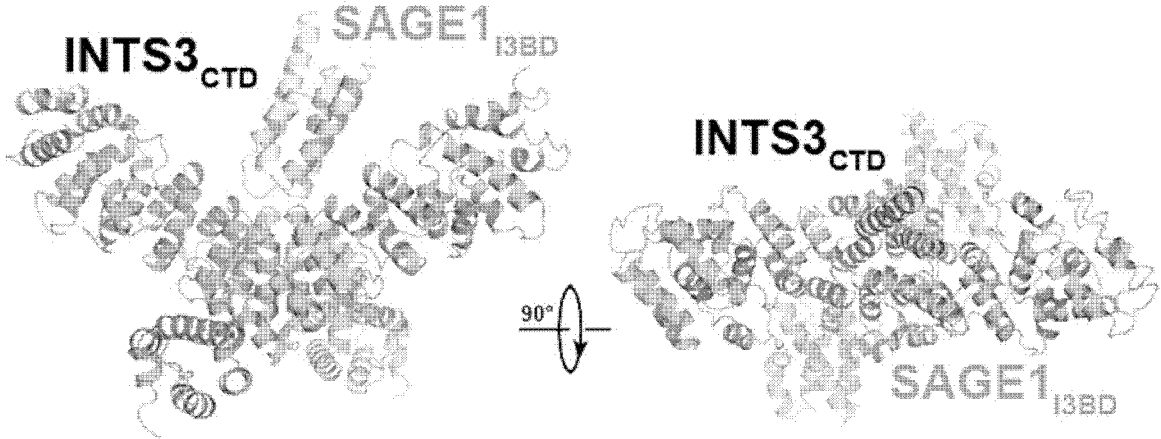
Figure 7C:
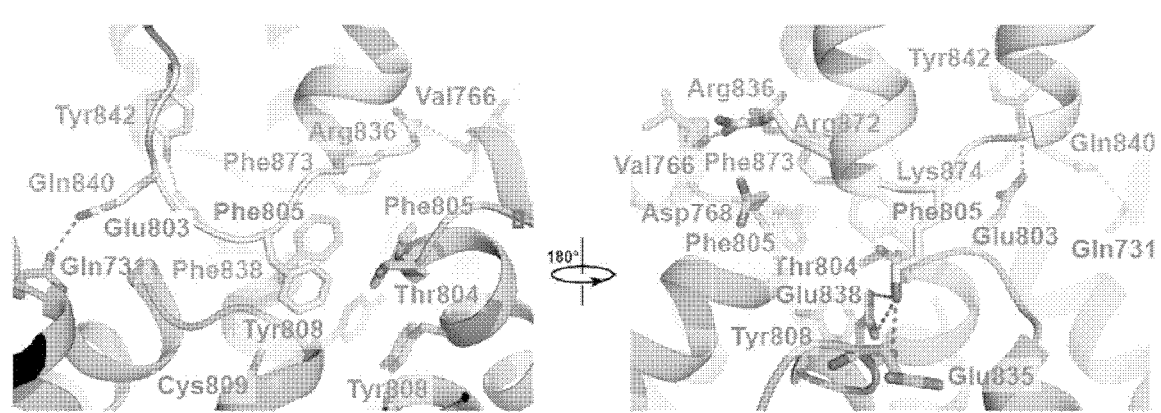
FIG. 7C illustrates details of the interactions between $SAGE1_{\beta BD}$ and the $INTS3_{CTD}$ dimer.
Figure 7D:
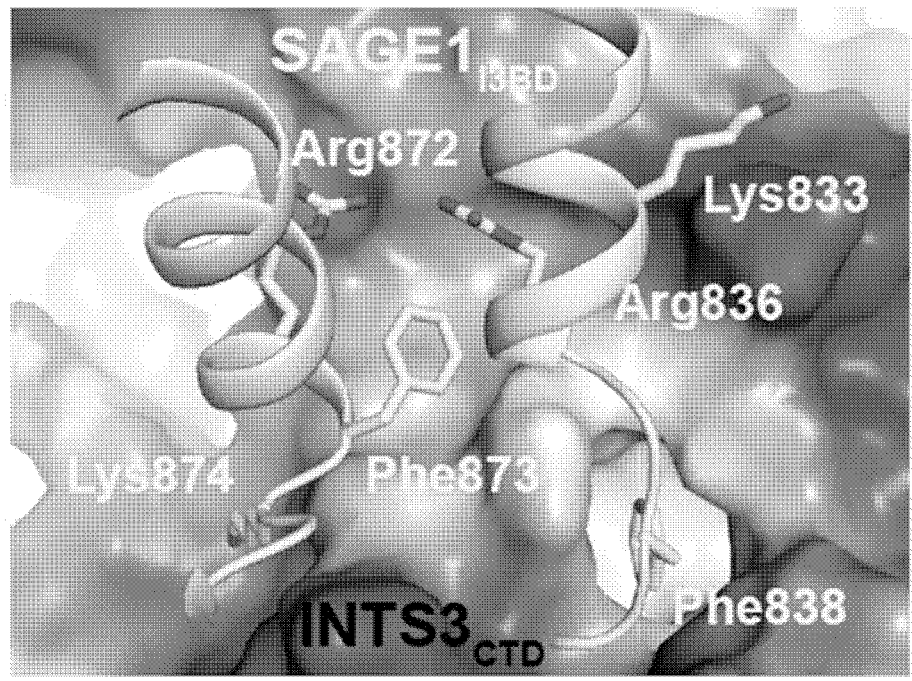
FIG. 7D illustrates electrostatic surface potential of the $SAGE1_{\beta BD}$-binding pocket of $INTS3_{CTD}$.
Figure 7E:
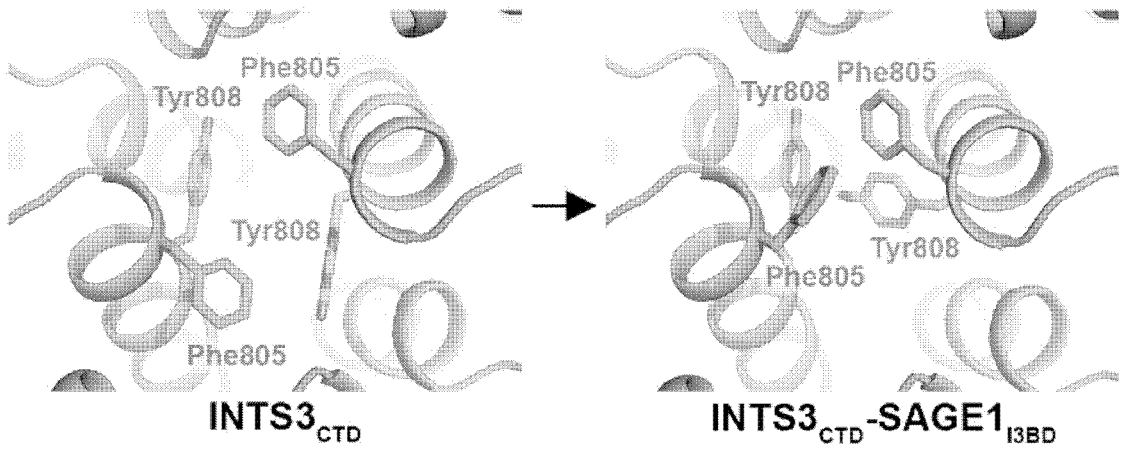
FIG. 7E illustrates binding of $SAGE1_{\beta BD}$ induces a symmetric-to-asymmetric transition of the side chains of Phe805 and Tyr807 in $INTS3_{CTD}$ dimer.
Figure 7F:
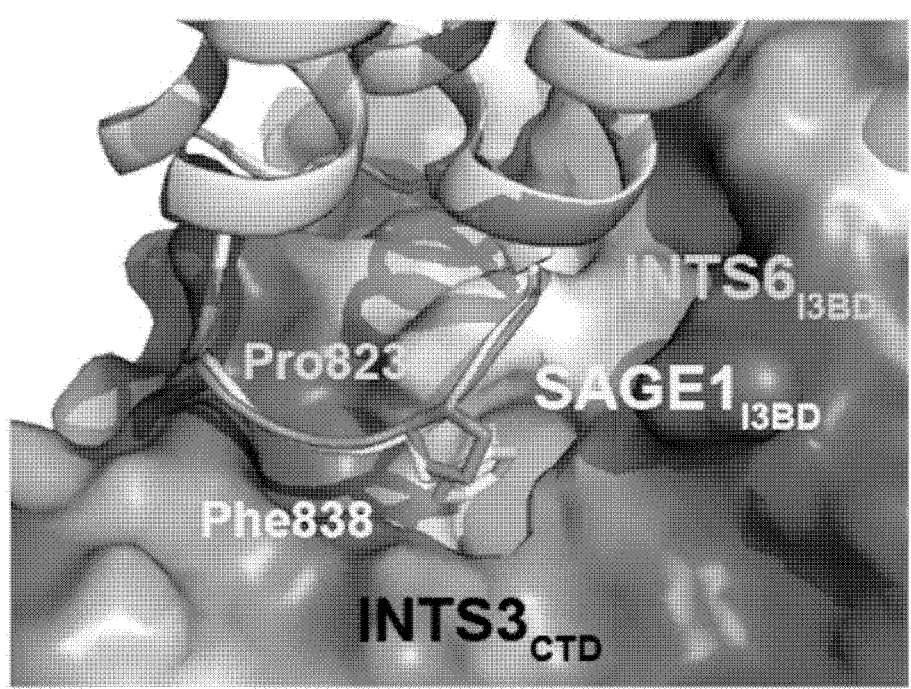
FIG. 7F illustrates superposition of the structural model of $INTS6_{\beta BD}$ onto $SAGE1_{\beta BD}$ highlights the difference between Phe838 SAGE1 and Pro823 INTS6.
Figure 7G:
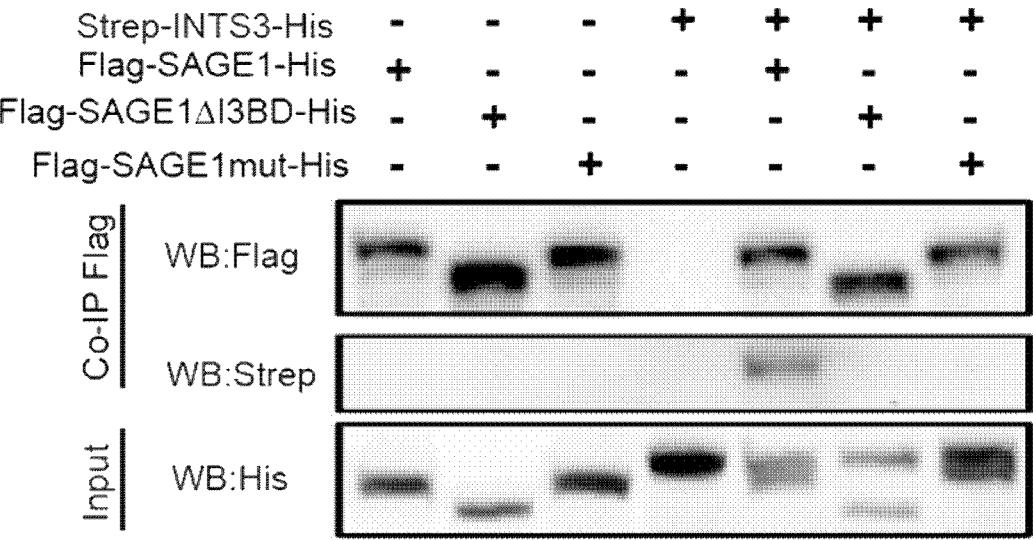
FIG. 7G illustrates Co-IP analysis of the interactions of WT SAGE1, $SAGE1D_{\beta BD}$ and SAGE1mut with INTS3.
Figure 7H:
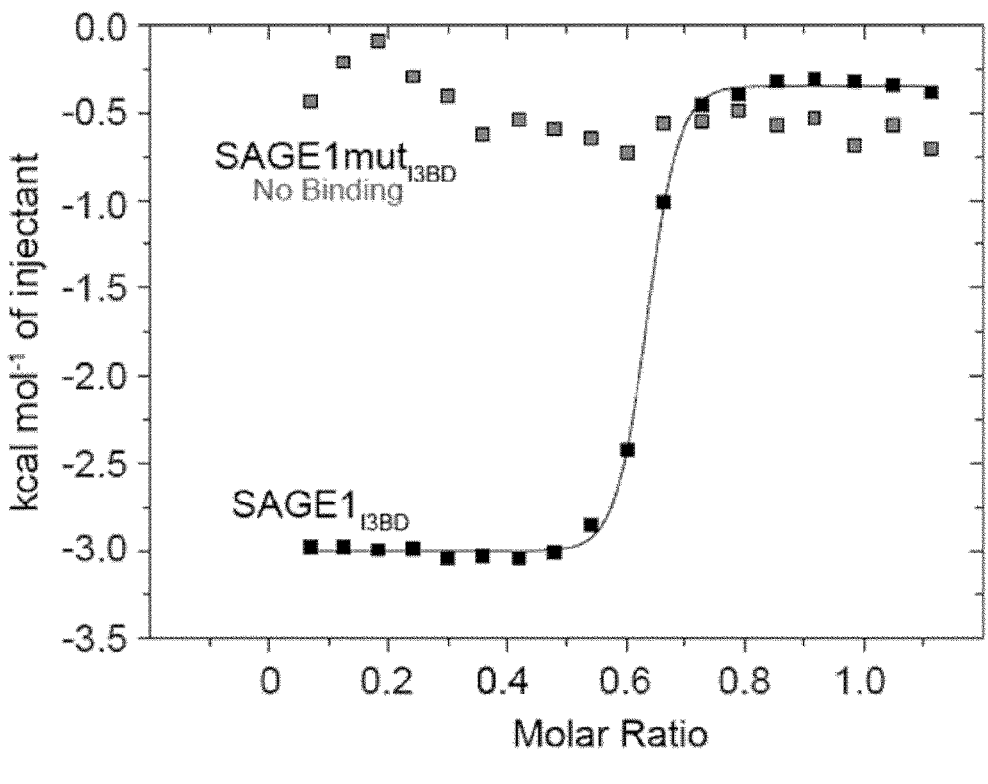
FIG. 7H illustrates comparison of ITC measurements of the interactions between WT or mutant $SAGE1_{\beta BD}$ and $INTS3_{CTD}$.
Figure 8F:
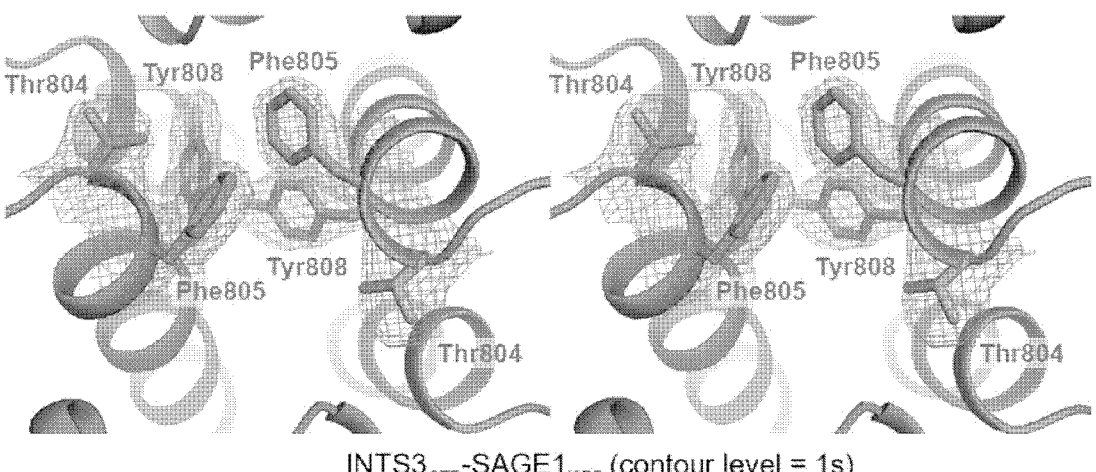
Figure 8G:
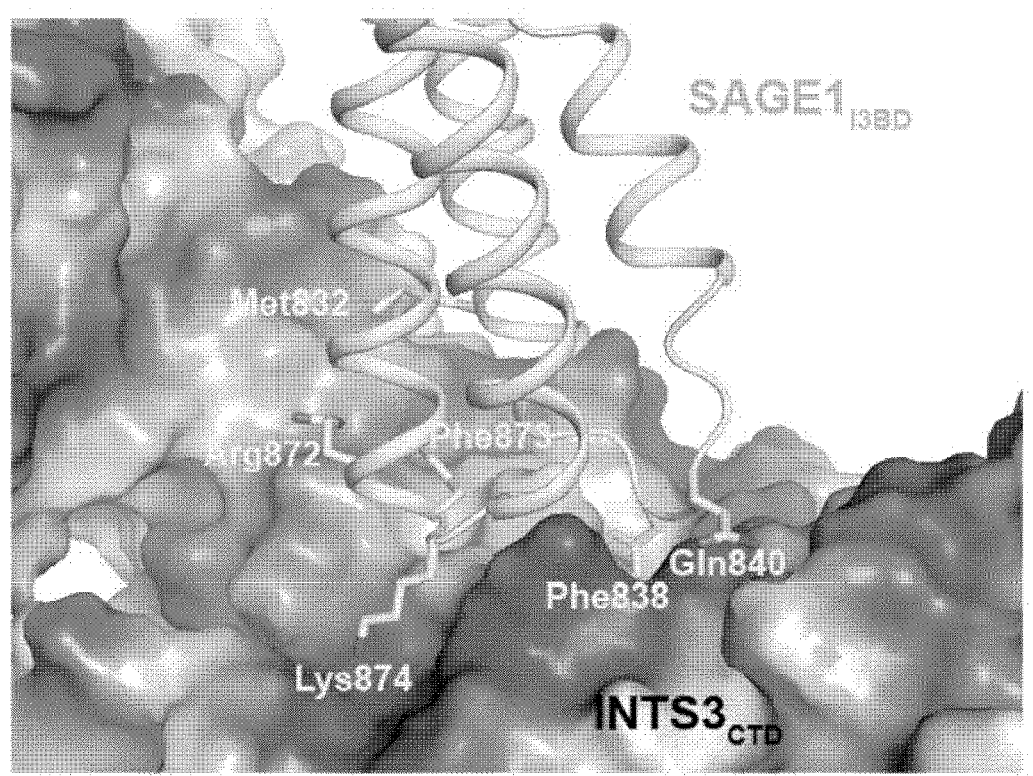
FIG. 8G illustrates close-up view of the $SAGE1_{\beta BD}$-$INTS3_{CTD}$ interface. Six key interacting residues that were substituted to alanine in SAGE1mut are highlighted in stick models.

Next, we crystallized the SAGE1$_{I3BD}$-INTS3$_{CTD}$ complex and determined its structure at a resolution of 2.9 Å by molecular replacement (FIGS. 7B-7D and FIG. 12, the coordinates deposited in PDB under code: 7C5U). In the INTS3$_{CTD}$-SAGE1$_{I3BD}$ complex structure, one SAGE1$_{I3BD}$ molecule binds to a dimer of INTS3$_{CTD}$ with a 1:2 stoichiometry (FIG. 7B). It is noteworthy that ITC measurement also unveiled a 1:2 stoichiometry in the SAGE1$_{I3BD}$-INTS3$_{CTD}$ interaction (FIG. 7H). SAGE1$_{I3BD}$ is a four-helix bundle, sitting on the joint of the INTS3$_{CTD}$ dimer (FIGS. 7B-7D). The internal two loops that connect the helices in SAGE1$_{I3BD}$ mediate contacts with the INTS3$_{CTD}$ dimer through both hydrophobic and electrostatic interactions (FIGS. 7E and 8F). The contact surface on the INTS3$_{CTD}$ dimer is highly acidic and interacts with a panel of basic residues of SAGE1$_{I3BD}$ (Lys833, Arg836, Arg872, and Lys874) via both charge and shape complementarity (FIGS. 8F and 8G). There are two adjacent hydrophobic pockets at the center of this acidic INTS3$_{CTD}$ surface. The sidechain of Phe838$^{SAGE1}$ sticks into one pocket with a deeper cavity, whereas another phenylalanine Phe873$^{SAGE1}$ sits in the shallower one. It is noteworthy that, although SAGE1$_{I3BD}$ does not interfere with the dimeric state of INTS3$_{CTD}$, its binding on the INTS3$_{CTD}$ dimer induces a symmetric-to-asymmetric conformational transition of the aromatic sidechains of Phe805$^{INTS3}$ and Tyr808$^{INTS3}$, which in turn shape the two hydrophobic pockets for efficient binding with SAGE1$_{I3BD}$ (FIGS. 7E, 8C, 8E and 8F). The residues involved in the interaction between INTS3$_{CTD}$ dimer and SAGE1$_{I3BD}$-INTS3$^{CTD}$ complex are identified (FIG. 13A and FIG. 13B).

Given the high sequence identity between INTS6$_{I3BD}$ and SAGE1$_{I3BD}$, we modeled the INTS3$_{CTD}$-INTS6$_{I3BD}$ interface based on the SAGE1$_{I3BD}$-INTS3$_{CTD}$ complex structure. Not surprisingly, except for a proline substitute (Phe838$^{SAGE1}$ $^{to}$ Pro823$^{INTS6}$), the INTS6$_{I3BD}$-INTS3$_{CTD}$ interface is almost identical to that between SAGE1$_{I3BD}$ and INTS3$_{CTD}$ (FIG. 7F). Notably, this proline substitution is expected to produce an energetically unfavorable cavity, explaining the weaker interaction between INTS6$_{I3BD}$ and INTS3$_{CTD}$ (FIG. 7F). Thus, these structural data provide solid evidence supporting why SAGE1 expression in cancer cells can disrupt the INTS3-INTS6 interaction and form the new SAGE1-INTS3 complex.

Example 10: The SAGE1-INTS3 Interaction is Essential for Cancer Cell Proliferation To study the in vivo function of the SAGE1-INTS3 interaction, we first examined the interaction between INTS3 and a deletion mutant of SAGE1 (SAGE1$_{ΔI3BD}$). Co-IP experiments showed that the I3BD domain of SAGE1 is required for the SAGE1-INTS3 interaction (FIG. 7G). Next, we generated a mutant SAGE1 (SAGE1mut) with alanine substitutions of six key interface residues, including Phe838 and found that these mutations completely abolished the SAGE1-INTS3 interaction (FIGS. 7G and 7H). In accordance with the co-IP data, ITC analysis revealed no detectable interaction between INTS3$_{CTD}$ and mutant SAGE1$_{I3BD}$ (FIG. 7H), confirming that the observed interface between SAGE1 and INTS3 in the crystal structure is essential for the SAGE1-INTS3 interaction.

Figure 7I:
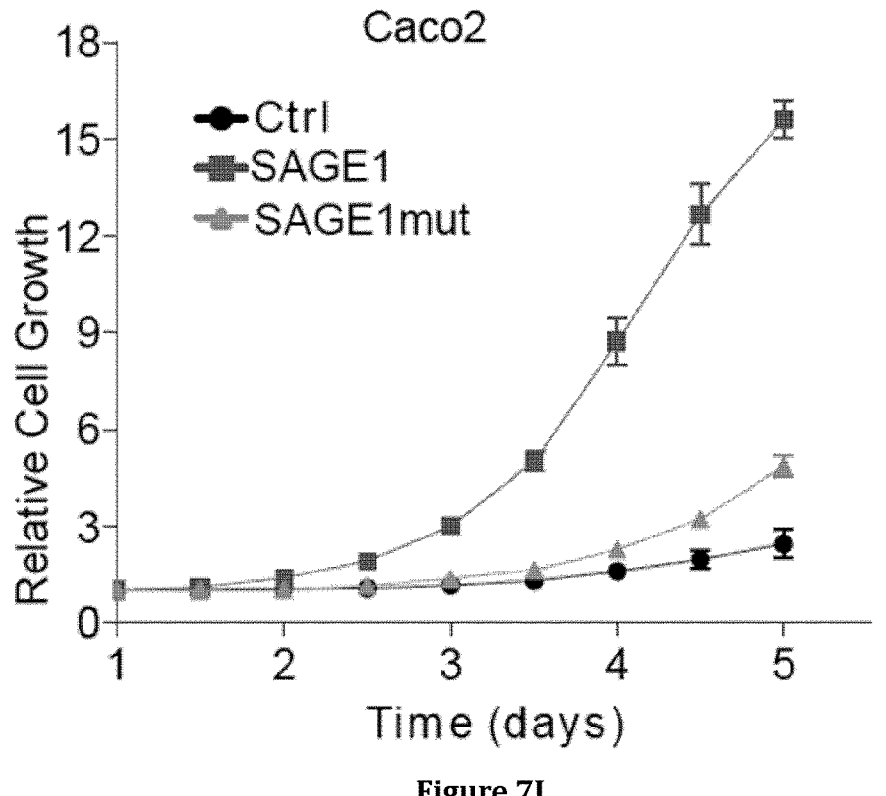
Figure 7L:
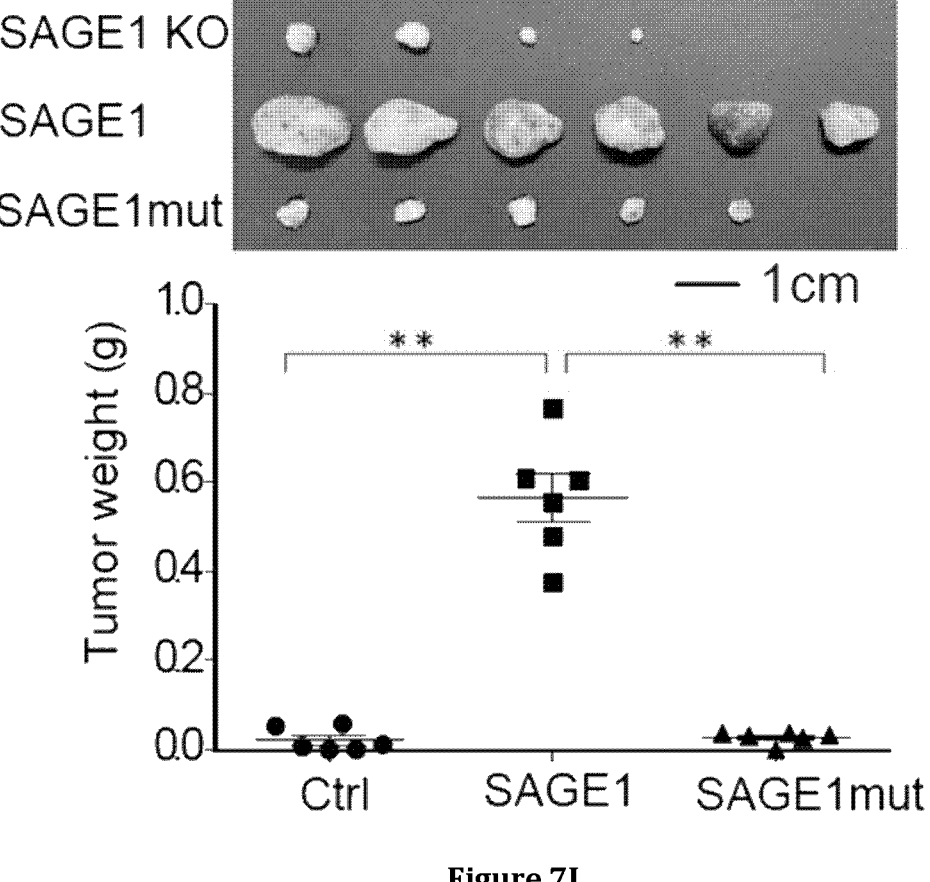

To examine whether the interaction between SAGE1 and INTS3 is important for cancer cell proliferation, wild type (WT) and mutant SAGE1 were introduced back in SAGE1-KO HuTu 80 and SAGE1-KD Caco2 cells, respectively. Expression of WT SAGE1 successfully restored cell growth in both cell lines, confirming that the observed suppression in SAGE1-KO HuTu 80 and SAGE1-KD Caco2 cells was SAGE1 specific (FIGS. 7I and 7J). In sharp contrast, SAGE1mut failed to regain cell proliferation capacity, although expressed at even higher levels than WT SAGE1. Next, we further examined the impact of the SAGE1-INTS3 interaction by using SAGE1-KO HuTu 80 cells restored with WT or mutant SAGE1 in soft agar and xenograft assays. Consistent with the cell growth data, ectopic expression of WT but not mutant SAGE1 rescued the anchorage-independent growth of SAGE1-KO HuTu 80 cells and resulted in an increase in tumor volume and weight (FIGS. 7K and 7L). Collectively, these mutational analyses show that the SAGE1-INTS3 interaction is essential for cancer cell proliferation and that disruption of this interaction could attenuate the pro-oncogenic function of SAGE1.

Example 11: In Vivo Metastasis Analysis Via Tail Vein Injection Assay

Figure 5A:
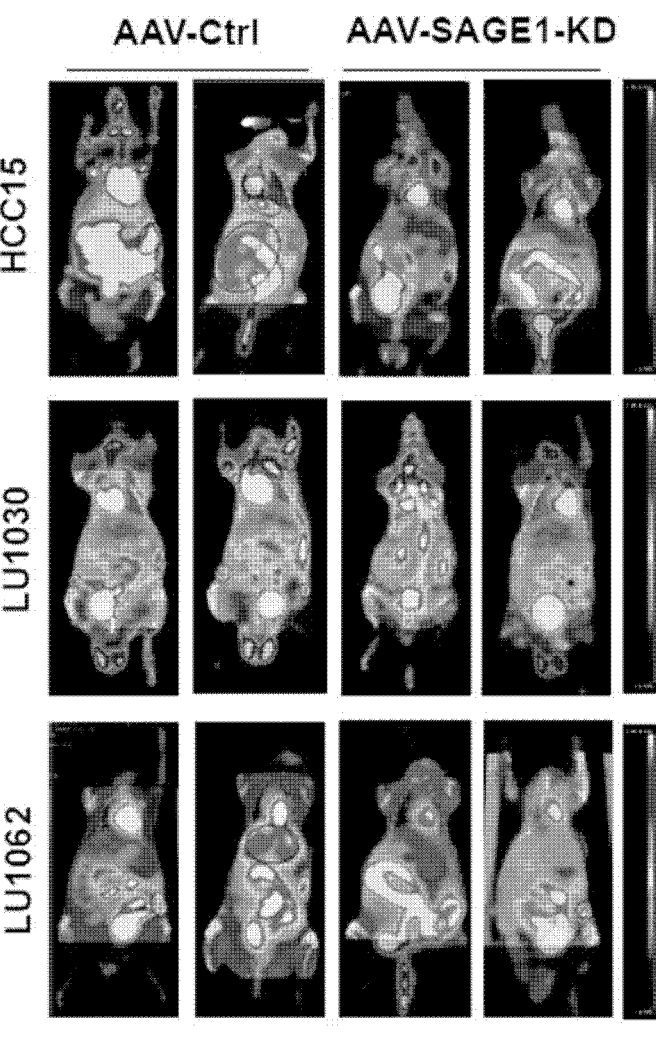
FIG. 5A, FIG. 5B and FIG. 5C illustrate the shSAGE1 treatment which suppressed tumor metastasis in experimental metastasis model. HCC-P, LUAD-P, LUSC-P PDX derived cells were injected into the tail vein. After 7 to 10 days, the recipients were treated with AAV-control or AAV-SAGE1 at $4 \times 10^{11}$ genome copies per mouse via tail vein injection. After 70-90 days, the animals were evaluated by PET-CT for the presence of metastatic tumors. When a mouse showed a poor condition, assessment was performed earlier (FIG. 5A).
Figure 5B:
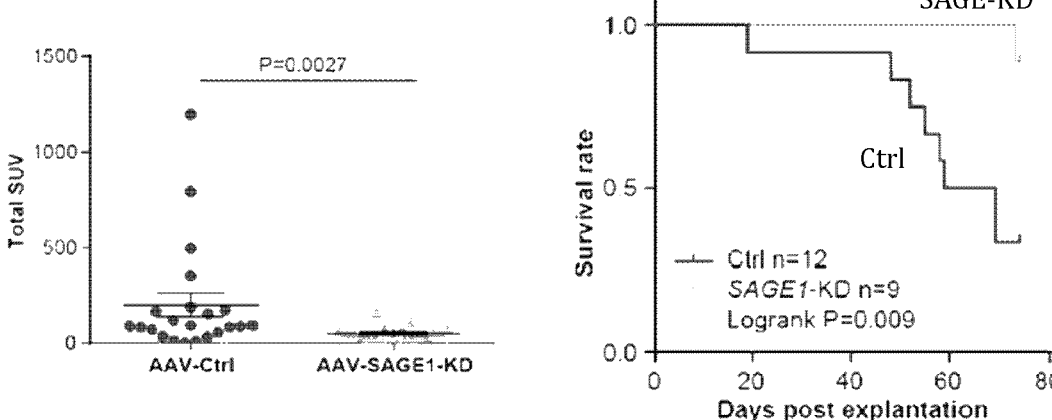
Figure 5C:
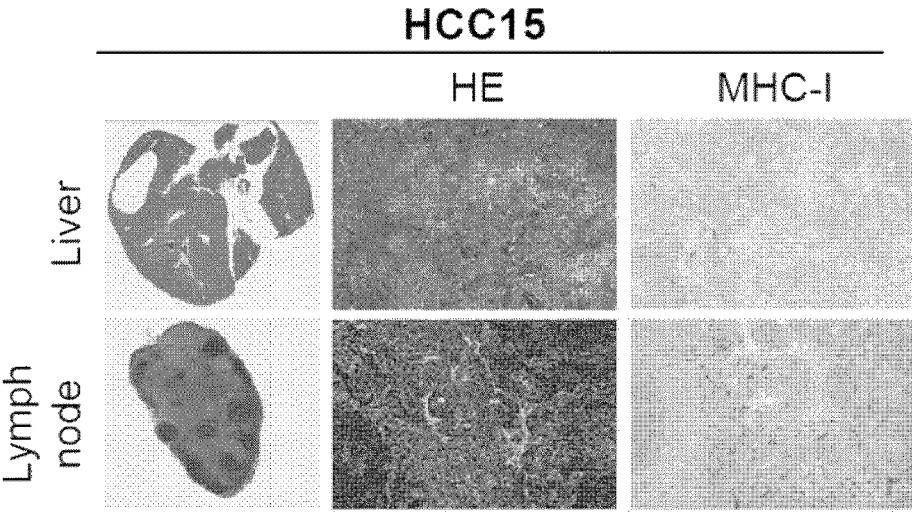

The experiment indicate that SAGE1 is crucial for oncogenic metastasis in vivo. The fact that SAGE1 knockdown blunted tumor metastasis suggests such tumors have become addictive to SAGE1, and that targeting SAGE1 could serve as a novel therapeutic strategy against SAGE1 positive tumors in vivo.

shSAGE1 treatment suppressed tumor metastasis in experimental metastasis model. HCC-P, LUAD-P, LUSC-P PDX derived cells were injected into the tail vein. After 7 to 10 days, the recipients were treated with AAV-control or AAV-SAGE1 (which carries shRNA Y12682 (SEQ ID NO: 128) targeting the sequence set forth in SEQ ID NO: 33 GCTGCAGTCACTCACAACA) at 4×10$^{11}$ genome copies per mouse via tail vein injection. After 70-90 days, the animals were evaluated by PET-CT for the presence of metastatic tumors. When a mouse showed a poor condition, assessment was performed earlier. Tumor burden was calculated by volume×mean SUV-bw and analyzed by T test. The survival time for HCC-P mice were calculated and analyzed by Kaplan-Meier analysis. The mice were euthanized and organs were dissected, and evaluated for the presence of metastatic tumors by hematoxylin-eosin and MHC-I staining (FIGS. 5A-5C).

Example 12

To further study whether the high expression of SAGE1 is associated with the tumor driver mutation, we carried out further analysise with TCGA data (FIGS. 10A and 10B). Somatic mutations in TP53 highly correlated with SAGE1 high expression (top 6% of SAGE1 expression level), and only protein coding mutations of TP53 retained in these SAGE1 high patient (Frame_Shift_Del, Frame_Shift_Ins, In_Frame_Del, In_Frame_Ins, Missense_Mutation, Nonsense_Mutation, Nonstop_Mutation, Splice_Site, and Translation_Start_Site).

Figure 11A:
FIG. 11A illustrates SAGE1 sarcoma antigen 1 [*Homo sapiens* (human)], Gene ID: 55511, located at Xq26.3, GRCh38.p13 (Genome Reference Consortium Human Build 38 patch release 13), the specific position in the human genome is ChrX: 135,893,700..135,913,062.

Example 13: The Analysis about SAGE1Gene Localization, Regulation and Methylation Sarcoma antigen 1 (SAGE1) is a CTA gene located in the X chromosome and encodes a putative 904-amino-acid protein illustrates SAGE1 sarcoma antigen 1 [*Homo sapiens* (human)], Gene ID: 55511, located at Xq26.3, GRCh38.p13 (Genome Reference Consortium Human Build 38 patch release 13), the specific position in the human genome is ChRX: 135,893,700..135,913,062 (FIG. 11A).

Figure 11B:
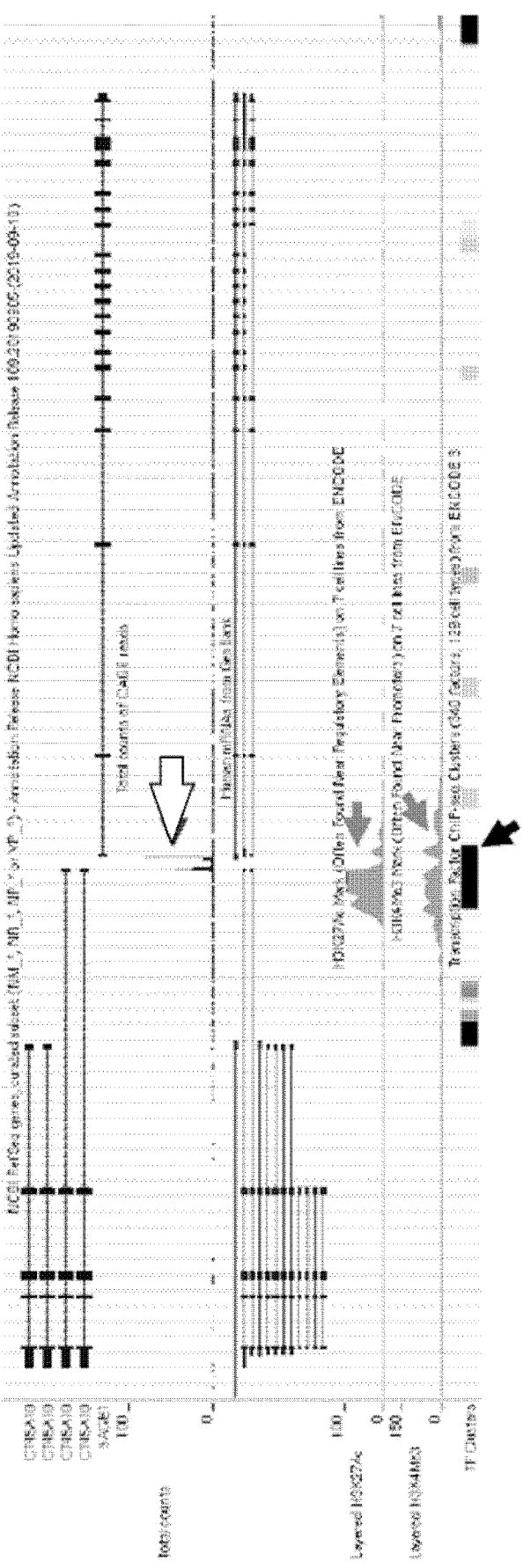
FIG. 11B illustrates CAGE (cap analysis of gene expression) analysis showing that the transcription start site of SAGE1 is located near ChrX: 135893700 (that is, the 5'end of the first exon) (white arrow). ChIP analysis showed that there were obvious H3K27Ac and H3K4Me3 modification signals (grey arrows) and a large number of transcription factor binding signals (black arrows) near the site.

Further CAGE (cap analysis of gene expression) analysis showing that in K562 transcription start site of SAGE1 is located near ChRX: 135893700 (that is, the 5'end of the first exon) (white arrow). ChIP analysis showed that there were obvious H3K27Ac and H3K4Me3 modification signals (grey arrows) and a large number of transcription factor binding signals (black arrows) near the site when SAGE1 is activated (FIG. 11B).

Figure 11C:
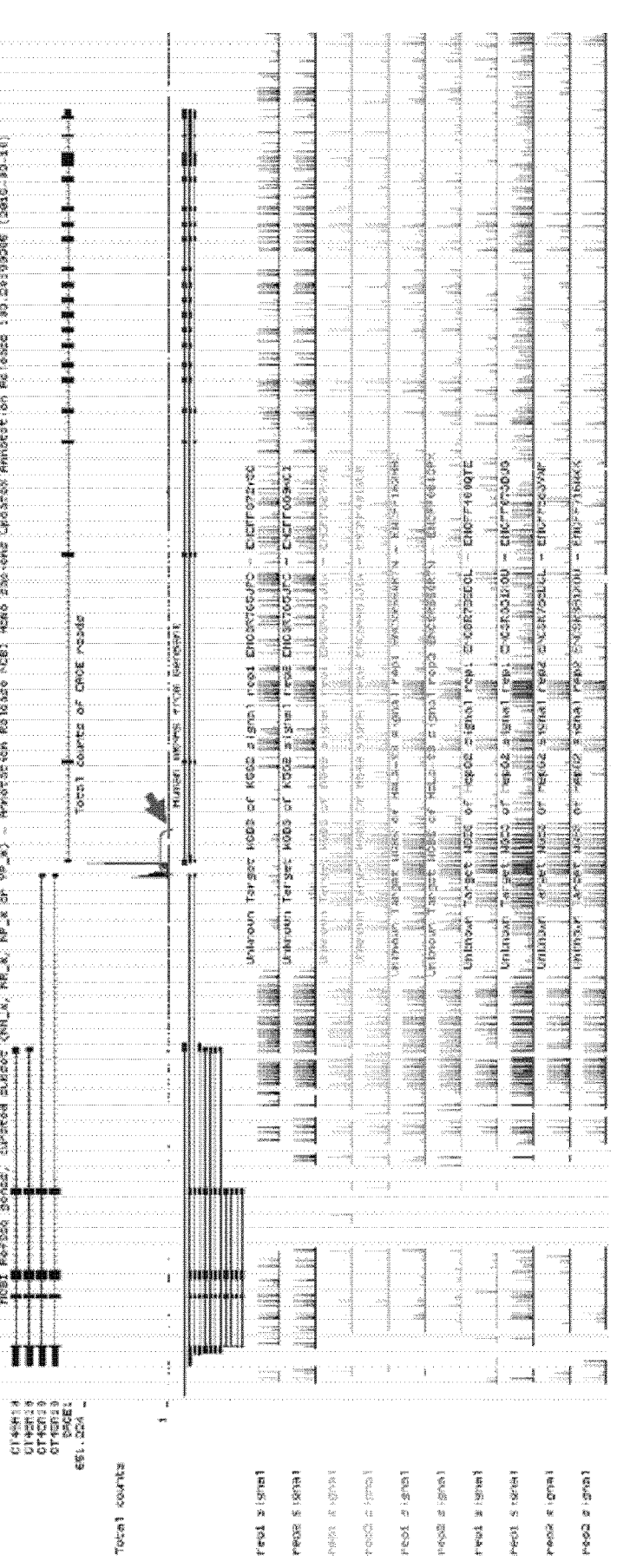
FIG. 11C illustrates the whole genome DNA methylation sequencing (Whole Genome Bisulfite Sequencing, WGBS) analysis showing that there are obvious differences in DNA methylation modification within 2 kb (-1 kb~1 kb) of the transcription start site of SAGE1 (chrX:135,892,700-135,894,700) (purple arrow): cells with high SAGE1 expression have low DNA methylation levels at this site; cells with low or no SAGE1 expression have high DNA methylation levels at this site. It indicates that DNA demethylation is involved in the regulation of SAGE1 expression.

The whole genome DNA methylation sequencing (Whole Genome Bisulfite Sequencing, WGBS) analysis showing that there are obvious differences in DNA methylation modification within 2 kb (−1 kb~1 kb) of the transcription start site of SAGE1 (chrX:135,892,700-135,894,700) (purple arrow): cells with high SAGE1 expression have low DNA methylation levels at this site; cells with low or no SAGE1 expression have high DNA methylation levels at this site. It indicates that DNA demethylation is involved in the regulation of SAGE1 expression (FIG. 11C).
Method:
1. Overall Survival Survival analyses were conducted by Kaplan-Meier method using the log-rank test. Overall survival was defined as the time interval from initial surgical excision to death or last follow-up time (censored). The TCGA database was divided into negative, low level and high level SAGE1 expression groups according to Negative (0 RESM), Low expression (0.1857-11.2969RESM), High expression (>11.30RESM).

All analyses were performed using R software, version 4.0.2. A two-sided p value <0.05 was considered statistically significant.
2. Anchorage-Independent Growth Assays For soft agar colony formation assay, $2 \times 103$ cells were added into growth medium containing 0.35% Fisher low-melt agar and overlayered onto 0.7% Sigma agar beds in six-well plates. Culture dishes were sequentially transferred to a refrigerator (4° C.) for 15 min, to room temperature for 10 min, and then to the cell culture incubator (37° C.). Cell culture media were replenished every three days. After 2-3 weeks, cultures were stained with piodonitroneotetrazolium violet (Sigma-Aldrich, #146-68-9) overnight, and imaged using a MiniCount Colony Counter (Imaging Products International, #013100708). The colonies were calculated, and data represented as mean±SD from three independent triplicate experiments.
3. WB Western blots were conducted using the following antibodies: rabbit anti-SAGE1 polyclonal antibody (Novus Biologicals, #NBP1-84355), rabbit anti-INTS3 polyclonal antibody (Novus Biologicals, #NBP1-19091), mouse anti-His monoclonal antibody (Proteintech, #66005-1-Ig), rabbit anti-FLAG polyclonal antibody (Proteintech, #20543-1-AP), mouse anti-STREPII monoclonal antibody (Abeam, #ab184224), rabbit anti-TLE3 polyclonal antibody (Proteintech, #11372-1-AP), mouse anti-GAPDH monoclonal antibody (Proteintech, #60004-1-Ig), goat antirabbit IgG (H+L), HRP conjugate (Proteintech, #SA00001-2), goat anti-mouse IgG (H+L), HRP conjugate (Proteintech, #SA00001-1). Proteins were resolved by 4-20% gradient SDS-PAGE gel (Genescript, #M42012C) and transferred to PVDF membranes. These membranes were then blocked with 5% skim milk in diluted 1×TBST buffer (Sangon, #tbst-0520009) and then probed overnight with primary antibodies at 4° C., followed by incubation of horseradish peroxidase (HRP)—conjugated donkey anti-mouse, anti-rabbit or anti-goat antibodies for 1 hour at room temperature. After 3 times of membrane wash, the immuno-complexes were detected by Western Lightning ECL Pro (PerkinElmer, #NEL122001EA) or ECL Prime Western Blotting Detection. Reagents (Amersham, #RPN2232).
4. Cell Cycle and Ki67 Test For in vivo SAGE1 knock down experiment, Streptavidin-Biotin Complex (SABC) method was used in immunohistochemistry to detect SAGE1 and ki67. For LUSC-P, Hematoxylin and Eosin staining were performed to show the histological changes in tumor residuals. Pan-cytokeratin staining showed fibro-inflammatory changes replacing neoplastic components in SAGE1 shRNA treated tissues. Primary antibodies against SAGE1, ki67 and pan-cytokeratin were used at a concentration of 1:300, 1:100 and 1:200, respectively. All antibodies used in this study were confirmed to be reactive only to the targets by the manufacturer.
5. IHC De-identified human normal and cancer tissues were obtained from Shanghai OUTDO Biotech Co. Ltd (Shanghai, China). The Streptavidin-Biotin Complex method was used in immunohistochemistry to detect SAGE1. For immunofluorescence staining, HuTu80 derived xenograft tissue and HCC PDX tissue sections were de-waxed twice in fresh xylene for 15 min each, rehydrated in 100%, 95%, 75%, 50% ethanol and PBS for 10 min each. Epitope retrieval was carried out by boiling sections in TUF TARGET UNMASKING FLUID (Invitrogen, Z00R.0000) for 20 min. Slides were then washed with PBST (PBS buffer supplemented with 0.5% Triton X-100) and blocked with 5% BSA at RT for 3 h, followed by incubation with rabbit anti-SAGE1 polyclonal antibody (Novus NBP1-84355), or rabbit anti-INTS3 polyclonal antibody (Novus NBP1-19091) at 4° C. for overnight, then washed and incubated with Alexa Fluor 555 or 488 conjugated secondary antibodies (Proteintech). Nuclei were counterstained with DAPI (Sigma). Slides were thoroughly washed in PBST and mounted and visualized using a laser scanning confocal microscope.
6. LC MS/MS Based Proteomics and Data Processing Cells were lysed in lysis buffer (8 M urea, 1% SDS, 100 mM Tris-HCl, pH 8.5, 1 mM PMSF, containing 1:100 (vol/vol) protease inhibitor cocktail (Roche, Switzerland)) with sonication. Lysates were incubated on ice for 30 min followed by centrifugation at 16,000 g for 30 min at 4° C. to remove insoluble debris. Protein concentration of the supernatant was determined by the Pierce™ BCA Protein Assay Kit (Thermo Scientific). Disulfide bridges were reduced using 10 mM tris(2-carboxyethyl)-phosphine (TCEP) at room temperature for 10 min, followed by alkylation with 15 mM iodoacetamide at room temperature in the dark for 30 min. Acetone precipitation was performed to remove the SDS. The protein samples were resuspended in 4M urea 40 mM Tris-HCl, pH 8.0. A 2-step digestion at 37° C. was performed by first adding 1:100 LysC (Wako) for 3 h and 1:50 trypsin (Promega) overnight. Digests were desalted using C18 RP solid-phase extraction cartridges (Waters), and the eluates were dried by vacuum centrifugation (Labconco). TMT labeling was performed according to manufacturer's instructions. Briefly, 100 mg of peptides was reconstituted in 100 mL of 50 mM TEAB buffer (pH 8.5). Each 0.8 mg of TMT 6-plex reagent (ThermoFisher) was reconstituted in 41 mL of acetonitrile and added to the corresponding aliquot of peptides. The labeling reaction was incubated for 1 h at room temperature, and then was quenched by adding 8 ml of 5% hydroxylamine. The labeled peptides were combined and desalted using C18 column cartridges (Waters). The TMT labeled peptides were fractionated by high-pH reversed phase chromatography on an Acquity BEH300 C18 Column (300 Å, 1.7 μm, 1 mm×150 mm Waters) using an Agilent 1200 HPLC. Peptides were separated into 32 fractions, which were pooled into 15 fractions. Each fraction was desalted using self-packed StageTip, dried via vacuum centrifugation, and reconstituted in 0.1% formic acid for LC-MS/MS analysis. Each fraction was separated by an EASY-nLC 1200 UHPLC (ThermoScientific) using an in-house packed capillary column (20 cm×75 μm i.d., ReproSil-Pur C18, 1.9 μm particle size, 120 Å pore size, Dr. Maisch) over a 150 min LC gradient at a flow rate of 250 nL/min (4-8% buffer B for 8 min, 8-25% buffer B for 105 min, 25-40% buffer B for 30 min, 40-80% buffer B for 7 min, buffer A: 0.1% formic acid in water, buffer B: 0.1% formic acid and 20% water in acetonitrile). The mass data was acquired on an Orbitrap Fusion Lumos mass spectrometer (ThermoScientific) using a SPS-MS3 method. MS1 scans were collected at 60K resolution, with a scan range of 375-1500 m/z, AGC target of 4×105, max ion injection time (MIT) of 20 ms, and dynamic exclusion set to 60 s. For the MS2 analysis, the MS1 precursor ions were isolated by the quadrupole with an isolation window of 0.7 m/z, AGC target of 1×104, MIT of 50 ms, and fragmented by collision induced dissociation at a normalized collision energy of 35%. The MS2 fragment ions were detected in the ion trap under the "rapid" scan rate. Following acquisition of each MS2 spectrum, a synchronous precursor selection (SPS) MS3 scan was performed on the top 10 most intense ions in the MS2 spectrum. SPS-MS3 precursors were isolated with an isolation window of 0.7 m/z, AGC target of 5×104, MIT of 100 ms, followed by the fragmentation using HCD at an activation energy of 65%, and detection using the Orbitrap at a resolution of 15k.

Identification, quantification and differential expression analyses were done using Proteome Discover 2.2 (Thermo-Scientific). Briefly, raw data of TMT quantification were processed using the Proteome Discoverer 2.2 (Ther-moFisher). The MS/MS spectra were searched against the human reference proteome (UP000005640) by the Sequest HT search engine. The MS1 tolerance was set to 10 ppm, the MS2 tolerance was set to 0.6. Trypsin was specified as the proteolytic enzyme, allowing for up to 2 missed cleavages. Carbamidomethylation (+57.0214 Da) of cysteine residues, and TMT tags (+229.1629 Da) on peptide N-termini and lysine residues were set as the fixed modifications. Oxidation on methionine and acetylation on protein N-termini were set as the dynamic modifications. The decoy database searches were also performed in parallel, and the false discovery rate (FDR) was set to 1% for both peptide-spectrum matches (PSMs) and proteins. The signal-to-noise (S/N) values of TMT reporter ions were exacted from the MS3 scans and paired with the MS2 peptide identifications. The PSMs with an average S/N less than 10 or co-isolation interference ions more than 25% were filtered out. The S/N measurements were adjusted according to the isotopic impurities of the different TMT reagents. For each protein, its abundance was calculated by summing the S/N values from all the PSMs matching to the protein. The protein abundances were normalized so that the sum of the signal for all proteins in each channel was equal. Two-sides t-tests were applied for each protein measure, followed by multiple testing correction using Benjamini-Hochberg method. Proteins with a fold change >1.5 and Benjamini-Hochberg adjusted p-value <0.05 were considered as differentially expressed proteins.

7. Experimental Animals

Housing and all procedures using BALB/c nude mice were approved by the Institutional Animal Care and Use Committee and in accordance with the Animals (Scientific Procedures) Act, 1986 (UK) (amended 2013). All sections of this report adhere to the ARRIVE Guidelines for reporting animal research. All mice were housed in individually ventilated cages (5 per cage) under specific pathogen free (SPF) condition. Housing was temperature-controlled, with a 12-h/12-h light/dark cycle. Animal weights were measured every other day.

8. Cell Line Derived Subcutaneous Xenografts

Male BALB/c athymic nude mice (4 to 6 weeks old) were obtained from the Experimental Animal Centre of SIBS. HuTu 80 parental and SAGE1-KO cells (3×106 cells in 100 μL) were injected subcutaneously into mouse flanks as previously described. At ending point, tumor tissue was excised from the mice and weighted. Data on tumor weight are presented as means±SD (n=6). The animal experiments were approved by the Animal Care and Use Committee of shanghai ninth people's hospital, Shanghai Jiaotong University School of Medicine (SH9H-2019-A727-1) and conducted following the animal policies of the Shanghai Jiao-Tong University in accordance with the guidelines established by the National Health and Family Planning Commission of China.

9. Cell Line Derived Intraocular Uveal Melanoma Xenografts

Uveal melanoma cell line MUM2B were pre-transfected with lentivirus encoded by plvx-luciferase-mCherry-Blasti-cidin vector. Cells were washed twice with PBS and harvested by trypsinization. BALB/c nude mice (male, 6 weeks old) were first anaesthetized of topical anesthetic Benoxil. Methocel eye drops were used to avoid drying of the eyes. Injections were performed using a surgical microscope. 2u1 of sterile phosphate buffered saline containing 3×104 uveal melanoma cells were injected into the suprachoroidal space of right eye through the sclera using a Hamilton syringe. After the injection, the eyes were treated with antibiotic eye drops. A bio-luminance imaging assay were performed before adenovirus administration (at day 5) and after adeno-virus administration (at day 12). The SAGE1-silenced or empty vector of adenovirus were injected into the vitreous body (3.2*1011 pfu/ml, 1.5u1 for each administration, at day 7, 9, 11). The survival time for each mouse has been calculated.

10. Patient Derived Xenograft (PDX) Tumors and In Vivo SAGE1 Knock Down Experiments PDX tumors were provided by Shanghai Sunstem Bio-technology Co., Ltd. and WuXi Apptec Co., Ltd., or established by our department (SH9H-2019-T279-2). Xenografts were allowed to grow until they reached a size of 50-100 mm3 and then mice were randomized into two groups (7-9 animals per group) for in vivo RNAi experiments as previously described. shSAGE adenovirus were given by multi-point intra-tumor injection every 3 days. Tumor size was measured at regular intervals with a digital caliper using the formula: tumor volume=(length×width2)/2. One day after the last dosage, animals were sacrificed and the tumors were weighted and fixed in formalin. IHC was performed to examine SAGE1 and ki67. Data on tumor volume and tumor weight are presented as means±SD or means±SE (n=7~9). ALL animal experiments were approved by the Shanghai Jiao Tong University Animal Care and Use Committee (SH9H-2019-A727-1) and conducted following the animal policies of the Shanghai JiaoTong University in accordance with the guidelines established by the National Health and Family Planning Commission of China.

11. PDX Derived Cells (PDC) Isolation and Sample Preparation for Single Cell RNA Sequencing Fresh PDX tissues were washed twice in 1×PBS, and digested with collagenase type IV (Sigma Aldrich cat #C5138-500MG) for 20-30 min at 37° C. with gentle agitation (250 rpm). The digestion was stopped by adding 10% FBS (Gibco cat #10082147). Single cells were obtained by filtering through strainers with mesh size 40 μm (Fisher Scientific cat #08-771-1). The cells were pelleted by centrifugation at 600×g for 15 min, and washed twice with 1×PBS. Cells were then cultured and infected with shRNA virus. Upon the ending point, the cells were trypsinized and resuspended in 1×PBS+10% FBS for single cell RNA sequencing.

12. Tissue Staining

De-identified human normal and cancer tissues were obtained from Shanghai OUTDO Biotech Co. Ltd (Shanghai, China). The Streptavidin-Biotin Complex method was used in immunohistochemistry to detect SAGE1. For immunofluorescence staining, HuTu80 derived xenograft tissue and HCC PDX tissue sections were de-waxed twice in fresh xylene for 15 min each, rehydrated in 100%, 95%, 75%, 50% ethanol and PBS for 10 min each. Epitope retrieval was carried out by boiling sections in TUF TARGET UNMASK-ING FLUID (Invitrogen, Z00R.0000) for 20 min. Slides were then washed with PBST (PBS buffer supplemented with 0.5% Triton X-100) and blocked with 5% BSA at RT for 3 h, followed by incubation with rabbit anti-SAGE1 polyclonal antibody (Novus NBP1-84355), or rabbit anti-INTS3 polyclonal antibody (Novus NBP1-19091) at 4° C. for overnight, then washed and incubated with Alexa Fluor 555 or 488 conjugated secondary antibodies (Proteintech). Nuclei were counterstained with DAPI (Sigma). Slides were thoroughly washed in PBST and mounted and visualized using a laser scanning confocal microscope.

13. In Vivo SAGE1 Knock Down Experiment IHC

Streptavidin-Biotin Complex (SABC) method was used in immunohistochemistry to detect SAGE1 and ki67. For LUSC-P, Hematoxylin and Eosin staining were performed to show the histological changes in tumor residuals. Pan-cytokeratin staining showed fibro-inflammatory changes replacing neoplastic components in SAGE1 shRNA treated tissues. Primary antibodies against SAGE1, ki67 and pan-cytokeratin were used at a concentration of 1:300, 1:100 and 1:200, respectively. All antibodies used in this study were confirmed to be reactive only to the targets by the manu-facturer.

14. Protein Expression and Purification

SAGE1I3BD (residues 818-904) and INTS3CTD (residues 572-978) were cloned into a modified pET28a vector with a SUMO protein fused at the N terminus after the 6×His tag (1). INTS6I3BD (residues 572-978) and SAGE1I3BD (residues 818-904) were cloned into a pGEX-6P-1vector with a GST tag. His-SUMO-INTS3CTD and GST-SAGE1I3BD were co-expressed in E. coli BL21(DE3) CodonPlus cells (Stratagene). After induction for 20 h with 0.1 mM IPTG at 20° C., the cells were harvested by centrifugation, and the pellets were resuspended in lysis buffer (50 mM Tris-HCl, pH 8.0, 400 mM NaCl, 10% glycerol, 1 mM PMSF, 5 mM benzamidine, 1 mg mL-1 leupeptin and 1 mg mL-1 pepstatin). The cells were then lysed by sonication and the cell debris was removed by ultracentrifugation. The supernatant was mixed with Ni-NTA agarose beads (QIAGEN) and rocked for 2 hours at 4° C. before elution with 250 mM imidazole. The ULP1 and 3C PreScission protease were added to remove the His-SUMO and GST tags. The SAGE1I3BD INTS3CTD complex was then further purified by size exclusion chromatography equilibrated with 25 mM Tris-HCl pH 8.0, 150 mM NaCl, and 2 mM dithiothreitol. The purified SAGE1I3BD INTS3CTD complex was concentrated to 15 mg mL-1 and stored at −80° C. Other proteins and protein complex (INTS3CTD, WT and mutant SAGE1I3BD and the INTS3CTD-INTS6I3BD complex) were purified similarly, concentrated to 10~20 mg mL-1 and stored at −80° C.

15. Crystallization, Data Collection and Structure Determination

Crystals of the INTS3CTD dimer and the SAGE1I3BD-INTS3CTD complex were grown by sitting drop vapor diffusion at 4° C. The precipitant well solution of INTS3CTD consisted of 25% Ethylene Glycol 3350, 0.01 mM EDTA and 150 mM NaCl. The precipitant well solution of the SAGE1I3BD-INTS3CTD complex consisted of 0.2 M Ammonium sulfate and 25% Ethylene Glycol 3350. Crystals were gradually transferred into a harvesting solution (25% Ethylene Glycol, 0.01 mM EDTA, 150 mM NaCl, 25% glycerol for INTS3CTD crystals and 0.2 M Ammonium sulfate, 25% Ethylene Glycol 3350 and 25% glycerol for the SAGE1I3BD-INTS3CTD complex crystals) followed by flash-freezing in liquid nitrogen for storage. Datasets were collected under cryogenic conditions (100K) at the Shanghai Synchrotron Radiation Facility (SSRF) beamlines BL18U1 and BL19U1. A 3.0-A SeMet-SAD dataset of INTS3CTD was collected at the Se peak wavelength (0.97853 A) and was processed by HKL3000 (2). Seven selenium atoms were located and refined, and the original SAD electron density map was calculated using HKL3000. (3). The initial SAD map was substantially improved by solvent flattening. The model was then refined against a native dataset with a 2.5-A resolution using Phenix (4). The SAGE1I3BDINTS3CTD complex crystal diffracted to 2.90 A resolution, and the structure was determined by the molecular replacement method.

16. GST Pull-Down Assay

Purified GST-SAGE1I3BD was added into the INTS3CTD-INTS6I3BD complex in an equal molar ratio, and the mixture was incubated with glutathione sepharose 4B beads (GE Healthcare) for 2 hr at 4° C. in 100 μL buffer (25 mM Tris-HCl pH 8.0, 150 mM NaCl and 2 mM MgCl2).

After extensive wash with the same buffer, the bound proteins were eluted in an elution buffer (25 mM Tris-HCl pH 8.0, 150 mM NaCl, 2 mM MgCl2 and 15 mM reduced glutathione). The proteins of input and eluted samples were visualized on 12% SDS-PAGE by Coomassie blue staining.

17. Isothermal Titration Calorimetry (ITC)

The equilibrium dissociation constant of the SAGE1I3BD-INTS3CTD interaction was determined using a MicroCal iTC200 calorimeter (Malvern). The binding enthalpy was measured at 16° C. in 25 mM Tris-HCl pH 8.0, 150 mM NaCl and 5 mM MgCl2. Two independent experiments were performed. ITC data were subsequently analyzed and fitted using Origin 7 software (OriginLab).

18. Cell Culture, Transfection and Lentiviral Transduction

Cell lines used in this study were purchased from Shanghai Gaining Biological Technology Ltd. (Shanghai, China) and verified using DNA fingerprinting. Human duodenal adenocarcinoma HuTu 80 cells were cultured in Minimum Essential Medium (Gibco, #42360032) supplemented with 10% fetal bovine serum (FBS, Gibco, #10091-148). HEK-293T, human malignant melanoma A375 and human colorectal adenocarcinoma Caco2 cells were cultured in Dulbecco's modified Eagle's medium (HyClone, #SH30022.01) containing 10% FBS respectively. Human immortalized primary hepatocyte L02, chronic myelogenous leukemia K-562, and osteosarcoma U2OS cells were maintained in RPMI-1640 medium (Gibco, #22400089) supplemented with 10% FBS. Human esophageal squamous carcinoma KYSE-30 cells were cultured in DMEM/F12 medium (Gibco, #11330032) containing 10% FBS.

Human His-SAGE1-Flag, His-INTS3-Strep were subcloned into a lentiviral pCDH-CMV vector (Addgene, Plasmid #72265) respectively. Mutant SAGE1 (SAGE1mut: R872A, F873A, K874A, M832A, F838A and Q840A) was derived from the WT SAGE1 plasmid using QuikChange II site-directed mutagenesis kit (Agilent, #200523) with primers containing desired mutations. To fluorescently label exogenous SAGE1 expressing cells, WT SAGE1, SAGE1mut were inserted into the BamHI-XbaI sites in a modified lentiviral pCDH-CMV-MCS-EF1-copGFP vector that allows fluorescent copGFP to be expressed in the same cells when lentiviral backbone incorporated into host cell genome. All plasmids were verified by sequencing analysis.

19. SAGE1 shRNA and siRNA

Human SAGE1 shRNA and siRNA were tested and many of them could sufficiently suppress endogenous SAGE1 expression (FIG. 16). pLK0.1 scramble shRNA vector was used as a negative control. The lentiviruses were produced in HEK-293T cells by transient transfection of the indicated pLK0.1-SAGE1 shRNA construct together with two packaging vectors: pCMV-dR8.2 dvpr (Addgene, Plasmid #8455) and pCMV-VSV-G (Addgene, Plasmid #8454). The supernatants were harvested after 48 hours post transfection and subjected to filtering using 0.45 μm sterile filter (Millipore, #SLHU033RB). The resultant lentiviral stocks were used to transduce HuTu 80, Caco2, A375, and LO2 cells, respectively. Twenty-four hours later, cells were selected by 3 μg mL-1 of puromycin (Gibco, #A11138-03) for 3-5 days.

FIG. 17 shows the SAGE1 siRNA and shRNA used in the present disclosure, and the target sequences of SAGE1 mRNA transcript by the SAGE1 shRNA and siRNA used in the present disclosure.

20. Flow Cytometry and Cell Sorting

To isolate exogenous SAGE1 or SAGE1mut expressing cells, we took advantage of copGFP expression in the same cells that allowed us to use fluorescence activated cell sorting (FACS) for the purification of these SAGE1-expressing cell populations. Briefly, SAGE1-KD and KO or control cells were infected with lentiviruses carrying WT SAGE1, SAGE1mut or empty vector for 24 hours and cultured for another 24 hours. Then, these cells were trypsinized, resuspended in sterile FCAS buffer containing 1% penicillin-streptomycin (Gibco, #15140122) and subjected to cell sorting by BD Influx. Sorted live coGFP+ cells were collected for further study.

21. SAGE1 Knockout by the CRISPR-Cas9 Method

To knock out endogenous SAGE1, two pairs of DNA oligos (Hum SAGE1 sg1-Up: ACCGaaggaagagtatgtcctcg (SEQ ID NO: 96), Hum SAGE1 sg1-D: AAACCGAGGA-CATACTCTTCCTT (SEQ ID NO: 98), Hum SAGE1 sg2-Up: ACCGaagtaaatctggttgcaac (SEQ ID NO: 97), Hum SAGE1 sg2-D: AAACGTTGCAACCAGATTTACTT (SEQ ID NO: 99) (The lower case letters show the targeting sequences at SAGE1 genome) both were used for producing single guide RNAs that were annealed and cloned into the AgeI-EcoRI sites of pX330-U6-Chimeric_BB-CBh-hSp-Cas9 vector (Addgene, Plasmid #42230). These SAGE1-targeting constructs were transfected into HuTu 80 cells using lipofectamine 2000 reagent (Invitrogen, #11668019) according to the manufacturer's instruction. After 48 hours, cells were detached, resuspended, and re-seeded into 96-well plates with dilution ensuring 1 cell per well. After culture of several days, individual colonies were split and half of total cells from each colony were subjected to genomic DNA extraction and T7 Endonuclease I cleavage assay (New England Biolabs, #M0302S) as previously described (5). Briefly, cells were lysed in 100 μL of lysis buffer (10 μM Tris-HCl, 0.4 M NaCl, 2 μM EDTA, 1% SDS, and 100 μg mL-1 Proteinase K). The genomic DNA was extracted by phenol-chloroform, precipitated by ethanol, and dissolved in elution buffer (1 mM Tris-HCl pH 8.3). DNA fragments harboring targeted sites were amplified by Q5 Hot Start High-Fidelity DNA polymerase (New England Biolabs, #M0493) and purified with PCR and DNA cleanup kit (New England Biolabs, #T1030). Purified PCR products were denatured and annealed in NEB Buffer 2. The resultant hybridized PCR products were digested by T7 endonuclease I for 30 minutes and separated by 2.5% agarose gel. SAGE1-null colonies were also verified by SAGE1 locus sequencing and Western blot.

22. Cell Growth Analysis

A real-time cell analyzer XCELLIGENCE (ACEA Biosciences) was used to monitor cell growth according to the manufacturer's instruction. Briefly, cells with the density of 3-6×103 per well were seeded in E-plate 96 and real-time electric resistance values were measured for 120 hours. As the increase of electric impedance in each well is positively associated with the increment of cell number, cell growth curves were presented as real-time measurement of unitless cell indices using the formula: cell index=(Rtn−Rt0)/15Ω (Rtn is the resistance measured at a time point Tn and Rt0 is the background resistance measured at a time point TO).

23. Tissue Staining

De-identified human normal and cancer tissues were obtained from Shanghai OUTDO Biotech Co. Ltd (Shanghai, China). The Streptavidin-Biotin Complex method was used in immunohistochemistry to detect SAGE1. For immunofluorescence staining, HuTu80 derived xenograft tissue and HCC PDX tissue sections were de-waxed twice in fresh xylene for 15 min each, rehydrated in 100%, 95%, 75%, 50% ethanol and PBS for 10 min each. Epitope retrieval was carried out by boiling sections in TUF TARGET UNMASK-ING FLUID (Invitrogen, Z00R.0000) for 20 min. Slides were then washed with PBST (PBS buffer supplemented with 0.5% Triton X-100) and blocked with 5% BSA at RT for 3 h, followed by incubation with rabbit anti-SAGE1 polyclonal antibody (Novus NBP1-84355), or rabbit anti-INTS3 polyclonal antibody (Novus NBP1-19091) at 4° C. for overnight, then washed and incubated with Alexa Fluor 555 or 488 conjugated secondary antibodies (Proteintech). Nuclei were counterstained with DAPI (Sigma). Slides were thoroughly washed in PBST and mounted and visualized using a laser scanning confocal microscope.

For in vivo SAGE1 knock down experiment, Streptavidin-Biotin Complex (SABC) method was used in immunohistochemistry to detect SAGE1 and ki67. For LUSC-P, Hematoxylin and Eosin staining were performed to show the histological changes in tumor residuals. Pan-cytokeratin staining showed fibro-inflammatory changes replacing neoplastic components in SAGE1 shRNA treated tissues. Primary antibodies against SAGE1, ki67 and pan-cytokeratin were used at a concentration of 1:300, 1:100 and 1:200, respectively. All antibodies used in this study were confirmed to be reactive only to the targets by the manufacturer.

24. qPCR and WB

To further investigate the function of SAGE1 in patient-derived primary tumor cells, we carried out qPCR and Western blotting analyses for samples with the following primers.

```
QPCR primer Sage-F:
                          (SEQ ID NO: 100)
ACTTCAAACGAGTCAACCAACT, Sage-R:
                          (SEQ ID NO: 101)
TCTAACCACGAGGACATACTCTT,

GAPDH-F:
                          (SEQ ID NO: 102)
ATCATCCCTGCCTCTACTGG,

GAPDH-R:
                          (SEQ ID NO: 103)
GTCAGGTCCACCACTGACAC.
```

Western blots were conducted using the following antibodies: rabbit anti-SAGE1 polyclonal antibody (Novus Biologicals, #NBP1-84355), rabbit anti-INTS3 polyclonal antibody (Novus Biologicals, #NBP1-19091), mouse anti-His monoclonal antibody (Proteintech, #66005-1-Ig), rabbit anti-FLAG polyclonal antibody (Proteintech, #20543-1-AP), mouse anti-STREPII monoclonal antibody (Abcam, #ab184224), rabbit anti-TLE3 polyclonal antibody (Proteintech, #11372-1-AP), mouse anti-GAPDH monoclonal antibody (Proteintech, #60004-1-Ig), goat antirabbit IgG (H+L), HRP conjugate (Proteintech, #SA00001-2), goat anti-mouse IgG (H+L), HRP conjugate (Proteintech, #SA00001-1). Proteins were resolved by 4-20% gradient SDS-PAGE gel (Genescript, #M42012C) and transferred to PVDF membranes. These membranes were then blocked with 5% skim milk in diluted 1×TBST buffer (Sangon, #tbst-0520009) and then probed overnight with primary antibodies at 4° C., followed by incubation of horseradish peroxidase (HRP)—conjugated donkey anti-mouse, anti-rabbit or anti-goat antibodies for 1 hour at room temperature. After 3 times of membrane wash, the immuno-complexes were detected by Western Lightning ECL Pro (PerkinElmer, #NEL122001EA) or ECL Prime Western Blotting Detection Reagents (Amersham, #RPN2232).

25. Tyramide Signal Amplification-Based Multiplexed Immunohistochemical Fluorescence Analysis Multiplexed immunohistochemical fluorescence (mIF) analysis was performed by sequential staining of 4 μm-thick deparaffined tissue sections with primary antibodies, paired with TSA 5-color kit (Yuanxibio, #D110051-50T). Briefly, after antigen retrieval and quenching of endogenous peroxidase activity, slides were blocked with 5% BSA in TBST buffer for 1 hour and incubated with anti-INTS3 antibody (Proteintech, #16620-1-AP) for 30 minutes and then probed with anti-rabbit horseradish peroxidase-conjugated (HRP) secondary antibody (Yuanxibio, #A10011-60) for 10 minutes. Fluorescence labelling using TSA 570 was developed for 10 minutes according to the manufacturer's instructions. Then, slides were washed in TBST buffer and transferred into sub-boiling 1 mM citrate solution for 15 minutes. Slides were cooled down, washed, blocked and used for another three rounds of staining for anti-histone H3K9me3 (Acam, #ab8898)/TSA 620, and anti-SAGE1 (Abcam, #ab233388)/ TSA 520. Finally, slides were treated with 2 drops of DAPI (ThermoFisher, #D1306), washed in distilled water, and mounted with Prolong Gold mounting medium. Images were taken under Zeiss LSM 880 laser scanning confocal microscope and analyzed using Indica Halo software.

26. Immunoprecipitation (IP) and Co-Immunoprecipitation (Co-IP)

For IP, 1×107 cells were lysed in lysis buffer (20 mM Tris-HCl, 150 mM NaCl, 10% Glycerol, 0.5% TritonX-100, 1 mM EDTA, 1 mM EGTA, pH7.4) supplemented with protease inhibitor cocktail (Sigma-Aldrich, #B14001), incubated in 4° C. for 10 min and sonicated by Bioruptor Plus (Diagenode) (5-10% amplitude/power, ON 5 sec-OFF 5 sec) for 1 min. After centrifugation (14,000 rpm, 15 min, 4° C., 1 mg of supernatants were incubated with 5 μg of rabbit anti-SAGE1 polyclonal antibody (Novus Biologicals, #NBP1-84355, or Abcam, #ab233388) and rabbit anti-INTS3 polyclonal antibody (Novus Biologicals, #NBP1-19091) for 16 hours respectively. Next day, 20 μL of Protein G beads (Millipore, #LSKMAGG02) were added into each tube and incubated for 3 more hours. Then beads were harvested and washed for three times with lysis buffer and eluted by 0.2 M Glycine (pH 2.2).

For Co-IP, HEK-293T cells were transfected with the indicated plasmids using X-tremeGENE HP DNA transfection reagent (Sigma-Aldrich, #6366546001). After 48 hours, cells were lysed in IP buffer containing 50 mM Tris-HCl pH 7.5, 150 mM NaCl, 0.1% Triton-X100, 1 mM EDTA and 1×Roche protease inhibitor. The supernatants were incubated overnight with mouse anti-His monoclonal antibody (Proteintech #66005-1-Ig), or rabbit anti-FLAG polyclonal antibody (Proteintech #20543-1-AP). Then, protein A/G agarose beads (Millipore, #LSKMAGAG02) were added and rotated for 2 more hours. The immunoprecipitated complexes were subjected to SDS-PAGE, followed by Western blot and/or MS analyses.

27. Protein Identification by Mass Spectrometry (MS) Analysis

Eluates of immunoprecipitation were reduced with 5 mM Tris (2-carboxyethyl) phosphine hydrochloride (TCEP) and alkylated with 25 mM Iodoacetamide. After protein precipitation by chilled acetone, the proteins were reconstituted in 25 mM ammonium bicarbonate buffer and digested by sequencing-grade trypsin (Promega) in an enzyme/substrate ratio of 1:50 at 37° C. overnight.

For liquid chromatography tandem mass spectrometry (LC-MS/MS) analysis, the digested peptide mixtures were loaded onto a trap column (2 cm×100 μm inner diameter (i.d.), C18, 3 μm particle size, 100 A pore size) for online desalting using the EASY-nLC 1000 UHPLC (Thermo Scientific). Peptides were then separated on a capillary column (15 cm×75 μm i.d., ReproSil-Pur C18, 1.9 μm particle size, 120 A pore size) at a flow rate of 300 nL min-1. The eluate was directly introduced into an Orbitrap Fusion mass spectrometer or Q Exactive HF mass spectrometer (Thermo Scientific). Mass spectra were acquired in a data-dependent mode, each full scan MS (m/z 350-1500, resolution 60 K) was followed by several higher collision induced dissociation MS/MS scans for the most intense precursor ions. The raw data were extracted and searched by Proteome Discoverer 2.2 (Thermo Scientific) with the SEQUEST search engine against the human UniProt database (UP000005640). Enzyme specificity was set to trypsin, allowing for up to 2 missed cleavages. Mass tolerance was set to 10 ppm for the precursor ions and 0.02 Da for fragment ions. The carbamidomethylation (+57.022 Da) of cysteine was set as static modifications, and oxidation of methionine residues (+15.995 Da) was set as a variable modification. The decoy database searches were also performed in parallel, and peptides less than 1% false discovery rate (FDR) were accepted.

28. Cell Line Derived Xenografts

Male BALB/c athymic nude mice (4 to 6 weeks old) were obtained from the Experimental Animal Centre of Shanghai Institutes of Biological Sciences (Shanghai, China). 1-3× 106 HuTu 80 parental, KO/SAGE1 and SAGE1mut cells were injected subcutaneously into mouse flanks. At end-points, tumor tissues were excised from sacrificed animals and calculated by weight and volume. Data of tumor weight were presented as means±SD.

29. TCGA Datasets

The cohort consisted of 10,207 samples of 32 TCGA projects, representing most major classes of human adult cancer. Level 3 RNA-seq data were downloaded for each of the following TCGA datasets: ACC (n=79), BLCA (n=414), BRCA (n=1,109), CESC (n=306), CHOL (n=36), COAD (n=480), DLBC (n=48), ESCA (n=162), GBM (n=169), HNSC (n=502), KICH (n=65), KIRC (n=539), KIRP (n=289), LAML (n=151), LGG (n=529), LIHC (n=374), LUAD (n=535), LUSC (n=502), MESO (n=86), OV (n=379), PAAD (n=178), PCPG (n=183), PRAD (n=499), READ (n=167), SARC (n=263), SKCM (n=471), STAD (n=375), THCA (n=510), THYM (n=119), UCEC (n=552), UCS (n=56), and UVM (n=80). Relevant clinical annotations were also downloaded and stored as an R object for reference. These mRNA sequencing FPKM datasets are all open access via R with 'TCGAbiolinks' package (v2.15.3) (26).

30. GTEx Datasets

The Genotype-Tissue Expression (GTEx) project (27) is an ongoing effort to build a comprehensive public resource to study tissue-specific gene expression and regulation. Gene read counts of RNA-seq data of 29 GTEx non-diseased tissue and gene-level model based on the GEN-CODE 26 transcript model were downloaded from GTEx website (https://www.gtexportal.org) including GTEx_Analysis_2017-06-

05_v8_RNASeQCv1.1.9_gene_reads.gct and gencode.v26.GRCh38.genes.gtf. The RNA expression values of 16,047 samples from 29 tissues normalized to the fragments per kilobase of transcript per million mapped reads (FPKM), and the samples including adipose (n=1, 204), adrenal gland (n=258), bladder (n=21), Blood (n=929), Brain (n=2,642), breast (n=459), cervix uteri (n=19), colon (n=779), esophagus (n=1,445), fallopian tube (n=9), heart (n=861), kidney (n=89), liver (n=226), lung (n=578), muscle (n=803), nerve (n=619), ovary (n=180), pancreas (n=328), pituitary (n=283), prostate (n=245), salivary gland (n=162), skin (n=1,809), small intestine (n=187), spleen (n=241), stomach (n=359), testis (n=361), thyroid (n=653), uterus (n=142), and vagina (n=156).

31. Quantification and Statistical Analysis

All statistical tests of experimental results were performed using the GraphPad Prism 7 unless noted. The statistical significance was calculated via unpaired two-tailed Student's t test. The dissociation constants (Kd) in ITC experiments were calculated using the Origin 7 software as mean±standard error from two independent experiments with a single site-specific binding model. The statistical analysis of in vivo experiments data was performed using nonparametric Mann-Whitney test. Results were represented as mean±standard deviation unless noted and $p < 0.05$ was considered statistically significant.

---

The invention claimed is:

1. A method of diagnosing a SAGE1 positive disorder in a subject, comprising:
   (a) lysing cells from a biological sample of a subject to obtain a supernatant;
   (b) contacting the supernatant with an anti-SAGE1 antibody to immunoprecipitate proteins;
   (c) separating the proteins by Sodium Dodecyl Sulfate Polyacrylamide Gel Electrophoresis (SDS-PAGE);
   (d) visualizing the proteins by silver staining; and
   (e) detecting INTS3 within the proteins by Mass Spectrometry (MS);
   wherein when INTS3 is detected, a SAGE1-INTS3 complex is identified in the biological sample, indicating a SAGE1 expression is detected in the biological sample, and the subject is diagnosed as having a SAGE1 positive disorder.

2. The method of claim 1, wherein the biological sample is of a type of sample that normally has no detectable SAGE1 expression.

3. The method of claim 1, wherein the subject has been determined to have a deficiency in TP53.

4. The method of claim 1, wherein the SAGE1 positive disorder is a SAGE1 positive tumor.

5. A method of assessing malignancy or malignancy potential of a tumor in a subject, comprising:
   (a) lysing cells from a biological sample of a subject to obtain a supernatant;
   (b) contacting the supernatant with an anti-SAGE1 antibody to immunoprecipitate proteins;
   (c) separating the proteins by Sodium Dodecyl Sulfate Polyacrylamide Gel Electrophoresis;
   (d) visualizing the proteins by silver staining; and
   (e) detecting INTS3 within the proteins by Mass Spectrometry;
   wherein when INTS3 is detected, a SAGE1-INTS3 complex is identified in the biological sample, indicating a SAGE1 expression is detected in the biological sample, and the tumor is assessed to be malignant or as having malignancy potential.

6. The method of claim 5, wherein the biological sample is of a type of sample that normally has no detectable SAGE1 expression.

7. The method of claim 5, wherein the malignancy is characterized as having one or more of the following features:
   a) expressing one or more stem cell marker;
   b) capable of metastasis;
   c) capable of uncontrolled cell proliferation;
   d) likely to experience disease progression;
   e) likely to develop resistance to an anti-cancer therapy;
   f) likely to relapse after treatment with an anti-cancer therapy, and
   g) having, or likely to develop, one or more cancer-related driver mutations.

8. The method of claim 5, wherein the subject has not shown any clinical manifestation of malignancy.

9. A SAGE1 inhibitor, comprising an oligonucleotide targeting SAGE1 nucleic acid, or a polynucleotide encoding the oligonucleotide, or a nucleic acid vector comprising the oligonucleotide or the polynucleotide; wherein the oligonucleotide comprises a sequence selected from SEQ ID NOs: 82-95, and 106-147, or the oligonucleotide comprises a pair of sense/antisense sequences selected from SEQ ID NOs: 70/71, 72/73, 74/75, 76/77, 78/79, and 80/81.

10. The method of claim 1, wherein when SAGE1 expression is not detected in the biological sample, the method further comprises monitoring SAGE1 expression in the subject after a course of time.

11. A method of treating or alleviating one or more symptoms of a SAGE1 positive disorder in a subject, comprising administering to the subject in need thereof a therapeutically effective amount of a SAGE1 inhibitor of claim 9.

12. A method of treating or alleviating one or more symptoms of a SAGE1 positive disorder in a subject, comprising administering to the subject in need thereof a therapeutically effective amount of a SAGE1 inhibitor, wherein the inhibitor comprises (a) a SAGE1-binding fragment of INTS3 comprising an amino acid sequence of SEQ ID NO: 9; (b) an INTS3-binding fragment of SAGE1 comprising an amino acid sequence of SEQ ID NO: 8; or (c) an INTS3-binding fragment of INTS6 or INTS6L comprising an amino acid sequence of SEQ ID NO: 10, SEQ ID NO: 104, or SEQ ID NO: 105.

13. A method of determining sensitivity of a tumor sample to a SAGE1 inhibitor, comprising:
- (a) lysing cells from the tumor sample of a subject to obtain a supernatant;
- (b) contacting the supernatant with an anti-SAGE1 antibody to immunoprecipitate proteins;
- (c) separating the proteins by Sodium Dodecyl Sulfate Polyacrylamide Gel Electrophoresis;
- (d) visualizing the proteins by silver staining; and
- (e) detecting INTS3 within the proteins by Mass Spectrometry;
- wherein when INTS3 is detected, a SAGE1-INTS3 complex is identified in the tumor sample, indicating a SAGE1 expression is detected in the tumor sample, and the tumor sample is determined to be sensitive to the SAGE1 inhibitor.

14. A method of identifying a subject having a tumor who is likely to benefit from treatment with a SAGE1 inhibitor, comprising:
- (a) lysing cells from a tumor sample of a subject to obtain a supernatant;
- (b) contacting the supernatant with an anti-SAGE1 antibody to immunoprecipitate proteins;
- (c) separating the proteins by Sodium Dodecyl Sulfate Polyacrylamide Gel Electrophoresis;
- (d) visualizing the proteins by silver staining; and
- (e) detecting INTS3 within the proteins by Mass Spectrometry;
- wherein when INTS3 is detected, a SAGE1-INTS3 complex is identified in the tumor sample, indicating a SAGE1 expression is detected in the tumor sample, and the subject is identified as being likely to benefit from treatment with the SAGE1 inhibitor.

15. The method of claim 14, wherein the subject has been determined to have a mutation in TP53.

16. The method of claim 14, further comprising providing or administering the SAGE1 inhibitor to the subject identified as being likely to benefit from treatment with the SAGE1 inhibitor; wherein the SAGE1 inhibitor comprises an oligonucleotide targeting SAGE1 nucleic acid, or a polynucleotide encoding the oligonucleotide, or a nucleic acid vector comprising the oligonucleotide or the polynucleotide; wherein the oligonucleotide comprises a sequence selected from SEQ ID NOs: 82-95, and 106-147, or the oligonucleotide comprises a pair of sense/antisense sequences selected from SEQ ID NOs: 70/71, 72/73, 74/75, 76/77, 78/79, and 80/81; or
- wherein the SAGE1 inhibitor comprises (a) a SAGE1-binding fragment of INTS3 comprising an amino acid sequence of SEQ ID NO: 9; (b) an INTS3-binding fragment of SAGE1 comprising an amino acid sequence of SEQ ID NO: 8; or (c) an INTS3-binding fragment of INTS6 or INTS6L comprising an amino acid sequence of SEQ ID NO: 10, SEQ ID NO: 104, or SEQ ID NO: 105.

17. A method of monitoring progression of a SAGE1 positive disorder in a subject, comprising:
- (a) lysing cells from a first biological sample and a second biological sample of a subject to obtain a first supernatant and a second supernatant, respectively; wherein the second biological sample is obtained after a course of time from the first sample;

- (b) contacting the first and the second supernatants with an anti-SAGE1 antibody to immunoprecipitate a first protein in the first supernatant and a second protein in the second supernatant;
- (c) separating the first and second proteins by Sodium Dodecyl Sulfate Polyacrylamide Gel Electrophoresis;
- (d) visualizing the first and second proteins by silver staining;
- (e) detecting INTS3 within the first and second proteins by Mass Spectrometry; if INTS3 in the first and second proteins is detected, a SAGE1-INTS3 complex is identified in the first and second biological samples, indicating a SAGE1 expression is detected in the first and second biological samples; and
- (f) measuring an amount of binding between the SAGE1 antibody and the first and second proteins to determine a level of SAGE1 expression in the first and second biological samples by using western blot;
- wherein when the level of SAGE1 expression in the second biological sample is higher than that in the first biological sample, the SAGE1 positive disorder is determined as having progressed.

18. A method of monitoring responsiveness of a subject having a SAGE1 positive disorder undergoing treatment with the method of claim 16 within a therapeutic period, comprising:
- (a) lysing cells from a first biological sample and a second biological sample of a subject to obtain a first supernatant and a second supernatant, respectively; wherein the first biological sample is obtained from the subject before the therapeutic period, and the second biological sample is obtained after the therapeutic period;
- (b) contacting the first and second supernatants with an anti-SAGE1 antibody to immunoprecipitate a first protein in the first supernatant and a second protein in the second supernatant;
- (c) separating the first and second proteins by Sodium Dodecyl Sulfate Polyacrylamide Gel Electrophoresis;
- (d) visualizing the first and second proteins by silver staining;
- (e) detecting INTS3 within the first and second proteins by Mass Spectrometry; if INTS3 within the first and second proteins is detected, a SAGE1-INTS3 complex is identified in the first and second biological samples, indicating a SAGE1 expression is detected in the first and second biological samples; and
- (f) measuring an amount of binding between the SAGE1 antibody and the first and second proteins to determine a level of SAGE1 expression in the first and second biological samples by using western blot;
- wherein when the level of SAGE1 expression in the second biological sample is lower than in the first, the subject is identified as being responsive to the treatment.

19. The method of claim 1, wherein the SAGE1 expression is detected at DNA level, RNA level, or protein level.

20. The method of claim 19, wherein the SAGE1 expression is further indicated by
- (a) presence or level of SAGE1 protein;
- (b) presence or level of SAGE1 mRNA;
- (c) presence or level of a SAGE1 complex;
- (d) level of demethylation of in the SAGE1 gene;
- (e) presence or level of histone acetylation of the SAGE1 gene;
- (f) presence or level of binding of a transcription factor to the SAGE1 gene,
- (g) or any combination thereof.

21. The method of claim 20, wherein the SAGE1 complex comprises SAGE1 and at least one component selected from INIP, NABP1/2, CREBBP, TLE1, TLE2, TLE3, TLE4, TLE5, GGA3, CNOT1, TAX1BP1, SEC16A, CYLD and PAXBP1.

22. The method of claim 20, wherein a level of demethylation is detected in a region that is within 3 kb upstream and 3 kb downstream of the transcription start site of SAGE1 gene.

23. The method of claim 20, where the histone acetylation is detected near an enhancer region, a promoter region or an expression region of the SAGE1 gene.

24. The method of claim 19, wherein the detection comprises an immunoassay, an amplification assay, a hybridization assay, or a sequencing assay.

25. The method of claim 1, wherein the biological sample is selected from a cell, a tissue, a bodily fluid and any combination thereof.

26. The method of claim 25, wherein body fluid is selected from blood, serum, plasma, ascites, cyst fluid, pleural fluid, peritoneal fluid, cerebrospinal fluid, tears, urine, saliva, sputum, nipple aspirates, lymph fluid, fluid of the respiratory, intestinal, and genitourinary trances, breast milk, intra-organ system fluid, peritoneal fluid, conditioned media from tissue explant culture, or combinations thereof.

27. The method of claim 5, wherein the tumor is selected from solid tumors or hematological tumors.

28. The method of claim 27, wherein the tumor is selected from adrenal cancer, lymphoepithelial neoplasia, adenoid cell carcinoma, lymphoma, acoustic neuroma, acute lymphocytic leukemia, acral lentiginous melanoma, acute myeloid leukemia, acrospiroma, chronic lymphocytic leukemia, acute eosinophilic leukemia, liver cancer, acute erythrocyte leukemia, small cell lung cancer, acute lymphocytic leukemia, non-small cell lung cancer, acute megakaryoblastic leukemia, MALT lymphoma, acute monocytic leukemia, malignant fibrous histiocytoma, acute promyelocytic leukemia, malignant peripheral schwannomas, mantle cell lymphoma, adenocarcinoma, marginal zone B-cell lymphoma, malignant hippocampal tumor, adenoid cystic carcinoma, gland tumor, adenoma-like odontogenic tumor, mast cell leukemia, adenosquamous carcinoma, mediastinal germ cell tumor, adipose tissue tumor, breast medullary carcinoma, adrenocortical carcinoma, medullary thyroid carcinoma, adult T cell leukemia/lymphoma, Medulloblastoma, invasive NK cell leukemia, melanoma, AIDS-related lymphoma, meningioma, lung rhabdomyosarcoma, Merkel cell carcinoma, alveolar soft tissue sarcoma, mesothelioma, ameloblastoma, metastatic urothelial carcinoma, anaplastic large cell lymphoma, mixed Müllerian tumor, thyroid undifferentiated carcinoma, mucinous neoplasm, angioimmunoblastic T-cell lymphoma, multiple myeloma, angiomyolipoma, muscle tissue tumor, angiosarcoma, mycosis fungoides, astrocytoma, myxoid liposarcoma, atypical deformed rhabdoid tumor, myxoma, B-cell chronic lymphocytic leukemia, mucinous sarcoma, B-cell lymphoblastic leukemia, nasopharyngeal carcinoma, B-cell lymphoma, schwannomas, basal cell carcinoma, neuroblastoma, biliary tract cancer, neurofibromatosis, bladder cancer, neuroma, blastoma, nodular melanoma, bone cancer, eye cancer, Brenner tumor, oligodendroxoma, brown tumor, oligodendroglioma, Burkitt's lymphoma, eosinophilic breast cancer, brain cancer, optic nerve tumor cancer, oral cancer carcinoma in situ, osteosarcoma, carcinosarcoma, ovarian cancer, cartilage tumor, pulmonary sulcus tumor, papillary thyroid carcinoma, myeloma, paraganglioma, chondroma, pineal blastoma, chordoma, pineal cell tumor, choriocarcinoma, pituitary tumor, choroid plexus papilloma, pituitary adenoma, kidney clear cell sarcoma, pituitary tumor, craniopharyngioma, plasmacytoma, cutaneous T-cell lymphoma, multiple embryonic cell tumor, cervical cancer, precursor T lymphoblastic lymphoma, colorectal cancer, primary central nervous system lymphoma, Degos disease, primary effusion lymphoma, proliferative small round cell tumor, primary preformed peritoneal cancer, diffuse large B-cell lymphoma, prostate cancer, embryonic dysplasia of neuroepithelial neoplasia, pancreatic cancer, anaplastic cell tumor, pharyngeal carcinoma, embryonic carcinoma, peritoneal pseudomyxoma, endocrine gland tumor, renal cell carcinoma, enteropathy-associated T-cell lymphoma, endodermal sinus tumor, renal medullary carcinoma, retinoblastoma, esophageal cancer, rhabdomyosarcoma, endadelphos, rhabdomyosarcoma, fibroids, Richter's transformation, fibrosarcoma, rectal cancer, follicular lymphoma, sarcoma, follicular thyroid cancer, schwannoma, ganglion cell tumor, seminoma, gastrointestinal cancer, Sertoli cell tum, germ cell tumor, sex cord-gonadal stromal tumor, pregnancy choriocarcinoma, signet ring cell carcinoma, giant cell fibroblastoma, skin cancer, bone giant cell tumor of bone, small blue round cell tumor, glioma, small cell carcinoma, glioblastoma multiforme, soft tissue sarcoma, glioma, somatostatin tumor, glioma brain, soot wart, pancreatic high glucagonoma, spinal tumor, Gonadoblastoma, spleen marginal lymphoma, granulosa cell tumor, squamous cell carcinoma, estrogen tumor, synovial sarcoma, gallbladder cancer, Sezary disease, gastric cancer, small intestine cancer, hairy cell leukemia, squamous cell carcinoma, hemangioblastoma, gastric cancer, head and neck cancer, T-cell lymphoma, vascular epithelioma, testicular cancer, hematological malignancies, sarcoma, hepatoblastoma, thyroid cancer, hepatosplenic T-cell lymphoma, transitional cell carcinoma, Hodgkin's lymphoma, laryngeal cancer, non-Hodgkin's lymphoma, urachal cancer, invasive lobular carcinoma, genitourinary cancer, intestinal cancer, urothelial carcinoma, renal cancer, uveal melanoma, laryngeal cancer, uterine cancer, malignant freckle-like sputum, verrucous carcinoma, lethal midline granuloma, visual pathway glioma, leukemia, vulvar cancer, testicular stromal tumor, vaginal cancer, liposarcoma, Waldenstrom's macroglobulinemia Disease, lung cancer, adenolymphoma lymphangioma, nephroblastoma, lymphangisarcoma, colon adenocarcinoma (coad), liver hepatocellular carcinoma (lihc), ovarian serous cystadenocarcinoma (ov), uterine corpus endometrial carcinoma (ucec), thyroid carcinoma (thca), skin cutaneous melanoma (skcm), lung adenocarcinoma (luad), head and neck squamous cell carcinoma (hnsc), glioblastoma multiforme (gbm), prostate adenocarcinoma (prad), thymoma (thym), brain lower grade glioma (lgg), rectum adenocarcinoma (read), pheochromocytoma and paraganglioma (pcpg), esophageal carcinoma (esca), kidney renal clear cell carcinoma (kirc), cervical squamous cell carcinoma and endocervical adenocarcinoma (cesc), bladder urothelial carcinoma (blca), kidney renal papillary cell carcinoma (kirp), pancreatic adenocarcinoma (paad), stomach adenocarcinoma (stad), kidney chromophobe (kich), breast invasive carcinoma (brca), lung squamous cell carcinoma (lusc), sarcoma (sarc), or acute myeloid leukemia (laml).

\* \* \* \* \*